(12) United States Patent
Ding et al.

(10) Patent No.: US 9,878,982 B2
(45) Date of Patent: Jan. 30, 2018

(54) PYRIDINE DERIVATIVES AND ANTI-MYCOBACTERIAL USE THEREOF

(71) Applicant: CISEN PHARMACEUTICAL CO., LTD., Jining (CN)

(72) Inventors: Zhaozhong Ding, Shanghai (CN); Shuhui Chen, Shanghai (CN); Zhigang Huang, Shanghai (CN); Wei Luo, Shanghai (CN); Zhe Cai, Shanghai (CN); Yepeng Wang, Shanghai (CN); Dongdong Tang, Shanghai (CN)

(73) Assignee: CISEN PHARMACEUTICAL CO., LTD., Jining (CN)

( * ) Notice: Subject to any disclaimer, the term of this patent is extended or adjusted under 35 U.S.C. 154(b) by 0 days.

(21) Appl. No.: 15/325,824

(22) PCT Filed: Jul. 9, 2015

(86) PCT No.: PCT/CN2015/083626
§ 371 (c)(1),
(2) Date: Jan. 12, 2017

(87) PCT Pub. No.: WO2016/008381
PCT Pub. Date: Jan. 21, 2016

(65) Prior Publication Data
US 2017/0174628 A1 Jun. 22, 2017

(30) Foreign Application Priority Data

Jul. 14, 2014 (CN) .......................... 2014 1 0335196
Jul. 2, 2015 (CN) .......................... 2015 1 0383612

(51) Int. Cl.
| | | |
|---|---|---|
| C07D 213/64 | (2006.01) | |
| C07D 401/04 | (2006.01) | |
| C07D 405/04 | (2006.01) | |
| C07D 409/04 | (2006.01) | |
| A61K 31/44 | (2006.01) | |
| C07D 213/643 | (2006.01) | |
| C07D 213/647 | (2006.01) | |
| C07D 213/57 | (2006.01) | |
| C07D 417/04 | (2006.01) | |

(52) U.S. Cl.
CPC .......... *C07D 213/643* (2013.01); *A61K 31/44* (2013.01); *C07D 213/57* (2013.01); *C07D 213/647* (2013.01); *C07D 401/04* (2013.01); *C07D 405/04* (2013.01); *C07D 409/04* (2013.01); *C07D 417/04* (2013.01)

(58) Field of Classification Search
None
See application file for complete search history.

(56) References Cited

U.S. PATENT DOCUMENTS

| | | |
|---|---|---|
| 7,498,343 B2 | 3/2009 | Van Gestel et al. |
| 7,709,498 B2 | 5/2010 | Andries et al. |
| 8,415,475 B2 | 4/2013 | Guillemont et al. |
| 2007/0249667 A1 | 10/2007 | Andries et al. |
| 2010/0069366 A1 | 3/2010 | Guillemont et al. |

FOREIGN PATENT DOCUMENTS

| | | |
|---|---|---|
| CN | 1671667 A | 9/2005 |
| CN | 1976704 A | 6/2007 |
| CN | 101232884 A | 7/2008 |
| CN | 101547907 A | 9/2009 |
| CN | 101553470 A | 10/2009 |

OTHER PUBLICATIONS

Mamolo et al, II Farmaco (1996), 51(1), pp. 65-71.*
Wu et al., Toxicology (2007), 236, pp. 1-6.*
International Search Report dated Oct. 22, 2015corresponding to International Patent Application No. PCT/CN2015/083626, filed on Jul. 9, 2015; 8 pages.

* cited by examiner

*Primary Examiner* — Zinna Northington-Davis
(74) *Attorney, Agent, or Firm* — Mintz Levin Cohn Ferris Glovsky and Popeo PC

(57) ABSTRACT

Disclosed are a method for preparing a series of novel pyridine derivatives and a use thereof. Such derivatives can be used in the treatment of related diseases caused by mycobacteria, in particular diseases caused by pathogenic mycobacteria, such as *Mycobacterium tuberculosis*, *Mycobacterium bovis*, *Mycobacterium avium* and *Mycobacterium marinum*.

13 Claims, 1 Drawing Sheet

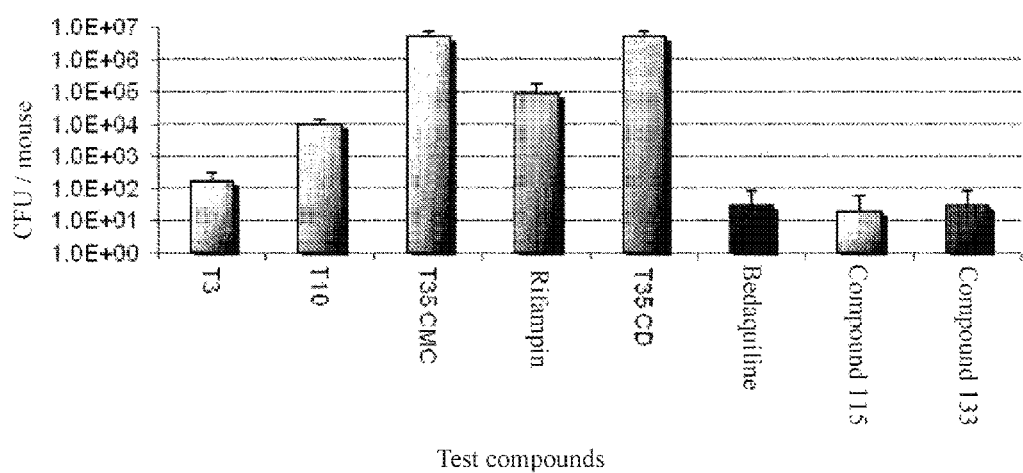

PYRIDINE DERIVATIVES AND ANTI-MYCOBACTERIAL USE THEREOF

TECHNICAL FIELD

The present invention relates to a preparation method and use of a series of novel pyridine derivatives. Such derivatives are useful for treating mycobacterium related diseases, especially for treating diseases caused by pathogenic mycobacteria, such as *M. tuberculosis, M. bovis, M. avium,* and *M. marinum*.

BACKGROUND ART

*Mycobacterium tuberculosis* is the pathogen of tuberculosis. As a globally widespread and a fatal infectious disease, about more than 8 million people were infected annually and 2 million people died from tuberculosis, according to the World Health Organization. In the last decade, tuberculosis cases have increased at a rate of 20% worldwide, particularly in poor areas. If this trend continues, tuberculosis cases are very likely to continue to increase at a rate of 41% over the next two decades. In the first 50 years after the initial application of chemotherapy, tuberculosis had always been the main infectious disease leading to adult death, only second to AIDS. The complications of tuberculosis led to the emergence of many resistant strains, which also developed a symbiotic relationship with AIDS. The population infected with tuberculosis whose HIV tests were positive is 30 times more likely to develop into active tuberculosis compared to the population whose HIV tests were negative. On average, one out of every three people who died of AIDS was caused by tuberculosis.

The current treatments for tuberculosis use a combination of multiple agents. For example, a formula recommended by the U.S. Public Health Service includes a combination of isoniazid, rifampicin, pyrazinamide and ethambutol for two months, followed by a combination of isoniazid and rifampicin for four months. For patients infected with AIDS, use of this drug combination needs to be extended to seven months. For patients infected with multidrug-resistant tuberculosis, the drug combination needs contain additional drugs, such as ethambutol tablets, streptomycin, kanamycin, amikacin, capreomycin, ethionamide, cycloserine, ciprofloxacin and ofloxacin.

For the benefit of patients and medical providers, new therapies that can improve the current treatment, such as a therapy that has a shorter treatment cycle or needs less supervision, are highly desired. During the first two months of treatment, the combined four drugs inhibited the bacteria, thereby greatly reducing the number of bacteria and making the patient non-infectious. In the next four to six months, the bacteria present in the patient's body were eliminated, thereby reducing the possibility of relapse. A potent antiseptic that shortens the treatment cycle to two months or less can bring huge benefits. At the same time, the drug should also require less supervision. Clearly, a drug that can shorten the treatment time while reduce the frequency of monitoring can bring the greatest benefit.

Complications of infectious tuberculosis cause multidrug-resistant tuberculosis. 4% of cases are associated with multidrug-resistant tuberculosis around the world. Multidrug-resistant tuberculosis is mainly resistant to isoniazid and rifampicin in the four standard therapy drugs. Multidrug-resistant tuberculosis can be fatal if leaving untreated or if the standard therapy for the common tuberculosis is used. Therefore, the treatment of such disease requires the use of second-line drugs to two years. Most of these second-line drugs are toxic, expensive, and of low efficacy. Due to the absence of effective treatment, patients with contagious drug-resistant tuberculosis continue to spread the disease. Therefore, for multidrug-resistant tuberculosis, a new drug having a new action mechanism is highly desired.

At present, in all clinical drugs, anti-tuberculosis ATP synthase inhibitors attract more and more attentions. WO2004/01436 described a compound which is effective for treating tuberculosis, in particular for tuberculosis infected with multidrug-resistant *Mycobacterium tuberculosis*. The compound has the formula (Ia):

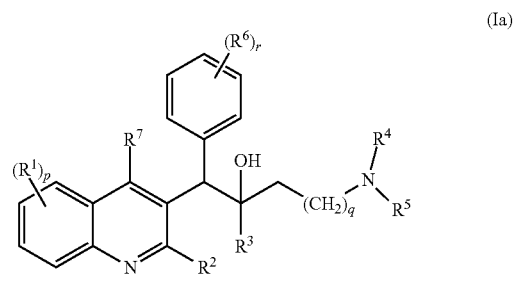

(Ia)

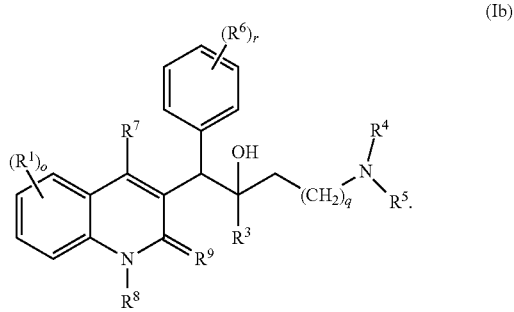

(Ib)

According to that study, a novel anti-tuberculosis weapon, TMC207, was developed. The compound has the formula (Ic).

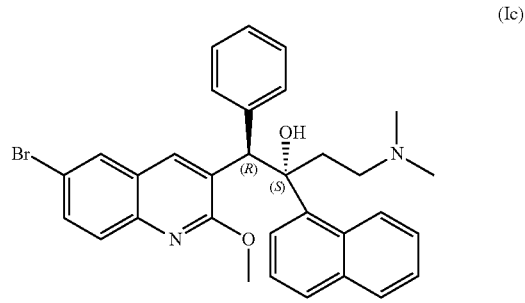

(Ic)

TMC207 (also known as R207910, or Compound 'J') is a diarylquinoline. The compound inhibits the proton pump of *M. tuberculosis* ATP synthase. TMC207 was obtained by Johnson & Johnson through screening more than 70,000 compounds against the saprophytic *Mycobacterium smegmatis* which grows more rapidly and controllably than *M. tuberculosis* does. TMC207 (Sirturo) is the first anti-tuberculosis and energy-metabolism-interfering drug that applied a new mechanism of action. The US Food and Drug Safety Agency and the European Commission approved Sirturo as part of a combination therapy for adult multidrug-resistant tuberculosis in late 2012 and March 2014, respectively.

The present invention aimed at developing a new type of pyridine derivatives which can inhibit the growth of mycobacterium, thereby achieving the effective treatment of the diseases caused by *M. tuberculosis, M. bovis, M. avium*, and *M. marinum*.

SUMMARY OF THE INVENTION

The present invention provides a compound of formula (I), or a pharmaceutically acceptable salt, hydrate, prodrug, stereoisomer or tautomer thereof,

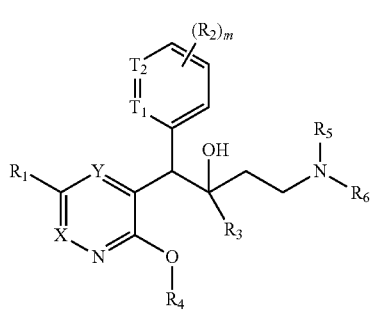

wherein,
$R^1$ is selected from H, F, Cl, Br, I, CN, OH, SH, $NH_2$, CHO, COOH, $C(=O)NH_2$, $S(=O)NH_2$, $S(=O)_2NH_2$, or the following group optionally substituted with 0, 1, 2 or 3 $R^{01}$: $C_{1-10}$ hydrocarbyl, $C_{1-10}$ heterohydrocarbyl, $C_{3-10}$ cyclohydrocarbyl, $C_{3-10}$ heterocyclohydrocarbyl, $C_{1-10}$ hydrocarbyl substituted with $C_{3-10}$ cyclohydrocarbyl or $C_{3-10}$ heterocyclohydrocarbyl, $C_{1-10}$ heterohydrocarbyl substituted with $C_{3-10}$ cyclohydrocarbyl or $C_{3-10}$ heterocyclohydrocarbyl;
m is 0, 1, 2 or 3;
$R^2$ is selected from H, halogen, haloalkyl, OH, CN, $NH_2$, or the following group optionally substituted with 0, 1, 2 or 3 $R^{01}$: $C_{1-10}$ alkyl, $C_{1-10}$ alkoxy or $C_{1-10}$ alkylthiol;
$R^3$ is selected from the following group optionally substituted with 0, 1, 2 or 3 $R^{01}$: 6-12 membered aryl, 6-12 membered heteroaryl, 6-12 membered aryl-alkylene, 6-12 membered heteroaryl-alkylene, 3-6 membered cycloalkyl, 3-6 membered heterocycloalkyl, 3-6 membered cycloalkyl-alkylene or 3-6 membered heterocycloalkyl-alkylene;
$R^4$ represents $C_{1-8}$ alkyl optionally substituted with 0, 1, 2 or 3 $R^{01}$;
$R^5$ and $R^6$ are each independently selected from H, $C_{1-8}$ alkyl or benzyl, wherein the $C_{1-8}$ alkyl is optionally substituted with 0, 1, 2 or 3 F, Cl, Br, I, CN, OH, $NH_2$ or $CF_3$;
$T_1$ and $T_2$ are each independently selected from CH and N;
X is selected from CH, —C($C_{6-12}$ aryl)-, —C(halogen)-, —C($C_{1-10}$ alkyl)-, —C($C_{1-10}$ alkoxy)-, —C[N(di-$C_{1-10}$ alkyl)]- and N;
Y is selected from CH and N;
$R^{01}$ is selected from F, Cl, Br, I, CN, OH, $N(CH_3)_2$, $NH(CH_3)$, $NH_2$, CHO, COOH, $C(=O)NH_2$, $S(=O)NH_2$, $S(=O)_2NH_2$, $CF_3$, $CF_3O$, $(NH_2)CH_2$, $(HO)CH_2$, $CH_3C(=O)$, $CH_3OC(=O)$, $CH_3S(=O)_2$, $CH_3S(=O)$ $C_{1-8}$ alkoxy and $C_{1-8}$ alkyl;
"hetero" represents a heteroatom or a heteroatom group selected from —C(=O)NH—, —NH—, —C(=NH)—, —S(=O)$_2$NH—, —S(=O)NH—, —O—, —S—, N, =O, —S—, —C(=O)O—, —C(=O)—, —C(=S)—, —S(=O)—, —S(=O)$_2$— or —NHC(=O)NH—;
the number of the hetero atoms or hetero atom groups is each independently selected from 0, 1, 2 or 3; optionally, $R^5$ and $R^6$ are together attached to the same atom to form a 3-6 membered ring.

In one embodiment of the present invention, the above $R^1$ is selected from H, F, Cl, Br, I, CN, OH, SH, $NH_2$, CHO, COOH, $C(=O)NH_2$, $S(=O)NH_2$, $S(=O)_2NH_2$, $R^{11}$ or

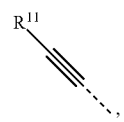

wherein, $R^{11}$ is selected from the following group optionally substituted with 0, 1, 2 or 3 $R^{01}$: $C_{1-6}$ alkyl, $C_{1-6}$ heteroalkyl, N,N-di($C_{1-6}$ alkyl)amino-$(CH_2)_{0-3}$, $C_{3-6}$ cycloalkyl, 3-6 membered heterocycloalkyl, 5-6 membered cyclohydrocarbyl and 5-6 heterocyclohydrocarbyl.

In one embodiment of the present invention, the above $R^1$ is selected from H, F, Cl, Br, I, $R^{101}$ and

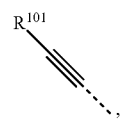

wherein, $R^{101}$ is selected from the following group optionally substituted with 1, 2 or 3 F, Cl, Br, I, $CH_3$, $CF_3$, $CH_3O$ or $CF_3O$: phenyl, pyridyl, thienyl, furyl, thiazolyl, isothiazolyl, $C_{1-6}$ alkyl, N,N-di($C_{1-6}$ alkyl)amino-$(CH_2)_{0-3}$, $C_{3-4}$ cycloalkyl,

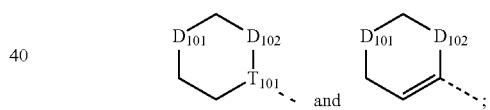

$D_{101}$ is selected from $CH_2$, O, S, NH and $N(CH_3)$;
$D_{102}$ is $CH_2$ or a single bond; and
$T_{101}$ is CH or N.

In one embodiment of the present invention, the above $R^1$ is selected from:

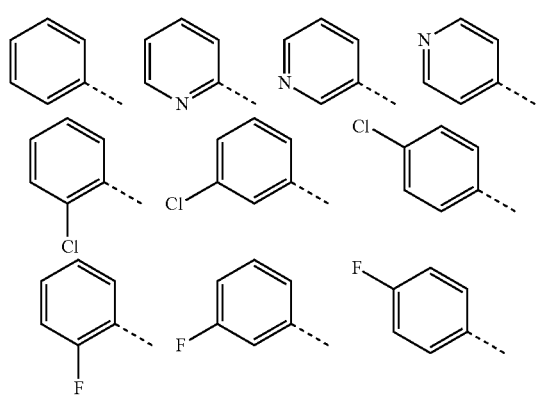

-continued

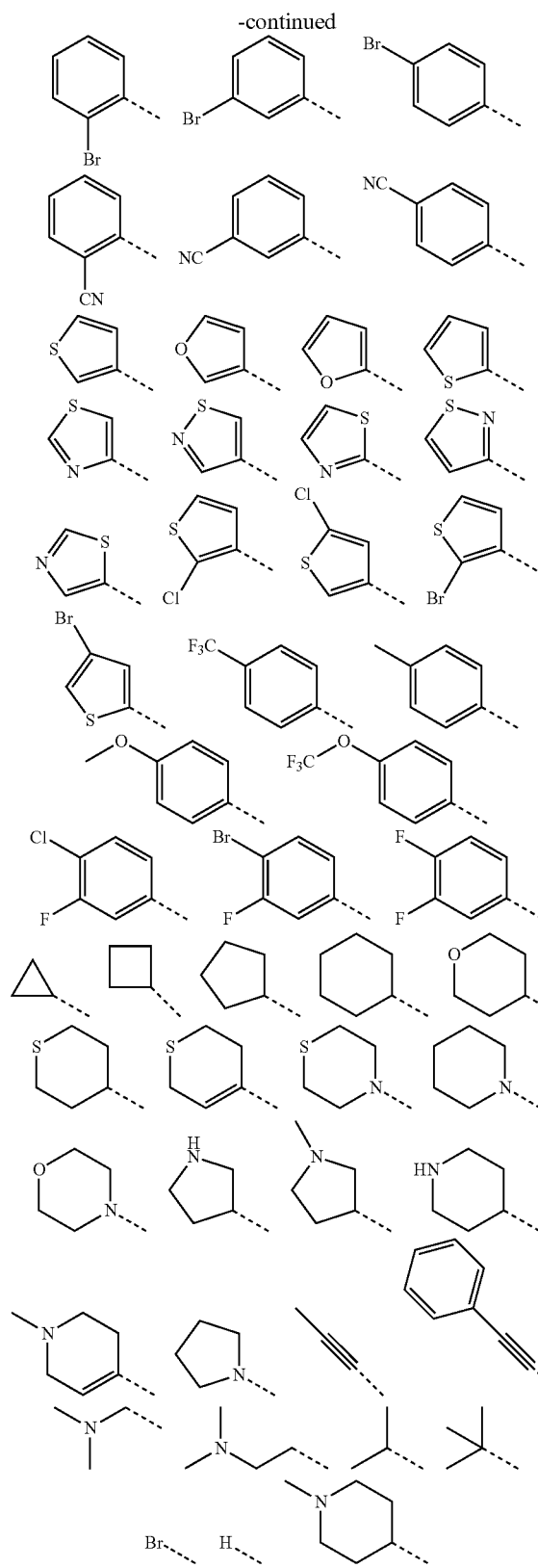

In one embodiment of the present invention, the above $R^2$ is selected from H, halogen, hydroxyl, or the following group optionally substituted with 0, 1, 2 or 3 $R^{01}$: $C_{1-6}$ alkyl or $C_{1-6}$ alkoxy.

In one embodiment of the present invention, the above $R^2$ is selected from H, halogen, hydroxyl, $CH_3O$ and $CF_3$.

In one embodiment of the present invention, the above $R^3$ is selected from the following group optionally substituted with 0, 1, 2 or 3 $R^{01}$: phenyl-$(CH_2)_{0-3}$, naphthyl-$(CH_2)_{0-3}$ and $C_{3-6}$ cycloalkyl-$(CH_2)_{0-3}$.

In one embodiment of the present invention, the above $R^3$ is selected from:

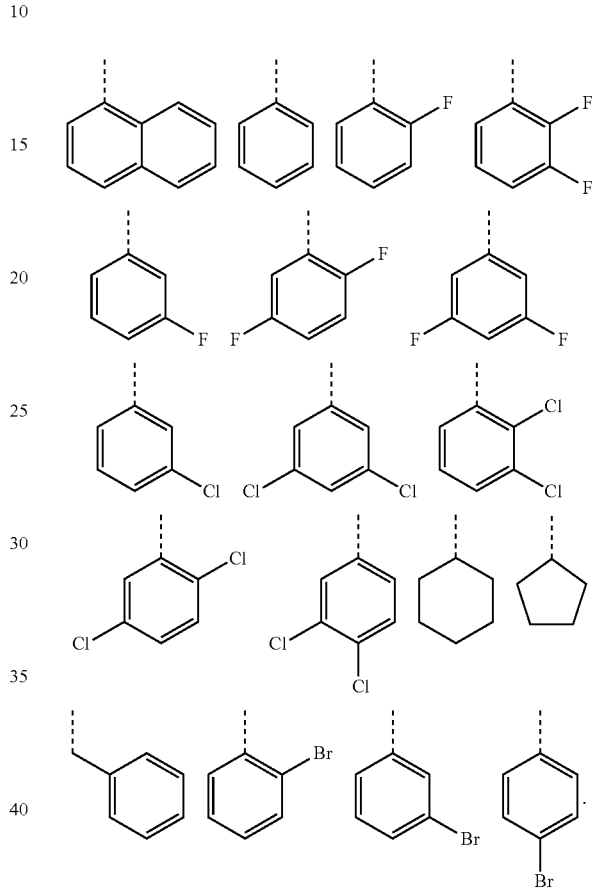

In one embodiment of the present invention, the above $R^4$, $R^5$ and $R^6$ are each independently selected from $C_{1-6}$ alkyl optionally substituted with 0, 1, 2 or 3 F, Cl, Br, I, CN, OH, SH, $NH_2$, CHO, COOH, C(=O)$NH_2$, S(=O)$NH_2$ or S(=O)$_2NH_2$.

In one embodiment of the present invention, the above $R^4$, $R^5$ and $R^6$ are each independently selected from $CH_3$ and

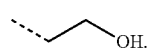

In one embodiment of the present invention, the above structure unit

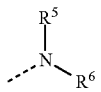

is selected from

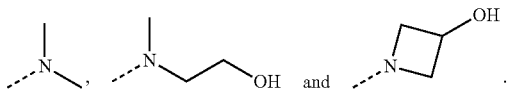

In one embodiment of the present invention, the above compound is selected from:
1) 2-(5-(4-(dimethylamino)-2-hydroxyl-2-(naphthalen-1-yl)-1-phenylbutyl)-3-(6-methoxypyridin-3-yl))benzonitrile;
2) 1-(5-(2-bromophenyl)-2-methoxypyridin-3-yl)-4-(dimethylamino)-2-(naphthalen-1-yl)-1-phenylbutan-2-ol;
3) 1-(5-cyclopropyl-2-methoxypyridin-3-yl)-4-(dimethylamino)-2-(naphthalen-1-yl)-1-phenylbutan-2-ol;
4) 4-(dimethylamino)-1-(6-methoxy-[3,4'-bipyridin]-5-yl)-2-(naphthalen-1-yl)-1-phenylbutan-2-ol;
5) 4-(dimethylamino)-1-(6-methoxy-[3,3'-bipyridin]-5-yl)-2-(naphthalen-1-yl)-1-phenylbutan-2-ol;
6) 4-(dimethylamino)-1-(2-methoxy-5-(pyrrolidin-3-yl)pyridin-3-yl)-2-(naphthalen-1-yl)-1-phenylbutan-2-ol;
7) 4-(dimethylamino)-1-(2-methoxy-5-(1-methylpyrrol-3-yl)pyridin-3-yl)-2-(naphthalen-1-yl)-1-phenylbutan-2-ol;
8) 1-(5-cyclopentyl-2-methoxypyridin-3-yl)-4-(dimethylamino-2-(naphthalen-1-yl)-1-phenylbutan-2-ol;
9) 4-(dimethylamino)-1-(2-methoxy-5-(tetrahydro-2H-pyran-4-yl)pyridin-3-yl)-2-(naphthalen-1-yl)-1-phenylbutan-2-ol;
10) 4-(dimethylamino)-1-(2-methoxy-5-(piperidin-4-yl)pyridin-3-yl)-2-(naphthalen-1-yl)-1-phenylbutan-2-ol;
11) 4-(dimethylamino)-1-(2-methoxy-5-(1-methylpiperidin-4-yl)pyridin-3-yl)-2-(naphthalen-1-yl)-1-phenylbutan-2-ol;
12) 4-(dimethylamino)-1-(6-methoxy-1'-methyl-1',2',3',6'-tetrahydro-[3,4'-bipyridin]-5-yl)-2-(naphthalen-1-yl)-1-phenylbutan-2-ol;
13) 4-(dimethylamino)-1-(5-(2-fluorophenyl)-2-methoxypyridin-3-yl)-2-(naphthalen-1-yl)-1-phenylbutan-2-ol;
14) 4-(dimethylamino)-1-(5-(3-fluorophenyl)-2-methoxypyridin-3-yl)-2-(naphthalen-1-yl)-1-phenylbutan-2-ol;
15) 4-(dimethylamino)-1-(5-(4-fluorophenyl)-2-methoxypyridin-3-yl)-2-(naphthalen-1-yl)-1-phenylbutan-2-ol;
16) 4-(dimethylamino)-1-(6'-methoxy-[2,3'-bipyridin]-5'-yl)-2-(naphthalen-1-yl)-1-phenylbutan-2-ol;
17) 4-(dimethylamino)-1-(5-((dimethylamino)methyl)-2-methoxypyridin-3-yl)-2-(naphthalen-1-yl-1-phenylbutan-2-ol;
18) 4-(dimethylamino)-1-(5-(2-(dimethylamino)ethyl)-2-methoxypyridin-3-yl)-2-(naphthalen-1-yl)-1-phenylbutan-2-ol;
19) 1-(5-cyclohexyl-2-methoxypyridin-3-yl)-4-(dimethylamino)-2-(naphthalen-1-yl)-1-phenylbutan-2-ol;
20) 1-5-(2-chlorophenyl)-2-methoxypyridin-3-yl)-4-(dimethylamino)-2-(naphthalen-1-yl)-1-phenylbutan-2-ol;
21) 1-5-(3-chlorophenyl)-2-methoxypyridin-3-yl)-4-(dimethylamino)-2-(naphthalen-1-yl)-1-phenylbutan-2-ol;
22) 1-(5-(4-chlorophenyl)-2-methoxypyridin-3-yl)-4-(dimethylamino)-2-(naphthalen-1-yl)-1-phenylbutan-2-ol;
23) 4-(dimethylamino)-1-(2-methoxypyridin-3-yl)-2-(naphthalen-1-yl)-1-phenylbutan-2-ol;
24) 1-(5-(3-bromophenyl)-2-methoxypyridin-3-yl)-4-(dimethylamino)-2-(naphthalen-1-yl)-1-phenylbutan-2-ol;
25) 1-(5-(4-bromophenyl)-2-methoxypyridin-3-yl)-4-(dimethylamino)-2-(naphthalen-1-yl)-1-phenylbutan-2-ol;
26) 4-(dimethylamino)-1-(2-methoxy-5-(thiophen-3-yl)pyridin-3-yl)-2-(naphthalen-1-yl)-1-phenylbutan-2-ol;
27) 4-(dimethylamino)-1-(2-methoxy-5-(thiophen-2-yl)pyridin-3-yl)-2-(naphthalen-1-yl)-1-phenylbutan-2-ol;
28) 4-(dimethylamino)-1-(5-(isothiazol-3-yl)-2-methoxypyridin-3-yl)-2-(naphthalen-1-yl)-1-phenylbutan-2-ol;
29) 3-(5-(4-(dimethylamino)-2-hydroxyl-2-(naphthalen-1-yl)-1-phenylbutyl)-6-methoxypyridin-3-yl)-benzonitrile;
30) 4-(5-(4-(dimethylamino)-2-hydroxyl-2-(naphthalen-1-yl)-1-phenylbutyl)-6-methoxypyridin-3-yl)-benzonitrile;
31) 4-(dimethylamino)-1-(2-methoxy-5-(thiazol-4-yl)pyridin-3-yl)-2-(naphthalen-1-yl)-1-phenylbutan-2-ol;
32) 4-(dimethylamino)-1-(5-(isothiazol-4-yl)-2-methoxypyridin-3-yl)-2-(naphthalen-1-yl)-1-phenylbutan-2-ol;
33) 4-(dimethylamino)-1-(2-methoxy-5-(thiazol-2-yl)pyridin-3-yl)-2-(naphthalen-1-yl)-1-phenylbutan-2-ol;
34) 4-(dimethylamino)-1-(2-methoxy-5-(thiazol-5-yl)pyridin-3-yl)-2-(naphthalen-1-yl)-1-phenylbutan-2-ol;
35) 4-(dimethylamino)-1-(5-isopropyl-2-methoxypyridin-3-yl)-2-(naphthalen-1-yl)-1-phenylbutan-2-ol;
36) 4-(dimethylamino)-1-(5-(furan-3-yl)-2-methoxypyridin-3-yl)-2-(naphthalen-1-yl)-1-phenylbutan-2-ol;
37) 4-(dimethylamino)-1-(5-(furan-2-yl)-2-methoxypyridin-3-yl)-2-(naphthalen-1-yl)-1-phenylbutan-2-ol;
38) 1-(5-bromo-2-methoxypyridin-3-yl)-4-(dimethylamino)-2-(naphthalen-1-yl)-1-phenylbutan-2-ol;
39) 1-(5-(5-chlorothiophen-3-yl)-2-methoxypyridin-3-yl)-4-(dimethylamino)-2-(naphthalen-1-yl)-1-phenylbutan-2-ol;
40) 1-(5-(2-chlorothiophen-3-yl)-2-methoxypyridin-3-yl)-4-(dimethylamino)-2-(naphthalen-1-yl)-1-phenylbutan-2-ol;
41) 1-(5-(3,6-dihydro-2H-thiopyran-4-yl)-2-methoxypyridin-3-yl)-4-(dimethylamino)-2-(naphthalen-1-yl)-1-phenyl butan-2-ol;
42) 4-(dimethylamino)-1-(2-methoxy-5-(tetrahydro-2H-thiopyran-4-yl)pyridin-3-yl)-2-(naphthalen-1-yl)-1-phenylbutan-2-ol;
43) 4-(dimethylamino)-1-(2-methoxy-5-(pyrrolidin-1-yl)pyridin-3-yl)-2-(naphthalen-1-yl)-1-phenylbutan-2-ol;
44) 4-(dimethylamino)-1-(2-methoxy-5-prop-1-ynyl-3-pyridyl)-2-(1-naphthyl)-1-phenylbutan-2-ol;
45) 1-(5-(5-bromothiophen-3-yl)-2-methoxypyridin-3-yl)-4-(dimethylamino)-2-(naphthalen-1-yl)-1-phenylbutan-2-ol;
46) 4-(dimethylamino)-1-(2-methoxy-5-(4-(trifluoromethyl)phenyl)pyridin-3-yl)-2-(naphthalen-1-yl)-1-phenylbutan-2-ol;
47) 4-(dimethylamino)-1-(2-methoxy-5-(4-methoxyphenyl)pyridin-3-yl)-2-(naphthalen-1-yl)-1-phenylbutan-2-ol;
48) 1-(5-(4-bromo-3-fluorophenyl)-2-methoxypyridin-3-yl)-4-(dimethylamino)-2-(naphthalen-1-yl)-1-phenylbutan-2-ol;
49) 1-(5-(4-chloro-3-fluorophenyl)-2-methoxypyridin-3-yl)-4-(dimethylamino)-2-(naphthalen-1-yl)-1-phenylbutan-2-al;
50) 4-(dimethylamino)-1-[2-methoxy-5-(2-phenylethynyl)-3-pyridyl]-2-(1-naphthyl)-1-phenyl-butan-2-ol;
51) 1-(5-(3,4-difluorophenyl)-2-methoxypyridin-3-yl)-4-(dimethoxyamino)-2-(naphthalen-1-yl)-1-phenylbutan-2-ol);
52) 4-(dimethylamino)-1-(2-methoxy-6-phenylpyridin-3-yl)-2-(naphthalen-1-yl)-1-phenylbutan-2-ol;
53) 4-(dimethylamino)-1-(2-methoxy-6-phenylpyridin-3-yl)-1,2-diphenylbutan-2-ol;
54) 4-(dimethylamino)-2-(2-fluorophenyl)-1-(2-methoxy-5-phenylpyridin-3-yl)-1-phenylbutan-2-ol;

55) 2-(2,3-difluorophenyl)-4-(dimethylamino)-1-(2-methoxy-5-phenylpyridin-3-yl)-1-phenylbutan-2-ol;
56) 2-(3,5-difluorophenyl)-4-(dimethylamino)-1-(2-methoxy-5-phenylpyridin-3-yl)-1-phenylbutan-2-ol;
57) 2-(2,5-difluorophenyl)-4-(dimethylamino)-1-(2-methoxy-5-phenylpyridin-3-yl)-1-phenylbutan-2-ol;
58) 4-dimethylamino-1-(2-methoxy-5-phenylpyridin-3-yl)-2-(naphthalen-1-yl)-1-phenylbutan-2-ol;
59) 4-dimethylamino-1-(2-ethoxy-5-phenylpyridin-3-yl)-2-(naphthalen-1-yl)-1-phenylbutan-2-ol;
60) 1-(4-chlorophenyl)-4-(dimethylamino)-1-(2-methoxy-5-phenylpyridin-3-yl)-2-phenylbutan-2-ol;
61) 1-(3-chlorophenyl)-4-(dimethylamino)-1-(2-methoxy-5-phenylpyridin-3-yl)-2-phenylbutan-2-ol;
62) 4-(dimethylamino)-1-(2-fluorophenyl)-1-(2-methoxy-5-phenylpyridin-3-yl)-2-phenylbutan-2-ol;
63) 4-(dimethylamino)-1-(3-fluorophenyl)-1-(2-methoxy-5-phenylpyridin-3-yl)-2-phenylbutan-2-ol;
64) 4-(dimethylamino)-1-(4-fluorophenyl)-1-(2-methoxy-5-phenylpyridin-3-yl)-2-phenylbutan-2-1;
65) 1-(2,3-dimethoxyphenyl)-4-(dimethylamino)-1-(2-methoxy-5-phenylpyridin-3-yl)-2-phenylbutan-2-ol;
66) 2-(3,5-difluorophenyl)-1-(2,3-dimethoxyphenyl)-4-(dimethylamino)-1-(2-methoxy-5-phenylpyridin-3-yl)butan-2-al;
67) 2-(3-chlorophenyl)-1-(2,3-dimethoxyphenyl)-4-(dimethylamino)-1-(2-methoxy-5-phenylpyridin-3-yl)butan-2-ol;
68) 2-(3,5-dichlorophenyl)-1-(2, 3-dimethoxyphenyl)-4-(dimethylamino)-1-(2-methoxy-5-phenylpyridin-3-yl)butan-2-al;
69) 4-(dimethylamino)-1-(2-fluoro-3-methoxyphenyl)-1-(2-methoxy-5-phenylpyridin-3-yl)-2-phenylbutan-2-ol;
70) 4-(dimethylamino)-1-(2-methoxy-5-phenylpyridin-3-yl)-2-phenyl-1-(pyridin-2-yl)butan-2-ol;
71) 4-(dimethylamino)-1-(2-methoxy-5-phenylpyridin-3-yl)-2-phenyl-1-(pyridin-3-yl)butan-2-ol;
72) 4-(dimethylamino)-1-(2-methoxy-5-phenylpyridin-3-yl)-1-(3-methoxyphenyl)-2-phenylbutan-2-ol;
73) 4-(dimethylamino)-1-(2-methoxy-5-phenylpyridin-3-yl)-1-(4-methoxyphenyl)-2-phenylbutan-2-ol;
74) 4-(dimethylamino)-1-(2-methoxy-5-phenylpyridin-3-yl)-2-phenyl-1-(2-(trifluoromethyl)phenyl)butan-2-ol;
75) 4-(dimethylamino)-1-(2-methoxy-5-phenylpyridin-3-yl)-2-(naphthalen-1-yl)-1-(3-trifluoromethyl)phenyl)butan-2-ol;
76) 1-(5-(4-chlorophenyl)-2-methoxypyridin-3-yl)-2-(3,5-dichlorophenyl)-4-(dimethylamino)-1-phenylbutan-2-ol;
77) 1-(5-(4-chlorophenyl)-2-methoxypyridin-3-yl)-2-(2,5-difluorophenyl)-4-(dimethylamino)-1-phenylbutan-2-ol;
78) 1-(5-(4-chlorophenyl)-2-methoxypyridin-3-yl)-4-(dimethylamino)-2-(3-fluorophenyl)-1-phenylbutan-2-ol;
79) 2-(3-chlorophenyl)-1-(5-(4-chlorophenyl)-2-methoxypyridin-3-yl)-4-(dimethylamino)-1-phenylbutan-2-ol;
80) 1-(5-(4-chlorophenyl)-2-methoxypyridin-3-yl)-2-(2,3-dichlorophenyl)-4-(dimethylamino)-1-phenylbutan-2-ol;
81) 1-(5-(4-chlorophenyl)-2-methoxypyridin-3-yl)-2-(2,5-dichlorophenyl)-4-(dimethylamino)-1-phenylbutan-2-ol;
82) 1-(5-(4-chlorophenyl)-2-methoxypyridin-3-yl)-2-(3,4-dichlorophenyl)-4-(dimethylamino)-1-phenylbutan-2-ol;
83) 1-(5-(4-bromophenyl)-2-methoxypyridin-3-yl)-2-(2,5-difluorophenyl)-4-(dimethylamino)-1-phenylbutan-2-ol;
84) 1-(5-(4-bromophenyl)-2-methoxypyridin-3-yl)-4-(dimethylamino)-2-(3-fluorophenyl)-1-phenylbutan-2-ol;
85) 1-(5-(4-bromophenyl)-2-methoxypyridin-3-yl)-2-(3,5-dichlorophenyl)-4-(dimethylamino)-1-phenylbutan-2-ol;
86) 1-(5-(4-bromophenyl)-2-methoxypyridin-3-yl)-2-(3-chlorophenyl)-4-(dimethylamino)-1-phenylbutan-2-ol;
87) 4-(dimethylamino)-1-(2-methoxy-5-thiomorpholinpyridin-3-yl)-2-(naphthalen-1-yl)-1-phenylbutan-2-ol;
88) 4-(dimethylamino)-1-(2-methoxy-5-morpholinopyridin-3-yl)-2-(naphthalen-1-yl)-1-phenylbutan-2-ol;
89) 1-(5-tert-butyl-2-methoxypyridin-3-yl)-4-dimethylamino-2-(naphthalen-1-yl)-1-phenylbutan-2-ol;
90) 1-(6-chloro-5-(4-chlorophenyl)-2-methoxypyridin-3-yl)-4-dimethylamino-2-(naphthalen-1-yl)-1-phenylbutan-2-ol;
91) 2-cyclohexyl-4-dimethylamino-1-(2-methoxy-5-phenylpyridin-3-yl)-1-phenylbutan-2-ol;
92) 2-cyclopentyl-4-(dimethylamino)-1-(2-methoxy-5-phenylpyridin-3-yl)-1-phenylbutan-2-ol;
93) 2-benzyl-4-dimethylamino-1-(2-methoxy-5-phenylpyridin-3-yl)-1-phenylbutan-2-ol;
94) 4-((2-hydroxylethyl)(methyl)amino)-1-(2-methoxy-5-phenylpyridin-3-yl)-2-(naphthalen-1-yl)-1-phenylbutan-2-ol;
95) 1-(3-hydroxyl-4-(2-methoxy-5-phenylpyridin-3-yl)-3-(naphthalen-1-yl)-4-phenylbutyl)azetidin-3-ol;
96) 1-(5-(4-bromophenyl)-2-methoxypyridin-3-yl)-2-(2,3-difluorophenyl)-4-(dimethylamino)-1-phenylbutan-2-ol;
97) 1-(5-(4-chlorophenyl)-2-methoxy-3-pyridyl)-2-(2,3-difluorophenyl)-4-dimethylamino-1-phenylbutan-2-ol;
98) 1-(5-(4-bromophenyl)-2-methoxypyridin-3-yl)-2-(3,5-difluorophenyl)-4-dimethylamino-1-phenylbutan-2-ol;
99) 1-(5-(4-chlorophenyl)-2-methoxypyridin-3-yl)-2-(3,5-difluorophenyl)-4-dimethylamino-1-phenylbutan-2-ol;
100) 1-(4-chlorophenyl)-1-(5-(4-chlorophenyl)-2-methoxypyridin)-3-yl)-4-dimethylamino-2-naphthalen-1-yl)butan-2-ol;
101) 1-(5-(4-bromophenyl)-2-methoxypyridin-3-yl)-1-(4-chlorophenyl)-4-dimethylamino-2-(naphthalen-1-yl)butan-2-ol;
102) 4-(dimethylamino)-1-(2-methoxy-5-(p-tolyl)pyridin-3-yl)-2-(naphthalen-1-yl)-1-phenylbutan-2-ol;
103) 4-(dimethylamino)-1-(2-methoxy-5-(4-(trifluoromethoxy)phenyl)pyridin-3-yl)-2-(naphthalen-1-yl)-1-phenylbutan-2-ol;
104) 1-(5-(4-chloro-3-methoxyphenyl)-2-methoxypyridin-3-yl)-4-(dimethylamino)-2-(naphthalen-1-yl)-1-phenylbutan-2-ol;
105) 2-(2-bromophenyl)-1-(5-(4-chlorophenyl)-2-methoxypyridin-3-yl)-4-(dimethylamino)-1-phenylbutan-2-ol;
106) 2-(3-bromophenyl)-1-(5-(4-chlorophenyl)-2-methoxypyridin-3-yl)-4-(dimethylamino)-1-phenylbutan-2-ol;
107) 2-(4-bromophenyl)-1-(5-(4-chlorophenyl)-2-methoxypyridin-3-yl)-4-(dimethylamino)-1-phenylbutan-2-ol;
108) 1-(5-(4-chlorophenyl)-2-methoxypyridin-3-yl)-2-(3,5-dichlorophenyl)-1-(2,3-dimethoxyphenyl)-4-(dimethylamino)butan-2-ol;
109) 2-(3-chlorophenyl)-1-(5-(4-chlorophenyl)-2-methoxypyridin-3-yl)-1-(2,3-dimethoxyphenyl)-4-(dimethylamino) butan-2-ol;
110) 1-(5-(4-chlorophenyl)-2,6-dimethoxypyridin-3-yl)-4-(dimethylamino)-2-(naphthalen-1-yl)-1-phenylbutan-2-ol.

The present invention also provides a method for preparing the above compounds, which is selected from:

a) preparing the compound of formula (I) from an intermediate of formula (II) in the presence of a suitable catalyst and solvent, wherein $W_1$ represents a suitable leaving group:

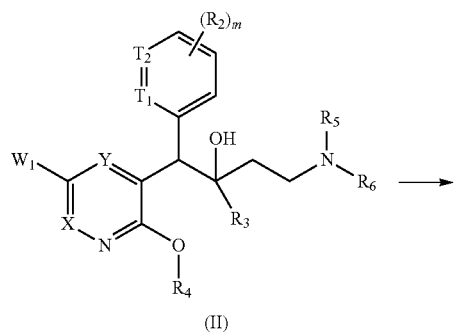

(II)

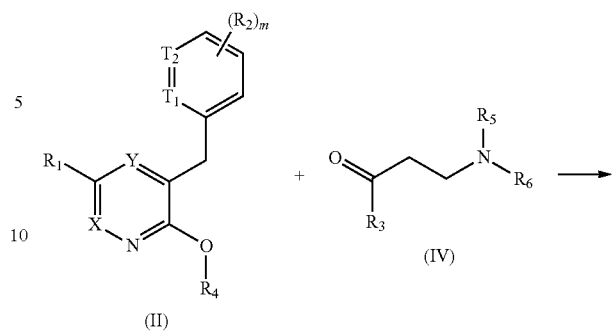

(II)     (IV)

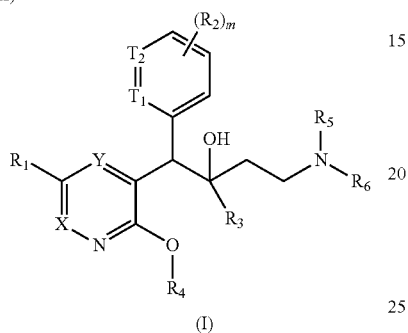

(I)

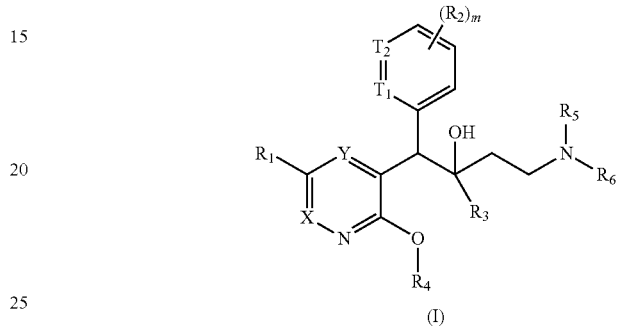

(I)

the other variables are as defined above;

b) preparing the compound of formula (I) by reacting a compound of formula (III) with a compound of formula (IV) in the presence of a suitable base and solvent:

the other variables are as defined above; or c) preparing the compound of formula (I) from the compound of formula (III) in five steps under appropriate conditions:

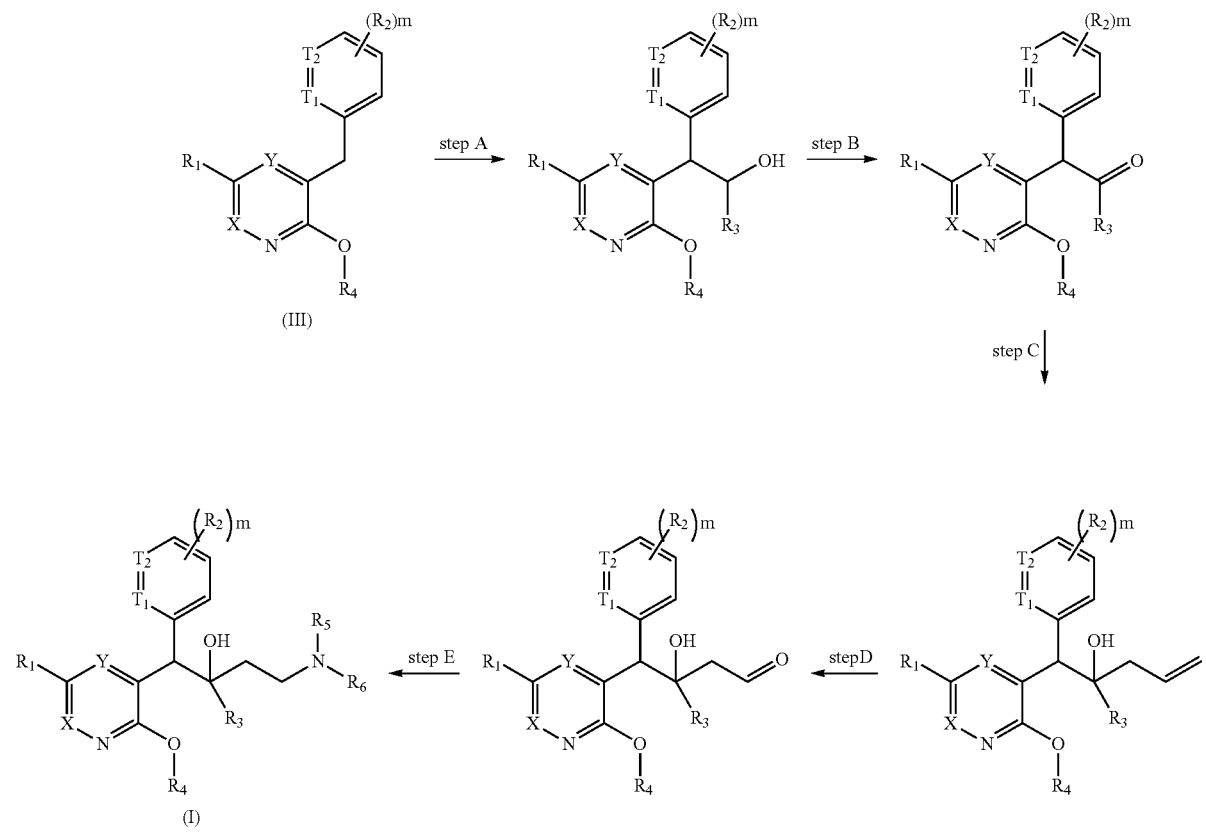

the other variables are as defined above.

The present invention further provides use of the above compounds in the manufacture of a medicament for the treatment of a *M. tuberculosis* disease.

Upon tested, the compounds of the present invention have shown a significant therapeutical efficacy on mycobacterial diseases, especially on the diseases caused by *M. tuberculosis, M. bovis, M. avium*, and *M. marinum*. Therefore, as a drug, in addition to the compounds of formula (I) defined above, the present invention also encompasses pharmaceutically acceptable acid addition salts or base addition salts, stereochemically isomeric forms, and tautomeric forms.

The present invention also comprises a pharmaceutically acceptable carrier, and effective components to achieve a therapeutic purpose. The compounds of the present invention may be made into different formulations. All applicable pharmaceutical ingredients may be used by systematic drug by reference. The preparation of the pharmaceutical ingredients of the present invention combines an effective dose of a particular compound (or salt form) as an active ingredient, and a pharmaceutically acceptable carrier which has a wide range of use forms according to examples of drug administration. The pharmaceutical ingredients are administered in the same dosage form, in particular orally or by injection. For example, for the preparation of a oral medicament, any usual pharmaceutical media may be used, such as water, glycerol, oil, alcohol, and the like to prepare an oral formulation (e.g., suspension, syrup, elixir, emulsion, solution); or starch, sugar, kaolin, diluent, lubricant, binder, disintegrating agent to prepare a solid carrier (e.g., powder, pill, capsule, and tablet). Because of convenience of use, for the solid oral medicament, tablets and capsules are the most advantageous pharmaceutical carrier. For an injectable formulation, in general, pure water accounts for the largest proportion of the carrier, and other materials are also included, for example, a medium to increase the solubility. The preparation of an injectable solution typically contains a physiological saline, glucose solution, or a combination thereof. The preparation of an injectable suspended solution contains a suitable liquid carrier, such as a suspension auxiliary agent and the like. A solid form prepared is usually converted into a liquid form immediately after use.

According to the administration mode of a medicament, the active ingredient should account for 0.05% to 99%, more preferably 0.1 to 70%, more preferably, 1 to 99.95%, yet more preferably 30 to 99.9%, of the total weight of the drug carrier.

Medicaments also may contain a number of added ingredients, such as lubricant, stabilizer, buffer, emulsifier, viscosity modifier, surfactant, preservative, flavoring or coloring agent. Generally, in order to facilitate the administration, the above additives will be kept in the same dosage form, but with different amounts. "The same dosage form" herein means a physically discrete unit relative to the dose, wherein each unit contains an effective dose calculated in advance to achieve a therapeutic purpose as well as the required drug carrier. Examples of such same dosage form include (scored, coated) tablet, capsule, pill, powder packet, wafer, anal suppository, injectable solution or injectable suspension, and other similar forms, or any combination thereof. The daily dose of the compound of the present invention should be adjusted according to the different compound, administration scheme, desired effect, and disease conditions. However, in general, in order to achieve satisfactory therapeutic results, the daily dose is recommended not to exceed 1 gram, such as 10 to 50 mg of per kilogram of body weight.

Furthermore, the present invention relates to use of the compounds of formula (I), pharmaceutically acceptable acid addition salts or base addition salts, stereochemically isomeric forms, tautomeric forms, as well as any medicament for treating mycobacterial diseases manufactured industrially through use of the above pharmaceutical ingredients.

Thus, from another perspective, the present invention provides a method for treating a patient afflicted or infected with mycobacterial diseases, which method comprises administering an effective dose or pharmaceutical components to the patient.

DEFINITIONS

Unless otherwise specified, the terms and words used herein have the following meanings. For any term or expression without a specified definition, it is rather to be understood as having its original meaning, but not to be construded as an unclear definition. Tradenames stated by the applicant include goods with such a brand name and the active pharmaceutical materials required by such goods.

$C_{1-10}$ is selected from the group consisting of $C_1$, $C_2$, $C_3$, $C_4$, $C_5$, $C_6$, $C_7$, $C_8$, $C_9$, and $C_{10}$; and $C_{3-10}$ is selected from the group consisting of $C_3$, $C_4$, $C_5$, $C_6$, $C_7$, $C_8$, $C_9$, and $C_{10}$.

$C_{1-10}$ alkyl, $C_{1-10}$ heteroalkyl, $C_{3-10}$ cycloalkyl, $C_{3-10}$ heterocycloalkyl, $C_{1-10}$ alkyl substituted with $C_{3-10}$ cycloalkyl or $C_{3-10}$ heterocycloalky, $C_{1-10}$ oxa-alkyl substituted with $C_{3-10}$ cycloalkyl or $C_{3-10}$ heterocycloalkyl are included, but not limited to: $C_{1-10}$ alkyl, $C_{1-10}$ alkylamino, N,N-di($C_{1-10}$ alkyl) amino, $C_{1-10}$ alkoxy, $C_{1-10}$ alkanoyl, $C_{1-10}$ alkyloxyacyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkoxy, $C_{3-10}$ cycloalkanoyl, $C_{3-10}$ cycloalkyloxyacyl, $C_{3-10}$ cycloalkylsulfonyl, and $C_{3-10}$ cycloalkylsulfinyl;

methyl, ethyl, n-propyl, isopropyl, $—CH_2C(CH_3)(CH_3)(OH)$, cyclopropyl, cyclobutyl, propylmethylene, cyclopropionyl, benzyloxy, cyclopropenyl, trifluoromethyl, aminoethyl, hydroxymethyl, methoxy, formyl, methoxycarbonyl, methylsulfonyl, methylsulfinyl, ethoxy, acetyl, ethanesulfonyl, ethoxycarbonyl, dimethylamino, diethylamino, dimethylaminocarbonyl, and diethylaminocarbonyl;

$N(CH_3)_2$, $NH(CH_3)$, $—CH_2CF_3$, $—CH_2CH_2CF_3$, $—CH_2CH_2F$, $—CH_2CH_2S(=O)_2CH_3$, $—CH_2CH_2CN$,

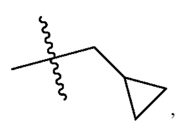

,
,
,
,
,
, $—CH_2CH(OH)(CH_3)_2$, $—CH_2CH(F)(CH_3)_2$, $—CH_2CH_2F$, $—CH_2CF_3$, $—CH_2CH_2CF_3$, $—CH_2CH_2NH_2$, $—CH_2CH_2OH$, $—CH_2CH_2OCH_3$, $—CH_2CH_2CH_2OCH_3$, $—CH_2CH_2N(CH_3)_2$, $—S(=O)_2CH_3$, $—CH_2CH_2S(=O)_2CH_3$,

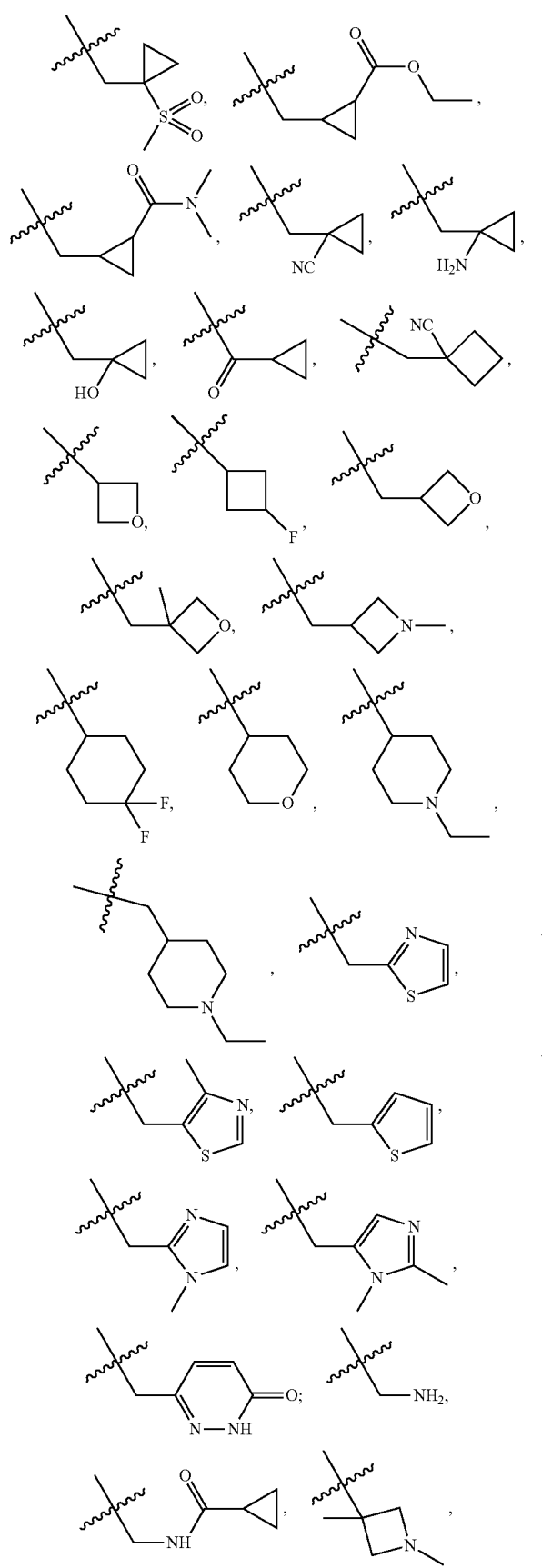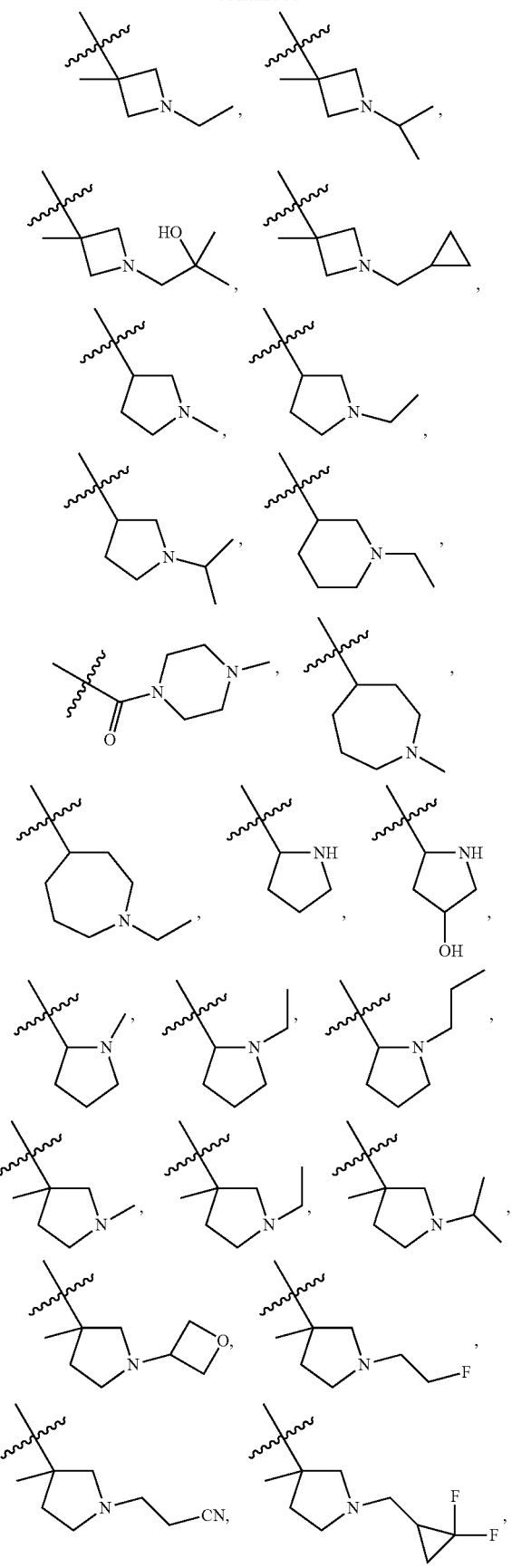

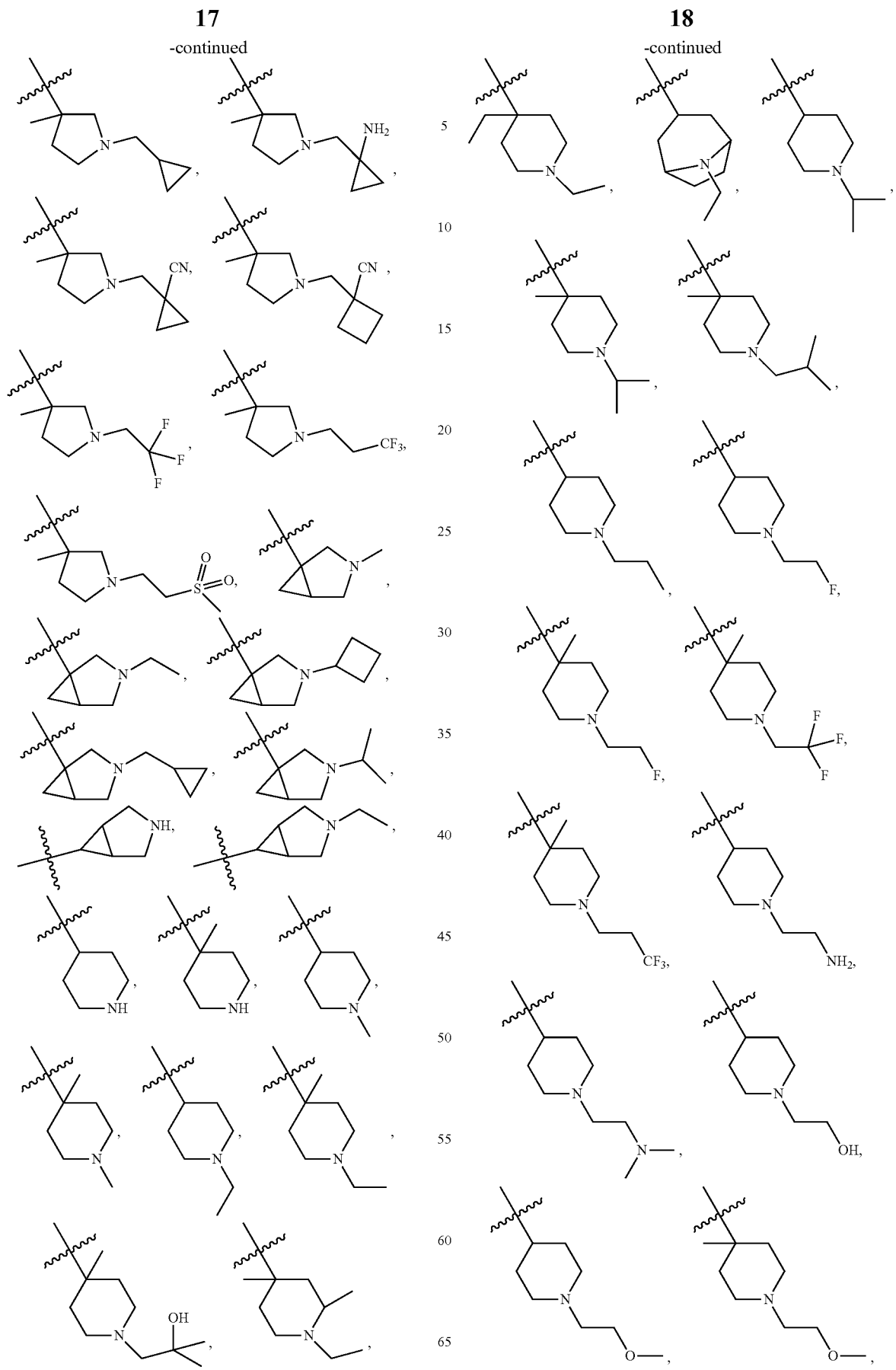

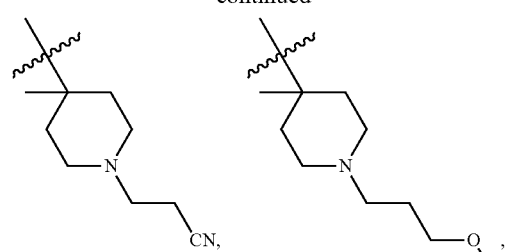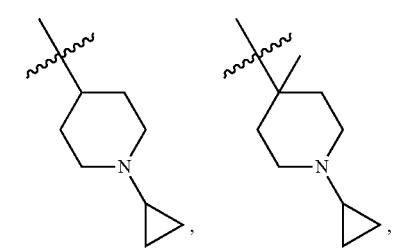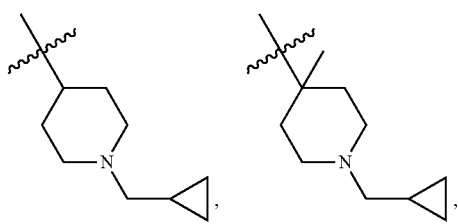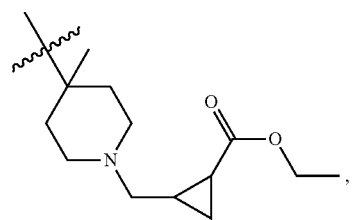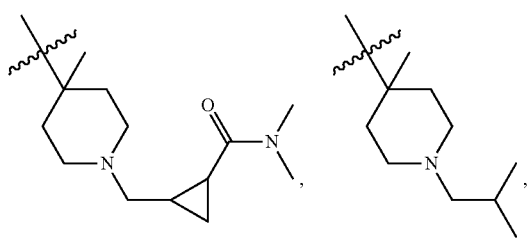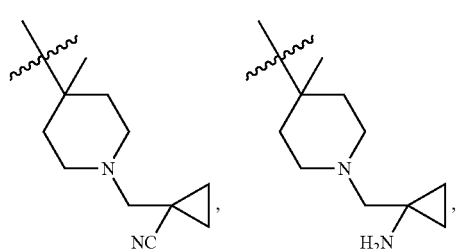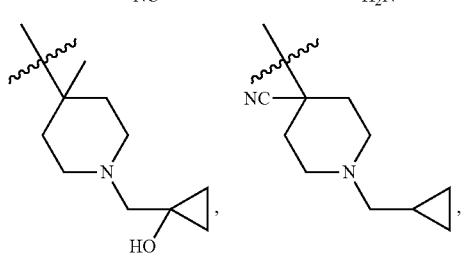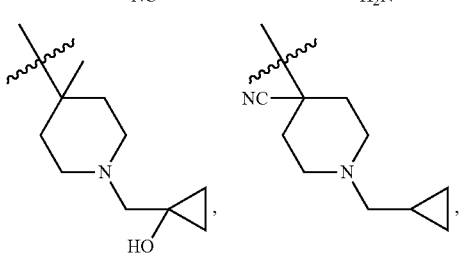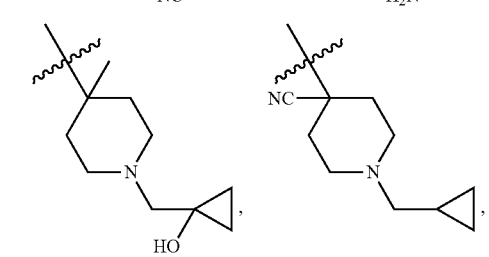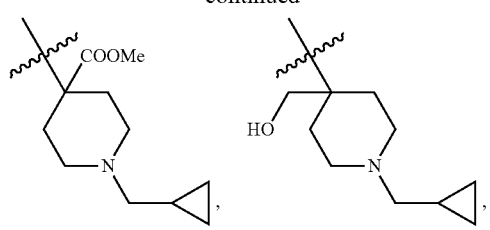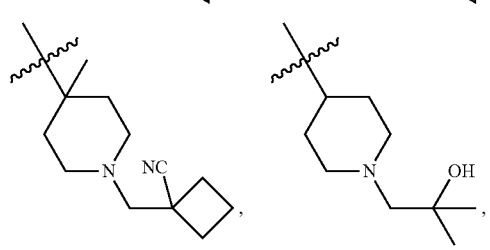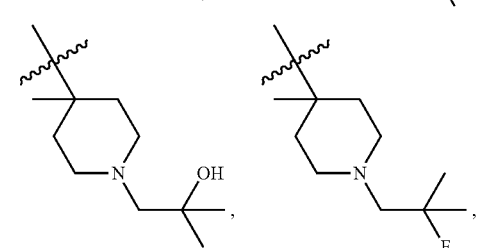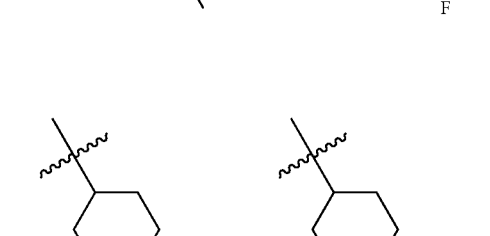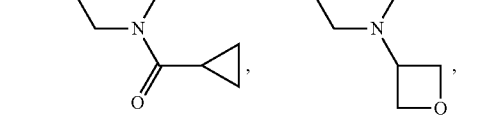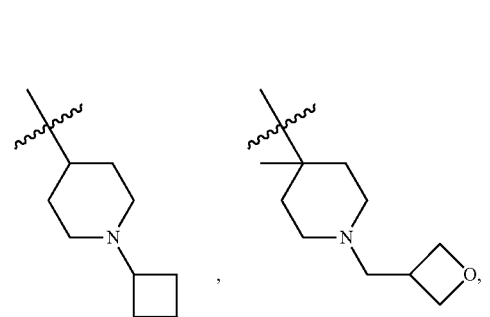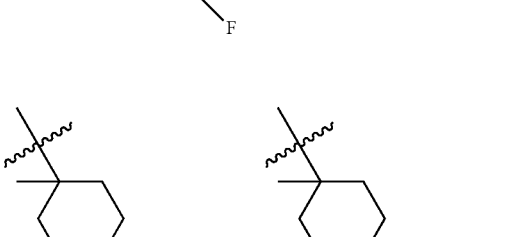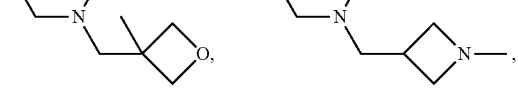

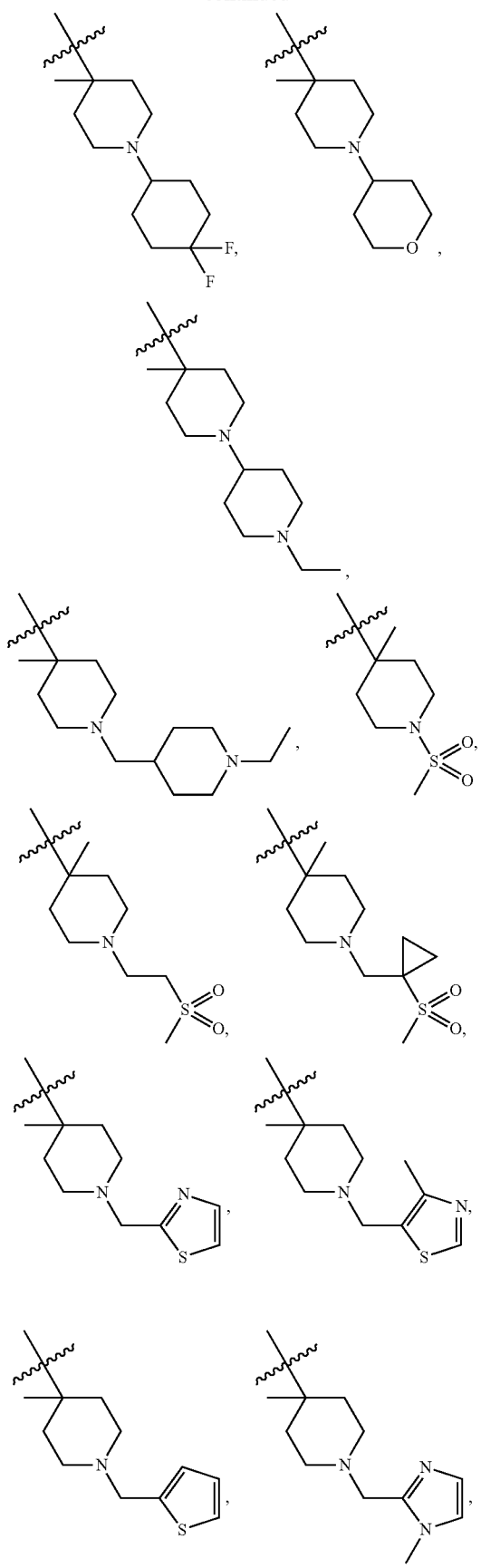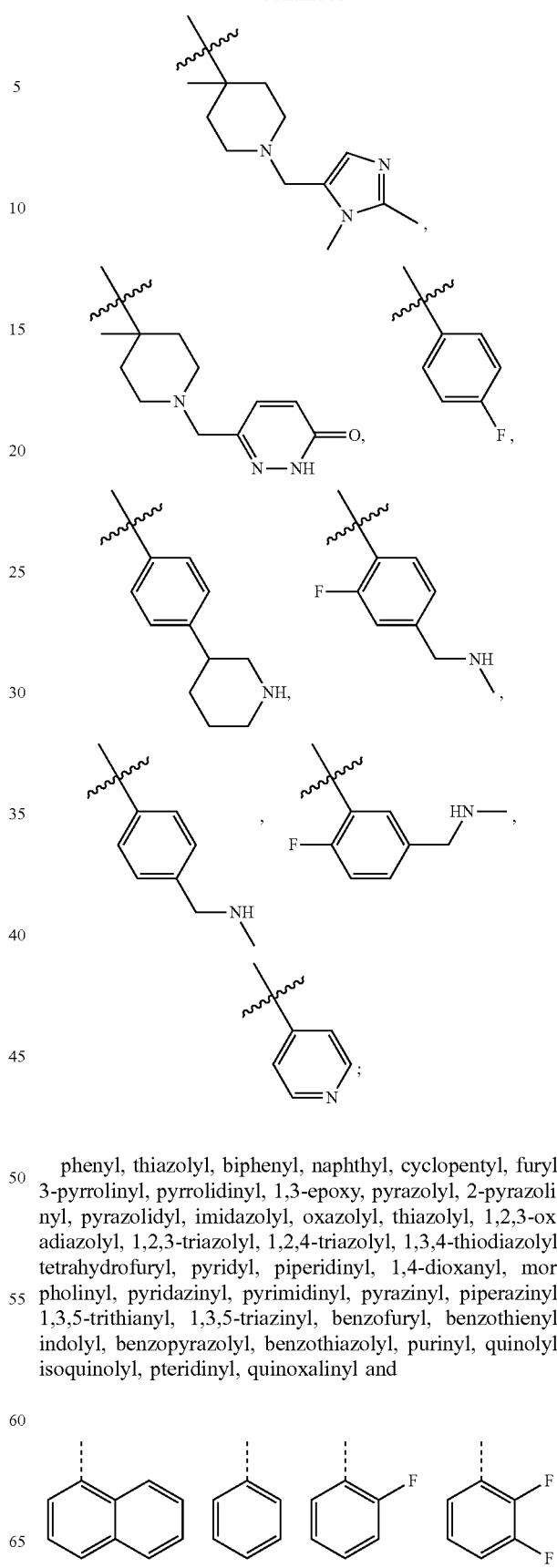

phenyl, thiazolyl, biphenyl, naphthyl, cyclopentyl, furyl, 3-pyrrolinyl, pyrrolidinyl, 1,3-epoxy, pyrazolyl, 2-pyrazolinyl, pyrazolidyl, imidazolyl, oxazolyl, thiazolyl, 1,2,3-oxadiazolyl, 1,2,3-triazolyl, 1,2,4-triazolyl, 1,3,4-thiodiazolyl, tetrahydrofuryl, pyridyl, piperidinyl, 1,4-dioxanyl, morpholinyl, pyridazinyl, pyrimidinyl, pyrazinyl, piperazinyl, 1,3,5-trithianyl, 1,3,5-triazinyl, benzofuryl, benzothienyl, indolyl, benzopyrazolyl, benzothiazolyl, purinyl, quinolyl, isoquinolyl, pteridinyl, quinoxalinyl and -continued

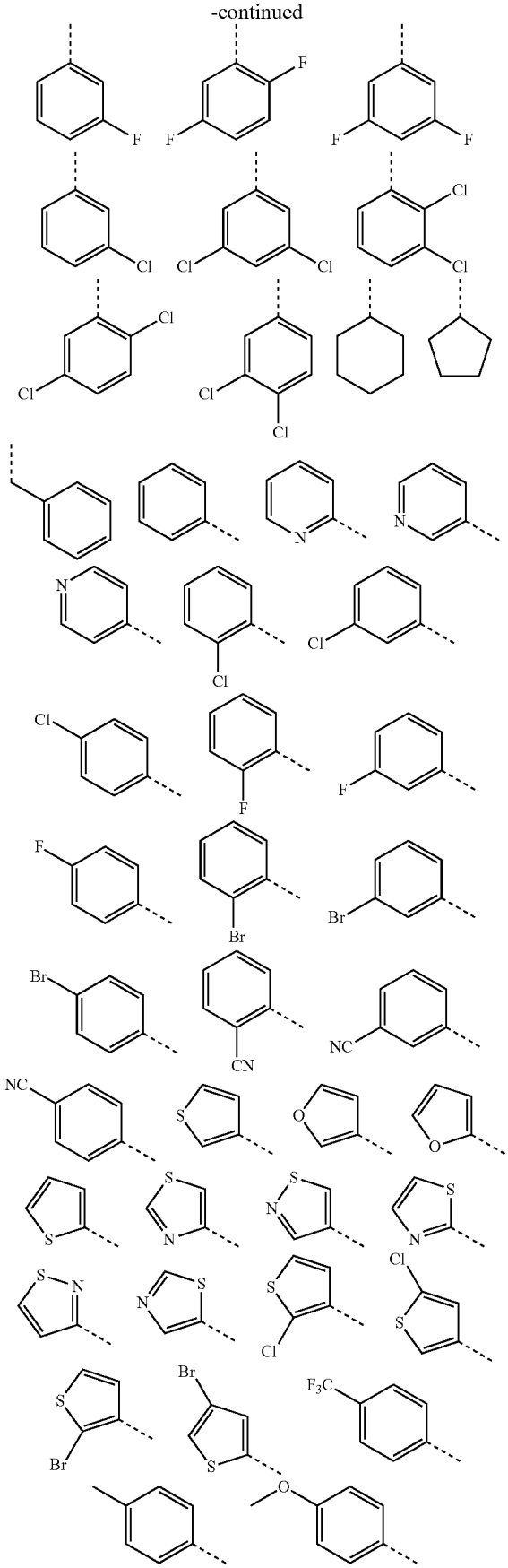

-continued

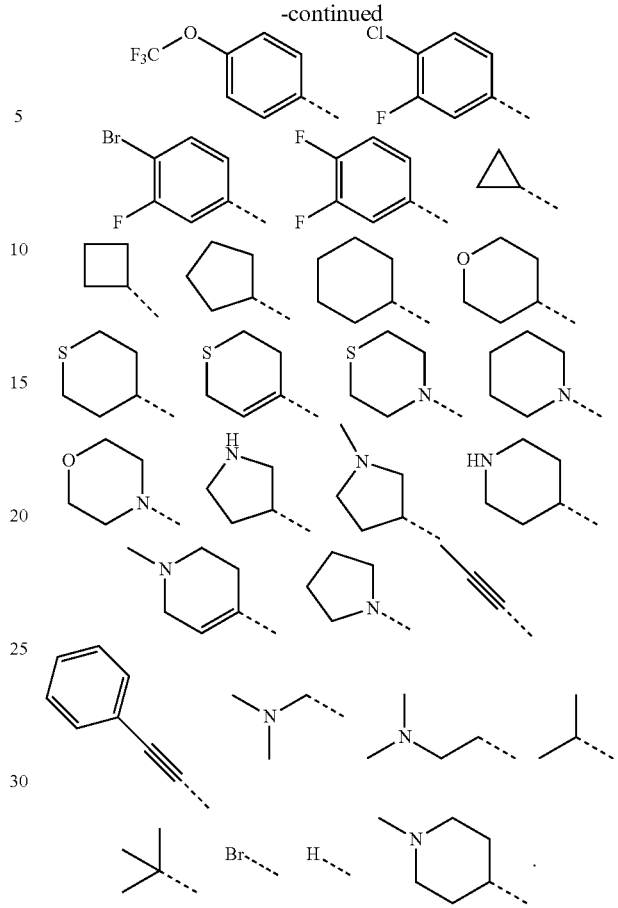

The term "pharmaceutically acceptable" used herein means that the referenced compounds, materials, compositions, and/or dosage forms are, within the scope of reliable medical judgment, suitable for access by human and animal tissues without excessive toxicity, irritation, allergic reaction or other problems or complications, and commensurate with reasonable benefit/risk ratio.

The term "pharmaceutically acceptable salt" refers to salts of the compounds of the present invention which are prepared from the compounds having particular substituent moieties found in the present invention and relatively nontoxic acids or bases. When compounds of the present invention contain relatively acidic functionalities, base addition salts can be obtained by contacting a sufficient amount of base with the neutral form of such compounds in a neat solution or in a suitable inert solvent. The pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting a sufficient amount of acid with the neutral form of such compounds in a neat solution or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, phosphorous acids and the like; as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic acid and the like (see, Berge et al, "Pharmaceutical salts", Journal of Pharmaceutical Science 66: 1-19 (1977)). Certain specific compounds of the present invention contain both basic and acidic functionalities that allow the compounds to be converted into either base or acid addition salts.

The neutral forms of the parent compounds are easily prepared by the reaction of the salt with a base or acid and then isolation. The prototype of a compound differs from its various salt forms in physical properties (such as the solubility in a polar solvent).

The term "pharmaceutically acceptable salt" refers to derivatives of the compounds disclosed, while the prototype of the compound is derived from the transformation of an acid or basic salt. The pharmaceutically acceptable salt includes, but is not limited to—an organic acid salt of mineral, or a basic residue (e.g., amines); an organic base salt of alkali metal or acidic residue (e.g., carboxylic acid). Pharmaceutically acceptable salts include common nontoxic salt or a quaternary ammonium salt derived from a prototype compound (eg, non-toxic inorganic/organic acid). Common non-toxic salts include, but are not limited to—a salt derived from inorganic or organic acid, e.g., carbethoxybenzoic, isethionic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycolic p-arsanilic acid, hexylisophthalic, hydrabaminic, hydrobromic, hydrochloric, hydroiodic, hydroxylmaleic, hydroxylnaphthoic, hydroxylsulfonic, lactic, lactose, dodecyl sulfonic, maleic, malic, mandelic, methanesulfonic, naphthalene sulfonic, nitric, oxalic, Pamoic, pantothenic, phenylacetic, phosphoric, polygalacturonic, propionic, salicylic, stearic, alkali acetic, succinic, aminosulfonic, sulfanilic, sulfuric, tannic, tartaric, toluenesulfonic acid.

The pharmaceutically acceptable salts can be prepared from the parent compounds containing acid radical or base radical. In general, such salts can be prepared by the reaction of a free acid or base with another suitable base or acid in water or in an organic solvent (non-aqueous medium such as ether, ethyl acetate, ethanol, isopropanol, or acetonitrile) or a mixture of both.

In addition to salt forms, the compounds provided by the present invention have prodrug forms. Prodrugs of the compounds described herein readily undergo chemical changes under physiological conditions to provide the compounds of the present invention. Additionally, prodrugs can be converted to the compounds of the present invention by chemical or biochemical methods in an in vivo environment.

Certain compounds of the present invention may be presented in non-solvated form or solvated form including hydrate form. In general, the non-solvated form is equivalent to the solvated form, and both forms are within the scope of the present invention. Certain compounds of the present invention may exist in polycrystalline or amorphous form.

Certain compounds of the present invention may have asymmetric carbon atoms (optical centers) or double bonds. Racemate, diastereomer, geometric isomer and individual isomer are included within the scope of the present invention. The graphic representations of racemic, ambiscalemic and scalemic or enantiomerically pure compounds used herein are taken from Maehr J. Chem. Ed. 62, 114-120 (1985). Unless otherwise stated, solid and broken wedges are used to denote the absolute configuration of a chiral element. Unless otherwise stated, when the compounds in the present invention contain olefinic double bond and other geometric asymmetry centers, they contain E, and Z geometric isomers. Likewise, all tautomeric forms are included within the scope of the present invention.

The compounds of the present invention may have particular geometric or stereoisomeric forms. The present invention contemplates all such compounds, including cis and trans isomers, (−)- and (+)-enantiomers, (R)- and (S)-enantiomers, diastereoisomers, (D)-isomers, (L)-isomers, and racemic mixtures and other mixtures, for example, enantiomers or diastereoisomers enriched mixtures, all of which belong to the scope of the present invention. The substituents such as alkyl, etc. may have additional asymmetric carbon atoms. All these isomers and mixtures thereof are included within the scope of the present invention.

Optically active (R)- and (S)-isomers, or (D)- and (L)-isomers may be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or acidic functional group (such as a carboxyl), the compound reacts with an appropriate optically active acid or base to form a salt of diastereomeric isomer, then the diastereomeric isomer is subjected to resolution through fractional crystallization or chromatography well known in the art and recover to give pure enantiomer. In addition, the enantiomers and diastereoisomers are generally separated through chromatography which uses a chiral stationary phase and optionally a chemical derivative method (for example, carbamate generated by amine).

Ideally, the compound of formula I is a particular mixture of enantiomers (hereinafter referred to as diastereoisomer A or B), thereby distinguished from other diastereomers. Since the compound of formula I has two chiral centers, the compound is determined to be a mixture, particularly a racemic mixture of (R, S) and (S, R) enantiomers, or of (R, R) and (S, S) enantiomers. In the description below, the two enantiomers in the mixture are called diastereoisomer A or B. Whether the racemic mixture is defined as A or B depends on which one (A or B) is firstly separated in the synthesis step. More ideally, the compound of formula I is a particular enantiomer (different from other enantiomers). Since the compound of formula I has two chiral centers, the compound is determined to be (R, S), (S, R), (R, R) or (S, S) enantiomer which corresponds to A1, A2, B1 or B2 described hereinafter respectively. Whether the enantiomer is defined as A1, A2, B1 or B2 depends on whether such enantiomer is separated firstly or secondly from the synthesis step and whether isolated from diastereomer A or B.

Of particular interest is that these compounds have the structure of formula (I), and the compounds having a single configuration.

According to the CAS standard nomenclature, when there are two stereocenters in the known absolute configuration in a molecule, R or S symbol should be marked on the chiral center having the lowest numbering, namely reference center (according to Cahn-Ingold-Prelog Rule). Comparatively, the [R*, R*] or [R*, S*] mark indicates the configuration of the second stereocenter, R* commonly referred to as the reference center. [R*, R*] represents that the compound has identical chiral centers, and [R*, S*] represents that the compound has different chiral centers. For example, if the lowest-numbered chiral center in the molecule has S configuration and the second chiral center has R configuration, the corresponding symbol is S-[S*, S*]. When "α" and "β" signa are also used, on the asymmetric carbon atom in the ring with the minimum numbered element, the highest priority substituent position always be marked as "a" position of plane in the ring system. Relative to the highest priority substituent position on the reference carbon atom, the highest priority substituent position on another asymmetric carbon atom on the same side of the plane is marked as "α", and that of the other side of the plane is marked as "β".

When a particular stereoisomer is specified, it indicates that the amount of this specific structure is free, that is to say, the content of other isomers is less than 50%, preferably less than 20%, more preferably less than 10%, still more preferably less than 5%, yet more preferably less than 2%, most preferably less than 1%. Thus, when a compound of formula (I) is identified as (R, S), it indicates that the (S, R) isomer of the compound is not contained.

The compound of formula I and some intermediate compounds always have at least two stereocenters to derive at least four different structures.

Compound of formula I can be synthesized in a form of an enantiomeric mixture (in particular a racemic mixture), and also may be isolated according to conventional procedures. The reaction of the racemic compound of formula I with a chiral acid may convert the compound into the corresponding diastereomeric salt. The diastereomeric salt can be isolated in a subsequent step, e.g., by selective crystallization or fractional crystallization, and the enantiomer may be separated with an alkali metal. Another method for separating the diastereomeric salt of the compound of formula I is liquid phase separation using a chiral stationary phase. Preferably, if a particular stereoisomer is desired, the compound can be prepared by specific stereo methods. The advantage of such method is to introduce the stereo conformation from pure raw materials.

The tautomeric form of the compound of formula I is also included in the compounds having formula (I). For example, an enol is converted to a ketone (ketone-enol tautomerism). The tautomers of the compounds of formula I or of the intermediate compounds disclosed herein are also within the protection scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The term "pharmaceutically acceptable carrier" refers to any agent or carrier medium which is capable of delivering an effective amount of the active substances of the present invention, does not interfere with the biological activity of the active substances and has no toxic side effects on the host or patient. The representative carrier includes water, oil, vegetable and mineral, cream base, lotion base, ointment base and the like. These bases include suspending agents, thickeners, penetration enhancers and the like. Their formulations are well known to the skilled in the cosmetic field or topical pharmaceutical field. The additional informations about the carrier can be referred to Remington: The Science and Practice of Pharmacy, 21st Ed, Lippincott, Williams & Wilkins (2005), the disclosure of which is incorporated herein by reference.

The term "excipient" generally refers to a carrier, diluent and/or vehicle required for formulating an effective pharmaceutical composition.

For drug or pharmacologically active agent, the term "effective amount" or "therapeutically effective amount" refers to a nontoxic but sufficient amount to achieve the desired effect of the drug or agent. For oral dosage forms of the present invention, an "effective amount" of an active substance in the composition refers to an amount required for achieving the desired effect when combining with another active substance in the composition. An effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Substituted" as used herein means one or more hydrogen atoms on an atom are substituted with a particular group, such case including deuterium (D) atom, an isotope of hydrogen atom, such that the valence of the original atom does not overflow, thus rendering the compound more stable. When the substituent group is a ketone (eg, =O), the two hydrogen atoms are substituted. Positions on an aromatic ring can not be substituted with a ketone. As used herein, the term "optionally substituted" means, unless otherwise specified, the type and number of the substituents are not limited as long as it can be achieved in chemistry whether an atom can be replaced by a substituent or not.

When an arbitrary variable (eg, R) occurs in the structure or formula of the compound for multiple times, the definition of the variable at each occurrence is independent from that for other occurrences. Thus, if a group is substituted with 0-2 R groups, the group may be optionally substituted with up to two R, wherein the definition of the arbitrary R and the original definition of (R) are independent of each other. Moreover, a combination of substituents and/or variables is allowed only when the combination results in a stable compound.

When one of the variables is selected from a single bond, it represents that the two groups linked by the single bond are connected directly. For example, when L in A-L-Z represents a single bond, the structure of A-L-Z is actually A-Z.

When a bond of a substituent crosses with a bond that links two atoms on a ring, it indicates that such substituent can bond to any atom of the ring. When the atom linked by a substituent is not specified, the substituent can form a bond with any atom. A combination of substituents and/or variants is allowed only when such combination can result in a stable compound. For example, the structural unit

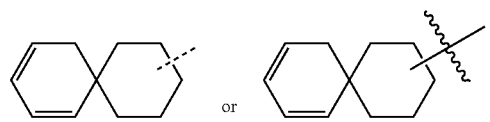

represents that any position on cyclohexyl or cyclohexadiene can be substituted.

The substituents of alkyl and heteroalkyl radicals (including those groups commonly referred to as alkylene, alkenyl, heteroalkylene, heteroalkenyl, alkynyl, cycloalkyl, heterocycloalkyl, cycloalkenyl and heterocycloalkenyl) are generally known as "alkyl substituents", which may be selected from, but not limited to one or more of the following groups: —R', —OR', =O, =NR', =N—OR', —NR'R", —SR', halogen, —SiR'R"R'", OC(O)R', —C(O)R', —CO$_2$R', —CONR'R", —OC(O)NR'R", —NR"C(O)R', NR' C(O) NR"R'", —NR"C(O)$_2$R', —NR""—C(NR'R"R'")=NR"", NR""C(NR'R")=NR'", —S(O)R', —S(O)$_2$R', —S(O)$_2$ NR'R", NR"SO$_2$R', —CN, —NO$_2$, —N$_3$, —CH(Ph)$_2$ and fluoro(C$_1$-C$_4$) alkyl, the number of substituents is 0~(2m'+1), wherein m' is the total number of carbon atoms in such radical. R', R", R'", R"" and R""' are each independently and preferably hydrogen, substituted or unsubstituted heteroalkyl, substituted or unsubstituted aryl (e.g., 1 to 3 halogens-substituted aryl), substituted or unsubstituted alkyl, alkoxy, thioalkoxy or aralkyl. When the compound of the present invention includes more than one R, for example, each R is to be selected independently as each of these groups when more than one R', R", R'", R"", and R""' exist. When R' and R" are attached to the same nitrogen atom, they can form a 5-, 6- or 7-membered ring together with the nitrogen atom. For example, —NR'R" is meant to include, but not limited to 1-pyrrolidinyl and 4-morpholinyl. According to the above discussion of substituents, one skilled in the art will appreciate that the term "alkyl" is meant to include a group formed by the linkage of carbon atom with a non-hydrogen group, such as haloalkyl (e.g., —CF$_3$, —CH$_2$CF$_3$) and acyl (e.g., —C(O)CH$_3$, —C(O)CF$_3$, —C(O)CH$_2$OCH$_3$, etc.).

Similar to the alkyl substituent, aryl and heteroaryl substituents are generally referred to as "aryl substituents", and selected from, for example —R', —OR', —NR'R", —SR', -halogen, —SiR'R"R'", OC(O)R', —C(O)R', —CO2R', —CONR'R", —OC(O)NR'R", —NR"C(O)R', NR'C(O) NR"R'", —NR"C(O)2R', —NR""—C(NR'R"R'")=NR"", NR""C(NR'R")=NR"", —S(O)R', —S(O)$_2$R', —S(O)$_2$ NR'R", NR"SO$_2$R', —CN, —NO$_2$, —N$_3$, —CH(Ph)$_2$, fluoro (C$_1$-C$_4$) alkoxy and fluoro(C$_1$-C$_4$) alkyl and the like, and the number of substituents is between 0 and the total number of open valences on the aromatic ring, wherein R', R", R'", R"" and R""' are each independently and preferably selected from hydrogen, substituted or unsubstituted alkyl, substituted or unsubstituted heteroalkyl, substituted or unsubstituted aryl and substituted or unsubstituted heteroaryl. When the compound of the present invention includes more than one R, for example, each R is to be selected independently as each of these groups when more than one R', R", R'", R"", and R""' exist. Two substituents of the adjacent atoms on an aryl or heteroaryl ring may optionally be substituted by a substituent of the formula -T-C(O)—(CRR')q-U—, wherein T and U are independently selected from —NR—, —O—, CRR'— or a single bond, and q is an integer of 0-3.

Unless on special conditions, the term "halogen" or "halo" by itself or as part of another substituent refers to fluorine, chlorine, bromine or iodine atom. Furthermore, the term "haloalkyl" is meant to include monohaloalkyl and polyhaloalkyl. For example, the term "halo(C1-C4)alkyl" is intended to include, but not limited to, trifluoromethyl, 2,2,2-trifluoroethyl, 4-chlorobutyl, 3-bromopropyl and the like.

Examples of haloalkyl include, but not limited to: trifluoromethyl, trichloromethyl, pentafluoroethyl and pentachloroethyl. "Alkoxy" represents any alkyl defined above and having the specified number of carbon atoms attached by oxygen. C$_{1-6}$alkoxy means alkoxy including C$_1$, C$_2$, C$_3$, C$_4$, C$_5$ and C$_6$ alkoxy. Examples of alkoxy include, but not limited to: methoxy, ethoxy, n-propoxy, isopropoxy, n-butoxy, sec-butoxy, tert-butoxy, n-pentyloxy and sec-pentoxy. "Cycloalkyl" means a saturated ring, such as cyclopropyl, cyclobutyl or cyclopentyl. 3-7 cycloalkyl means cycloalkyl including C$_3$, C$_4$, C$_5$, C$_6$ and C$_7$. "Alkenyl" means straight or branched hydrocarbon chain, wherein one or more carbon-carbon double bonds may be present in any stable site on the chain, such as vinyl and propenyl.

The term "halo" or "halogen" used herein refers to fluoro, chloro, bromo and iodo.

Unless otherwise specified, the term "hetero" used herein means a hetero atom or hetero radical (i.e., free radical containing a hetero atom), including all atoms except carbon (C) and hydrogen (H), and also including free radicals containing the above hetero atoms. The related examples include oxygen (O), nitrogen (N), sulfur (S), silicon (Si), germanium (Ge), aluminum (Al), boron (B), and optionally substituted —C(=O)N(H)—, —N(H)—, —C(=NH)—, —S(=O)$_2$N(H)— or —S(=O)N(H)—.

The term "ring" used herein represents a substituted or unsubstituted cycloalkyl, a substituted or unsubstituted heterocycloalkyl, a substituted or unsubstituted aryl or a substituted or unsubstituted heteroaryl. The so-called ring includes fused ring. The number of ring atoms is usually defined as the member number of the ring, for example, "5-7 membered ring" means that 5 to 7 atoms are arranged surrounding the ring. Unless otherwise specified, the ring optionally contains 1 to 3 hetero atoms. Therefore, "5-7 membered ring" includes for example, phenyl pyridine and piperidinyl; on the other hand, the term "5-7 membered heterocycloalkyl ring" includes pyridyl and piperidyl, but excluding phenyl. The term "ring" also includes a ring system containing at least one ring, wherein each ring independently meets the above definition.

The term "heterocycle" or "heterocyclo" used herein means a stable 5-, 6- or 7-membered mono-cycle, or bi-cycle or 7-, 8-, 9- or 10-membered bi-cycle heterocycle, which may be saturated, partially unsaturated or unsaturated (aromatic) and contain carbon atoms and 1, 2, 3 or 4 ring heteroatoms independently selected from N, O and S, wherein the above any heterocycle may be fused to a benzene ring to form a bi-cycle. Nitrogen and sulfur heteroatoms may optionally be oxidized (i.e., NO and S(O)p). Nitrogen atom may be substituted or unsubstituted (i.e., N or NR, wherein R is H or other substituents already defined herein). The heterocycle may be attached to the pendant group of any heteroatom or carbon atom to form a stable structure. If the resulting compound is stable, the heterocycle described herein may have a substitution on a carbon or nitrogen position. Nitrogen atom in the heterocycle is optionally quaternized. In a preferred embodiment, when the total number of S and O atoms in the heterocycle is more than 1, these heteroatoms are not adjacent to each other. In another preferred embodiment, the total number of S and O atoms in the heterocycle is not more than 1. As used herein, the term "aromatic heterocyclic group" or "heteroaryl" refers to a stable 5-, 6- or 7-membered mono-cycle, or bi-cycle or aromatic ring of 7-, 8-, 9- or 10-membered bi-cycle heterocyclic group which contains carbon atoms and 1, 2, 3 or 4 ring heteroatoms independently selected from N, O and S. Nitrogen atom may be substituted or unsubstituted (i.e., N or NR, wherein R is H or other substituents already defined herein). Nitrogen and sulfur heteroatoms may optionally be oxidized (i.e., NO and S(O) p). It is worth noting that the total number of S and O atoms in an aromatic heterocycle is not more than one.

Bridged ring is also included in the definition of heterocycle. Bridged ring is formed when one or more atoms (ie, C, O, N or S) link two non-adjacent carbon or nitrogen atoms. Preferred bridged ring includes, but not limited to: one carbon atom, two carbon atoms, one nitrogen atom, two nitrogen atoms and one carbon-nitrogen group. It is worth noting that one bridge always converts a monocycle to a tricycle. In a bridged ring, the substituents on the ring may also be present on the bridge.

Examples of the heterocyclic compounds include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, pyranyl, isoindolyl, isoindolinyl, isoindolyl, indolyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, oxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrimidyl, pyrrolidinyl, pyrrolinyl, 2H-pyrrolyl, pyrrolyl, pyrazolyl, quinazolinyl, quinolinyl, 411-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thieno-oxazolyl, thieno-thiazolyl, thieno-imidazolyl, thienyl, 1,2,3-triazolyl, 1,2,4-triazolyl, 1,2,5-triazolyl, 1,3,4-triazolyl and xanthenyl. Also included are fused ring and spiro-ring compounds, e.g. the above heterocycles.

Unless otherwise specified, the term "hydrocarbyl" or lower-level terms thereof (such as alkyl, alkenyl, alkynyl, and phenyl, etc.), by itself or as part of another substituent, means a straight, branched chain or cyclic hydrocarbon radicals or any combinations thereof. They may be fully saturated, mono- or polyunsaturated, can be mono-, di- or poly-substituted, may be a monovalent (such as methyl), divalent (such as methylene) or multivalent (such as methenyl), may also includes divalent or multivalent free radical and have a specified number of carbon atoms (for example, $C_1$-$C_{10}$ indicates 1 to 10 carbon atoms). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to an alkyl, alkenyl, and alkynyl. The aromatic hydrocarbyl includes but is not limited to 6-12 membered aromatic hydrocarbyl such as phenyl, and dimethyl fumarate. In some embodiments, the term "alkyl" means a straight or branched radical or a combination thereof which may be fully saturated, mono- or polyunsaturated, and may include a divalent or multivalent radical. Examples of saturated hydrocarbyl radical include, but are not limited to, the group such as methyl, ethyl, n-propyl, isopropyl, n-butyl, tert-butyl, isobutyl, sec-butyl, cyclohexyl, (cyclohexyl)methyl, cyclopropylmethyl, n-amyl, n-hexyl, n-heptyl, n-octyl and homologs or isomers thereof.

The unsaturated alkyl has one or more double or triple bonds. Examples of unsaturated alkyl include but are not limited to, ethenyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless otherwise specified, the term "heterohydrocarbyl" or lower-level terms thereof (such as heteroalkyl, heteroalkenyl, heteroalkynyl, and heteroaryl, etc.), by itself or as part of another substituent, means a stable straight, branched chain or cyclic hydrocarbon radicals or any combinations thereof, which have a specified number of carbon atoms and at least one hetero atom. In some embodiments, the term "heteroalkyl" by itself or in combination with another term represents a stable straight chain, branched chain hydrocarbon radical or combinations thereof which have a specified number of carbon atoms and at least one hetero atom. Typically, a hetero atom is selected from B, O, N and S, wherein nitrogen and sulfur atoms are optionally oxidized and the nitrogen atom is optionally quaternized. Heteroatom B, O, N and S may be replaced at any interior position in a heterohydrocarbyl (including the position where the hydrocarbyl attaches to the rest part of the molecule). Examples include, but are not limited to, —CH2-CH2-O—CH3, —CH2-CH2-NH—CH3, —CH2-CH2-N(CH3)-CH3, —CH2-S—CH2-CH3, —CH2-CH2, —S(O)—CH3, —CH2-CH2-S(O)2-CH3, —CH=CH—O—CH3, —CH2-CH=N—OCH3, and —CH=CH—N(CH3)-CH3. Up to two consecutive heteroatoms can be present, such as, —CH$_2$—NH—OCH$_3$.

The terms "alkoxy", "alkylamino" and "alkylthio" (or thioalkyl) are used by their conventional meanings and refer to those alkyl groups connected to the remainder of the molecule via an oxygen atom, an amino or a sulfur atom, respectively.

Unless otherwise specified, the term "cyclohydrocarbyl", "heterocyclohydrocarbyl" or lower-level terms thereof (such as aryl, heteroaryl, cycloalkyl, heterocycloalkyl, cycloalkenyl, heterocycloalkenyl, cycloalkynyl, heterocycloalkynyl, etc.) by itself or in combination with another term represents cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2, 5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydrothiophen-3-yl, 1-piperazinyl and 2-piperazinyl.

Unless otherwise specified, the term "aryl" means a polyunsaturated aromatic substituent which is a single ring or multiple rings (preferably 1-3 rings) wherein they are fused together or linked covalently. The term "heteroaryl" refers to an aryl (or ring) containing one to four hetero atoms. The exemplary hetero atom is usually B, O, N and S, wherein nitrogen and sulfur atoms are optionally oxidized and the nitrogen atom is optionally quaternized. A heteroaryl may attach to the rest part of a molecule via a heteroatom. Non-limiting examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituents of all the above aryl and heteroaryl rings are selected from the substituents described below.

For the sake of convenience, when combined with other terms (e.g. aryloxy, arylthio, arylalkyl), the aryl includes all the aryl and heteroaryl ring as defined above. Thus, the term "aralkyl" is meant to include free radicals formed from one aryl attached to one alkyl (e.g. benzyl, phenethyl, pyridylmethyl, and the like). The carbon atom of an alkyl (e.g., methylene) can be replaced (by one oxygen atom, e.g., phenoxymethyl, 2-pyridyloxy, 3-(1-naphthyloxy)propyl, and the like).

The term "leaving group" refers to a functional group or atom which can be substituted by another functional group or atom through a substitution reaction (such as a nucleophilic substitution reaction). For example, representative leaving groups include triflate; chlorine, bromine and iodine; sulfonate groups, such as mesylate, tosylate, brosylate, tosylate and the like; acyloxy, such as acetoxy, trifluoroacetoxy and the like.

The term "protecting group" includes, but is not limited to "nitrogen protecting group", "hydroxyl protecting group" or "sulphur protecting group." The term "amino protecting group" means a protecting group suitable for blocking side reactions on nitrogen of the amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like.

The term "hydroxy protecting group" refers to a protecting group suitable for blocking side reactions on the hydroxyl group. Representative hydroxy protecting groups include, but are not limited to: alkyl such as methyl, ethyl and t-butyl; acyl, e.g. alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The present invention employs the following abbreviations: LDA represents lithium diisopropylamide; TMPLi represents lithium 2,2,6,6-tetramethylpiperidide. DCM represents dichloromethane; EtOAc represents ethyl acetate; EtOH represents ethanol; MeOH represents methanol; TFA represents trifluoroacetic acid; PCC represents pyridinium chlorochromate; $NaCNBH_3$ represents sodium cyanoborohydride; THF represents tetrahydrofuran; DCE represents 1,2-dichloroethane; FA represents formic acid; MeCN represents acetonitrile; Pd/C represents palladium on carbon; $BF_3$-Et2O represents boron trifluoride-diethyl ether complex; TBAF represents tetra-butylammonium fluoride; TLC represents thin layer chromatography; HPLC represents high performance liquid chromatography; SFC represents supercritical fluid chromatography; $Pd(dppf)Cl_2$ represents [1,1'-bis(diphenylphosphino)ferrocene]palladium dichloride; $Pd(PPh_3)Cl_2$ represents bis(triphenylphosphino) palladium dichloride.

BRIEF DESCRIPTION OF DRAWINGS

FIG. 1 shows the results of the in vivo pharmacodynamic evaluation experiment of the compounds in a mice model infected with spray of *M. tuberculosis*. After the mice were infected for 35 days, all mice were euthanized, the lung tissue was taken out and ground, and the amount of bacteria load was calculated after spotting on a plate.

SYNTHESIS METHOD

The compounds of the present invention can be synthesized by a variety of methods and through a series of synthetic steps well known to those skilled in the art.

In general, compounds of formula (I) can be prepared from the intermediate of formula (II). W represents a suitable leaving group, for example halogen (eg, bromine) which can react with aryl boric acid or aryl borate.

Conversely, W may also represent an aryl borate which can react with an aryl halide. The reaction requires a suitable catalyst (eg, Pd $(dppf)Cl_2$), a suitable base (e.g., $K_2CO_3$), and a suitable solvent (eg, 1,4-dioxane/water). According to Reaction Scheme 1, the reaction is preferably carried out at a high temperature.

Reaction Scheme 1

(II)

(I)

All variables have the same definitions as formula (I).

The starting material, compound of formula (II), can be prepared through the general reaction steps well known to those skilled in the art. One of the examples is Reaction Scheme 2.

Reaction Scheme 2:

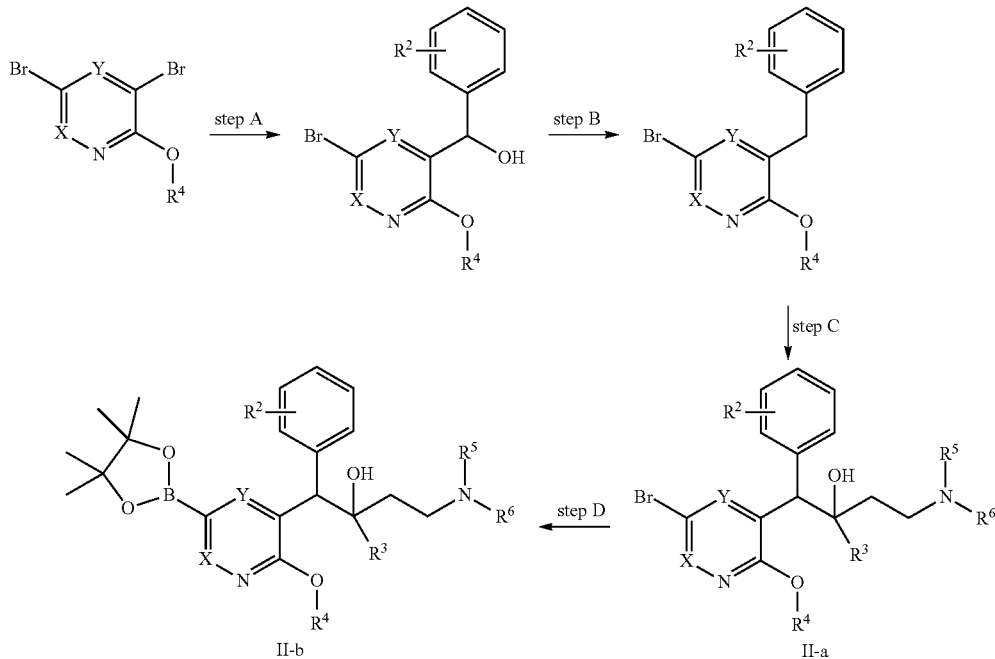

All variables have the same definitions as in formula (I). Dibromoheterocycle is reacted with benzaldehyde in step A of Reaction Scheme 2. The reaction is carried out in a suitable base (such as n-butyl lithium), and a suitable solvent (eg, THF) at −78° C. to −50° C. In the next step B, the adduct obtained from the above step is reacted with triethylsilane and boron trifluoride in DCM at a high temperature. DIPA is reacted with n-butyl lithium in THF in step C at −78° C. to −50° C. Bromide 11-a is reacted with bis(pinacolato) diboron in a suitable catalyst (such as Pd(dppf)Cl$_2$), a suitable base (such as potassium acetate) and a suitable solvent (such as 1,4-dioxane) in the next step D. The reaction is preferably carried out at a high temperature.

It is obvious that, in the reactions mentioned earlier and later, the reaction products can be isolated from the reaction medium and if desired, can be purified by using the purification methods well known to the skilled in the art, such as extraction, crystallization and chromatography. More obviously, for the reaction products having more than one enantiomers, the compound of formula (I) can be separated into isomers thereof by the separation methods well known by the skilled in the art, in particular, preparative chromatography, such as preparative HPLC, SFC and the like.

The compound of formula (I) can also be prepared from the intermediate of formula (II) and the intermediate of formula (IV) according to Reaction Scheme 3:

Reaction Scheme 3:

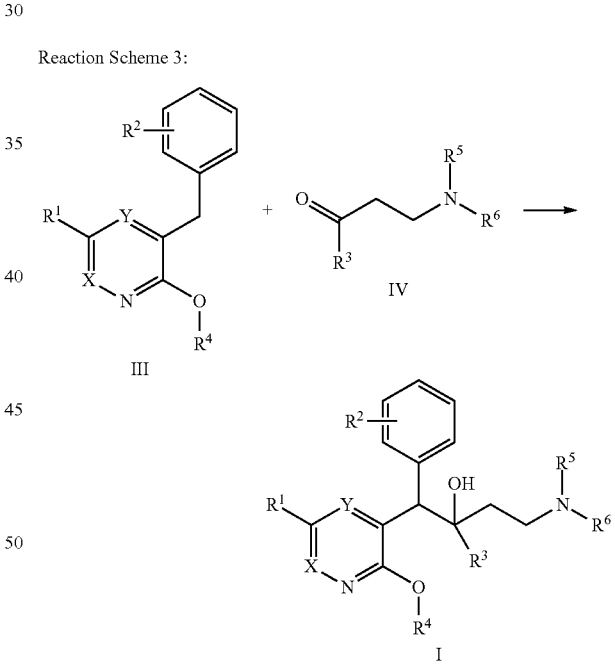

N-butyllithium was added to a suitable base (eg, diisopropylamine) and a suitable solvent (such as tetrahydrofuran). All variables have the same definitions as in formula (I). The reaction rate can be elevated by stirring. The reaction temperature is −78° C. to −50° C.

The intermediates of formula (III) and (IV) or the starting materials for their synthesis can either be purchased from the market or prepared by the general reactions well known to the skilled in the art. For example, the intermediate of formula (III) can be prepared according to Reaction Scheme 4:

Reaction Scheme 4:

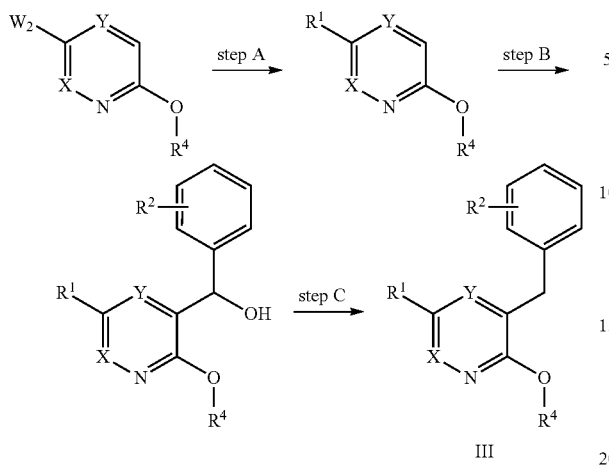

The intermediate of formula (IV) can be purchased from the market or prepared by the general reaction schemes well known to the skilled in the art. For example, the intermediate of formula (IV) can be prepared according to Reaction Scheme 5:

Reaction Scheme 5

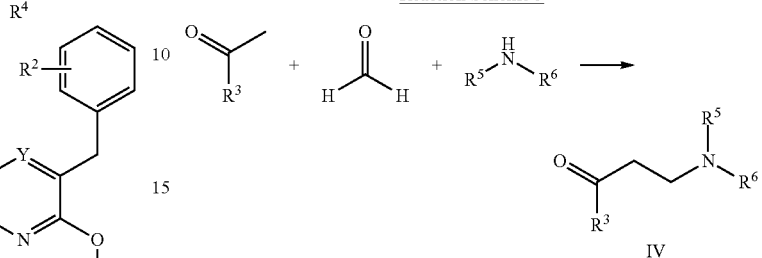

Reaction Scheme 5 comprises the reaction of acetyl derivative of $R^3$ (eg, cyclohexylethyl ketone), polymethanol, and a primary or secondary amine $HNR_4R_5$ (preferably a salt form) in a suitable acid (e.g., hydrochloric acid) and an appropriate solvent (e.g., alcohols, such as ethanol). The reaction is preferably carried out in a high temperature environment.

All variables have the same definitions as in formula (I). In step A of Reaction Scheme 4, W of the raw material represents a suitable leaving group, for example halogen (eg, bromine) which can be reacted with aryl boric acid or aryl borate. The reaction requires a suitable catalyst (eg, Pd(dppf)Cl$_2$), a suitable base (e.g., K$_2$CO$_3$), and a suitable solvent (eg, 1,4-dioxane/water). The reaction is preferrably carried The compound of formula (I) can also be prepared from the intermediate of formula (III) as raw material according to Reaction Scheme 6:

Reaction Scheme 6

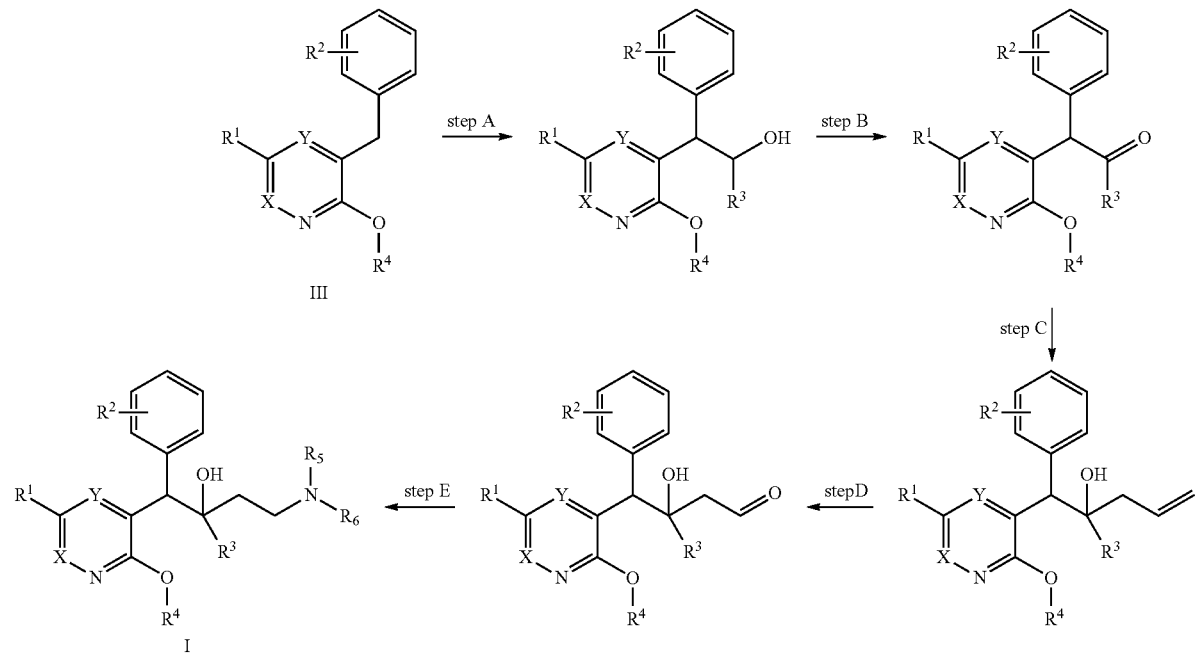

out at a high temperature. In the next step B, the adduct is reacted with a benzaldehyde derivative. The reaction requires a suitable base (e.g., TMPLi or LDA) and a suitable solvent (such as THF) and is carried out at −78° C. to 20° C.

In the next step C, hydroxyl is reduced in silane (eg, triethylsilane). The reaction is carried out in TFA at a high temperature.

The compounds which can not be prepared successfully according to Reaction Scheme 3 can be prepared according to Reaction Scheme 6. All variables have the same definitions as in formula (I). The compound of formula III as raw material of step A in Reaction Scheme 6 is reacted with a benzaldehyde derivant. The reaction is carried out in a suitable base (such as TMPLi or LDA), and a suitable solvent (eg, THF) at −78° C. to 20° C. In the next step B, the alcohol is oxidized by an oxidant (e.g., PCC or Dess-Martin). The reaction solvent is DCM and the like. In step C, the carbonyl is subjected to an addition reaction in an organometallic reagent (e.g., allylmagnesium bromide) and an appropriate solvent (e.g., THF). In step D, the olefin is oxidized by an oxidant (e.g., $OsO_4/NaIO_4$) in a suitable solvent, which typically requires the addition of 2,6-lutidine. In the next step E, the intermediate obtained from step D and the salt form of a primary or secondary amine ($HNR_5R_6$) are reacted to introduce the amino ($—NR_5R_6$) under a reductive amination condition. The reaction is carried out in a suitable reducing agent (such as, $NaBH_3CN$ or $NaBH(OAc)_3$) and a suitable solvent (eg, dichloroethane, methanol or dichloroethane).

The chemical reactions in the specific embodiments of the present invention are performed in suitable solvents, and the solvents must be suitable for the chemical changes of the present invention as well as the reagents and materials required. In order to obtain the compounds of the present invention, it is sometimes necessary for the skilled in the art to modify or select the synthesis steps or reaction schemes based on the existing embodiments.

The compound of formula (I) can also be formed from the compound per se by conversion of functional groups well known by the skilled in the art.

The compounds of the present invention may be prepared by a variety of synthetic methods well known to the skilled, including the following specific embodiments, the embodiments formed by the following specific embodiments in combination with other chemical synthesis methods and the equivalent replacement well known to the skilled in the art. The preferred embodiments include, but are not limited to, the examples of the present invention.

The chemical reactions in the specific embodiments of the present invention are performed in suitable solvents, and the solvents must be suitable for the chemical changes of the present invention as well as the reagents and materials required. In order to obtain the compounds of the present invention, it is sometimes necessary for the skilled in the art to modify or select the synthesis steps or reaction schemes based on the existing embodiments.

One important consideration in any synthetic route in the art is to select a suitable protecting group for a reactive functional group (such as amino in the present invention). For a trained practitioner, (Protective Groups In Organic Synthesis, Wiley and Sons, 1991) of Greene and Wuts is the authority in this regard. All references cited herein are incorporated herein as a whole.

The present invention will be specifically described below by way of examples, and these examples do not imply any limitation of the present invention.

All solvents used in the present invention are commercially available and used without further purification. The reaction is generally conducted under inert nitrogen in an anhydrous solvent. Proton nuclear magnetic resonance data are recorded on a Bruker Avance 111 400 (400 MHz) spectrometer, wherein chemical shifts are indicated as (ppm) of tetramethylsilane at low field. Mass spectra are measured on Agilent 1200 Series plus 6110 (& 1956A). LC/MS or Shimadzu MS contains a DAD: SPD-M20A (LC) and Shimadzu Micromass 2020 detector. Mass spectrometer is equipped with an electrospray ionization source (ESI) operated under a positive or negative mode.

Compounds are named manually or by ChemDraw® software. The commercially available compounds use their vendor directory names.

HPLC analysis was conducted using Shimadzu LC20AB system equipped with Shimadzu SIL-20A autosampler and Shimadzu DAD: SPD-M20A LC20AB detector through Xtimate C18 column (3 μm packing material, 2.1×300 mm). 0-60AB_6 min method was carried out using linear gradient elution from 100% A (A is 0.0675% TFA in water) to 60% B (B is 0.0625% TFA solution in MeCN) over 4.2 minutes, and then 60% B was used to elute for 1 minute. The column was re-equilibrated for 0.8 minutes to 100:0 and the total run time was 6 minutes. 10-80AB 6 min method was carried out using linear gradient elution from 90% A (A is 0.0675% TFA in water) to 80% B (B is 0.0625% TFA solution in MeCN) over 4.2 minutes, and then 80% B was used to elute for 1 minute. The column was re-equilibrated for 0.8 minutes to 90:10 and the total run time was 6 minutes. The column temperature was 50° C., and the flow rate was 0.8 mL/min. The scanning wavelength of diode array detector was 200-400 nm.

Thin layer chromatography (TLC) was conducted on Sanpont-group silica gel GF254. The spots were detected by irradiation of the commonly used ultraviolet light. In some cases, the spots were detected by other means. In these cases, iodine (formed from thorough blend of 10 g of silica gel and about 1 g iodine), vanillin (formed from dissolution of about 1 g vanillin in 100 mL of 10% $H_2SO_4$), ninhydrin (commercially available from Aldrich), or a special color-developing agent (formed from thorough blend of $(NH_4)_6.Mo_7O_{24}.4H_2O$, 5 g $(NH_4)_2Ce(IV)(NO_3)_6$, 450 mL of $H_2O$ and 50 mL of concentrated $H_2SO_4$) was used to develop the TLC plate to detect the compound. The flash column chromatography was conducted on 40-63 μm (230-400 mesh) silica gel from Silicycle using a method similar to the technique disclosed in Still, W. C.; Kahn, M.; and Mitra, M. Journal of Organic Chemistry, 1978, 43, 2923-2925. The typical solvent used in flash column chromatography or thin-layer chromatography was a mixture of dichloromethane/methanol, ethyl acetate/methanol, and hexane/ethyl acetate.

The preparative chromatography analysis was conducted by Gilson-281 Prep LC 322 system using Gilson UV/VIS-156 detector. The chromatographic column used was Agella Venusil ASB Prep C18, 5 μm, 150×21.2 mm; Phenomenex Gemini C18, 5 m, 150×30 mm; Boston Symmetrix C18, 5 L m, 150×30 mm; or Phenomenex Synergi C18, 4 μm, 150×30 mm. The flow rate was 25 mL/min and a low gradient of acetonitrile/water was used to elute the compound, wherein 0.05% HCl, 0.25% HCOOH or 0.5% $NH_3.H_2O$ was contained in the water. The total run time was 8-15 minutes.

SFC analysis was conducted using Agilent 1260 Infinity SFC system equipped with Agilent 1260 autosampler and Agilent DAD: 1260 detector. Chiralcel OD-H 250×4.6 mm I.D., 5 um or Chiralpak AS-H 250×4.6 mm I.D., 5 um or Chiralpak AD-H 250×4.6 mm I.D., 5 um was used as the chromatographic column. The chromatographic conditions for OD-H_5_40_2.35 ML: Chiralcel OD-H column (250× 4.6 mm I.D., 5 um packing material), 40% ethanol (0.05% DEA)—$CO_2$ as a mobile phase; 2.35 mL/min of flow rate; 220 nm of detection wavelength. The chromatographic conditions for AS-H_3_40_2.35 ML: Chiralpak AS-H column (250×4.6 mm I.D., 5 um packing material), 40% methanol (0.05% DEA)—$CO_2$ as a mobile phase; 2.35 mL/min of flow rate; 220 nm of detection wavelength. The chromatographic conditions for OD-H_3_40_2.35M: Chiralcel OD-H column (250×4.6 mm I.D, 5 um packing material), 40% methanol (0.05% DEA)—$CO_2$ as a mobile phase; 2.35 mL/min of flow rate; 220 nm of detection wavelength. The chromatographic conditions for AD-H_2_50_2.35 ML: Chiralpak AD-H column (250×4.6 mm I.D, 5 um packing material), 5% methanol (0.1% MEA)—$CO_2$ as a mobile phase; 2.35 mL/min of flow rate; 220 nm of detection wavelength.

The preparative SFC analysis was conducted using Waters Thar 80 Pre-SFC system equipped with Gilson UV detector. The chromatographic column used was Chiralcel OD-H (250×4.6 mm I.D, 5 μm packing material) or Chiralpak AD-H (250×4.6 mm I.D, 5 μm packing material). The flow rate was about 40-80 mL/min, the low gradient of ethanol-carbon dioxide or methanol-carbon dioxide was used to elute the compound, wherein methanol or ethanol contained 0.05% $NH_3 \cdot H_2O$, 0.05% DEA or 0.1% MEA and the total run time was 20-30 minutes.

The present invention provides novel compounds, primarily pyridine derivatives. Such compounds can inhibit the growth of mycobacteria so that they can be used to treat the related diseases caused by mycobacteria, especially by *M. tuberculosis*, *M. bovis*, *M. avium* and *M. marinum*.

DETAILED DESCRIPTION

The present invention will be described in detail through the following examples, but the scope of the present invention is not limited thereto.

EXPERIMENT SECTION

The absolute stereoconfiguration, or the configuration of the double bond, of the chiral center carbon atoms of certain compounds or intermediates has not been experimentally tested. In this case, the isomer separated firstly is labeled "A" and the next separated is labeled "B". Any person skilled in the art can distinguish between "A" and "B" isomers by some means, such as NMR. This method is the most suitable way to determine the stereoconfiguration.

When "A" and "B" are a mixture of isomers (especially enantiomers), they can be further separated. In this case, the portion firstly isolated is referred to as "A1" and "B1", and the second portion separated is referred to as "A2" and "B2". The "A1", "A2" and "B1", "B2" (enantiomeric) isomers can be clearly distinguished by a person skilled in the art using some methods such as X-ray diffraction.

When a diastereomeric or corresponding isomeric final compound or intermediate is converted to another final compound or intermediate, the diastereoisomer (A or B), or enantiomer (A1, A2, B1, B2) of the new product is from the corresponding part of the former product.

The examples set forth below are all prepared, separated and characterized by the methods described herein. The following examples are merely representative parts in the scope of the invention and are not intended to be exhaustive. The present invention has been described in detail herein, and specific embodiments thereof are also disclosed. It is obvious for the skilled in the art to make various changes and modifications to the specific embodiments of the present invention without departing from the spirit and scope of the present invention.

Preparation of Intermediate a and Intermediate B

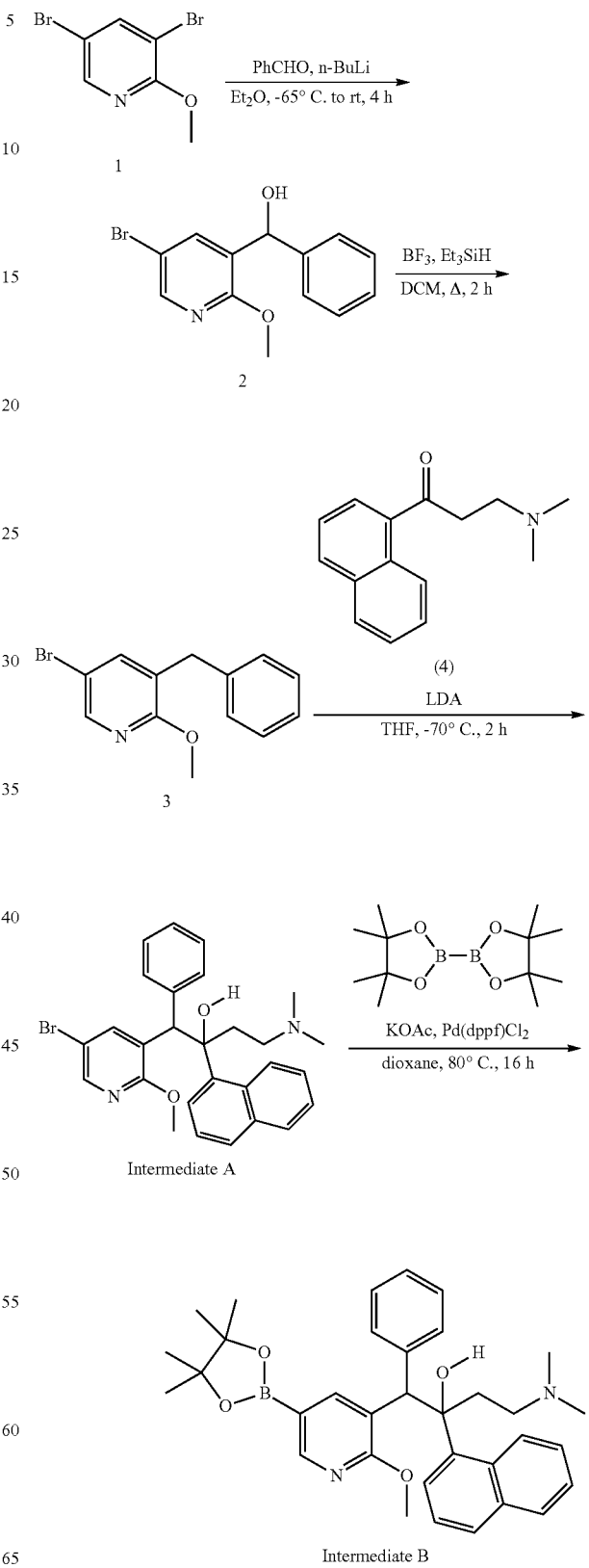

Intermediate A

Intermediate B

Step 1: (5-bromo-2-methoxypyridin-3-yl)(phenyl)methanol

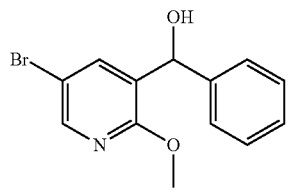 [SMILES: COc1ncc(Br)cc1C(O)c1ccccc1]

Under nitrogen, 3,5-dibromo-2-methoxypyridine (118 g, 443 mmol) was dissolved in 1.2 L of anhydrous ethyl ether, n-butyllithium (2.5M n-hexane solution, 195 mL, 487 mmol) was added slowly at −78° C. and stirred for 0.5 hours at −78° C. Benzaldehyde (47.0 g, 443 mmol) was dissolved in 100 mL of anhydrous ethyl ether and was added slowly to the reaction system at −78° C. The mixture was slowly warmed to 15-25° C. and stirred for 1 hour. The reaction was quenched using 600 mL of saturated ammonium chloride solution. The mixture was extracted with ethyl acetate for three times and 200 mL of ethyl acetate was used for each extraction. The combined organic phases were washed with brine, dried over anhydrous sodium sulfate, concentrated in vacuo, isolated by column chromatography (eluent: petroleum ether/ethyl acetate=50/1-10/1) to give (5-bromo-2-methoxypyridin-3-yl) (phenyl)methanol (73.5 g, 56.0% yield) as a white solid. LCMS (ESI) m/z: 294.0 (M+1).

Step 2: 3-benzyl-5-bromo-2-methoxypyridine

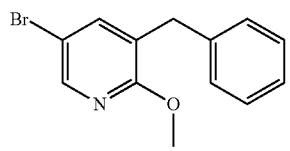 [SMILES: COc1ncc(Br)cc1Cc1ccccc1]

(5-bromo-2-methoxypyridin-3-yl) (phenyl)methanol (73.5 g, 264 mmol) was dissolved in 500 mL of dichloromethane, triethylsilane (61.3 g, 529 mmol) and boron trifluoride (103.2 mL, 872 mmol) were added and heated to 60° C. to react for 2 hours. TLC (petroleum ether/ethyl acetate=10/1) monitored that the reaction was complete. The reaction mixture was concentrated, neutralized with saturated sodium carbonate solution, extracted with 200 mL methylene chloride each time for three times. The combined organic phases were washed with brine, dried over anhydrous sodium sulfate, concentrated in vacuo, and isolated by column chromatography (eluent: petroleum ether/ethyl acetate=50/1-20/1) to give 3-benzyl-5-bromo-2-methoxy pyridine (65.0 g, 93.5% yield) as a colorless oil. LCMS (ESI) m/z: 278.0 (M+1).

Step 3: 1-(5-bromo-2-methoxypyridin-3-yl)-4-(dimethylamino)-2-(naphthalen-1-yl)-1-phenylbutan-2-ol Intermediate A

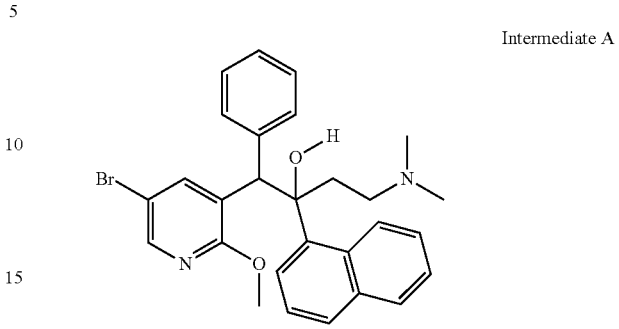

Under nitrogen, diisopropylamine (32.7 g, 324 mmol) was dissolved in 10 mL of anhydrous tetrahydrofuran, n-butyllithium (2.5 M n-hexane solution, 129 mL, 324 mmol) was added slowly at −70° C. and then stirred for 0.5 hours at −70° C. 3-benzyl-5-bromo-2-methoxypyridine (60.0 g, 216 mmol) was dissolved in 150 mL of anhydrous tetrahydrofuran and added slowly to the reaction system at −70° C. Then the reaction mixture was stirred for 1 hour at −70° C. 3-(dimethylamino)-1-(naphthalen-1-yl)propan-1-one (58.8 g, 259 mmol) was dissolved in 150 mL of anhydrous tetrahydrofuran and added slowly to the reaction system at −70° C. Then the reaction mixture was stirred for another 1-2 hours. The reaction was quenched using 600 mL of saturated aqueous ammonium chloride solution. The mixture was extracted with 200 mL ethyl acetate each time for three times. The combined organic phases were dried over anhydrous sodium sulfate, concentrated in vacuo, isolated by column chromatography (eluent: petroleum ether/ethyl acetate=100/1-30/1) to give 1-(5-bromo-2-methoxypyridin-3-yl)-4-(dimethylamino)-2-(naphthalen-1-yl)-1-phenylbutan-2-ol (Intermediate A) (48 g, 43.1% yield) as a white solid. LCMS (ESI) m/z: 505.1 (M+1).

Step 4: 4-(dimethylamino)-1-(2-methoxy-5-(4,4,5,5-tetramethyl-1,3,2-dioxaborolan-2-yl)pyridin-3-yl)-2-(naphthalen-1-yl)-1-phenylbutan-2-ol Intermediate B

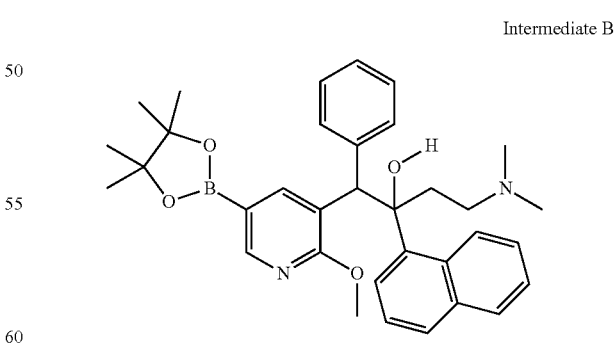

Under nitrogen, 1-(5-bromo-2-methoxypyridin-3-yl)-4-(dimethylamino)-2-(naphthalen-1-yl)-1-phenyl-butan-2-ol (Intermediate A) (10.0 g, 19.0 mmol), bis(pinacolato)diboron (9.04 g, 35.61 mmol) and potassium acetate (3.88 g, 39.5 mmol) were dissolved in 100 mL of dioxane, and Pd(dppf) Cl$_2$ (1.44 g, 1.97 mmol) was added. The reaction liquid was heated to 80° C. and stirred for 16 hours. 200 mL of water was added, the mixture was extracted with 100 mL of ethyl acetate each time for three times and then dried over anhydrous sodium sulfate, concentrated in vacuo, and isolated by column chromatography (eluent: petroleum ether/ ethyl acetate=20/1-1/1) to give 4-(dimethylamino)-1-(2-methoxy-5-(4,4,5,5-tetramethyl-1,3,2-dioxaborolan-2-yl) pyridin-3-yl)-2-(naphthalen-1-yl)-1-phenylbutan-2-ol (Intermediate B) (9.50 g, 86% yield). LCMS (ESI) m/z: 553.3 (M+1).

Example 1

2-(5-(4-(dimethylamino)-2-hydroxyl-2-(naphthalen-1-yl)-1-phenylbutyl)-3-(6-methoxypyridin-3-yl)) benzonitrile

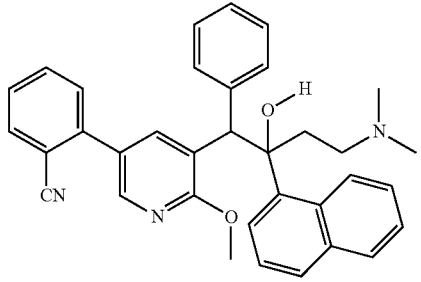

Compound 147 (A1)
Compound 148 (A2)
Compound 149 (B1)
Compound 150 (B2)

Under nitrogen, intermediate A (1.00 g, 1.98 mmol), (2-cyanophenyl)boronic acid (349 mg, 2.37 mmol), potassium acetate (388 mg, 3.96 mmol) and Pd(dppf)Cl₂ (92 mg, 0.1 mmol) were added to the mixed solvent of dioxane/water (10 mL×2 mL). The reaction liquid was heated to 80° C. and stirred at this temperature under nitrogen for 5 hours. Completion of the reaction was monitored by LCMS. The reaction mixture was added to water (30 mL) and extracted with ethyl acetate (10 mL×3). The combined organic phase was dried and concentrated to give the crude compound, and purified by preparative HPLC (GX-G; Phenomenex Synergi C18 150*30 mm*4 um; acetonitrile 15%-45%; water (0.225% formic acid); 25 mL/min) to give component A and component B. Component A was separated by chiral SFC (Berger MultiGram™ SFC, Mettler Toledo Co, Ltd, IC-10 um; supercritical CO₂/MeOH (0.05% aqueous ammonia) =60/40; 70 ml/min; 220 nm) to give compound 147 (A1) (42.14 mg, 4.14% yield) and compound 148 (A2) (30.89 mg, 2.96% yield) as white solid. Component B was separated by chiral SFC (Berger MultiGram™ SFC, Mettler Toledo Co, Ltd, IC-10 um; supercritical CO₂/MeOH (0.05% aqueous ammonia)=60/40; 70 ml/min; 220 nm) to give compound 149 (B1) (40.09 mg, 3.84% yield) and compound 150 (B2) (42.51 mg, 4.07% yield) as white solid. Compound 147 (A1)/compound 148 (A2): $^1$H NMR (400 MHz, methanol-d₄): δ 8.69-8.57 (m, 1H), 8.51 (br. s., 2H), 8.01 (d, J=7.53 Hz, 1H), 7.92-7.79 (m, 7H), 7.72-7.61 (m, 3H), 7.59-7.45 (m, 3H), 7.44-7.25 (m, 7H), 5.77 (s, 1H), 3.43-3.27 (m, 3H), 3.08-2.94 (m, 1H), 2.76-2.62 (m, 1H), 2.36 (s, 8H), 2.18 (m, 1H). Compound 149 (B1)/compound 150 (B2): $^1$H NMR (400 MHz, methanol-d₄): δ 8.80 (br. s., 1H), 8.65 (m, 1H), 7.92 (d, J=7.40 Hz, 2H), 7.83-7.48 (m, 7H), 7.29 (t, J=7.59 Hz, 1H), 7.06 (br. s., 2H), 6.88 (br. s., 3H), 5.94-5.81 (m, 1H), 4.16 (br. s., 3H), 2.82-2.97 (m, 1H), 2.65-2.48 (m, 1H), 2.27 (br. s., 7H), 2.05-2.15 (m, 1H). LCMS (ESI) m/z: 528.3 (M+1).

Example 2

1-(5-(2-bromophenyl)-2-methoxypyridin-3-yl)-4-(dimethylamino)-2-(naphthalen-1-yl)-1-phenylbutan-2-ol

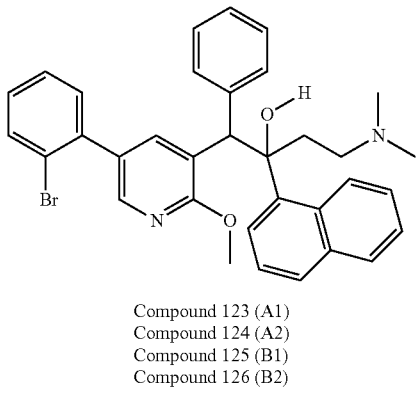 [SMILES: COc1ncc(-c2ccccc2Br)cc1C(c1ccccc1)C(O)(CCN(C)C)c1cccc2ccccc12]

Compound 123 (A1)
Compound 124 (A2)
Compound 125 (B1)
Compound 126 (B2)

Under nitrogen, intermediate B (2.00 g, 3.62 mmol), 1,2-dibromobenzene (1.02 g, 4.34 mmol), potassium acetate (710 mg, 7.24 mmol) and tetrakis(triphenylphosphine)palladium (209 mg, 0.18 mmol) were added to a mixed solution of dioxane/water. The temperature was raised to 80° C. and stirred at this temperature under nitrogen for 16 hours. Completion of the reaction was monitored by LCMS. The reaction mixture was added to water (40 mL) and extracted with ethyl acetate (30 mL×3). The combined organic phase was dried over anhydrous sodium sulfate and concentrated in vacuo to give the crude compound which was then purified by preparative HPLC (GX-G; Phenomenex Synergi C18 150*30 mm*4 um; acetonitrile 30%-60%; water (0.225% formic acid); 25 mL/min) to give component A and component B. Component A was separated by chiral SFC (Berger MultiGram™ SFC, Mettler Toledo Co, Ltd, IC-10 um; supercritical CO₂/MeOH (0.05% aqueous ammonia) =60/40; 70 ml/min; 220 nm) to give compound 123 (A1) (104.16 mg, 4.95% yield) and compound 124 (A2) (33.73 mg, 1.60% yield) as white solid. Component B was separated by chiral SFC (Berger MultiGram™ SFC, Mettler Toledo Co, Ltd, IC-10 um; supercritical CO₂/MeOH (0.05% aqueous ammonia)=60/40; 70 ml/min; 220 nm) to give compound 125 (B1) (13.73 mg, 0.65% yield) and compound 126 (B2) (26.50 mg, 1.26% yield) as white solid. Compound 123 (A1)/compound 124 (A2): $^1$H NMR (400 MHz, methanol-d₄): δ 8.63 (d, J=8.53 Hz, 1H), 8.49 (br. s., 1H), 8.31 (br. s., 1H), 7.99 (d, J=7.40 Hz, 1H), 7.90-7.78 (m, 4H), 7.75-7.59 (m, 6H), 7.50 (t, J=6.78 Hz, 1H), 7.44-7.24 (m, 8H), 7.10 (d, J=7.53 Hz, 1H), 5.75 (s, 1H), 3.36 (s, 3H), 3.10 (br. s., 1H), 2.81 (br. s., 1H), 2.44 (s, 6H), 2.34-2.18 (m, 2H). LCMS (ESI) m/z: 583.0 (M+1). Compound 125 (B1)/ compound 126 (B2): $^1$H NMR (400 MHz, methanol-d₄): δ 8.68 (br. s., 1H), 8.59 (s, 1H), 8.08 (d, J=2.38 Hz, 1H), 7.89 (d, J=8.16 Hz, 1H), 7.84 (d, J=7.15 Hz, 1H), 7.78-7.73 (m, 1H), 7.68 (d, J=7.91 Hz, 2H), 7.55-7.44 (m, 2H), 7.43-7.38 (m, 1H), 7.35-7.25 (m, 2H), 7.14 (br. s., 2H), 6.91-6.83 (m, 3H), 5.84 (br. s., 1H), 4.17 (s, 3H), 2.78 (d, J=12.42 Hz, 1H), 2.17-2.32 (m, 2H), 2.12 (s, 6H), 2.01 (br. s., 1H). LCMS (ESI) m/z: 583.0 (M+1).

Example 3

1-(5-cyclopropyl-2-methoxypyridin-3-yl)-4-(dimethylamino)-2-(naphthalen-1-yl)-1-phenylbutan-2-ol

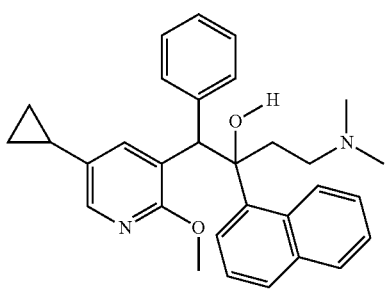

Compound 5 (A1)
Compound 6 (A2)
Compound 7 (B1)
Compound 8 (B2)

According to the method of Example 1, the product was prepared by the reaction of intermediate A and cyclopropyl boronic acid. The crude product was purified by preparative HPLC (GX-D; Agella Venusil ASB C18 150*21.2 mm*5 um; acetonitrile 70%-100%; water (0.225% HCl); 25 mL/min) to give component A and component B. Component A was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 5 (A1) (5.64 mg, 0.66% yield) and compound 6 (A2) (10.21 mg, 1.2% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 7 (B1) (17.62 mg, 2.09% yield) and compound 8 (B2) (18.30 mg, 2.14% yield) as white solid. Compound 5 (A1)/compound 6 (A2): $^1$H NMR (400 MHz, METHANOL-$d_4$): δ 8.64 (br. s., 1H), 8.17 (br. s., 1H), 7.81-7.94 (m, 3H), 7.56-7.71 (m, 2H), 7.48 (t, J=6.90 Hz, 1H), 7.28 (t, J=7.78 Hz, 1H), 7.10 (br. s., 2H), 6.91-6.80 (m, 3H), 5.75 (br. s., 1H), 4.14-4.01 (m, 3H), 2.64 (d, J=12.30 Hz, 1H), 2.21-1.81 (m, 11H), 1.31 (br. s., 1H), 1.05-0.94 (m, 2H), 0.75-0.62 (m, 2H). Compound 7 (B1)/compound 8 (B2): $^1$H NMR (400 MHz, METHANOL-$d_4$): δ 8.53 (d, J=8.78 Hz, 1H), 8.02 (d, J=7.28 Hz, 1H), 7.96 (s, 1H), 7.82 (d, J=8.03 Hz, 1H), 7.73 (d, J=7.53 Hz, 2H), 7.66 (d, J=7.78 Hz, 1H), 7.57 (t, J=7.78 Hz, 1H), 7.46-7.41 (m, 2H), 7.38-7.33 (m, 3H), 7.29-7.23 (m, 1H), 4.62 (br. s., 1H), 3.23 (s, 3H), 2.62 (d, J=13.05 Hz, 1H), 2.19 (t, J=13.43 Hz, 2H), 2.01 (s, 7H), 1.90 (br. s., 1H), 1.71 (d, J=4.77 Hz, 1H), 1.31 (s, 1H), 0.89 (d, J=7.53 Hz, 3H), 0.61-0.43 (m, 3H). LCMS (ESI) m/z: 467.3 (M+1).

Example 4

4-(dimethylamino)-1-(6-methoxy-[3,4'-bipyridin]-5-yl)-2-(naphthalen-1-yl)-1-phenylbutan-2-ol

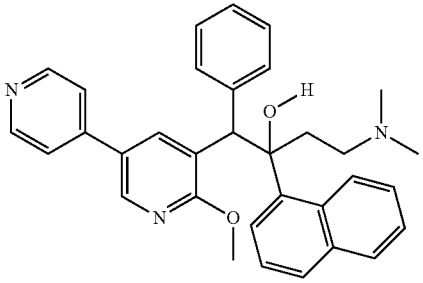

Compound 13 (A1)
Compound 14 (A2)
Compound 15 (B1)
Compound 16 (B2)

According to the method of Example 1, the product was prepared by the reaction of intermediate A and 4-pyridine boronic acid. The crude product was purified by preparative HPLC (GX-D; Boston Symmetrix C18 ODS-R 150*30 mm*5 um; MeCN: 15%-45%; $H_2O$ (+0.225% HCOOH); 25 mL/min) to give component A and component B. Component A was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 13 (A1) (50.24 mg, 1.2% yield) and compound 14 (A2) (47.56 mg, 1.19% yield) as white solid. Component B was separated by chiral SFC (Berger MultiGram™ SFC, Mettler Toledo Co, Ltd, AS-10 um; supercritical $CO_2$/MeOH (0.05% aqueous ammonia)=60/40; 70 ml/min; 220 nm) to give compound 15 (B1) (20.43 mg, 0.51% yield) and compound 16 (B2) (29.37 mg, 0.73% yield) as white solid. Compound 13 (A1)/compound 14 (A2): $^1$H NMR (400 MHz, METHANOL-$d_4$): δ 8.83-8.59 (m, 4H), 8.54 (d, J=2.26 Hz, 1H), 8.47 (s, 1H), 7.96-7.80 (m, 2H), 7.73 (d, J=8.03 Hz, 4H), 7.53 (t, J=7.15 Hz, 1H), 7.33 (t, J=7.78 Hz, 1H), 7.14 (br. s., 2H), 6.98-6.84 (m, 3H), 5.89 (br. s., 1H), 4.21 (s, 3H), 3.06 (br. s., 1H), 2.76 (br. s., 1H), 2.40 (s, 6H), 2.20 (d, J=8.03 Hz, 2H). Compound 15 (B1)/compound 16 (B2): $^1$H NMR (400 MHz, METHANOL-$d_4$): δ 8.74 (d, J=2.51 Hz, 1H), 8.58 (d, J=6.27 Hz, 3H), 8.13 (d, J=7.28 Hz, 1H), 8.02 (d, J=2.51 Hz, 1H), 7.86-7.78 (m, 3H), 7.67-7.57 (m, 4H), 7.46 (t, J=7.53 Hz, 1H), 7.40-7.34 (m, 3H), 7.31-7.26 (m, 1H), 5.70 (s, 1H), 2.65 (d, J=14.18 Hz, 1H), 2.30-2.15 (m, 2H), 2.01 (s, 6H), 1.96-1.88 (m, 1H). LCMS (ESI) m/z: 504.3 (M+1).

Example 5

4-(dimethylamino)-1-(6-methoxy-[3,3'-bipyridin]-5-yl)-2-(naphthalen-1-yl)-1-phenylbutan-2-ol

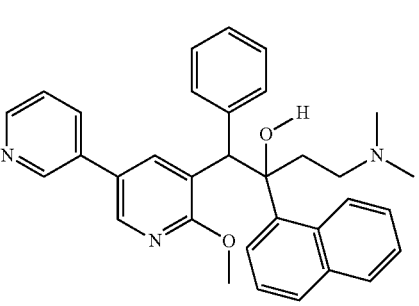

Compound 17 (A1)
Compound 18 (A2)
Compound 19 (B1)
Compound 20 (B2)

According to the method of Example 1, the product was prepared by the reaction of intermediate A and 4-pyridine boronic acid. The crude product was purified by preparative HPLC (GX-D; Boston Symmetrix C18 ODS-R 150*30 mm*5 um; MeCN: 30%-54%; H₂O (+0.25% HCl); 25 mL/min) to give component A and component B. Component A was separated by chiral SFC (sfc 80, AD-10 um; supercritical CO₂/MeOH (0.05% aqueous ammonia)=60/40; 70 ml/min; 220 nm) to give compound 17 (A1) (64.8 mg, 1.8% yield) and compound 18 (A2) (83.3 mg, 2.4% yield) as white solid. Component B was separated by chiral SFC (Berger MultiGram™ SFC, Mettler Toledo Co, Ltd, AS-10 um; supercritical CO₂MeOH (0.05% aqueous ammonia)=60/40; 70 ml/min; 220 nm) to give compound 19 (B1) (64.38 mg, 1.8% yield) and compound 20 (B2) (69.52 mg, 2.0% yield) as white solid. Compound 17 (A1)/compound 18 (A2): $^1$H NMR (400 MHz, METHANOL-$d_4$): δ 8.70 (d, J=1.6 Hz, 1H), 8.63 (d, J=2.4 Hz, 1H), 8.57 (d, J=6.4 Hz, 2H), 8.14 (d, J=6.4 Hz, 1H), 8.00 (s, 1H), 7.91-7.82 (m, 2H), 7.75 (d, J=6.4 Hz, 2H), 7.68-7.57 (m, 2H), 7.49-7.20 (m, 6H), 5.60 (s, 1H), 3.64 (s, 3H), 2.18-1.86 (m, 10H). Compound 19 (B1)/compound 20 (B2): $^1$H NMR (400 MHz, METHANOL-$d_4$): δ 8.74 (d, J=2.51 Hz, 1H), 8.58 (d, J=6.27 Hz, 3H), 8.13 (d, J=7.28 Hz, 1H), 8.02 (d, J=2.51 Hz, 1H), 7.86-7.78 (m, 3H), 7.67-7.57 (m, 4H), 7.46 (t, J=7.53 Hz, 1H), 7.40-7.34 (m, 3H), 7.31-7.26 (m, 1H), 5.70 (s, 1H), 2.65 (d, J=14.18 Hz, 1H), 2.30-2.15 (m, 2H), 2.01 (s, 6H), 1.96-1.88 (m, 1H). LCMS (ESI) m/z: 504.3 (M+1).

Example 6

4-(dimethylamino)-1-(2-methoxy-5-(pyrrolidin-3-yl)pyridin-3-yl)-2-(naphthalen-1-yl)-1-phenylbutan-2-ol

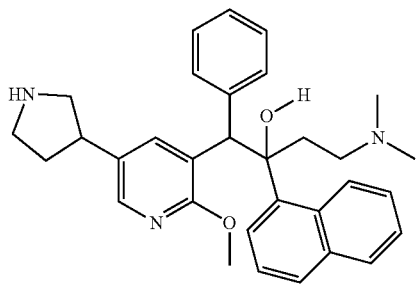

Compound 57 (A1)
Compound 58 (A2)
Compound 59 (B1)
Compound 60 (B2)

Step 1: tert-butyl 3-((((trifluoromethyl)sulfonyl)oxy)-2, 5-dihydro-1H-pyrrol-1-carbonate

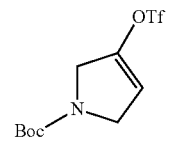

Under nitrogen, the solution of tert-butyl 3-pyrrolidinone-1-carboxylate in tetrahydrofuran (50 mL) was slowly added dropwise to the solution of LiHMDS (30 mL, 30 mmol, 1M in THF) in tetrahydrofuran (100 mL) at −78° C. After addition, the mixture was stirred at this temperature for 15 minutes and then the solution of 1,1,1-trifluoro-N-phenyl-N-((trifluoromethyl)sulfonyl)methanesulfonic acid (11.35 g, 30 mmol) in tetrahydrofuran (100 mL) was added to the reaction liquid and stirred at −78° C. for 3 hours. Then the temperature was raised to 30° C. for 1 hour. The reaction liquid was quenched with sodium bicarbonate solution (10%, 500 mL), and extracted with ethyl acetate (100 mL×2). The combined organic phase was washed with brine (100 mL×2) and the organic phase was dried over anhydrous sodium sulfate, and concentrated to give the crude product which was purified by silica gel column chromatography (eluent: petroleum ether/ethyl acetate=100/1-10/1) to give tert-butyl 3-((((trifluoromethyl)sulfonyl)oxy)-2,5-dihydro-1H-pyrrol-1-carbonate (5.1 g, 60% yield) as a yellow liquid. $^1$H NMR (400 MHz, CHLOROFORM-d): δ 5.73-5.61 (m, 1H), 4.22-4.08 (m, 4H), 1.41 (s, 9H).

Step 2: tert-butyl 3-(4,4,5,5-tetramethyl-1,3,2-dioxaborolan-2-yl)-2,5-dihydro-1H-pyrrol-1-carbonate

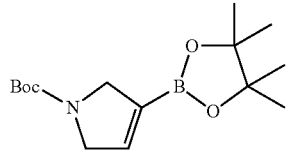 [SMILES: CC(C)(C)OC(=O)N1CC=C(B2OC(C)(C)C(C)(C)O2)C1]

At 25° C., tert-butyl 3-(((trifluoromethyl)sulfonyl)oxy)-2,5-dihydro-1H-pyrrol-1-carbonate (600 mg, 1.9 mmol), pinacol borate (480 mg, 1.9 mmol), Pd(dppf)Cl$_2$ (140 mg, 0.19 mmol), diphenylphosphino ferrocene (100 mg, 0.19 mmol) and potassium acetate (550 mg, 0.57 mmol) were dissolved in dioxane (10 mL). The reaction system was displaced with nitrogen for three times and then heated to 80° C. for 4 hours. The reaction liquid was concentrated and directly separated by silica gel column chromatography (petroleum ether/ethyl acetate=50/1-10/1) to give tert-butyl 3-(4,4,5,5-tetramethyl-1,3,2-dioxaborolan-2-yl)-2,5-dihydro-1H-pyrrol-1-carbonate (400 mg, 72% yield) as a yellow liquid.

Step 3: tert-butyl 3-(5-(4-(dimethylamino)-2-hydroxyl-2-(naphthalen-1-yl)-1-phenylbutyl)-6-methoxypyridin-3-yl)-2, 5-dihydro-1H-pyrrol-1-carbonate

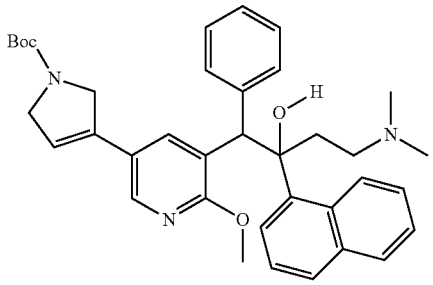 [SMILES: COc1ncc(C2=CCN(C(=O)OC(C)(C)C)C2)cc1C(c1ccccc1)C(O)(CCN(C)C)c1cccc2ccccc12]

Under nitrogen, 1-(5-bromo-2-methoxypyridin-3-yl)-4-(dimethylamino)-2-(naphthalen-1-yl)-1-phenylbutan-2-ol (1.00 g, 1.98 mmol), tert-butyl 3-(4,4,5,5-tetramethyl-1,3,2-dioxaborolan-2-yl)-2,5-dihydro-1H-pyrrol-1-carbonate (643 mg, 2.18 mmol), Pd(dppf)Cl$_2$ (144.88 mg, 198 umol) and potassium acetate (582.95 mg, 5.94 mmol) were mixed in dioxane (10 mL) and water (2 mL), heated to 80-90° C. and stirred for 16 hours. The reaction liquid was cooled and poured in water and extracted with ethyl acetate (20 mL×3). The combined organic phase was washed with saturated saline solution (20 mL×3), dried over anhydrous sodium sulfate, and concentrated under reduced pressure to give the crude product which was then separated by silica gel column chromatography (petroleum ether/ethyl acetate: 30/1-5/1) to give tert-butyl 3-(5-(4-(dimethylamino)-2-hydroxyl-2-(naphthalen-1-yl)-1-phenylbutyl)-6-methoxypyridin-3-yl)-2,5-dihydro-1H-pyrrol-1-carbonate (500 mg, 42.7% yield) as yellow solid. LCMS (ESI) m/z: 594.3 (M+1).

Step 4: tert-butyl 3-(5-(4-(dimethylamino)-2-hydroxyl-2-(naphthalen-1-yl)-1-phenylbutyl)-6-methoxypyridin-3-yl)pyrrol-1-carbonate

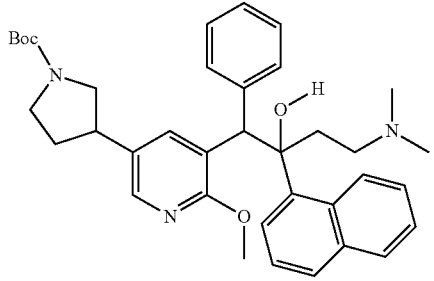 [SMILES: COc1ncc(C2CCN(C(=O)OC(C)(C)C)C2)cc1C(c1ccccc1)C(O)(CCN(C)C)c1cccc2ccccc12]

Tert-butyl 3-(5-(4-(dimethylamino)-2-hydroxyl-2-(naphthalen-1-yl)-1-phenylbutyl)-6-methoxypyridin-3-yl)-2, 5-dihydro-1H-pyrrol-1-carbonate (500 mg, 0.84 mmol) and dry palladium on carbon (100 mg) were added to methanol (10 mL) and the reaction was conducted at 25-30° C. under 15 psi hydrogen atmosphere for hours. The reaction mixture was filtered and concentrated to give tert-butyl 3-(5-(4-(dimethylamino)-2-hydroxyl-2-(naphthalen-1-yl)-1-phenylbutyl)-6-methoxypyridin-3-yl)pyrrol-1-carbonate (500 mg, crude) as a white solid. The crude product was used directly in the next step without further purification. LCMS (ESI) m/z: 596.3 (M+1).

Step 5: 4-(dimethylamino)-1-(2-methoxy-5-(pyrrolidin-3-yl)pyridin-3-yl)-2-(naphthalen-1-yl)-1-phenylbutan-2-ol

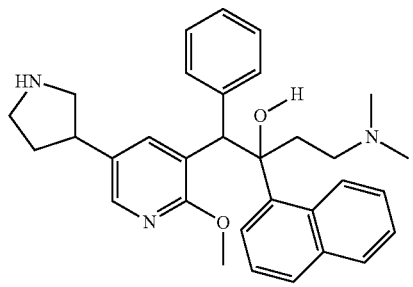

Compound 57 (A1)
Compound 58 (A2)
Compound 59 (B1)
Compound 60 (B2)

Tert-butyl 3-(5-(4-(dimethylamino)-2-hydroxyl-2-(naphthalen-1-yl)-1-phenylbutyl)-6-methoxypyridin-3-yl)pyrrol-1-carbonate (500 mg, 0.84 mmol) was dissolved in the mixed solvent of dichloromethane (10 ml) and trifluoroacetic acid (2 mL) at 20-30° C. and stirred for 2 hours. The reaction liquid was then concentrated and purified by preparative HPLC (GX-D; Boston Symmetrix C18 ODS-R 150*30 mm*5 um; acetonitrile 10%-40%; water (0.225% formic acid); 25 mL/min) to give component A and component B. Component A was separated by chiral SFC (sfc 80; AD-10 um; supercritical CO$_2$/MeOH (0.1% aqueous ammonia)=50/50; 70 ml/min; 220 nm) to give compound 57 (A1) (46.6 mg, 11.2% yield) and compound 58 (A2) (64.7 mg, 15.5% yield) as white solid. Component B was separated by chiral SFC (Berger MultiGram™ SFC, Mettler Toledo Co, Ltd; IC 250 mm*20 mm, 10 um; supercritical $CO_2$/MeOH (0.05% aqueous ammonia)—50/50; 70 ml/min; 220 nm) to give compound 59 (B1) (26.9 mg, 6.46% yield) and compound (B2) (19.47 mg, 4.68% yield) as white solid. Compound 57 (A1)/compound 58 (A2): $^1$H NMR (400 MHz, METHANOL-$d_4$): δ 8.66 (br. s., 1H), 8.50 (s, 2H), 8.33 (br. s., 1H), 8.06 (s, 1H), 7.88 (d, J=7.7 Hz, 2H), 7.69 (d, J=7.7 Hz, 2H), 7.55-7.46 (m, 1H), 7.31 (t, J=7.7 Hz, 1H), 7.15 (br. s., 2H), 6.88 (br. s., 3H), 5.81 (br. s., 1H), 4.14 (s, 3H), 3.75 (t, J=9.7 Hz, 1H), 3.64-3.53 (m, 2H), 3.46-3.39 (m, 1H), 3.30-3.02 (m, 1H), 2.94 (br. s., 1H), 2.66-2.43 (m, 2H), 2.31 (br. s., 6H), 2.22-1.99 (m, 3H). Compound 59 (B1)/compound 60 (B2): $^1$H NMR (400 MHz, METHANOL-$d_4$): δ 8.58 (d, J=8.8 Hz, 1H), 8.44 (br. s., 3H), 8.20-8.07 (m, 2H), 7.82 (d, J=8.0 Hz, 1H), 7.72-7.53 (m, 6H), 7.47-7.31 (m, 5H), 5.71 (s, 1H), 3.62-3.42 (m, 5H), 3.30-3.10 (m, 2H), 3.07-2.89 (m, 2H), 2.63-2.54 (m, 7H), 2.40-2.20 (m, 3H), 1.90 (d, J=5.9 Hz, 1H). LCMS (ESI) m/z: 496.3 (M+1).

Example 7

4-(dimethylamino)-1-(2-methoxy-5-(1-methylpyrrol-3-yl)pyridin-3-yl)-2-(naphthalen-1-yl)-1-phenylbutan-2-ol

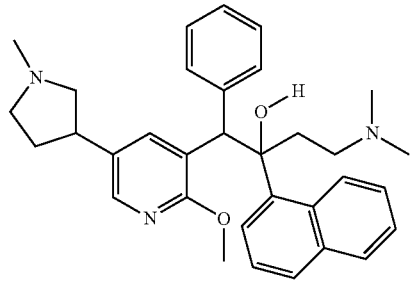

Compound 61 (A)
Compound 62 (B)

Under nitrogen, 4-(dimethylamino)-1-(2-methoxy-5-(pyrrol-3-yl)pyridin-3-yl)-2-(naphthalen-1-yl)-1-phenylbutan-2-ol (500 mg, 1.0 mmol) and sodium cyanoborohydride (100 mg, 1.5 mmol) were dissolved in methanol (5 mL), then added with 2 mL of aqueous formaldehyde solution and stirred at 25-30° C. for 5 h. Then the reaction liquid was filtered and the filtrate was dried by rotary evaporation and purified by preparative HPLC (GX-G; Phenomenex Synergi C18 150*30 mm*4 um; acetonitrile; 10%-40%; water (0.225% FA); 25 mL/min) to give compound 61 (A) (222.21 mg, 43.2% yield) and compound 62 (B) (124.27 mg, 29.5% yield) as white solid. Compound 61 (A): $^1$H NMR (400 MHz, METHANOL-$d_4$): δ 8.67 (br. s., 1H), 8.47 (s, 2H), 8.30 (br. s., 1H), 8.07 (s, 1H), 7.95-7.77 (m, 2H), 7.71 (d, J=8.0 Hz, 2H), 7.57-7.47 (m, 1H), 7.31 (t, J=7.8 Hz, 1H), 7.12 (br. s., 2H), 6.90 (br. s., 3H), 5.81 (br. s., 1H), 4.12 (br. s., 3H), 3.80-3.37 (m, 5H), 3.13-2.98 (m, 4H), 2.88 (br. s., 1H), 2.58-2.44 (m, 7H), 2.35-2.06 (m, 3H). Compound 62 (B): $^1$H NMR (400 MHz, METHANOL-$d_4$): δ 8.58 (d, J=8.8 Hz, 1H), 8.45 (s, 3H), 8.19-8.07 (m, 2H), 7.81 (d, J=7.9 Hz, 1H), 7.74-7.67 (m, 3H), 7.53 (s, 1H), 7.49-7.28 (m, 6H), 5.71 (s, 1H), 3.67-3.37 (m, 7H), 3.26-2.96 (m, 6H), 2.57 (s, 6H), 2.45-2.23 (m, 3H), 2.06-1.89 (m, 1H). LCMS (ESI) m/z: 510.3 (M+1).

Example 8

1-(5-cyclopentyl-2-methoxypyridin-3-yl)-4-(dimethylamino-2-(naphthalen-1-yl)-1-phenylbutan-2-ol

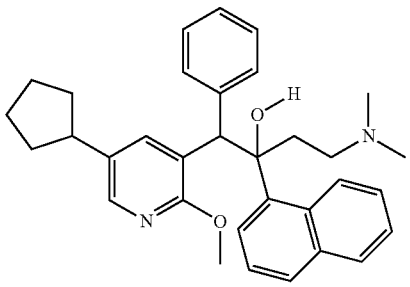

Compound 63 (A1)
Compound 64 (A2)
Compound 65 (B1)
Compound 66 (B2)

Step 1: 1-(5-(cyclopentyl-1-en-1-yl)-2-methoxypyridin-3-yl)-4-(dimethylamino)-2-(naphthalen-1-yl)-1-phenylbutan-2-ol

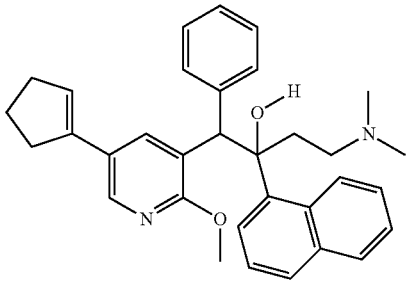 [SMILES: COc1ncc(C2=CCCC2)cc1C(c1ccccc1)C(O)(CCN(C)C)c1cccc2ccccc12]

Under nitrogen, intermediate A (1.00 g, 1.98 mmol), cyclopentyl-1-en-1-yl boronic acid (243.6 mg, 2.18 mmol), Pd(dppf)Cl$_2$ (144.88 mg, 198 umol) and potassium acetate (582.95 g, 5.94 mmol) were added to dioxane(10 mL) and water (2 mL), heated to 80-90° C. and stirred for 16 h. The reaction liquid was cooled and poured into water (20 mL) and extracted with ethyl acetate (10 mL×2). The combined organic phases were washed with saturated brine (10 mL×2), dried over anhydrous sodium sulfate, and concentrated under reduced pressure to give crude product. The crude product was separated by silica gel column chromatography (eluent: petroleum ether/ethyl acetate: 30/1-5/1) to give 1-(5-(cyclopentyl-1-en-1-yl)-2-methoxypyridin-3-yl)-4-(dimethylamino)-2-(naphthalen-1-yl)-1-phenylbutan-2-ol (750 mg, 76.89% yield) as yellow solid. LCMS (ESI) m/z: 493.3 (M+1).

Step 2: 1-(5-cyclopentyl-2-methoxypyridin-3-yl)-4-(dimethylamino-2-(naphthalen-1-yl)-1-phenylbutan-2-ol

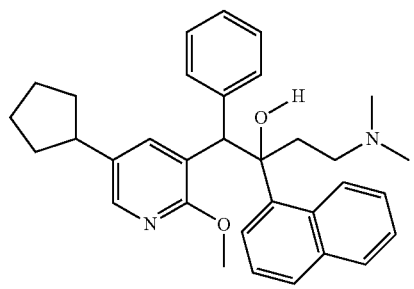

Compound 63 (A1)
Compound 64 (A2)
Compound 65 (B1)
Compound 66 (B2)

1-(5-(cyclopentyl-1-en-1-yl)-2-methoxypyridin-3-yl)-4-(dimethylamino)-2-(naphthalen-1-yl)-1-phenylbutan-2-ol (750 mg, 1.52 mmol) and dry palladium on carbon (100 mg) were added to methanol (10 mL) and stirred at 25-30° C. under hydrogen atmosphere (15 psi) for 5 h. The reaction liquid was filtered and the filtrate was dried by rotary evaporation and purified by preparative HPLC (GX-D; Boston Symmetrix C18 ODS-R 150*30 mm*5 um; acetonitrile 34%-64%; water (0.225% formic acid); 25 mL/min) to give component A and component B. Component A was separated by chiral SFC (Berger MultiGram™ SFC, Mettler Toledo Co, Ltd; IC-10 um; supercritical $CO_2$/MeOH (0.05% aqueous ammonia)=60/40; 70 ml/min; 220 nm) to give compound 63 (A1) (43.63 mg, 5.8% yield) and compound 64 (A2) (43.96 mg, 5.85% yield) as white solid. Component B was separated by chiral SFC (Berger MultiGram™ SFC, Mettler Toledo Co, Ltd; IC-10 um; supercritical $CO_2$/MeOH (0.05% aqueous ammonia)=60/40; 70 ml/min; 220 nm) to give compound 65 (B1) (32.98 mg, 4.39% yield) and compound 66 (B2) (31.3 mg, 4.16% yield) as white solid. Compound 63 (A1)/compound 64 (A2): $^1$H NMR (400 MHz, METHANOL-$d_4$): δ 8.65 (br. s., 1H), 8.55 (br. s., 1H), 8.44 (br. s., 1H), 7.99-7.77 (m, 3H), 7.73-7.58 (m, 2H), 7.50 (t, J=7.72 Hz, 1H), 7.29 (t, J=7.78 Hz, 1H), 7.08 (br. s., 2H), 6.94-6.80 (m, 3H), 5.78 (br. s., 1H), 4.09 (s, 3H), 3.06 (quin, J=8.38 Hz, 1H), 2.71 (br. s., 1H), 2.30 (br. s., 1H), 2.19-1.56 (m, 16H). Compound 65 (B1)/compound 66 (B2): $^1$H NMR (400 MHz, METHANOL-$d_4$): δ 8.61-8.45 (m, 1H), 8.17 (br. s., 1H), 8.06 (d, J=7.28 Hz, 1H), 7.82 (d, J=8.28 Hz, 1H), 7.75-7.53 (m, 4H), 7.49-7.25 (m, 6H), 5.65 (s, 1H) 3.34 (d, J=5.65 Hz, 3H), 2.93 (d, J=8.91 Hz, 1H), 2.85-2.73 (m, 1H), 2.64 (d, J=10.04 Hz, 1H), 2.45-2.23 (m, 7H), 2.15 (d, J=12.17 Hz, 1H), 1.97-1.66 (m, 5H), 1.40 (d, J=8.91 Hz, 1H). LCMS (ESI) m/z: 495.3 (M+1).

Example 9

4-(dimethylamino)-1-(2-methoxy-5-(tetrahydro-2H-pyran-4-yl)pyridin-3-yl)-2-(naphthalen-1-yl)-1-phenylbutan-2-ol

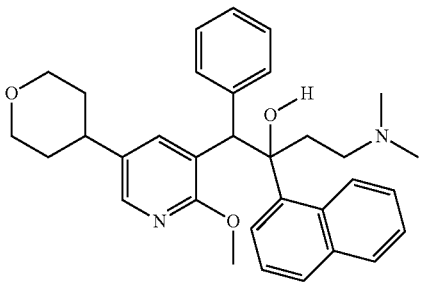

Compound 75 (A1)
Compound 76 (A2)
Compound 77 (B1)
Compound 78 (B2)

Step 1: 1-(5-(3,6-dihydro-2H-pyran-4-yl)-2-methoxypyridin-3-yl)-4-(dimethylamino)-2-(naphthalen-1-yl)-1-phenylbutan-2-ol

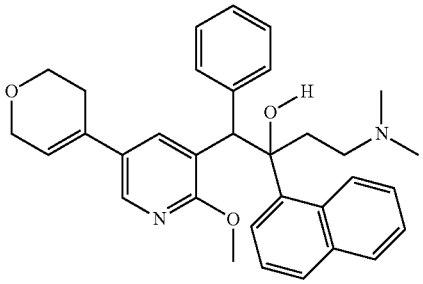

Intermediate A (1.2 g, 2.37 mmol), 2-(3,6-dihydro-2H-pyran-4-yl)-4,4,5,5-tetramethyl-1,3,2-dioxaborolane (0.55 g, 2.61 mmol) and potassium acetate (704 mg, 7.11 mmol) were dissolved in the mixed solution of dioxane (10 mL) and water (2 mL). Under nitrogen, Pd(dppf)Cl$_2$(176 mg, 0.24 mmol) was added to the reaction liquid. The reaction liquid was heated to 80° C. and stirred for 2 h. Water (100 mL) was added to the reaction liquid and the reaction mixture was extracted with ethyl acetate (100 mL×3), dried over anhydrous sodium sulfate, and concentrated under reduced pressure to give crude product which was then separated and purified by silica gel column chromatography (eluent: petroleum ether/ethyl acetate=20/1-2/1) to give 1-(5-(3,6-dihydro-2H-pyran-4-yl)-2-methoxypyridin-3-yl)-4-(dimethylamino)-2-(naphthalen-1-yl)-1-phenylbutan-2-ol (0.70 g, 58%) as a white solid. LCMS (ESI) m/z: 509.3 (M+1).

Step 2: 4-(dimethylamino)-1-(2-methoxy-5-(tetrahydro-2H-pyran-4-yl)pyridin-3-yl)-2-(naphthalen-1-yl)-1-phenylbutan-2-ol

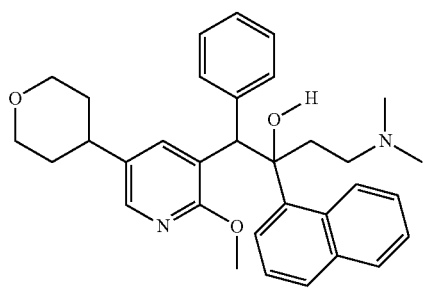 [SMILES: COc1ncc(C2=CCOCC2)cc1C(c1ccccc1)C(O)(CCN(C)C)c1cccc2ccccc12]

Compound 75 (A1)
Compound 76 (A2)
Compound 77 (B1)
Compound 78 (B2)

1-(5-(3,6-dihydro-2H-pyran-4-yl)-2-methoxypyridin-3-yl)-4-(dimethylamino)-2-(naphthalen-1-yl)-1-phenylbutan-2-ol (0.7 g, 1.38 mmol) and dry palladium on carbon (70 mg) were added to methanol (20 mL) and stirred at 25-30° C. under hydrogen atmosphere (50 psi) for 5 h. The reaction liquid was filtered and the filtrate was dried by rotary evaporation and purified by preparative HPLC (GX-D; Boston Symmetrix C18 ODS-R 150*30 mm*5 um; MeCN: 27%-57%; H₂O (+0.0023 FA); 25 mL/min) to give component A and component B. Component A was separated by chiral SFC (Berger MultiGram™ SFC, Mettler Toledo Co, Ltd, ID-5 um; supercritical CO₂/MeOH (0.05% aqueous ammonia)=60/40; 70 ml/min; 220 nm) to give compound 75 (A1) (29.60 mg, 16.9% yield) and compound 76 (A2) (33.08 mg, 18.9% yield) as white solid. Component B was separated by chiral SFC (Berger MultiGram™ SFC, Mettler Toledo Co, Ltd; IC-10 um; supercritical CO₂/MeOH (0.05% aqueous ammonia)—60/40; 70 ml/min; 220 nm) to give compound 77 (B1) (12.08 mg, 6.9% yield) and compound 78 (B2) (12.75 mg, 7.3% yield) as white solid. Compound 75 (A1)/compound 76 (A2): ¹H NMR (400 MHz, METHANOL-d₄): δ 8.66 (s, 1H), 8.53 (s, 1H), 8.40 (br. s., 1H), 8.07-7.87 (m, 4H), 7.76-7.58 (m, 3H), 7.58-7.42 (m, 2H), 7.30 (t, J=7.78 Hz, 2H), 7.09 (br. s., 3H), 6.88 (d, J=2.01 Hz, 4H), 5.80 (br. s., 1H), 4.22-3.96 (m, 5H), 3.74-3.51 (m, 2H), 2.99-2.66 (m, 2H), 2.41 (br. s., 2H), 2.21 (s, 9H), 2.14-1.96 (m, 3H), 1.94-1.66 (m, 6H). Compound 77 (B1)/compound 78 (B2): ¹H NMR (400 MHz, METHANOL-d₄): δ 8.56 (d, J=8.53 Hz, 1H), 8.25 (s, 1H), 8.07 (d, J=7.15 Hz, 1H), 7.87-7.70 (m, 3H), 7.69-7.51 (m, 3H), 7.50-7.21 (m, 9H), 5.63 (s, 1H), 4.05 (d, J=11.04 Hz, 2H), 3.64-3.47 (m, 2H), 3.30 (s, 3H), 2.81-2.52 (m, 2H), 2.40-2.17 (m, 2H), 2.13 (s, 6H) 2.04-1.92 (m, 1H), 1.60-1.48 (m, 4H). LCMS (ESI) m/z: 511.2 (M+1).

Example 10

4-(dimethylamino)-1-(2-methoxy-5-(piperidin-4-yl)pyridin-3-yl)-2-(naphthalen-1-yl)-1-phenylbutan-2-ol

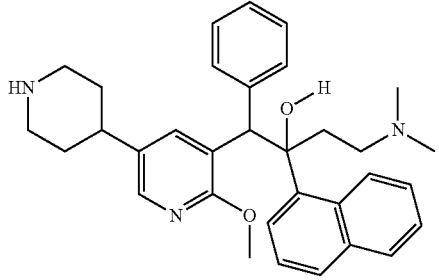

Compound 79 (A)
Compound 80 (B)

Step 1: tert-butyl 5-(4-(dimethylamino)-2-hydroxyl-2-(naphthalen-1-yl)-1-phenylbutyl)-6-methoxy-5',6'-dihydro-[3,4'-bipyridyl]-1'(2'H)-carboxylate

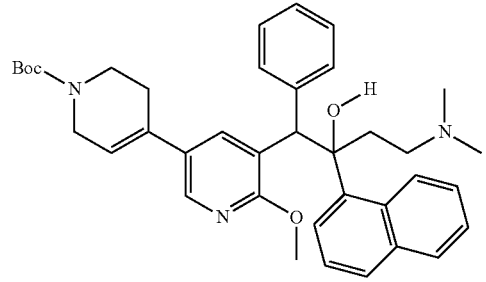 [SMILES: COc1ncc(C2=CCN(C(=O)OC(C)(C)C)CC2)cc1C(c1ccccc1)C(O)(CCN(C)C)c1cccc2ccccc12]

Intermediate A (3.6 g, 7.11 mmol), tert-butyl 4-(4,4,5,5-tetramethyl-1,3,2-dioxaborolan-2-yl)-5,6-dihydropyridyl-1(2H)-carboxylate (2.4 g, 7.84 mmol) and potassium acetate (2.2 g, 22 mmol) were dissolved in the mixed solution of dioxane (30 mL) and water (6 mL). Under nitrogen, Pd(dppf)Cl₂ (0.53 g, 0.71 mmol) was added. The reaction liquid was heated to 80° C. and stirred for 2 h. Water (200 mL) was added and the reaction mixture was extracted with ethyl acetate (200 mL×3), dried over anhydrous sodium sulfate, concentrated in vacuo to give crude product which was then separated by silica gel column chromatography (eluent: petroleum ether/ethyl acetate=0/1-2/1) to give tert-butyl 5-(4-(dimethylamino)-2-hydroxyl-2-(naphthalen-1-yl)-1-phenylbutyl)-6-methoxy-5',6'-dihydro-[3,4'-bipyridyl]-1'(2'H)-carboxylate (3.3 g, 77% yield) as a white solid. LCMS (ESI) m/z: 608.3 (M+1).

Step 2: 4-(dimethylamino)-1-(6-methoxy-1',2',3',6'-tetrahydro-[3,4'-bipyridin]-5-yl)-2-(naphthalen-1-yl)-1-phenylbutan-2-ol

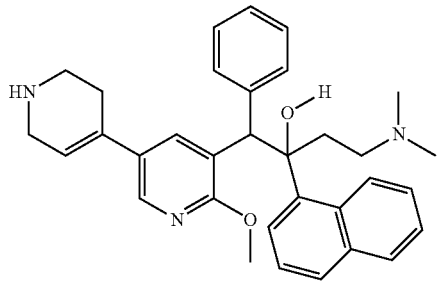 [SMILES: COc1ncc(C2=CCNCC2)cc1C(c1ccccc1)C(O)(CCN(C)C)c1cccc2ccccc12]

5-(4-(dimethylamino)-2-hydroxyl-2-(naphthalen-1-yl)-1-phenylbutyl)-6-methoxy-5',6'-dihydro-[3,4'-bipyridyl]-1'(2'H)-carboxylate (3.3 g, 1.38 mmol) was dissolved in dichloromethane (30 mL) and trifluoroacetic acid (10 mL) and stirred at 20° C. for 1 hour. The reaction liquid was concentrated to give 4-(dimethylamino)-1-(6-methoxy-1',2',3',6'-tetrahydro-[3,4'-bipyridin]-5-yl)-2-(naphthalen-1-yl)-1-phenylbutan-2-ol (2.8 g, crude product), which was used directly in the next step without further purification. LCMS (ESI) m/z: 508.3 (M+1).

Step 3: 4-(dimethylamino)-1-(2-methoxy-5-(piperidin-4-yl)pyridin-3-yl)-2-(naphthalen-1-yl)-1-phenylbutan-2-ol

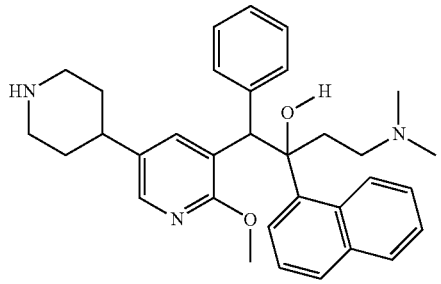

Compound 79 (A)
Compound 80 (B)

4-(dimethylamino)-1-(6-methoxy-1',2',3',6'-tetrahydro-[3,4'-bipyridin]-5-yl)-2-(naphthalen-1-yl)-1-phenylbutan-2-ol (2 g, 3.9 mmol) was dissolved in methanol (60 mL) and palladium on carbon (100 mg) was added and stirred at 30° C. under hydrogen atmosphere (50 psi) for 20 h. The reaction liquid was filtered and the filtrate was concentrated to give crude product (0.5 g) which was purified by preparative HPLC (GX-D; Boston Symmetrix C18 ODS-R 150*30 mm*5 um; MeCN: 15%-50%; H$_2$O (+0.0023 FA); 25 ml/min) to give compound 79 (A) (57.27 mg, 23.4% yield) and compound 80 (B) (77.82 mg, 26.9% yield) as a white solid. Compound 79 (A): $^1$H NMR (400 MHz, METHANOL-d$_4$): δ 8.66-8.43 (m, 1H), 8.25-8.04 (m, 1H), 7.82 (d, J=8.03 Hz, 1H), 7.76-7.55 (m, 5H), 7.54-7.23 (m, 8H), 5.68 (s, 1H), 3.59-3.46 (m, 2H), 3.37 (s, 3H), 3.22-2.91 (m, 4H), 2.71 (d, J=2.89 Hz, 2H), 2.52-2.10 (m, 9H), 2.02-1.68 (m, 4H). Compound (B): $^1$H NMR (400 MHz, METHANOL-d$_4$): δ 8.66 (br. s., 1H), 8.21 (br. s., 1H), 8.06-7.84 (m, 3H), 7.84-7.65 (m, 5H), 7.53 (t, J=7.28 Hz, 2H), 7.32 (t, J=7.78 Hz, 2H), 7.11 (br. s., 3H), 6.90 (br. s., 5H), 5.83 (br. s., 1H), 4.14 (br. s., 4H), 3.69-3.44 (m, 3H), 2.90-3.28 (m, 5H), 2.62 (d, J=11.17 Hz, 6H), 2.27-1.78 (m, 5H). LCMS (ESI) m/z: 510.3 (M+1).

Example 11

4-(dimethylamino)-1-(2-methoxy-5-(1-methylpiperidin-4-yl)pyridin-3-yl)-2-(naphthalen-1-yl)-1-phenylbutan-2-ol

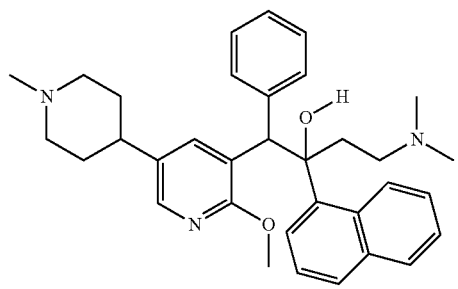

Compound 81 (A)
Compound 82 (B)

4-(dimethylamino)-1-(2-methoxy-5-(piperidin-4-yl)pyridin-3-yl)-2-(naphthalen-1-yl)-1-phenylbutan-2-ol (1.00 g, 1.96 mmol) and aqueous formaldehyde solution (5 mL) were dissolved in methanol (20 mL) and then sodium cyanoborohydride (160 mg, 4 mmol) was added and stirred at 30° C. for 2 h. Then the reaction liquid was filtered and the filtrate was concentrated and separated by preparative HPLC (GX-D; Boston Symmetrix C18 ODS-R 150*30 mm*5 um; MeCN: 25%-55%; H$_2$O (+0.0023 FA); 25 mL/min) to give compound 81 (A) (222.21 mg, 43.2% yield) and compound 82 (B) (124.27 mg, 29.5% yield) as white solid. Compound 81 (A): $^1$H NMR (400 MHz, METHANOL-d$_4$): δ 8.80-8.25 (m, 1H), 8.12-7.78 (m, 2H), 7.76-7.76 (m, 2H), 7.40-7.03 (m, 2H), 6.97-6.73 (m, 2H), 5.80 (br s, 1H), 4.12 (s, 3H), 3.05-2.63 (m, 10H), 2.52-1.72 (m, 13H). Compound (B): $^1$H NMR (400 MHz, METHANOL-d$_4$): δ 8.67-8.30 (m, 1H), 8.24-7.99 (m, 1H), 7.82 (d, J=7.78 Hz, 1H), 7.77-7.55 (m, 5H), 78254-7.18 (m, 8H), 5.68 (s, 1H), 3.54 (br s, 2H), 3.40 (s, 3H), 3.20-2.94 (m, 3H), 2.73-2.41 (m, 8H), 2.41-2.15 (m, 2H), 2.01-1.69 (m, 4H). LCMS (ESI) m/z: 524.3 (M+1).

Example 12

4-(dimethylamino)-1-(6-methoxy-1'-methyl-1',2',3', 6'-tetrahydro-[3,4'-bipyridin]-5-yl)-2-(naphthalen-1-yl)-1-phenylbutan-2-ol

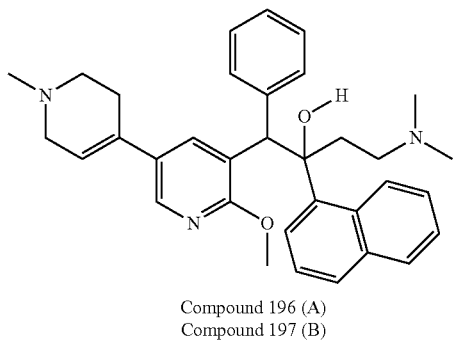

Compound 196 (A)
Compound 197 (B)

According to the method of Example 11, 4-(dimethylamino)-1-(6-methoxy-1',2',3',6'-tetrahydro-[3,4'-bipyridin]-5-yl)-2-(naphthalen-1-yl)-1-phenylbutan-2-ol and aqueous formaldehyde solution were used to prepare the crude product which was separated by preparative HPLC (GX-D; Boston Symmetrix C18 ODS-R 150*30 mm*5 um; MeCN: 15%-45%; H₂O (+0.0023 FA); 25 mL/min) to give compound 196 (A) (45.62 mg, 9.00% yield) and compound 197 (B) (66.75 mg, 13.1% yield) as white solid. Compound 196 (A): ¹H NMR (400 MHz, METHANOL-d₄): δ 8.82-8.31 (m, 1H), 8.19 (s, 1H), 7.96-7.76 (m, 2H), 7.71 (d, J=8.03 Hz, 2H), 7.52 (t, J=7.22 Hz, 1H), 7.31 (t, J=7.78 Hz, 1H), 7.12 (br s, 2H), 6.69-6.96 (m, 3H), 6.14 (br s, 1H), 5.82 (br s, 1H), 4.15 (s, 5H), 3.71 (br s, 3H), 3.20-2.60 (m, 10H), 2.40 (s, 9H), 2.16 (br. s., 2H). Compound 197 (B): ¹H NMR (400 MHz, METHANOL-d₄): δ 8.72-8.28 (m, 1H), 8.05 (d, J=7.28 Hz, 1H), 7.92-7.13 (m, 15H), 5.93 (br s, 1H), 5.69 (s, 1H), 3.69 (d, J=8.16 Hz, 2H), 3.36 (s, 3H), 3.21-2.96 (m, 2H), 2.96-2.68 (m, 5H), 2.66-2.15 (m, 7H). LCMS (ESI) m/z: 522.3 (M+1).

Example 13

4-(dimethylamino)-1-(5-(2-fluorophenyl)-2-methoxypyridin-3-yl)-2-(naphthalen-1-yl)-1-phenylbutan-2-ol

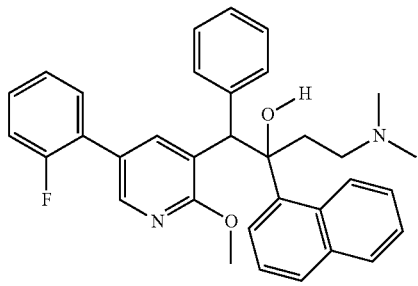

Compound 83 (A1)
Compound 84 (A2)
Compound 85 (B1)
Compound 86 (B2)

According to the method of Example 1, intermediate A and (2-fluorophenyl) boronic acid were used to prepare the crude product which was separated by preparative HPLC (GX-D; Boston Symmetrix C18 ODS-R 150*30 mm*5 um; acetonitrile 30%-60%; water (0.225% formic acid); 25 mL/min) to give component A and component B. Component A was separated by chiral SFC (Berger MultiGram™ SFC, Mettler Toledo Co, Ltd; IC 250 mm*20 mm, 10 um; supercritical CO₂/EtOH (0.05% aqueous ammonia)=60/40; 70 ml/min; 220 nm) to give compound 83 (A1) ((A1) (95.89 mg, 7.90% yield) and compound 84 (A2) (105.59 mg, 8.80% yield) as white solid. Component B was separated by chiral SFC (Berger MultiGram™ SFC, Mettler Toledo Co, Ltd; IC-10 um; supercritical CO₂/EtOH (0.05% aqueous ammonia)=50/50; 70 ml/min; 220 nm) to give compound 85 (B1) (75.10 mg, 6.18% yield) and compound 86 (B2) (5.10 mg, 1.61% yield) as white solid. Compound 83 (A1)/compound 84 (A2): ¹H NMR (400 MHz, METHANOL-d₄): δ 8.88 (s., 1H), 8.65 (d, J=8.80 Hz, 1H), 8.29 (s, 2H), 7.90 (d, J=7.60 Hz, 2H), 7.68-7.61 (m, 2H), 7.53-7.47 (m, 2H), 7.37-7.31 (m, 2H), 7.26-7.31 (m, 4H), 6.90 (t, J=4.00 Hz, 3H), 5.84 (s., 1H), 4.01-4.14 (m, 3H), 2.55 (d, J=14.00 Hz, 1H), 2.19 (t, J=13.20 Hz, 1H), 2.02 (s, 8H). Compound 85 (B1)/compound 86 (B2): ¹H NMR (400 MHz, METHANOL-d₄): δ 8.61 (d, J=8.00 Hz, 2H), 8.09 (d, J=4.00 Hz, 1H), 7.86-7.79 (m, 4H), 7.68 (d, J=8.00 Hz, 1H), 7.62 (t, J=8.00 Hz, 1H), 7.46 (t, J=8.00 Hz, 1H), 7.40-7.33 (m, 5H), 7.28 (d, J=8.00 Hz, 2H), 7.21 (t, J=8.00 Hz, 1H), 5.69 (s, 1H), 3.29 (s, 3H), 2.68-2.65 (m, 1H), 2.28-2.15 (m, 2H), 2.01 (s, 6H), 1.92-1.89 (m, 1H). LCMS (ESI) m/z: 521.2 (M+1).

Example 14

4-(dimethylamino)-1-(5-(3-fluorophenyl)-2-methoxypyridin-3-yl)-2-(naphthalen-1-yl)-1-phenylbutan-2-ol

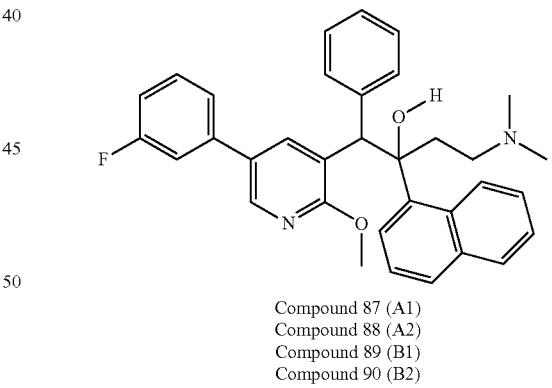

Compound 87 (A1)
Compound 88 (A2)
Compound 89 (B1)
Compound 90 (B2)

According to the method of Example 1, intermediate A and (4-fluorophenyl) boronic acid were used to prepare. The crude product was separated by preparative HPLC (GX-D; Boston Symmetrix C18 ODS-R 150*30 mm*5 um; acetonitrile 25%-55%; water (0.225% FA); 25 mL/min) to give component A and component B. Component A was separated by chiral SFC (Berger MultiGram™ SFC, Mettler Toledo Co, Ltd; IC-10 um; supercritical CO₂/EtOH (0.05% aqueous ammonia)=50/50; 70 ml/min; 220 nm) to give compound 87 (A1) (107 mg, 8.63% yield) and compound 88 (A2) (144 mg, 11.6% yield) as white solid. Component B was separated by chiral SFC (Berger MultiGram™ SFC, Mettler Toledo Co, Ltd; IC-10 um; supercritical CO₂/EtOH (0.05% aqueous ammonia)=50/50; 70 ml/min; 220 nm) to give compound 89 (B1) (123 mg, 9.92% yield) and compound 90 (B2) (91 mg, 7.34% yield) as white solid. Compound 87 (A1)/compound 88 (A2): ¹H NMR (400 MHz, METHANOL-d₄): δ 8.73 (s., 1H), 8.66 (d, J=8.00 Hz, 1H), 8.35 (d, J=4.00 Hz, 1H), 7.95 (d, J=8.00 Hz, 1H), 7.87 (d, J=8.00 Hz, 1H), 7.68-7.61 (m, 2H), 7.53-7.44 (m, 3H), 7.37 (d, J=8.00 Hz, 1H), 7.30 (t, J=8.00 Hz, 1H), 7.19 (s, 2H), 7.12 (t, J=8.00 Hz, 1H), 6.89-6.87 (m, 3H), 5.84 (s., 1H), 4.18 (s, 3H), 2.73 (m, 1H), 2.17-2.08 (m, 2H), 2.00 (s, 6H), 1.85-1.83 (m, 1H). Compound 89 (B1)/compound 90 (B2): ¹H NMR (400 MHz, METHANOL-d₄): δ8.61 (d, J=8.00 Hz, 1H), 8.53 (d, J=8.00 Hz, 1H), 8.12 (d, J=8.00 Hz, 1H), 7.85-7.83 (m, 2H), 7.77 (d, J=8.00 Hz, 2H), 7.68 (d, J=8.00 Hz, 1H), 7.63 (t, J=8.00 Hz, 1H), 7.47 (t, J=8.00 Hz, 2H), 7.42-7.37 (m, 3H), 7.31-7.25 (m, 2H), 7.16-7.14 (m, 1H), 7.08 (t, J=8.00 Hz, 1H), 5.72 (s., 1H), 3.36 (s, 3H), 2.88-2.83 (m, 1H), 2.48-2.46 (m, 1H), 2.34-2.27 (m, 2H), 2.23 (s, 5H), 2.11-2.06 (m, 1H). LCMS (ESI) m/z: 521.2 (M+1).

Example 15

4-(dimethylamino)-1-(5-(4-fluorophenyl)-2-methoxypyridin-3-yl)-2-(naphthalen-1-yl)-1-phenylbutan-2-ol

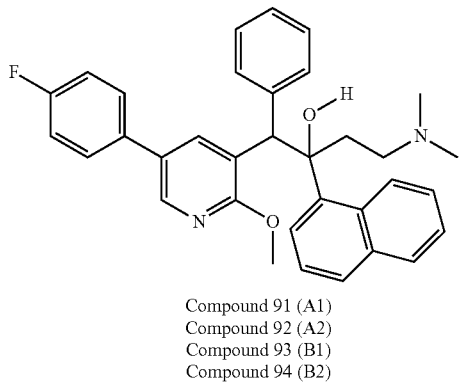 [SMILES: COc1ncc(-c2ccc(F)cc2)cc1C(c1ccccc1)C(O)(CCN(C)C)c1cccc2ccccc12]

Compound 91 (A1)
Compound 92 (A2)
Compound 93 (B1)
Compound 94 (B2)

According to the method of Example 1, the product was prepared by intermediate A and (4-fluorophenyl) boronic acid. The crude product was separated by preparative HPLC (GX-D; Boston Symmetrix C18 ODS-R 150*30 mm*5 um; acetonitrile 25%-55%; water (0.225% formic acid); 25 mL/min) to give component A and component B. Component A was separated by chiral SFC (Berger MultiGram™ SFC, Mettler Toledo Co, Ltd, IC-10 um; supercritical CO₂/MeOH (0.05% aqueous ammonia)=65/35; 60 ml/min; 220 nm) to give compound 91 (A1) (34.41 mg, 10.5% yield) and compound 92 (A2) (43.97 mg, 13.5% yield) as white solid. Component B was separated by chiral SFC (Berger MultiGram™ SFC, Mettler Toledo Co, Ltd, IC-10 um; supercritical CO₂/MeOH (0.05% aqueous ammonia)=70/30; 60 ml/min; 220 nm) to give compound 93 (B1) (16.8 mg, 18.0% yield) and compound 94 (B2) (75.01 mg, 23.1% yield) as white solid. Compound 91 (A1)/compound 92 (A2): ¹HNMR (400 MHz, methanol-d₄): δ 8.69 (br. s., 1H), 8.29 (d, J=2.38 Hz, 1H), 8.05-7.77 (m, 2H), 7.76-7.41 (m, 5H), 7.38-7.05 (m, 5H), 6.98-6.69 (m, 3H), 5.84 (br. s., 1H), 4.18 (s, 3H), 2.73 (br. s., 1H), 2.24-1.96 (m, 7H), 1.87 (br. s., 2H). Compound 93 (B1)/compound 94 (B2): ¹HNMR (400 MHz, methanol-d₄): δ 8.50-8.63 (m, 1H), 8.12 (d, J=7.40 Hz, 1H), 7.91-7.74 (m, 5H), 7.72-7.53 (m, 3H), 7.51-7.31 (m, 8H), 7.31-7.12 (m, 4H), 5.68 (s, 1H), 3.29 (s, 3H), 2.65 (d, J=14.18 Hz, 1H), 2.34-2.09 (m, 2H), 2.01 (s, 6H), 1.96-1.83 (m, 1H). LCMS (ESI) m/z: 521.2 (M+1).

Example 16

4-(dimethylamino)-1-(6'-methoxy-[2,3'-bipyridin]-5'-yl)-2-(naphthalen-1-yl)-1-phenylbutan-2-ol

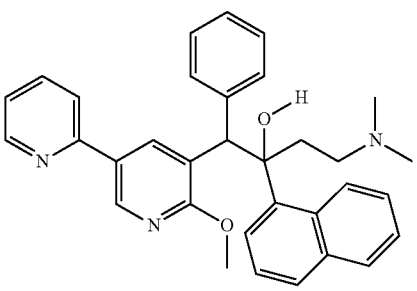

Compound 95 (A1)
Compound 96 (A2)
Compound 97 (B1)
Compound 98 (B2)

According to the method of Example 2, intermediate B was reacted with 2-bromopyridine to prepare the crude product which was separated by preparative HPLC (GX-D; Boston Symmetrix C18 ODS-R 150*30 mm*5 um; acetonitrile 30%-60%; water (0.225% formic acid); 25 mL/min) to give component A and component B. Component A was separated by chiral SFC (sfc-80; AD-10 um; supercritical CO₂/EtOH (0.1% aqueous ammonia)=80/20; 55 ml/min; 220 nm) to give compound 95 (A1) (8.07 mg, 0.88% yield) and compound 96 (A2) (15.13 mg, 0.70% yield) as white solid. Component B was separated by chiral SFC (sfc-80; AD-10 um; supercritical CO₂/EtOH (0.1% aqueous ammonia)=70/30; 60 ml/min; 220 nm) to give compound 97 (B1) (41.67 mg, 0.40% yield) and compound 98 (B2) (51.37 mg, 4.5% yield) as white solid. Compound 95(A1)/compound 96 (A2): ¹H NMR (400 MHz, METHANOL-d₄): δ 9.03 (br. s., 1H), 8.76-8.61 (m, 3H), 8.55 (br. s., 1H), 8.01-7.81 (m, 4H), 7.70 (d, J=8.0 Hz, 2H), 7.53 (d, J=6.8 Hz, 1H), 7.41 (dd, J=5.5, 7.0 Hz, 1H), 7.31 (t, J=7.8 Hz, 1H), 7.16 (br. s., 2H), 6.95-6.83 (m, 3H), 5.88 (br. s., 1H), 4.20 (s, 3H), 2.87 (br. s., 1H), 2.41 (br. s., 1H), 2.19 (br. s., 7H), 2.02 (br. s., 1H). Compound 97 (B1)/compound 98 (B2): ¹H NMR (400 MHz, METHANOL-d₄) δ 8.83 (d, J=2.3 Hz, 1H), 8.66-8.57 (m, 2H), 8.53 (br. s., 1H), 8.20 (d, J=2.4 Hz, 1H), 8.03 (d, J=7.0 Hz, 1H), 7.95-7.80 (m, 4H), 7.69-7.60 (m, 3H), 7.50-7.27 (m, 6H), 5.74 (s, 1H), 3.29 (s, 3H), 2.90-2.79 (m, 1H), 2.45 (br. s., 1H), 2.36-2.18 (m, 7H), 2.07 (dd, J=5.2, 11.9 Hz, 1H). LCMS (ESI) m/z: 504.3 (M+1).

Example 17

4-(dimethylamino)-1-(5-((dimethylamino)methyl)-2-methoxypyridin-3-yl)-2-(naphthalen-1-yl)-1-phenylbutan-2-ol

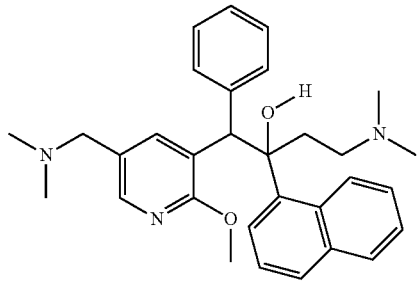

Compound 99 (A)
Compound 100 (B)

Step 1: 4-(dimethylamino)-1-(2-methoxy-5-vinylpyridin-3-yl)-2-(naphthalen-1-yl)-1-phenylbutan-2-ol

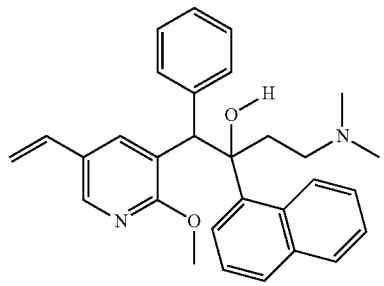 [SMILES: C=Cc1cnc(OC)c(C(c2ccccc2)C(O)(CCN(C)C)c2cccc3ccccc23)c1]

1-(5-bromo-2-methoxypyridin-3-yl)-4-(dimethylamino)-2-(naphthalen-1-yl)-1-phenylbutan-2-ol (2.00 g, 3.96 mmol) and 4,4,5,5-tetramethyl-2-vinyl-1,3,2-dioxaborolane (0.61 g, 3.96 mmol) were mixed in 1,4-dioxane (60 mL) and water (6 mL), and Pd(dppf)Cl$_2$ (289 mg, 0.39 mmol) and potassium acetate (0.78 g, 7.8 mmol) were added and heated to 75-85° C. for 8 h. After LCMS showed the reaction was complete, the reaction mixture was cooled to 15-35° C. and then concentrated at 45° C. under reduced pressure. The mixture was separated by silica gel column chromatography (eluent: petroleum ether/ethyl acetate=30/1~0/1) to give 4-(dimethylamino)-1-(2-methoxy-5-vinylpyridin-3-yl)-2-(naphthalen-1-yl)-1-phenylbutan-2-ol (1.5 g, 83.7% yield) as yellow solid. LCMS (ESI) m/z: 453.2 (M+1).

Step 2: 5-(4-(dimethylamino)-2-hydroxyl-2-(naphthalen-1-yl)-1-phenylbutyl)-6-methoxynicotinaldehyde

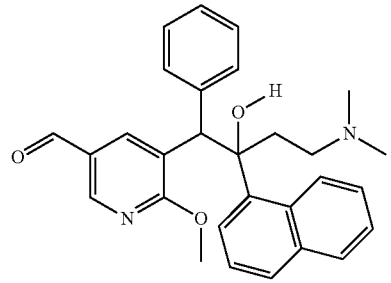 [SMILES: COc1ncc(C=O)cc1C(c1ccccc1)C(O)(CCN(C)C)c1cccc2ccccc12]

The mixture of 4-(dimethylamino)-1-(2-methoxy-5-vinylpyridin-3-yl)-2-(naphthalen-1-yl)-1-phenylbutan-2-ol (0.4 g, 0.88 mmol), 2,6-lutidine (189 mg, 1.76 mol) and osmium tetroxide (0.5 mL, 0.5 g in 100 mL toluene) were added to 1,4-dioxane (9 mL) and water (3 mL). Potassium periodate (760 mg, 3.52 mmol) was added at 15-35° C. and stirred for 2 h. TLC (petroleum ether/ethyl acetate=15:1) detected that the reaction was complete. The reaction mixture was poured into 20 mL of water and the mixture was extracted with dichloromethane (20 mL×3), dried over anhydrous sodium sulfate and concentrated under reduced pressure to give 5-(4-(dimethylamino)-2-hydroxyl-2-(naphthalen-1-yl)-1-phenylbutyl)-6-methoxynicotinaldehyde (0.6 g, crude product) which was used directly in the next step without further purification. LCMS (ESI) m/z: 455.2 (M+1).

Step 3: 4-(dimethylamino)-1-(5-((dimethylamino)methyl)-2-methoxypyridin-3-yl)-2-(naphthalen-1-yl)-1-phenylbutan-2-ol

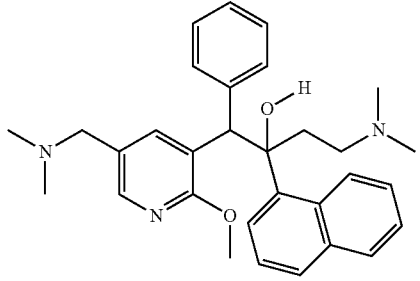

Compound 99 (A)
Compound 100 (B)

5-(4-(dimethylamino)-2-hydroxyl-2-(naphthalen-1-yl)-1-phenylbutyl)-6-methoxynicotinaldehyde (0.6 g, 0.88 mmol) and dimethylamine hydrochloride (0.36 g, 4.4 mmol) were dissolved in methanol (20 mL) and sodium cyanoborohydride (83.16 mg, 1.32 mmol) was added at 15-35° C. and stirred for 2 h. TLC (petroleum ether/ethyl acetate=4/1) detected that the reaction was complete. The reaction mixture was concentrated under reduced pressure, and separated by preparative HPLC (GX-G; Phenomenex Synergi C18 150*30 mm*4 um; acetonitrile 10%-40%; water (0.225% formic acid); 25 mL/min) to give compound 99 (A) (60.33 mg, 14.1% yield) and compound 100 (B) (105.82 mg, 24.7% yield) as white solid. Compound 99 (A): $^1$H NMR (400 MHz, METHANOL-d$_4$) 8.85-8.56 (m, 1H), 8.53-8.35 (m, 3H), 8.20 (s, 1H), 7.90 (d, J=8.0 Hz, 1H), 7.84-7.75 (m, 1H), 7.71 (d, J=8.0 Hz, 2H), 7.53 (s, 1H), 7.30 (t, J=7.8 Hz, 1H), 7.12 (br. s., 2H), 6.90 (d, J=3.5 Hz, 3H), 5.94-5.70 (m, 1H), 4.39-4.27 (m, 1H), 4.26-4.03 (m, 4H), 3.25-3.09 (m, 1H), 3.02 (d, J=10.4 Hz, 1H), 2.83 (s, 6H), 2.55 (s, 6H), 2.24 (d, J=6.8 Hz, 2H). Compound 100 (B): $^1$H NMR (400 MHz, METHANOL-d$_4$) δ 8.63 (d, J=8.8 Hz, 1H), 8.45-8.34 (m, 4H), 8.05 (d, J=6.9 Hz, 1H), 7.86 (d, J=8.2 Hz, 1H), 7.81-7.75 (m, 3H), 7.70 (t, J=7.5 Hz, 2H), 7.51 (t, J=7.5 Hz, 1H), 7.45-7.37 (m, 3H), 7.36-7.29 (m, 2H), 5.77 (s, 1H), 4.21-3.97 (m, 2H), 3.37 (s, 3H), 3.23-3.12 (m, 1H), 2.99 (s, 1H), 2.70-2.52 (m, 14H), 2.30 (s, 1H). LCMS (ESI) m/z: 484.2 (M+1).

Example 18

4-(dimethylamino)-1-(5-(2-(dimethylamino)ethyl)-2-methoxypyridin-3-yl)-2-(naphthalen-1-yl)-1-phenylbutan-2-ol

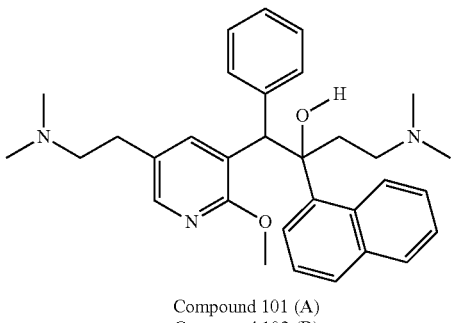

Compound 101 (A)
Compound 102 (B)

Step 1: 4-(dimethylamino)-1-5-(2-ethoxyvinyl-2-methoxypyridin-3-yl)-2-(naphthalen-1-yl)-phenylbutan-2-ol

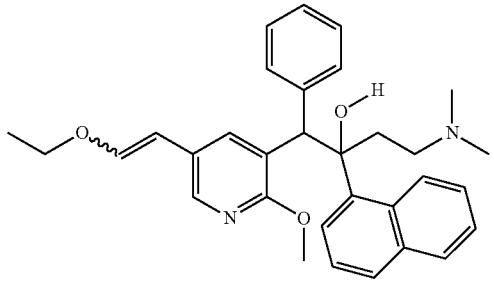 [SMILES: CCOC=Cc1cnc(OC)c(C(c2ccccc2)C(O)(CCN(C)C)c2cccc3ccccc23)c1]

Intermediate A (1.0 g, 1.98 mmol), 2-(2-ethoxyvinyl)-4,4,5,5-tetramethyl-1,3,2-dioxaborolane (0.49 g, 2.37 mmol), (+)-2,2'-bis-(diphenylphosphino)-1,1'-binaphthalene (100 mg) and potassium phosphate (835 mg, 3.96 mmol) were dissolved in the mixed solvent of 1,4-dioxane/H$_2$O (20.0 mL×5.0 mL). Under nitrogen, palladium acetate (100 mg, 0.2 mmol) was added. The reaction mixture was heated to 80° C. and stirred for 16 h. Water (20.0 mL) was added and the mixture was extracted with ethyl acetate (20 mL×2), dried over anhydrous sodium sulfate and concentrated under reduced pressure. The crude product was separated by silica gel column chromatography (eluent: petroleum ether/ethyl acetate: 20/1-2/1) to give 4-(dimethylamino)-1-5-(2-ethoxyvinyl)-2-methoxypyridin-3-yl)-2-(naphthalen-1-yl)-phenylbutan-2-ol (600 mg, 61.7% yield) as white solid. LCMS (ESI) m/z: 497.3 (M+1).

Step 2: 2-(5-(4-(dimethylamino)-2-hydroxyl-2-(naphthalen-1-yl)-1-phenylbutyl)-6-methoxypyridin-3-yl)acetaldehyde

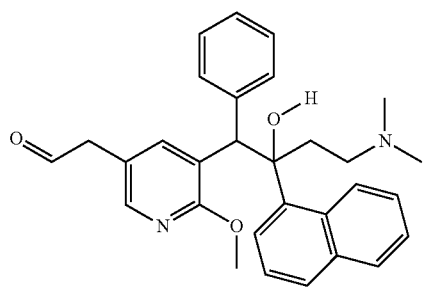 [SMILES: COc1ncc(CC=O)cc1C(c1ccccc1)C(O)(CCN(C)C)c1cccc2ccccc12]

4-(dimethylamino)-1-(5-(2-ethoxyvinyl)-2-methoxypyridin-3-yl)-2-(naphthalen-1-yl)-phenylbutan-2-ol (0.6 g, 1.2 mmol) was dissolved in THF (3 mL) and water (3 mL) and hydrochloric acid solution (6N, 3 mL) was added. The mixture was heated to reflux and stirred for 2 h, then cooled in ice water, adjusted with saturated sodium bicarbonate solution to pH 7. Then the mixture was extracted with ethyl acetate (10 mL×3), dried over sodium sulfate, filtered, and concentrated to give 2-(5-(4-(dimethylamino)-2-hydroxyl-2-(naphthalen-1-yl)-1-phenylbutyl)-6-methoxypyridin-3-yl) acetaldehyde (500 mg, 88.5% yield) as a yellow oil which was used directly in the next step without further purification.

Step 3: 4-(dimethylamino)-1-(5-(2-(dimethylamino)ethyl)-2-methoxypyridin-3-yl)-2-(naphthalen-1-yl)-1-phenylbutan-2-ol

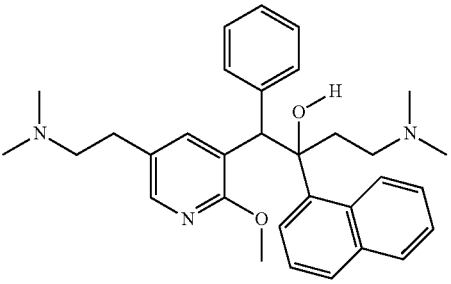

Compound 101 (A)
Compound 102 (B)

2-(5-(4-(dimethylamino)-2-hydroxyl-2-(naphthalen-1-yl)-1-phenylbutyl)-6-methoxypyridin-3-yl)acetaldehyde (0.5 g, 1.06 mmol) and dimethylamine hydrochloride (104 mg, 1.28 mmol) were mixed in methanol (30 mL) and stirred at 25° C. for 1 h. Sodium triacetoxyborohydride (271 mg, 1.28 mmol) was added and then stirred for 16 h. The mixture was cooled in ice water and adjusted with saturated sodium bicarbonate solution to pH 7, then extracted with ethyl acetate (30 mL×3), dried over sodium sulfate and concentrated under reduced pressure to give crude product which was then separated by preparative HPLC (HPLC-D; Boston Symmetrix C18 ODS-R 150*30 mm*5 um; acetonitrile 25%-55%; water (0.225% formic acid); 80 mL/min) to give compound 101 (A) (41.74 mg, 8.72% yield) and compound 102 (B) (78.27 mg, 5.48% yield) as white solid. Compound 101 (A): $^1$H NMR (400 MHz, METHANOL-d$_4$): δ 8.66 (br. s., 1H), 8.46 (br. s., 2H), 8.19 (br. s., 1H), 8.05 (s, 1H), 7.88 (d, J=8.0 Hz, 2H), 7.69 (d, J=8.0 Hz, 2H), 7.51 (t, J=7.5 Hz, 1H), 7.31 (t, J=7.8 Hz, 1H), 7.17 (br. s., 2H), 6.89 (d, J=3.0 Hz, 3H), 5.82 (br. s., 1H), 4.14 (br. s., 3H), 3.38-3.34 (m, 2H), 3.19-3.00 (m, 3H), 2.97-2.87 (m, 7H), 2.50 (s, 6H), 2.20 (d, J=8.3 Hz, 2H). Compound 102 (B): $^1$H NMR (400 MHz, METHANOL-d$_4$): δ 8.58 (d, J=8.7 Hz, 1H), 8.49 (br. s., 2H), 8.16-8.06 (m, 2H), 7.84 (d, J=8.2 Hz, 1H), 7.77-7.69 (m, 3H), 7.67-7.57 (m, 2H), 7.53 (d, J=2.0 Hz, 1H), 7.50-7.45 (m, 1H), 7.41 (t, J=7.7 Hz, 3H), 7.34-7.29 (m, 1H), 5.69 (s, 1H), 3.37 (s, 3H), 3.16-3.06 (m, 1H), 3.04-2.74 (m, 11H), 2.51 (s, 6H), 2.40-2.21 (m, 2H). LCMS (ESI) m/z: 498.3 (M+1).

Example 19

1-(5-cyclohexyl-2-methoxypyridin-3-yl)-4-(dimethylamino)-2-(naphthalen-1-yl)-1-phenylbutan-2-ol

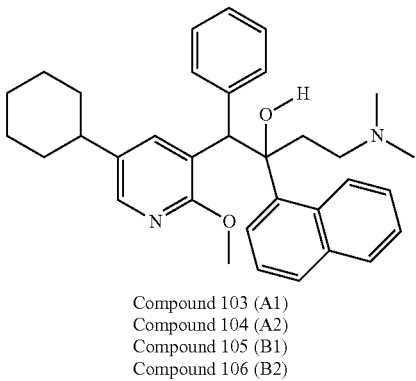 [SMILES: COc1ncc(C2CCCCC2)cc1C(c1ccccc1)C(O)(CCN(C)C)c1cccc2ccccc12]

Compound 103 (A1)
Compound 104 (A2)
Compound 105 (B1)
Compound 106 (B2)

Step 1: 1-(5-(cyclohex-1-en-1-yl)-2-methoxypyridin-3-yl)-4-(dimethylamino)-2-(naphthalen-1-yl)-1-phenylbutan-2-ol

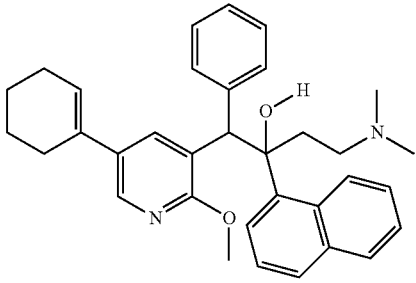 [SMILES: COc1ncc(C2=CCCCC2)cc1C(c1ccccc1)C(O)(CCN(C)C)c1cccc2ccccc12]

1-(5-bromo-2-methoxypyridin-3-yl)-4-(dimethylamino)-2-(naphthalen-1-yl)-1-phenylbutan-2-ol (1.00 g, 1.98 mmol), cyclohex-1-en-1-ylboronic acid (280 mg, 2.18 mmol), Pd(dppt)Cl$_2$ (144.88 mg, 198 umol) and potassium acetate (582.95 mg, 5.94 mmol) was suspended in 1,4-dioxane (10 mL) and water (2 mL) and purged with nitrogen, heated to 80-90° C. and stirred for 16 h. The reaction mixture was cooled with 20 mL of water, and extracted with ethyl acetate (20 mL×2). The combined organic phase was washed with saturated saline solution (20 mL), filtered, dried over anhydrous sodium sulfate, concentrated under reduced pressure and separated by silica gel column chromatography (eluent: petroleum ether/ethyl acetate: 30/1/5/1) to give pure 1-(5-(cyclohex-1-en-1-yl)-2-methoxypyridin-3-yl)-4-(dimethylamino)-2-(naphthalen-1-yl)-1-phenylbutan-2-ol (500 mg, 49.7% yield) as a yellow oil. LCMS (ESI) m/z: 507.3 (M+1).

Step 2: 1-(5-cyclohexyl-2-methoxypyridin-3-yl)-4-(dimethylamino)-2-(naphthalen-1-yl)-1-phenylbutan-2-ol

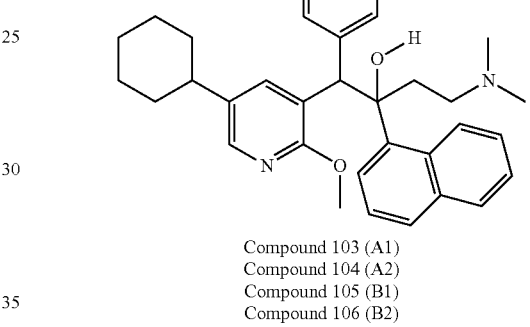

Compound 103 (A1)
Compound 104 (A2)
Compound 105 (B1)
Compound 106 (B2)

1-(5-cyclohexyl-2-methoxypyridin-3-yl)-4-(dimethylamino)-2-(naphthalen-1-yl)-1-phenylbutan-2-ol (500 mg, 0.98 mmol) and dry Pd/C catalyst (100 mg) were mixed in methanol (10 mL) and stirred under hydrogen (15 psi) at 25-30° C. for 5 h. The reaction mixture was filtered. The filtrate was dried by rotary evaporation, and separated by preparative HPLC (GX-D; Boston Symmetrix C18 ODS-R 150*30 mm*5 um; acetonitrile 34%-64%; water (0.225% formic acid); 25 mL/min) to give component A and component B. Component A was separated by chiral SFC (Berger MultiGram™ SFC, Mettler Toledo Co, Ltd; IC-10 um; supercritical CO$_2$/MeOH (0.05% aqueous ammonia) =60/40; 70 ml/min; 220 nm) to give compound 103 (A1) (13.98 mg, 2.8% yield) and compound 104 (A2) (13.52 mg, 2.70% yield) as white solid. Component B was separated by chiral SFC (Berger MultiGram™ SFC, Mettler Toledo Co, Ltd; IC-10 um; supercritical CO$_2$/MeOH (0.05% aqueous ammonia)=60/40; 70 ml/min; 220 nm) to give compound 105 (B1) (16.11 mg, 3.2% yield) and compound 106 (B2) (17.52 mg, 3.5% yield) as white solid. Compound 103 (A1)/compound 104 (A2): $^1$H NMR (400 MHz, METHANOL-d$_4$): δ 8.71-8.50 (m, 1H), 8.43 (br. s., 1H), 7.94-7.80 (m, 3H), 7.73-7.57 (m, 2H), 7.54-7.45 (m, 1H), 7.29 (t, J=7.8 Hz, 1H), 7.08 (br. s., 2H), 6.92-6.80 (m, 3H), 5.78 (br. s., 1H), 4.08 (s, 3H), 2.78-2.48 (m, 2H), 2.25-1.78 (m, 14H), 1.56-1.31 (m, 5H). Compound 105 (B1)/compound 106 (B2): $^1$H NMR (400 MHz, METHANOL-d$_4$): δ 8.55 (d, J=8.8 Hz, 1H), 8.21 (s, 1H), 8.05 (d, J=7.2 Hz, 1H), 7.81 (d, J=7.4 Hz, 1H), 7.73 (d, J=7.5 Hz, 2H), 7.68-7.55 (m, 2H), 7.46-7.26 (m, 6H), 5.62 (s, 1H), 3.29 (s, 3H), 2.78 (d, J=11.9

Hz, 1H), 2.49-2.10 (m, 10H), 2.01 (br s, 1H), 1.87-1.61 (m, 4H), 1.53-1.24 (m, 5H). LCMS (ESI) m/z: 509.3 (M+1).

Example 20

1-5-(2-chlorophenyl)-2-methoxypyridin-3-yl)-4-(dimethylamino)-2-(naphthalen-1-yl)-1-phenylbutan-2-ol

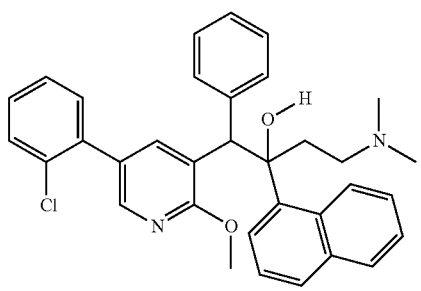

Compound 107 (A1)
Compound 108 (A2)
Compound 109 (B1)
Compound 110 (B2)

According to the method of Example 1, intermediate A was reacted with (2-chlorophenyl)boronic acid to prepare the crude product which was separated and purified by preparative HPLC (GX-D; Boston Symmetrix C18 ODS-R 150*30 mm*5 um; acetonitrile 26%-56%; water (0.225% formic acid); 25 mL/min) to give component A and component B. Component A was separated by chiral SFC (Berger MultiGram™ SFC, Mettler Toledo Co, Ltd; IC 250 mm*20 mm, 10 um; supercritical $CO_2$/EtOH (0.05% aqueous ammonia)=60/40; 70 ml/min; 220 nm) to give compound 107 (A1) (73.2 mg, 8.13% yield) and compound 108 (A2) (87.15 mg, 9.68% yield) as white solid. Component B was separated by chiral SFC (Berger MultiGram™ SFC, Mettler Toledo Co, Ltd; IC 250 mm*20 mm, 10 um; supercritical $CO_2$/EtOH (0.05% aqueous ammonia)=80/20; 70 ml/min; 220 nm) to give final product 109 (B1) (28.13 mg, 3.12% yield) and compound 110 (B2) (24.34 mg, 2.7% yield) as white solid. Compound 107 (A1)/compound 108 (A2): $^1$H NMR (400 MHz, METHANOL-$d_4$): δ 8.76-8.49 (m, 2H), 8.11 (d, J=2.4 Hz, 1H), 7.89 (d, J=8.2 Hz, 2H), 7.68 (d, J=8.0 Hz, 2H), 7.59-7.46 (m, 2H), 7.45-7.35 (m, 3H), 7.28 (t, J=7.7 Hz, 1H), 7.14 (br. s., 2H), 6.91-6.78 (m, 3H), 5.84 (br. s., 1H), 4.17 (s, 3H), 2.74 (br. s., 1H), 2.33-1.83 (m, 9H). Compound 109 (B1)/compound 110 (B2): $^1$H NMR (400 MHz, METHANOL-$d_4$): δ 8.61 (d, J=8.9 Hz, 1H), 8.55 (d, J=5.6 Hz, 1H), 8.43 (s, 1H), 8.02 (d, J=7.4 Hz, 1H), 7.92-7.75 (m, 3H), 7.71-7.61 (m, 3H), 7.56-7.44 (m, 2H), 7.43-7.23 (m, 7H), 7.21-7.12 (m, 1H), 5.73 (s, 1H), 3.32 (br. s., 3H), 2.83 (d, J=8.5 Hz, 1H), 2.42 (br. s., 1H), 2.27-2.16 (m, 7H), 2.05 (d, J=5.9 Hz, 1H). LCMS (ESI) m/z: 537.2 (M+1).

Example 21

1-5-(3-chlorophenyl)-2-methoxypyridin-3-yl)-4-(dimethylamino)-2-(naphthalen-1-yl)-1-phenylbutan-2-ol

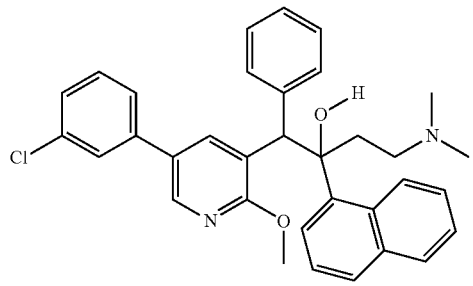

Compound 111 (A1)
Compound 112 (A2)
Compound 113 (B1)
Compound 114 (B2)

According to the method of Example 1, intermediate A and (3-chlorophenyl)boronic acid were used to prepare crude product which was separated by preparative HPLC (GX-D; Boston Symmetrix C18 ODS-R 150*30 mm*5 um; acetonitrile 29%-59%; water (0.225% formic acid); 25 mL/min) to give component A and component B. Component A was separated by chiral SFC (sfc 80; AD-10 um; supercritical $CO_2$/MeOH (0.1% aqueous ammonia)=50/50; 70 ml/min; 220 nm) to give compound 111 (A1) (46.6 mg, 5.17% yield) and compound 112 (A2) (64.1 mg, 7.18% yield) as white solid. Component B was separated by chiral SFC (Berger MultiGram™ SFC, Mettler Toledo Co, Ltd; IC-10 um; supercritical $CO_2$/EtOH (0.05% aqueous ammonia)=60/40; 70 ml/min; 220 nm) to give compound 113 (B1) (13.1 mg, 1.45% yield) and compound 114 (B2) (7.32 mg, 0.81% yield) as white solid. Compound 111 (A1)/compound 112 (A2): $^1$H NMR (400 MHz, METHANOL-$d_4$): δ 8.75-8.51 (m, 2H), 8.35 (d, J=2.5 Hz, 1H), 7.90 (d, J=8.5 Hz, 2H), 7.74-7.61 (m, 3H), 7.60-7.45 (m, 3H), 7.45-7.37 (m, 1H), 7.35-7.27 (m, 1H), 7.16 (br. s., 2H), 6.97-6.83 (m, 3H), 5.85 (br. s., 1H), 4.18 (s, 3H), 2.82 (br. s., 1H), 2.44-2.27 (m, 1H), 2.23-1.88 (m, 8H). Compound 113 (B1)/compound (B2): $^1$H NMR (400 MHz, METHANOL-$d_4$): δ 8.61-8.52 (m, 2H), 8.14 (d, J=7.3 Hz, 1H), 7.87-7.74 (m, 4H), 7.69-7.60 (m, 2H), 7.46-7.27 (m, 9H), 5.70 (s, 1H), 3.35 (s, 3H), 2.83-2.68 (m, 1H), 2.40-1.93 (m, 10H). LCMS (ESI) m/z: 537.2 (M+1).

Example 22

1-(5-(4-chlorophenyl)-2-methoxypyridin-3-yl)-4-(dimethylamino)-2-(naphthalen-1-yl)-1-phenylbutan-2-ol

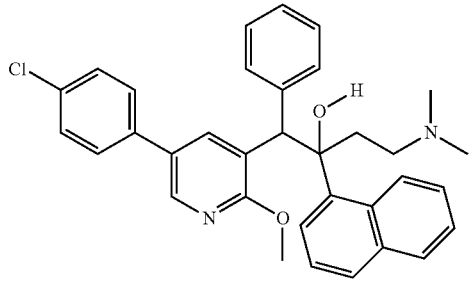

Compound 115 (A1)
Compound 116 (A2)
Compound 117 (B1)
Compound 118 (B2)

According to the method of Example 1, intermediate A and (4-chlorophenyl)boronic acid were used to prepare crude product which was separated by preparative HPLC (GX-D; Boston Symmetrix C18 ODS-R 150*30 mm*5 um; acetonitrile 30%-60%; water (0.225% formic acid); 25 mL/min) to give component A and component B. Component A was separated by chiral SFC (Berger MultiGram™ SFC, Mettler Toledo Co, Ltd; IC-10 um; supercritical $CO_2$/EtOH (0.05% aqueous ammonia)=60/40; 70 ml/min; 220 nm) to give compound 115 (A1) (95.89 mg, 7.9% yield) and compound 116 (A2) (105.59 mg, 8.8% yield) as white solid. Component B was separated by chiral SFC (Berger MultiGram™ SFC, Mettler Toledo Co, Ltd; IC 250 mm*20 mm, 10 um; supercritical $CO_2$/EtOH (0.05% aqueous ammonia)=80/20; 70 ml/min; 220 nm) to give compound 117 (B1) (43.78 mg, 3.65% yield) and compound 118 (B2) (19.36 mg, 1.61% yield) as white solid. Compound 115 (A1)/compound 116 (A2): $^1$H NMR (400 MHz, METHANOL-$d_4$): δ 8.69 (br. s., 2H), 8.53 (br. s., 1H), 8.34 (d, J=2.4 Hz, 1H), 7.90 (d, J=7.8 Hz, 2H), 7.74-7.57 (m, 4H), 7.51 (d, J=8.5 Hz, 3H), 7.31 (t, J=7.8 Hz, 1H), 7.16 (br. s., 2H), 6.92-6.82 (m, 3H), 5.86 (br. s., 1H), 4.18 (s, 3H), 2.84 (br. s., 1H), 2.53-1.83 (m, 9H). Compound 117 (B1)/compound 118 (B2): $^1$H NMR (400 MHz, METHANOL-$d_4$): δ 8.60 (d, J=8.9 Hz, 1H), 8.52 (br. s., 1H), 8.11 (d, J=7.4 Hz, 1H), 7.89-7.72 (m, 4H), 7.71-7.58 (m, 2H), 7.52-7.23 (m, 9H), 5.71 (s, 1H), 3.35 (s, 3H), 2.85 (br. s., 1H), 2.48 (br. s., 1H), 2.37-2.03 (m, 8H). LCMS (ESI)m/z: 537.2 (M+1).

Example 23

4-(dimethylamino)-1-(2-methoxypyridin-3-yl)-2-(naphthalen-1-yl)-1-phenylbutan-2-ol

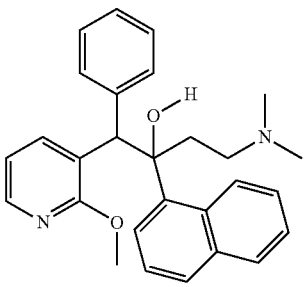

Compound 119 (A1)
Compound 120 (A2)
Compound 121 (B1)
Compound 122 (B2)

Intermediate A (1.50 g, 2.97 mmol) was dissolved in 50 mL of methanol and Pd/C (150 mg) was added. The mixture was stirred at 30° C. under hydrogen atmosphere (50 psi) for 20 h. The reaction mixture was filtered and the filtrate was concentrated to give crude product. The crude product was separated and purified by preparative HPLC (GX-D; Boston Symmetrix C18 ODS-R 150*30 mm*5 um; MeCN: 25%-65%; $H_2O$ (+0.0023 FA); 25 mL/min) to give component A and component B. Component A was separated by chiral SFC (sfc 80, AD-10 um; supercritical $CO_2$/EtOH (0.05% aqueous ammonia)=70/30; 60 g/min; 220 nm) to give compound 119 (A1) (120.71 mg, 9.54% yield) and compound 120 (A2) (93.85 mg, 7.41% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 121 (B1) (70.83 mg, 5.60% yield) and compound 122 (B2) (90.07 mg, 7.12% yield) as white solid. Compound 119 (A1)/compound 120 (A2): $^1$H NMR (400 MHz, methanol-$d_4$): δ 8.59 (d, J=8.2 Hz, 1H), 8.26 (dd, J=1.6, 7.3 Hz, 1H), 8.10 (d, J=3.5 Hz, 1H), 7.94-7.86 (m, 2H), 7.70 (d, J=8.0 Hz, 2H), 7.51 (t, J=6.9 Hz, 1H), 7.34 (t, J=7.7 Hz, 1H), 7.14 (d, J=5.5 Hz, 2H), 7.05 (dd, J=5.0, 7.3 Hz, 1H), 6.92-6.82 (m, 3H), 5.70 (br. s., 1H), 4.08 (br. s., 3H), 2.69-2.57 (m, 1H), 2.18-1.80 (m, 9H). Compound 121 (B1)/compound 122 (B2): $^1$H NMR (400 MHz, methanol-$d_4$): δ 8.54 (d, J=8.8 Hz, 1H), 8.35-8.26 (m, 2H), 7.97 (d, J=7.0 Hz, 1H), 7.86 (d, J=8.2 Hz, 1H), 7.75 (d, J=7.4 Hz, 2H), 7.68 (d, J=8.2 Hz, 1H), 7.64-7.58 (m, 2H), 7.47 (t, J=7.3 Hz, 1H), 7.35 (t, J=7.7 Hz, 3H), 7.28-7.22 (m, 1H), 6.68 (dd, J=4.9, 7.4 Hz, 1H), 5.55 (s, 1H), 3.15 (s, 3H), 2.53-2.51 (m, 1H), 2.10-2.00 (m, 1H), 1.98-1.92 (m, 1H), 1.89 (s, 6H), 1.86-1.78 (m, 1H). LCMS (ESI) m/z: 427.2 (M+1).

Example 24

1-(5-(3-bromophenyl)-2-methoxypyridin-3-yl)-4-(dimethylamino)-2-(naphthalen-1-yl)-1-phenylbutan-2-ol

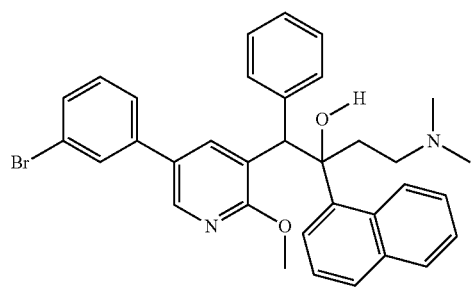

Compound 127 (A1)
Compound 128 (A2)
Compound 129 (B1)
Compound 130 (B2)

According to the method of Example 2, intermediate B and 1,3-dibromobenzene were used to prepare crude product which was separated and purified by preparative HPLC (GX-D; Boston Symmetrix C18 ODS-R 150*30 mm*5 um; acetonitrile 30%-60%; water (0.225% formic acid); 25 mL/min) to give component A and component B. Component A was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 127 (A1) (44.44 mg, 2.11% yield) and compound 128 (A2) (51.23 mg, 2.43% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 129 (B1) (21.87 mg, 1.04% yield) and compound 130 (B2) (32.10 mg, 1.52% yield) as white solid. Compound 127 (A1)/compound 128 (A2): $^1$H NMR (400 MHz, methanol-$d_4$): δ 8.59 (d, J=8.66 Hz, 1H), 8.49 (d, J=2.26 Hz, 1H), 8.16 (d, J=6.78 Hz, 1H), 7.88-7.72 (m, 4H), 7.71-7.59 (m, 3H), 7.56-7.25 (m, 10H), 5.71 (s, 1H) 3.38 (s, 3H), 2.92-2.82 (m, 1H), 2.57-2.47 (m, 1H), 2.33 (br. s., 1H), 2.23 (s, 6H), 2.08 (br. s., 1H). Compound 129 (B1)/compound 130 (B2): $^1$HNMR (400 MHz, methanol-$d_4$): δ 8.74-8.68 (m, 1H), 8.32-8.36 (m, 1H), 7.94-7.87 (m, 2H), 7.81-7.77 (m, 1H), 7.72-7.67 (m, 2H), 7.64-7.59 (m, 1H), 7.57-7.53 (m, 1H), 7.46-7.39 (m, 1H), 7.31 (t, J=7.78 Hz, 1H), 7.19-7.12 (m, 2H), 6.91-6.86 (m, 3H), 5.88-5.83 (m, 1H), 4.17 (s, 3H), 2.88-2.75 (m, 1H), 2.30 (br. s., 1H), 2.13 (s, 8H), 2.01-1.86 (m, 1H). LCMS (ESI) m/z: 581.0/583.0 (M+1).

Example 25

1-(5-(4-bromophenyl)-2-methoxypyridin-3-yl)-4-(dimethylamino)-2-(naphthalen-1-yl)-1-phenylbutan-2-ol

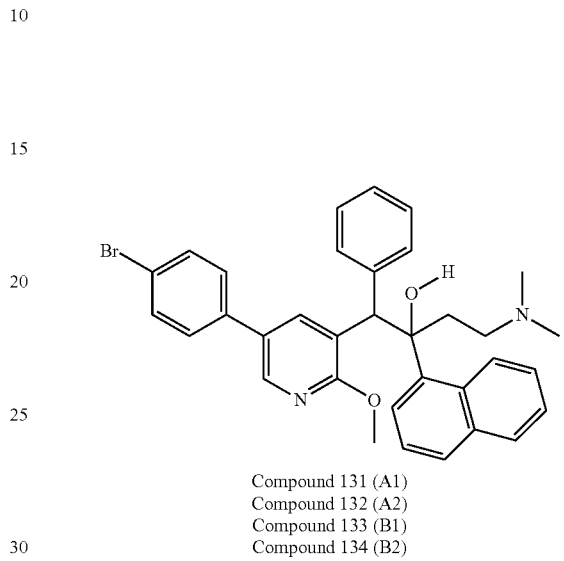

Compound 131 (A1)
Compound 132 (A2)
Compound 133 (B1)
Compound 134 (B2)

According to the method of Example 2, intermediate B and 1,4-dibromobenzene were used to prepare crude product which was separated and purified by preparative HPLC (HPLC-A; SYNERGI; acetonitrile 25%-50%; water (0.225% formic acid); 80 mL/imin) to give component A and component B. Component A was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 131 (A1) (145.96 mg, 6.93% yield) and compound 132 (A2) (164.11 mg, 7.80% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 133 (B1) (79.23 mg, 3.76% yield) and compound 134 (B2) (90.10 mg, 4.28% yield) as white solid. Compound 131 (A1)/compound 132 (A2): $^1$H NMR (400 MHz, methanol-$d_4$): δ 8.52 (d, J=2.38 Hz, 2H), 8.23 (s, 1H), 8.12 (s, 1H), 7.89-7.75 (m, 4H), 7.69-7.52 (m, 4H), 7.44-7.26 (m, 7H), 5.64 (s, 1H), 3.29 (s, 3H), 2.79-2.68 (m, 1H), 2.63-2.52 (m, 1H), 2.39-2.27 (m, 2H), 2.20 (s, 6H), 2.05-1.94 (m, 1H). Compound 133 (B1)/compound 134 (B2): $^1$H NMR (400 MHz, methanol-$d_4$): δ 8.70 (d, J=2.13 Hz, 1H), 8.65-8.59 (m, 1H), 8.30 (d, J=2.38 Hz, 1H), 8.18 (s, 1H), 7.97 (d, J=7.28 Hz, 1H), 7.89 (d, J=7.91 Hz, 1H), 7.69-7.58 (m, 4H), 7.56-7.48 (m, 3H), 7.36-7.27 (m, 2H), 7.20 (d, J=3.26 Hz, 2H), 6.95-6.88 (m, 3H), 5.82 (s, 1H), 4.17 (s, 3H), 2.84-2.73 (m, 1H), 2.49 (br. s., 1H), 2.26-2.10 (m, 8H), 2.00-1.90 (m, 1H). LCMS (ESI) m/z: 581.0/583.0 (M+1).

Example 26

4-(dimethylamino)-1-(2-methoxy-5-(thiophen-3-yl)pyridin-3-yl)-2-(naphthalen-1-yl)-1-phenylbutan-2-ol

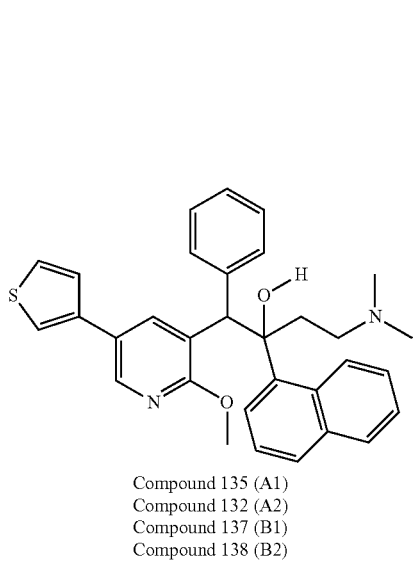 [SMILES: COc1ncc(-c2ccsc2)cc1C(c1ccccc1)C(O)(CCN(C)C)c1cccc2ccccc12]

Compound 135 (A1)
Compound 132 (A2)
Compound 137 (B1)
Compound 138 (B2)

According to the method of Example 1, intermediate A and 3-thiopheneboronic acid were used to prepare crude product which was separated and purified by preparative HPLC (GX-G; Phenomenex Synergi C18 150*30 mm*4 um; acetonitrile 33%-63%; water (0.225% formic acid); 25 mL/min) to give component A and component B. Component A was separated by chiral SFC (SFC 80; AD-10 um; supercritical $CO_2$/i-prOH (0.05% aqueous ammonia)=60/40; 70 ml/min; 220 nm) to give compound 135 (A1) (118.93 mg, 11.89% yield) and compound 136 (A2) (54.62 mg, 5.46% yield) as white solid. Component B was separated by chiral SFC (SFC 80; AD-10 um; supercritical $CO_2$/i-prOH (0.05% aqueous ammonia)=50/50; 70 ml/min; 220 nm) to give compound 137 (B1) (127.90 mg, 12.79% yield) and compound 138 (B2) (142.35 mg, 14.23% yield) as white solid. Compound 135 (A1)/compound 136 (A2): $^1$H NMR (400 MHz, methanol-$d_4$): δ 8.70 (br. s., 2H), 8.50 (s, 1H), 8.40 (d, J=2.26 Hz, 1H), 7.91 (d, J=8.03 Hz, 1H), 7.85-7.60 (m, 4H), 7.59-7.43 (m, 3H), 7.32 (t, J=7.78 Hz, 1H), 7.11 (br. s., 2H), 6.95-6.85 (m, 3H), 6.00-5.72 (m, 1H), 4.16 (s, 3H), 3.08-2.83 (m, 1H), 2.73-2.57 (m, 1H), 2.42-2.08 (m, 8H). Compound 137 (B1)/compound 138 (B2): $^1$H NMR (400 MHz, methanol-$d_4$): δ 8.68-8.47 (m, 2H), 8.10 (d, J=7.53 Hz, 1H), 7.92-7.74 (m, 4H), 7.70-7.56 (m, 2H), 7.52-7.19 (m, 8H), 5.69 (s, 1H), 3.34-3.33 (m, 3H), 2.98-2.75 (m, 1H), 2.48 (br. s., 1H), 2.37-2.03 (m, 8H). LCMS (ESI) m/z: 509.2 (M+1).

Example 27

4-(dimethylamino)-1-(2-methoxy-5-(thiophen-2-yl)pyridin-3-yl)-2-(naphthalen-1-yl)-1-phenylbutan-2-ol

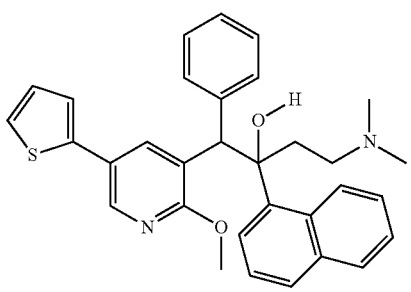

Compound 139 (A1)
Compound 140 (A2)
Compound 141 (B1)
Compound 142 (B2)

According to the method of Example 2, intermediate B and 2-bromothiophene were used to prepare crude product which was separated and purified by preparative HPLC (GX-G; Phenomenex Synergi C18 150*30 mm*4 um; acetonitrile 30%-60%; water (0.225% formic acid); 25 mL/min) to give component A and component B. Component A was separated by chiral SFC (sfc 80, AD-10 um; supercritical $CO_2$/EtOH (0.05% aqueous ammonia)=60/40; 70 ml/min; 220 nm) to give compound 139 (A1) (67.17 mg, 3.71% yield) and compound 140 (A2) (50.12 mg, 2.77% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 141 (B1) (31.69 mg, 1.76% yield) and compound 142 (B2) (32.81 mg, 2.04% yield) as white solid. Compound 139 (A1)/compound 140 (A2): $^1$H NMR (400 MHz, methanol-$d_4$): δ 8.61-8.55 (m, 2H), 8.52 (br. s., 1H), 8.11 (d, J=7.28 Hz, 1H), 7.88-7.81 (m, 2H), 7.78 (d, J=7.40 Hz, 2H), 7.69-7.60 (m, 2H), 7.46 (t, J=7.34 Hz, 1H), 7.43-7.33 (m, 5H), 7.32-7.27 (m, 1H), 7.19 (d, J=3.01 Hz, 1H), 7.11-7.07 (m, 1H), 5.68 (s, 1H), 3.33 (s, 3H), 2.93-2.82 (m, 1H), 2.56-2.45 (m, 1H), 2.28-2.20 (m, 7H), 2.13-2.04 (m, 1H). Compound 141 (B1)/compound 142 (B2): $^1$H NMR (400 MHz, methanol-$d_4$): δ 8.74 (m, 1H), 8.66 (m, 1H), 8.37 (d, J=2.26 Hz, 1H), 7.94-7.79 (m, 2H), 7.71 (d, J=8.03 Hz, 2H), 7.52 (t, J=7.34 Hz, 1H), 7.43 (d, J=5.14 Hz, 1H), 7.37 (d, J=3.14 Hz, 1H), 7.31 (t, J=7.78 Hz, 1H), 7.17-7.07 (m, 3H), 6.91-6.86 (m, 3H), 5.83 (br. s., 1H), 4.15 (s, 3H), 2.88 (br. s., 1H), 2.47 (br. s., 1H), 2.25 (s, 6H), 2.13-2.21 (m, 1H), 2.07 (m, 1H). LCMS (ESI) m/z: 509.2 (M+1).

Example 28

4-(dimethylamino)-1-(5-(isothiazol-3-yl)-2-methoxypyridin-3-yl)-2-(naphthalen-1-yl)-1-phenylbutan-2-ol

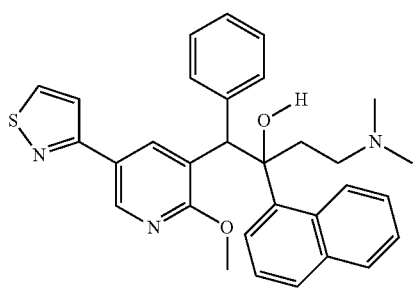

Compound 143 (A1)
Compound 144 (A2)
Compound 145 (B1)
Compound 146 (B2)

According to the method of Example 2, intermediate B and 3-bromoisothiazole were used to prepare crude product which was separated and purified by preparative HPLC (GX-G; Phenomenex Synergi C18 150*30 mm*4 um; acetonitrile 24%-54%; water (0.225% formic acid); 25 mL/min) to give component A and component B. Component A was separated by chiral SFC (sfc 80, AD-10 um; supercritical $CO_2$/EtOH (0.05% aqueous ammonia)=80/20; 55 mL/min; 220 nm) to give compound 143 (A1) (14.79 mg, 0.803% yield) and compound 144 (A2) (12.89 mg, 0.7% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 145 (B1) (52.37 mg, 2.84% yield) and compound 146 (B2) (49.58 mg, 2.69% yield) as white solid. Compound 143 (A1)/compound 144 (A2): $^1$H NMR (400 MHz, methanol-$d_4$): δ 8.94 (s, 1H), 8.72 (s, 1H), 8.62 (d, J 2.4 Hz, 1H), 8.58 (d, J=8.3 Hz, 1H), 8.12 (d, J=7.5 Hz, 1H), 7.95 (d, J=2.4 Hz, 1H), 7.86-7.79 (m, 3H), 7.68-7.65 (m, 1H), 7.61 (t, J=7.8 Hz, 1H), 7.48-7.43 (m, 1H), 7.37 (td, J=7.5, 12.6 Hz, 4H), 7.31-7.26 (m, 1H), 5.68 (s, 1H), 3.30 (s, 3H), 2.66 (d, J=14.1 Hz, 1H), 2.32-2.17 (m, 2H), 2.03 (s, 6H), 1.93 (d, J=12.2 Hz, 1H). Compound 145 (B1)/compound 146 (B2): $^1$H NMR (400 MHz, methanol-$d_4$): δ 9.09 (s, 1H), 8.88 (s, 1H), 8.76 (br. s., 1H), 8.66 (d, J=7.5 Hz, 1H), 8.45 (d, J=2.4 Hz, 1H), 7.97-7.84 (m, 2H), 7.67 (d, J=8.2 Hz, 2H), 7.53-7.46 (m, 1H), 7.30 (t, J=7.7 Hz, 1H), 7.19 (br. s., 2H), 6.92-6.84 (m, 3H), 5.84 (br. s., 1H), 4.18 (s, 3H), 2.73 (br. s., 1H), 2.18-2.04 (m, 2H), 2.00 (s, 6H), 1.86 (br. s., 1H). LCMS (ESI) m/z: 510.2 (M+1).

Example 29

3-(5-(4-(dimethylamino)-2-hydroxyl-2-(naphthalen-1-yl)-1-phenylbutyl)-6-methoxypyridin-3-yl)-benzonitrile

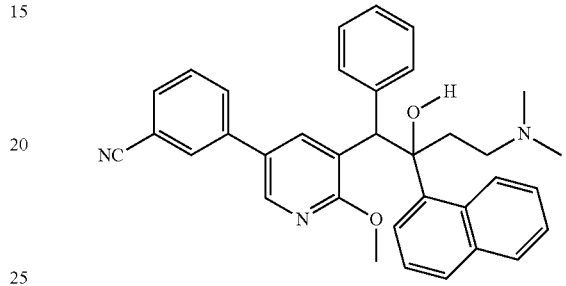

Compound 151 (A1)
Compound 152 (A2)
Compound 153 (B1)
Compound 154 (B2)

According to the method of Example 1, intermediate A and 3-cyanophenylboronic acid were used to prepare crude product which was separated and purified by preparative HPLC (GX-B; Phenomenex Synergi C18 150*30 mm*4 um; acetonitrile 25%-55%; water (0.225% formic acid); 25 mL/min) to give component A and component B. Component A was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 151 (A1) (144.84 mg, 13.87% yield) and compound 152 (A2) (92.24 mg, 8.84% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 153 (B1) (124.21 mg, 11.90% yield) and compound 154 (B2) (139.29 mg, 13.34% yield) as white solid. Compound 151 (A1)/compound 152 (A2): $^1$H NMR (400 MHz, methanol-$d_4$): δ 8.57-8.54 (m, 1H), 8.54-8.46 (m, 2H), 8.18-8.12 (m, 1H), 7.88-7.85 (m, 1H), 7.84-7.81 (m, 1H), 7.79-7.75 (m, 2H), 7.74-7.57 (m, 7H), 7.50-7.46 (m, 1H), 7.40 (s, 3H), 7.33-7.26 (m, 1H), 5.73 (s, 1H), 3.39 (s, 3H), 2.98-2.86 (m, 1H), 2.64-2.54 (m, 1H), 2.29 (s, 7H), 2.17-2.08 (m, 1H). Compound 153 (B1)/compound 154 (B2): $^1$H NMR (400 MHz, methanol-$d_4$): δ 8.70 (br. s., 2H), 8.38 (d, J=2.13 Hz, 1H), 8.03-7.85 (m, 4H), 7.78-7.61 (m, 4H), 7.51 (t, J=7.22 Hz, 1H), 7.31 (t, J=7.72 Hz, 1H), 7.17 (br. s., 2H), 6.95-6.83 (m, 3H), 5.87 (s., 1H), 4.19 (s., 3H), 2.89 (br. s., 1H), 2.44 (br. s., 1H), 2.26-2.08 (m, 7H), 2.03 (br. s., 1H). LCMS (ESI) m/z: 528.3 (M+1).

Example 30

4-(5-(4-(dimethylamino)-2-hydroxyl-2-(naphthalen-1-yl)-1-phenylbutyl)-6-methoxypyridin-3-yl)-benzonitrile

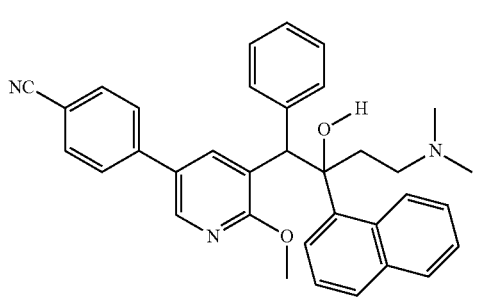

Compound 155 (A1)
Compound 156 (A2)
Compound 157 (B1)
Compound 158 (B2)

According to the method of Example 1, intermediate A and 4-cyanophenylboronic acid were used to prepare crude product which was separated and purified by preparative HPLC (GX-B; Phenomenex Synergi C18 150*30 mm*4 um; acetonitrile 31%-61%; water (0.225% formic acid); 25 mL/min) to give component A and component B. Component A was separated by chiral SFC (Berger MultiGram™ SFC, Mettler Toledo Co, Ltd, IC-10 um; supercritical $CO_2$/MeOH (0.05% aqueous ammonia)=50/50; 70 ml/min; 220 nm) to give compound 155 (A1) (81.22 mg, 7.78% yield) and compound 156 (A2) (102.83 mg, 8.84% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 157 (B1) (165.41 mg, 15.84% yield) and compound 158 (B2) (151.07 mg, 14.47% yield) as white solid. Compound 155 (A1)/compound 156 (A2): $^1$HNMR (400 MHz, $CDCl_3$): δ 8.59 (d, J=2.5 Hz, 1H), 8.49 (d, J=8.7 Hz, 1H), 8.10 (dd, J=1.1, 7.4 Hz, 1H), 7.91 (d, J=2.5 Hz, 1H), 7.88-7.82 (m, 3H), 7.72 (d, J=8.4 Hz, 2H), 7.65 (d, J=8.0 Hz, 1H), 7.61-7.54 (m, 3H), 7.49-7.44 (m, 1H), 7.43-7.38 (m, 2H), 7.36-7.30 (m, 2H), 5.65 (s, 1H), 3.25 (s, 3H), 2.62-2.53 (m, 1H), 2.35-2.25 (m, 2H), 2.09 (s, 6H), 2.02-1.97 (m, 1H). Compound 157 (B1)/compound 158 (B2): $^1$HNMR (400 MHz, $CDCl_3$): δ 8.69 (d, J=2.3 Hz, 1H), 8.60 (d, J=8.8 Hz, 1H), 8.35 (d, J=2.4 Hz, 1H), 8.15 (s, 1H), 8.00 (d, J=7.2 Hz, 1H), 7.89 (d, J=7.9 Hz, 1H), 7.80-7.74 (m, 4H), 7.70-7.61 (m, 2H), 7.55-7.49 (m, 1H), 7.33 (t, J=7.8 Hz, 1H), 7.27-7.20 (m, 2H), 6.95-6.88 (m, 3H), 5.83 (s, 1H), 4.20 (s, 3H), 2.93-2.82 (m, 1H), 2.72-2.61 (m, 1H), 2.24 (s, 6H), 2.18 (dd, J=7.1, 14.1 Hz, 1H), 1.99-1.90 (m, 1H). LCMS (ESI) m/z: 528.3 (M+1).

Example 31

4-(dimethylamino)-1-(2-methoxy-5-(thiazol-4-yl)pyridin-3-yl)-2-(naphthalen-1-yl)-1-phenylbutan-2-ol

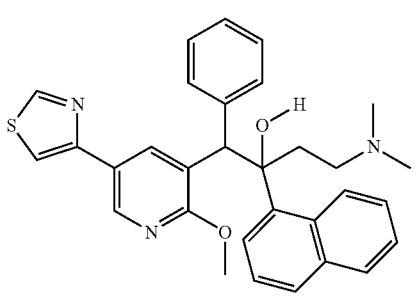

Compound 159 (A1)
Compound 160 (A2)
Compound 161 (B1)
Compound 162 (B2)

According to the method of Example 2, intermediate B and 4-bromothiazole were used to prepare crude product which was separated and purified by preparative HPLC (GX-B; Phenomenex Synergi C18 150*30 mm*4 um; acetonitrile 20%-50%; water (0.225% formic acid); 25 mL/min) to give component A and component B. Component A was separated by chiral SFC (sfc 80, AD-10 um; supercritical $CO_2$/MeOH (0.05% aqueous ammonia)=60/40; 70 ml/min; 220 nm) to give compound 159 (A1) (172.03 mg, 8.17% yield) and compound 160 (A2) (189.75 mg, 8.83% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 161 (B1) (135.61 mg, 6.44% yield) and compound 162 (B2) (147.77 mg, 7.02% yield) as white solid. Compound 159 (A1)/compound 160 (A2): $^1$H NMR (400 MHz, methanol-$d_4$): δ 9.05 (s, 1H), 8.79 (s, 1H), 8.60 (d, J=8.66 Hz, 1H), 8.51 (br. s., 1H), 8.19 (d, J=1.88 Hz, 1H), 8.04 (d, J=7.40 Hz, 1H), 7.88-7.79 (m, 3H), 7.71-7.65 (m, 4H), 7.47 (t, J=7.40 Hz, 1H), 7.43-7.38 (m, 2H), 7.31 (d, J=7.53 Hz, 2H), 5.72 (s, 1H), 3.28 (s, 3H), 2.96-2.85 (m, 1H), 2.60-2.49 (m, 1H), 2.33 (d, J=7.91 Hz, 1H), 2.27 (s, 6H), 2.11 (m, 1H). Compound 161 (B1)/compound 162 (B2): $^1$H NMR (400 MHz, methanol-$d_4$): δ 9.13 (br. s., 1H), 8.98 (br. s., 1H), 8.67 (br. s., 2H), 8.49 (br. s., 1H), 7.95-7.77 (m, 3H), 7.72 (d, J=6.65 Hz, 2H), 7.54 (br. s., 1H), 7.31 (t, J=7.78 Hz, 1H), 7.12 (br. s., 2H), 6.90 (br. s., 3H), 5.88 (br. s., 1H), 4.17 (br. s., 3H), 3.00 (br. s., 1H), 2.69 (br. s., 1H), 2.37 (br. s., 6H), 2.08-2.26 (m, 2H). LCMS (ESI) m/z: 510.2 (M+1).

Example 32

4-(dimethylamino)-1-(5-(isothiazol-4-yl)-2-methoxypyridin-3-yl)-2-(naphthalen-1-yl)-1-phenylbutan-2-ol

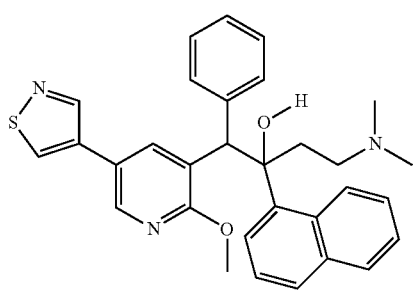

Compound 163 (A1)
Compound 164 (A2)
Compound 165 (B1)
Compound 166 (B2)

According to the method of Example 2, intermediate B and 4-bromoisothiazole were used to prepare crude product which was separated and purified by preparative HPLC (GX-G; Phenomenex Synergi C18 150*30 mm*4 um; acetonitrile 25%-55%; water (0.225% formic acid); 25 mL/min) to give component A and component B. Component A was separated by chiral SFC (sfc 80, AD-10 um; supercritical $CO_2$/EtOH (0.05% aqueous ammonia)=70/30; 60 g/min; 220 nm) to give compound 163 (A1) (54.92 mg, 2.98% yield) and compound 164 (A2) (53.62 mg, 2.91% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 165 (B1) (35.32 mg, 1.73% yield) and compound 166 (B2) (31.97 mg, 2.04% yield) as white solid. Compound 163 (A1)/compound 164 (A2): $^1$H NMR (400 MHz, METHANOL-$d_4$) 8.99-8.94 (m, 1H), 8.59 (d, J=8.8 Hz, 1H), 8.23 (d, J=2.4 Hz, 1H), 8.05 (d, J=7.4 Hz, 1H), 7.88-7.81 (m, 3H), 7.67-7.59 (m, 3H), 7.50-7.43 (m, 1H), 7.42-7.36 (m, 2H), 7.32-7.25 (m, 2H), 5.69 (s, 1H), 3.25 (s, 3H), 2.72-2.67 (m, 1H), 2.30-2.15 (m, 2H), 2.04 (s, 6H), 1.95-1.91 (m, 1H). Compound 165 (B1)/compound 166 (B2): $^1$H NMR (400 MHz, METHANOL-$d_4$) □□9.16 (br. s., 1H), 9.03 (d, J=4.6 Hz, 1H), 8.71 (d, J=2.1 Hz, 2H), 7.90 (d, J=7.7 Hz, 2H), 7.80 (d, J=4.6 Hz, 1H), 7.70 (d, J=7.9 Hz, 2H), 7.56-7.47 (m, 1H), 7.30 (t, J=7.7 Hz, 2H), 7.14 (br. s., 2H), 6.92-6.86 (m, 3H), 5.85 (br. s., 1H), 4.18 (br. s., 3H), 2.79 (br. s., 1H), 2.31 (br. s., 1H), 2.15 (s, 7H), 2.00 (br. s., 1H). LCMS (ESI) m/z: 510.2 (M+1).

Example 33

4-(dimethylamino)-1-(2-methoxy-5-(thiazol-2-yl)pyridin-3-yl)-2-(naphthalen-1-yl)-1-phenylbutan-2-ol

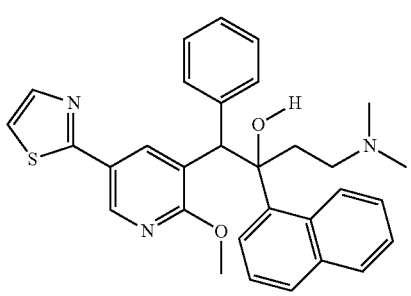

Compound 167 (A1)
Compound 168 (A2)
Compound 169 (B1)
Compound 170 (B2)

According to the method of Example 2, intermediate B and 2-bromothiazole were used to prepare crude product which was separated and purified by preparative HPLC (GX-D; Boston Symmetrix C18 ODS-R 150*30 mm*5 um; acetonitrile 30%-55%; water (0.225% formic acid); 25 mL/min) to give component A and component B. Component A was separated by chiral SFC (sfc 80, AD-10 um; supercritical $CO_2$/EtOH (0.05% aqueous ammonia)=70/30; 60 ml/min; 220 nm) to give compound 167 (A1) (97.61 mg, 5.40% yield) and compound 168 (A2) (103.57 mg, 5.73% yield) as white solid. Component B was separated by chiral SFC (Berger MultiGram™ SFC, Mettler Toledo Co, Ltd, IC-10 um; supercritical $CO_2$/MeOH (0.05% aqueous ammonia)—60/40; 70 ml/min; 220 nm) to give compound 169 (B1) (34.56 mg, 1.91% yield) and compound 170 (B2) (32.81 mg, 1.81% yield) as white solid. Compound 167 (A1)/compound 168 (A2): $^1$H NMR (400 MHz, methanol-$d_4$): δ 8.85 (d, J=2.13 Hz, 1H), 8.60 (d, J=8.78 Hz, 1H), 8.51 (br. s., 1H), 8.22 (br. s., 1H), 8.08 (d, J=7.40 Hz, 1H), 7.82 (d, J=7.65 Hz, 4H), 7.68-7.54 (m, 3H), 7.50-7.38 (m, 3H), 7.31 (t, J=6.84 Hz, 2H), 5.71 (s, 1H), 3.33 (s, 3H), 2.97-2.87 (m, 1H), 2.63-2.48 (m, 1H), 2.31-2.28 (m, 7H), 2.11 (br. s., 1H). Compound 169 (B1)/compound 170 (B2): $^1$H NMR (400 MHz, methanol-$d_4$): δ 9.07 (br. s., 1H), 8.74-8.60 (m, 2H), 7.97-7.87 (m, 3H), 7.73-7.60 (m, 3H), 7.52 (d, J=7.15 Hz, 1H), 7.30 (t, J=7.78 Hz, 1H), 7.15 (br. s., 2H), 6.95-6.81 (m, 3H), 5.83 (hr. s., 1H), 4.19 (br. s., 3H), 2.79 (br. s., 1H), 2.33 (br. s., 1H), 2.15 (s, 7H), 2.01 (hr. s., 1H). LCMS (ESI) m/z: 510.2 (M+1).

Example 34

4-(dimethylamino)-1-(2-methoxy-5-(thiazol-5-yl)pyridin-3-yl)-2-(naphthalen-1-yl)-1-phenylbutan-2-ol

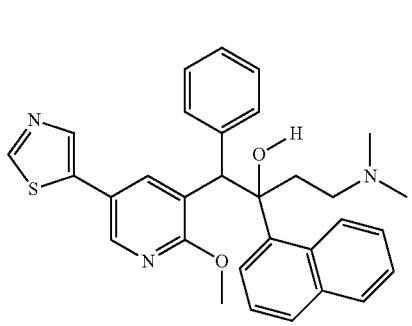

Compound 171 (A1)
Compound 172 (A2)
Compound 173 (B1)
Compound 174 (B2)

According to the method of Example 2, intermediate B and 5-bromothiazole were used to prepare crude product which was separated and purified by preparative HPLC (GX-D; Boston Symmetrix C18 ODS-R 150*30 mm; acetonitrile 25%-55%; water (0.225% formic acid); 25 mL/min) to give component A and component B. Component A was separated by chiral SFC (Berger MultiGram™ SFC, Mettler Toledo Co, Ltd, IC-10 um; supercritical $CO_2$/MeOH (0.05% aqueous ammonia)=60/40; 70 ml/min; 220 nm) to give compound 171 (A1) (72.84 mg, 3.95% yield) and compound 172 (A2) (69.51 mg, 3.77% yield) as white solid. Component B was separated by chiral SFC (Berger MultiGram™ SFC, Mettler Toledo Co, Ltd, IC-10 um; supercritical $CO_2$/MeOH (0.05% aqueous ammonia)=50/50; 70 ml/min; 220 nm) to give compound 173 (B1) (91.96 mg, 4.98% yield) and compound 174 (B2) (56.90 mg, 3.08% yield) as white solid. Compound 171 (A1)/compound 172 (A2): $^1$H NMR (400 MHz, methanol-$d_4$): δ 9.00 (d, J=5.27 Hz, 1H), 8.76-8.58 (m, 2H), 8.50 (br. s., 1H), 8.40 (m, 1H), 8.15 (m, 1H), 7.88 (m, 2H), 7.69 (d, J=7.03 Hz, 2H), 7.51 (br. s., 1H), 7.31 (t, J=7.53 Hz, 1H), 7.14 (br. s., 2H), 6.89 (s, 3H), 5.84 (br. s., 1H), 4.17 (s, 3H), 2.90 (br. s., 1H), 2.47 (br. s., 1H), 2.24 (s., 6H), 2.19-1.97 (m, 2H). Compound 173 (B1)/compound 174 (B2): $^1$H NMR (400 MHz, methanol-$d_4$): δ 8.96 (s, 1H), 8.59 (d, J=8.66 Hz, 1H), 8.52 (s, 1H), 8.12 (d, J=7.28 Hz, 1H), 7.96 (s, 1H), 7.90 (d, J=2.38 Hz, 1H), 7.83 (d, J=7.91 Hz, 1H), 7.77 (d, J=7.40 Hz, 2H), 7.70-7.60 (m, 3H), 7.47 (t, J=7.40 Hz, 1H), 7.43-7.35 (m, 4H), 7.33-7.28 (m, 1H), 5.70 (s, 1H), 3.37 (s, 3H), 2.96 (br. s., 1H), 2.63 (br. s., 1H), 2.37-2.25 (m, 7H), 2.16 (m, 1H). LCMS (ESI) m/z: 510.2 (M+1).

Example 35

4-(dimethylamino)-1-(5-isopropyl-2-methoxypyridin-3-yl)-2-(naphthalen-1-yl)-1-phenylbutan-2-ol

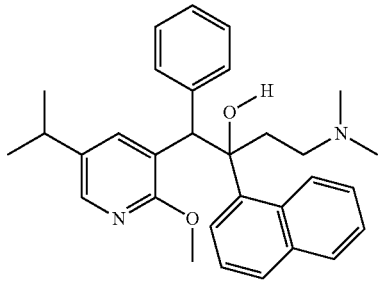

Compound 175 (A)
Compound 176 (B)

Step 1: 4-(dimethylamino)-1-(2-methoxy-5-(prop-1-en-2-yl)pyridin-3-yl)-2-(naphthalen-1-yl)-1-phenylbutan-2-ol

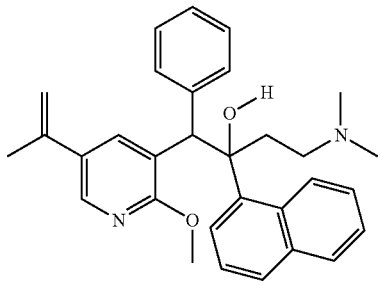 [SMILES: C=C(C)c1cnc(OC)c(C(c2ccccc2)C(O)(CCN(C)C)c2cccc3ccccc23)c1]

1-(5-bromo-2-methoxypyridin-3-yl)-4-(dimethylamino)-2-(naphthalen-1-yl)-1-phenylbutan-2-ol (1.3 g, 2.57 mmol), 4,4,5,5-tetramethyl-2-(prop-1-en-2-yl)-1,3,2-dioxaborolane (0.65 g, 3.09 mmol) and potassium acetate (760 mg, 7.72 mmol) were dissolved in 12.0 mL of 1,4-dioxane and 2.0 mL of water and a catalytic amount of Pd(dppf)Cl$_2$ (190 mg, 0.26 mmol, cat.) was added under nitrogen. The reaction liquid was stirred at 80° C. for 23 h. Then the reaction liquid was added with 20 mL of water and extracted with ethyl acetate (20 mL×3). The combined organic phase was dried over anhydrous sodium sulfate, concentrated and purified by column chromatography (eluent: petroleum ether/ethyl acetate=20/12/1) to give 4-(dimethylamino)-1-(2-methoxy-5-(prop-1-en-2-yl)pyridin-3-yl)-2-(naphthalen-1-yl)-1-phenylbutan-2-ol (1.45 g, crude product) as a yellow oil. LCMS (ESI) m/z: 467.2 (M+1).

Step 2: 4-(dimethylamino)-1-(5-isopropyl-2-methoxypyridin-3-yl)-2-(naphthalen-1-yl)-1-phenylbutan-2-ol

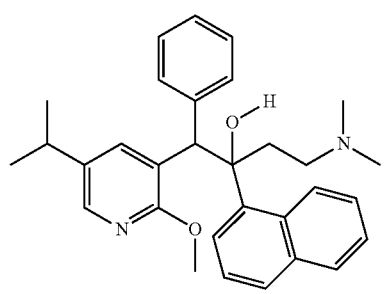

Compound 175 (A)
Compound 176 (B)

4-(dimethylamino)-1-(2-methoxy-5-(prop-1-en-2-yl)pyridin-3-yl)-2-(naphthalen-1-yl)-1-phenylbutan-2-ol (500 mg, 1.07 mmol) and cobalt chloride hexahydrate (1.2 g, 5.3 mmol) were dissolved in 25 mL of ethanol and sodium borohydride (1.16 g, 32.1 mmol) was added at 50° C. in two portions. Then the reaction liquid was stirred at this temperature for 2 h. The reaction liquid was adjusted with 5 M hydrochloric acid to pH 1 and then stirred until no bubbles emerged. The reaction liquid was concentrated and then adjusted with ammonium chloride solution to pH 9.20 mL of water was added and then the mixture was extracted with dichloromethane/methanol (10/1, 50 mL×3). The combined organic phase was washed with 50 mL of saturated brine twice, dried over anhydrous sodium sulfat and concentrated to give 4-(dimethylamino)-1-(5-isopropyl-2-methoxypyridin-3-yl)-2-(naphthalen-1-yl)-1-phenylbutan-2-ol (200 mg, 25%). The crude product was separated and purified by preparative HPLC (GX-D; Boston Symmetrix C18 ODS-R 150*30 mm*5 um; acetonitrile 25%-55%; water (0.223% FA); 25 mL/min) to give compound 175 (A) (13.5 mg, 2.72% yield) and compound 176 (B) (10.2 mg, 2.06% yield) as white solid. Compound 175 (A): $^1$H NMR (400 MHz, METHANOL-$d_4$): δ 8.66 (s., 1H), 8.50 (s., 1H), 8.38 (s., 1H), 7.95 (s., 1H), 7.90 (d, J=4.00 Hz, 1H), 7.79 (d, J=8.00 Hz, 1H), 7.73-7.67 (m, 2H), 7.52 (t, J=8.00 Hz, 1H), 7.31 (t, J=8.00 Hz, 1H), 7.06 (s, 2H), 6.89-6.88 (m, 3H), 5.81 (s, 1H), 4.09 (s, 3H), 2.99-2.91 (m, 2H), 2.63-2.62 (m, 1H), 2.36 (s, 6H), 2.20-2.13 (m, 2H), 1.34-1.29 (m, 5H). Compound 176 (B): $^1$H NMR (400 MHz, METHANOL-$d_4$): δ 8.56 (d, J=8.00 Hz, 1H), 8.21-8.05 (m, 1H), 7.83 (t, J=8.00 Hz, 1H), 7.77-7.59 (m, 5H), 7.44-7.31 (m, 7H), 7.79 (d, J=8.00 Hz, 1H), 7.73-7.67 (m, 2H), 7.52 (t, J=8.00 Hz, 1H), 5.63 (s, 1H), 3.30 (s, 3H), 2.79-2.68 (m, 2H), 2.42-2.62 (m, 3H), 2.20 (s, 6H), 2.05 (s, 2H), 1.16-1.11 (m, 4H). LCMS (ESI) m/z: 469.3 (M+1).

Example 36

4-(dimethylamino)-1-(5-(furan-3-yl)-2-methoxypyridin-3-yl)-2-(naphthalen-1-yl)-1-phenylbutan-2-ol

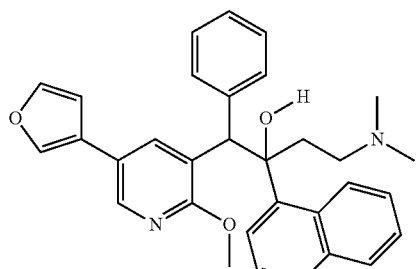

Compound 178 (A1)
Compound 179 (A2)
Compound 180 (B1)
Compound 181 (B2)

According to the method of Example 1, intermediate A and furan-3-yl boronic acid were used to prepare crude product which was separated and purified by preparative HPLC (GX-G; Phenomenex Synergi C18 150*30 mm*4 um; acetonitrile 25%-55%; water (0.225% formic acid); 25 mL/min) to give component A and component B. Component A was separated by chiral SFC (SFC 80; AD-10 um; supercritical $CO_2$/EtOH (0.05% aqueous ammonia)=70/30; 60 g/min; 220 nm) to give compound 178 (A1) (95.30 mg, 8.14% yield) and compound 179 (A2) (98.4 mg, 8.41% yield) as white solid. Component B was separated by chiral SFC (SFC 80; AD-10 um; supercritical $CO_2$/EtOH (0.05% aqueous ammonia)=70/30; 60 g/min; 220 nm) to give compound 180 (B1) (123 mg, 10.5% yield) and compound 181 (B2) (145 mg, 12.4% yield) as white solid. Compound 178 (A1)/compound 179 (A2): $^1$H NMR (400 MHz, METHANOL-$d_4$): δ 8.59 (d, J=8.00 Hz, 1H), 8.53 (s, 1H), 8.38 (s, 1H), 8.19 (s, 1H), 8.16 (s, 1H), 7.89 (d, J=8.00 Hz, 2H), 7.80 (s, 1H), 7.72 (d, J=8.00 Hz, 2H), 7.54 (t, J=8.00 Hz, 1H), 7.34 (t, J=8.00 Hz, 1H), 7.15 (d, J=4.00 Hz, 2H), 6.93-6.86 (m, 4H), 5.70 (s, 1H), 4.09 (s, 3H), 2.58 (t, J=16.0 Hz, 1H), 1.96 (s, 8H), 1.84 (d, J=8.00 Hz, 1H). Compound 180 (B1)/compound 181 (B2): $^1$H NMR (400 MHz, METHANOL-$d_4$): δ 8.58 (d, J=12.0 Hz, 1H), 8.48 (s, 1H), 8.09 (d, J=8.00 Hz, 1H), 7.84-7.76 (m, 5H), 7.64 (d, J=8.00 Hz, 1H), 7.60 (t, J=8.00 Hz, 1H), 7.56 (s, 1H), 7.45 (t, J=8.00 Hz, 1H), 7.40-7.32 (m, 4H), 7.28 (t, J=8.00 Hz, 1H), 6.67 (s, 1H), 5.65 (s, 1H), 3.26 (s, 3H), 2.69-2.65 (m, 1H), 2.29-2.16 (m, 2H), 2.03 (s, 6H), 1.93-1.90 (m, 1H). LCMS (ESI) m/z: 493.2 (M+1).

Example 37

4-(dimethylamino)-1-(5-(furan-2-yl)-2-methoxypyridin-3-yl)-2-(naphthalen-1-yl)-1-phenylbutan-2-ol

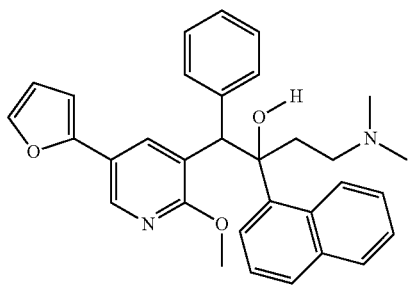

Compound 182 (A1)
Compound 183 (A2)
Compound 184 (B1)
Compound 185 (B2)

According to the method of Example 1, intermediate A and furan-2-yl boronic acid were used to prepare crude product which was separated and purified by preparative HPLC (GX-G; Phenomenex Synergi C18 150*30 mm*4 um; acetonitrile 24%-54%; water (0.223% formic acid); 25 mL/min) to give component A and component B. Component A was separated by chiral SFC (SFC 80; AD-10 um; supercritical $CO_2$/EtOH (0.05% aqueous ammonia)=80/20; 55 mL/min; 220 nm) to give compound 182 (A1) (61.90 mg, 5.29% yield) and compound 183 (A2) (71.90 mg, 6.14% yield) as white solid. Component B was separated by chiral SFC (SFC 80; AD-10 um; supercritical $CO_2$/EtOH (0.05% aqueous ammonia)=70/30; 60 g/min; 220 nm) to give compound 184 (B1) (37.6 mg, 3.13% yield) and compound 185 (B2) (36.6 mg, 3.12% yield) as white solid. Compound 182 (A1)/compound 183 (A2): $^1$H NMR (400 MHz, METHANOL-$d_4$): δ 8.81 (s, 1H), 8.65 (d, J=4.00 Hz, 1H), 8.42 (s, 1H), 7.90 (t, J=8.00 Hz, 2H), 7.69-7.61 (m, 3H), 7.49 (t, J=4.00 Hz, 1H), 7.30 (d, J=8.00 Hz, 1H), 7.15 (s, 2H), 6.87 (s, 3H), 6.75 (d, J=4.00 Hz, 1H), 6.57-6.55 (m, 1H), 5.80 (s, 1H), 4.15 (s, 3H), 2.69 (d, J=8.00 Hz, 1H), 2.12 (t, J=8.00 Hz, 2H), 2.03 (s, 6H), 1.88 (s, 1H). Compound 184 (B1)/compound 185 (B2): $^1$H NMR (400 MHz, METHANOL-$d_4$): δ 8.58 (d, J=12.0 Hz, 1H), 8.48 (s, 1H), 8.09 (d, J=8.00 Hz, 1H), 7.84-7.76 (m, 5H), 7.64 (d, J=8.00 Hz, 1H), 7.60 (t, J=8.00 Hz, 1H), 7.56 (s, 1H), 7.45 (t, J=8.00 Hz, 1H), 7.40-7.32 (m, 4H), 7.28 (t, J=8.00 Hz, 1H), 6.67 (s, 1H), 5.65 (s, 1H), 3.26 (s, 3H), 2.69-2.65 (m, 1H), 2.29-2.16 (m, 2H), 2.03 (s, 6H), 1.93-1.90 (m, 1H). LCMS (ESI) m/z: 493.2 (M+1).

Example 38

1-(5-bromo-2-methoxypyridin-3-yl)-4-(dimethylamino)-2-(naphthalen-1-yl)-1-phenylbutan-2-ol

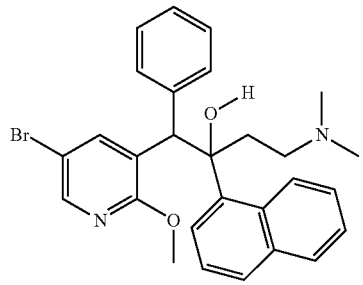

Compound 194 (A)
Compound 195 (B)

Intermediate A was separated and purified by preparative HPLC (HPLC-D; SYNERGI-C 200*50 10 um; acetonitrile 30%-60%; water (0.225% formic acid); 70 mL/min) to give compound 194 (A) and compound 195 (B) as white solid. Compound 194 (A): $^1$H NMR (400 MHz, METHANOL-$d_4$): δ 8.59 (d, J=8.7 Hz, 1H), 8.52 (br. s., 2H), 8.17 (d, J=2.4 Hz, 1H), 7.90 (d, J=8.0 Hz, 1H), 7.82 (d, J=6.8 Hz, 1H), 7.73-7.63 (m, 3H), 7.55-7.48 (m, 1H), 7.33-7.27 (m, 1H), 7.06 (br. s., 2H), 6.92-6.86 (m, 3H), 5.77 (br. s., 1H), 4.11 (s, 3H), 2.95 (br. s., 1H), 2.70-2.56 (m, 1H), 2.35 (s, 6H), 2.18-2.06 (m, 2H). Compound 195 (B): $^1$HNMR (400 MHz, METHANOL-$d_4$): δ 8.56 (d, J=8.8 Hz, 1H), 8.38 (d, J=2.4 Hz, 1H), 7.97 (d, J=7.7 Hz, 1H), 7.87 (d, J=7.7 Hz, 1H), 7.77-7.71 (m, 3H), 7.68-7.62 (m, 2H), 7.49 (t, J=7.5 Hz, 1H), 7.45-7.40 (m, 3H), 7.39-7.30 (m, 2H), 5.64 (s, 1H), 3.22 (s, 3H), 2.99 (t, J=9.5 Hz, 1H), 2.68 (br. s., 1H), 2.38 (s, 6H), 2.30-2.14 (m, 2H). LCMS (ESI) m/z: 505.1 (M+1).

Example 39

1-(5-(5-chlorothiophen-3-yl)-2-methoxypyridin-3-yl)-4-(dimethylamino)-2-(naphthalen-1-yl)-1-phenylbutan-2-ol

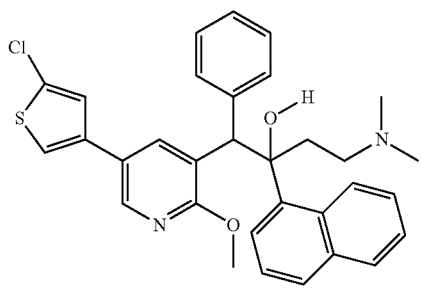

Compound 245 (A1)
Compound 246 (A2)
Compound 247 (B1)
Compound 248 (B2)

Step 1: (5-chlorothiophen-3-yl)boronic acid

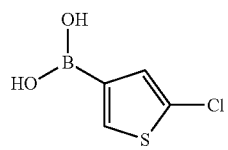

3-thienylboronic acid (750.00 mg, 5.86 mmol) and N-chlorosuccinimide (938.98 mg, 7.03 mmol) were mixed in 5 mL of tetrahydrofuran, heated to 60° C. and stirred for 12 h. TLC (developing solvent:petroleum ether/ethyl acetate=50/1) showed the reaction was complete. Then the reaction liquid was concentrated, washed with 20 mL of mixed solvent (petroleum ether/ethyl acetate=20/1) once, filtered and dried to give (5-chloro-3-thienyl)boronic acid (500 mg, crude product) as a pale yellow solid which was used directly in the next step without further purification.

Step 2: 1-(5-(5-chlorothiophen-3-yl)-2-methoxypyridin-3-yl)-4-(dimethylamino)-2-(naphthalen-1-yl)-1-phenylbutan-2-ol

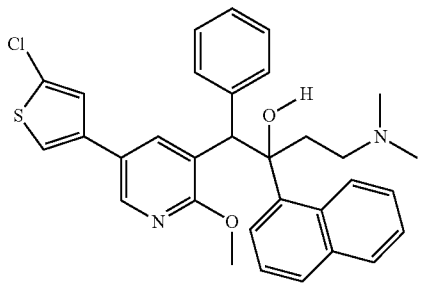

Compound 245 (A1)
Compound 246 (A2)
Compound 247 (B1)
Compound 248 (B2)

According to the method of Example 1, intermediate A and (5-chloro-3-thienyl)boronic acid were used to prepare crude product which was separated and purified by preparative HPLC (GX-G; Phenomenex Synergi C18 150*30 mm*4 um; acetonitrile 30%-59%; water (0.225% formic acid); 25 mL/min) to give component A and component B. Component A was separated by chiral SFC (Berger MultiGram™ SFC, Mettler Toledo Co, Ltd, IC-10 um; supercritical CO$_2$/MeOH (0.05% aqueous ammonia)=50/50; 70 ml/min; 220 nm) to give compound 245 (A1) (55.7 mg, 16.1% yield) and compound 246 (A2) (40.28 mg, 11.6% yield) as white solid. Component B was separated by chiral SFC (Berger MultiGram™ SFC, Mettler Toledo Co, Ltd, IC-10 um; supercritical CO$_2$/MeOH (0.05% aqueous ammonia)=50/50; 70 ml/min; 220 nm) to give compound 247 (B1) (70.48 mg, 20.4% yield) and compound 248 (B2) (44.37 mg, 12.8% yield) as white solid. Compound 245 (A1)/compound 246 (A2): $^1$H NMR (400 MHz, methanol-d$_4$): δ 8.66 (br. s., 2H), 8.34 (d, J=2.26 Hz, 1H), 7.89 (d, J=7.65 Hz, 2H), 7.69 (d, J=8.16 Hz, 2H), 7.57-7.42 (m, 2H), 7.40-7.26 (m, 2H), 7.14 (br. s., 2H), 6.94-6.83 (m, 3H), 5.83 (br. s., 1H), 4.15 (s, 3H), 2.95-268 (m, 1H), 2.43-2.27 (m, 1H), 2.15 (s, 7H), 2.03-1.88 (m, 1H). Compound 247 (B1)/compound 248 (B2): $^1$H NMR (400 MHz, methanol-d$_4$): δ 8.77 (br. s., 2H), 8.52 (br. s., 1H), 8.29 (d, J=2.38 Hz, 1H), 7.89 (d, J=7.91 Hz, 2H), 7.69 (d, J=8.03 Hz, 2H), 7.51 (s, 1H), 7.41 (d, J=5.77 Hz, 1H), 7.30 (t, J=7.78 Hz, 1H), 7.21-7.08 (m, 3H), 6.92-6.82 (m, 3H), 5.83 (br. s., 1H), 4.17 (s, 3H), 2.93-2.69 (m, 1H), 2.48-2.28 (m, 1H), 2.16 (s, 8H). LCMS (ESI) m/z: 543.2 (M+1).

Example 40

1-(5-(2-chlorothiophen-3-yl)-2-methoxypyridin-3-yl)-4-(dimethylamino)-2-(naphthalen-1-yl)-1-phenylbutan-2-ol

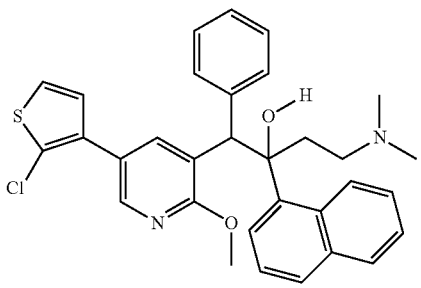

Compound 249 (A1)
Compound 250 (A2)
Compound 251 (B1)
Compound 252 (B2)

According to the method of Example 2, intermediate B was reacted with 3-bromo-2-chlorothiophene to produce crude product which was separated and purified by preparative HPLC (HPLC-D; SYNERGI-C 200*50 10 um; acetonitrile 25%-50%; water (0.225% formic acid); 80 mL/min) to give component A and component B. Component A was separated by chiral SFC(Chiralpak AD 250×30 mm I.D., 10 um; supercritical CO$_2$/i-PrOH (0.1% aqueous ammonia) =70/30; 60 g/min; 220 nm) to give compound 249 (A1) (60.91 mg, 3.09% yield) and compound 250 (A2) (65.42 mg, 3.32% yield) as white solid. Component B was separated by chiral SFC (Chiralpak AD 250×30 mm, I.D-5 um; supercritical CO$_2$/IPA (0.1% aqueous ammonia)=70/30; 60 g/min; 220 nm) to give compound 251 (B1) (18.08 mg, 0.92% yield) and compound 252 (B2) (32.55 mg, 1.65% yield) as white solid. Compound 249 (A1)/compound 250 (A2): $^1$HNMR (400 MHz, CHLOROFORM-d): δ 8.55-8.44 (m, 2H), 8.07 (d, J=7.53 Hz, 1H), 7.94-7.80 (m, 4H), 7.65 (d, J=7.78 Hz, 1H), 7.58 (t, J=7.65 Hz, 1H), 7.49-7.31 (m, 4H), 7.14 (d, J=5.52 Hz, 1H), 6.94 (d, J=5.52 Hz, 1H), 5.65 (s, 1H) 3.22 (s, 3H) 2.57 (d, J=12.30 Hz, 1H), 2.35-2.20 (m, 3H), 2.07 (s, 6H), 1.33-1.20 (m, 1H). Compound 251 (B1)/compound 252 (B2): $^1$HNMR (400 MHz, METHANOL-d$_4$): δ 8.80-8.74 (m, 1H), 8.73-8.64 (m, 1H), 8.33-8.26 (m, 1H), 7.96-7.81 (m, 2H), 7.75-7.74 (m, 1H), 7.70 (d, J=8.03 Hz, 2H), 7.56-7.48 (m, 1H), 7.42 (d, J=5.77 Hz, 1H), 7.30 (s, 1H), 7.21-7.08 (m, 3H), 6.92-6.83 (m, 3H), 5.89-5.81 (m, 1H), 4.17 (s, 3H), 2.91-2.79 (m, 1H), 2.47-2.34 (m, 1H), 2.20 (br. s., 7H). LCMS (ESI) m/z: 543.2 (M+1).

Example 41

1-(5-(3,6-dihydro-2H-thiopyran-4-yl)-2-methoxy-pyridin-3-yl)-4-(dimethylamino)-2-(naphthalen-1-yl)-1-phenylbutan-2-ol

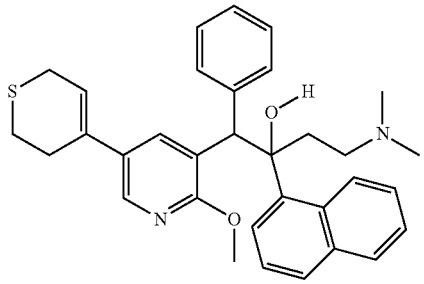

Compound 257 (A1)
Compound 258 (A2)
Compound 259 (B1)
Compound 260 (B2)

According to the method of Example 1, intermediate A was reacted with 2-(3,6-dihydro-2H-thiopyran-4-yl)-4,4,5,5,-tetramethyl-1,3,2-dioxaborolane to produce crude product which was isolated by column chromatography (column height: 250 mm; diameter: 100 mm; 100-200 mesh silica gel; eluent: petroleum ether/ethyl acetate=100/11/1) to give component A and component B. Component A was separated by chiral SFC (Chiralpak AD 250×30 mm I.D., 10 um; supercritical $CO_2$/EtOH (0.1% aqueous ammonia)=70/30; 60 ml/min; 220 nm) to give compound 257 (A1) (43.72 mg, 3.53% yield) and compound 258 (A2) (38.88 mg, 3.14% yield) as white solid. Component B was separated by chiral SFC (Chiralpak IC 250×30 mm I.D., 10 um; supercritical $CO_2$/MeOH (0.1%/aqueous ammonia)=50/50; 70 ml/min; 220 nm) to give compound 259 (B1) (13.52 mg, 1.09% yield) and compound 260 (B2) (13.43 mg, 1.08% yield) as white solid. Compound 257 (A1)/compound 258 (A2): $^1$H NMR (400 MHz, METHANOL-$d_4$): δ 8.61-8.54 (m, 1H), 8.52-8.45 (m, 1H), 8.28-8.17 (m, 1H), 8.08-8.01 (m, 1H), 7.88-7.80 (m, 1H), 7.77-7.55 (m, 6H), 7.50-7.29 (m, 6H), 6.03-5.95 (m, 1H), 5.68 (s, 1H), 4.68-4.60 (m, 1H), 3.35 (br. s., 3H), 3.17-3.01 (m, 2H), 2.86 (t, J=5.65 Hz, 3H), 2.69-2.52 (m, 3H), 2.46 (s, 6H), 2.39-2.21 (m, 3H). Compound 259 (B1)/compound 260 (B2): $^{11}$HNMR (400 MHz, METHANOL-$d_4$): δ 8.74-8.61 (m, 1H), 8.46 (br. s., 1H), 8.09 (d, J=2.01 Hz, 1H), 7.90 (d, J=8.03 Hz, 2H), 7.70 (d, J=8.03 Hz, 2H), 7.56-7.47 (m, 1H), 7.31 (s, 1H), 7.09 (br. s., 2H), 6.89 (d, J=2.26 Hz, 1H), 6.25 (br. s., 1H), 5.81 (br. s., 1H), 4.63 (br. s., 1H), 4.21-4.03 (m, 3H), 2.96-2.82 (m, 3H), 2.70 (br. s., 2H), 2.54 (br. s., 1H), 2.28 (s, 6H), 2.17-2.02 (m, 2H). LCMS (ESI) m/z: 525.2 (M+1).

Example 42

4-(dimethylamino)-1-(2-methoxy-5-(tetrahydro-2H-thiopyran-4-yl)pyridin-3-yl)-2-(naphthalen-1-yl)-1-phenylbutan-2-ol

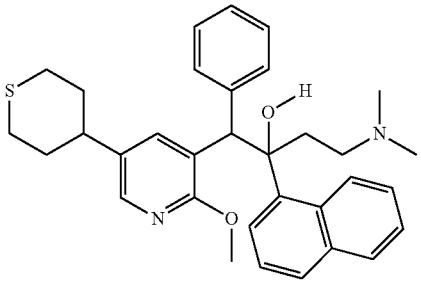

Compound 253 (A1)
Compound 254 (A2)
Compound 255 (B1)
Compound 256 (B2)

Under nitrogen, 1-(5-(3,6-dihydro-2H-thiopyran-4-yl)-2-methoxy-3-pyridyl)-4-(dimethylamino)-2-(1-naphthyl)-1-phenyl-butan-2-ol (200.0 mg, 381.16 umol) (the mixture of compound 257 and compound 258) was dissolved in 50 mL of methanol and platinum dioxide (20.00 mg, 88.07 umol) was added. The reaction liquid was evacuated and repeatedly charged with hydrogen and then stirred at 50° C. under hydrogen (50 psi) for 24 h. LCMS showed the starting material was completely consumed. The reaction liquid was filtered and the filtrate was concentrated to give component A. Like the previous reaction step, component B was produced by the reaction of 1-(5-(3,6-dihydro-2H-thiopyran-4-yl)-2-methoxy-3-pyridyl)-4-(dimethylamino)-2-(1-naphthyl)-1-phenyl-butan-2-ol (the mixture of compound 257 and compound 258). Component A was separated by chiral SFC (Chiralpak IC 250×30 mm I.D., 10 um; supercritical $CO_2$/MeOH (0.1% aqueous ammonia)=60/40; 70 g/min; 220 nm) to give compound 253 (A1) (20.76 mg, 10.34% yield) and compound 254 (A2) (35.47 mg, 17.67% yield) as white solid. Component B was separated by chiral SFC (Chiralpak IC 250×30 mm I.D., 10 um; supercritical $CO_2$/MeOH (0.1% aqueous ammonia)=60/40; 70 ml/min; 220 nm) to give compound 255 (B1) (21.3 mg, 10.61% yield) and compound 256 (B2) (16.18 mg, 8.06% yield) as white solid. Compound 253 (A1)/compound 254 (A2): $^1$H NMR (400 MHz, CHLOROFORM-d): δ 8.49-8.43 (m, 1H), 8.29-8.22 (m, 1H), 8.09 (d, J=6.78 Hz, 1H), 7.80 (d, J=7.78 Hz, 2H), 7.64-7.58 (m, 1H), 7.56-7.50 (m, 1H), 7.48-7.30 (m, 5H), 5.60-5.54 (m, 1H), 3.25 (br. s., 3H), 2.90-2.67 (m, 4H), 2.00 (br. s., 6H), 1.91-1.71 (m, 4H), 1.28 (br. s., 3H), 0.95-0.79 (m, 2H). Compound 255 (B1)/compound 256 (B2): $^1$HNMR (400 MHz, CHLOROFORM-d): δ 8.65-8.58 (m, 1H), 8.55-8.47 (m, 1H), 7.96-7.85 (m, 3H), 7.71-7.64 (m, 1H), 7.63-7.58 (m, 1H), 7.53-7.64 (m, 1H), 7.37-7.30 (m, 1H), 7.11 (br. s., 2H), 6.91 (d, J=3.01 Hz, 3H), 5.81-5.77 (m, 1H), 4.09 (s, 3H), 2.90 (br. s., 2H), 2.77 (br. s., 2H), 2.61-2.46 (m, 2H), 2.08-1.90 (m, 10H). LCMS (ESI) m/z: 527.2 (M+1).

Example 43

4-(dimethylamino)-1-(2-methoxy-5-(pyrrolidin-1-yl)pyridin-3-yl)-2-(naphthalen-1-yl)-1-phenylbutan-2-ol

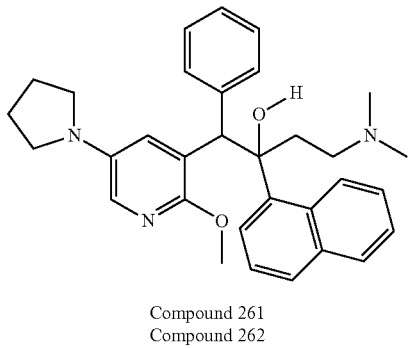 [SMILES: COc1ncc(N2CCCC2)cc1C(c1ccccc1)C(O)(CCN(C)C)c1cccc2ccccc12]

Compound 261
Compound 262

Step 1: (5-(4-(dimethylamino)-2-hydroxyl-2-(naphthalen-1-yl)-1-phenylbutyl)-6-methoxypyridin-3-yl)boronic acid

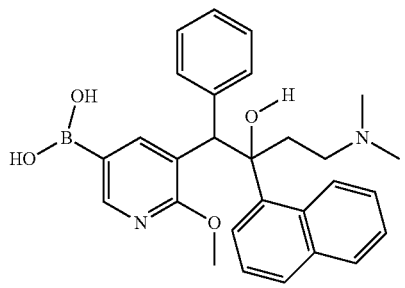 [SMILES: COc1ncc(B(O)O)cc1C(c1ccccc1)C(O)(CCN(C)C)c1cccc2ccccc12]

Intermediate B (700.00 mg, 1.27 mmol) was dissolved in 50 mL of acetone and sodium periodate (897 mg, 4.19 mmol) was added at 10-20° C. Then the mixture was stirred at this temperature for 36 h. LCMS showed the starting material was completely consumed. The reaction liquid was concentrated at 45° C. and then poured into 50 mL of water. The mixture was extracted with ethyl acetate (100 mL×3). The combined organic phase was washed with saturated brine (100 mL×2), dried over anhydrous sodium sulfate, filtered and concentrated to give (5-(4-(dimethylamino)-2-hydroxyl-2-(naphthalen-1-yl)-1-phenylbutyl)-6-methoxy-pyridin-3-yl)boronic acid (480.00 mg, 80.51% yield) as a tan solid. LCMS (ESI) m/z: 471.2 (M+1).

Step 2: 4-(dimethylamino)-1-(2-methoxy-5-(pyrrolidin-1-yl)pyridin-3-yl)-2-(naphthalen-1-yl)-1-phenylbutan-2-ol

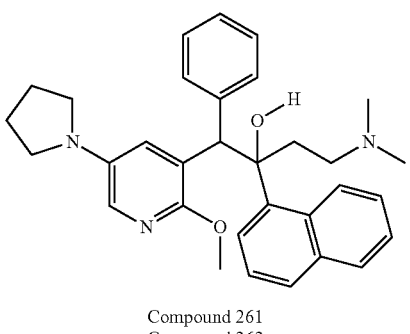

Compound 261
Compound 262

Under oxygen, (5-(4-(dimethylamino)-2-hydroxyl-2-(naphthalen-1-yl)-1-phenylbutyl)-6-methoxy pyridin-3-yl) boronic acid (200.00 mg, 425.2 umol), copper acetate (155 mg, 0.851 mmol), triethylamine (150 mg, 1.48 mmol) and 4 A molecular sieves (1 g) were dissolved in 8 mL of acetonitrile and stirred at 10-20° C. for 12 h. The reaction liquid was filtered and the filtrate was concentrated to give crude product which was separated and purified by preparative HPLC (GX-G; Phenomenex Synergi C18 150*30 mm*4 um; acetonitrile 30%-60%; water (0.225% formic acid); 25 mL/min) to give compound 261 (A) (2.7 mg, 1.3% yield) and compound 262 (B) (2.8 mg, 1.3% yield) as white solid. Compound 261 (A): $^1$H NMR (400 MHz, METHANOL-$d_4$): δ 8.56 (d, J=9.3 Hz, 1H), 8.08 (d, J=7.3 Hz, 1H), 7.88-7.72 (m, 4H), 7.71-7.57 (m, 2H), 7.51-7.42 (m, 1H), 7.36 (q, J=7.5 Hz, 4H), 7.32-7.24 (m, 1H), 6.92 (d, J=2.8 Hz, 1H), 5.61 (s, 1H), 3.23 (s, 2H), 3.13 (d, J=5.6 Hz, 2H), 2.71 (s, 1H), 2.46-2.11 (m, 9H), 2.00 (br. s., 4H). Compound 262 (B): $^1$H NMR (400 MHz, METHANOL-$d_4$): δ 8.56 (d, J=9.0 Hz, 1H), 8.09 (d, J=7.2 Hz, 1H), 7.87-7.72 (m, 4H), 7.68 (d, J=8.2 Hz, 1H), 7.59 (t, J=7.2 Hz, 1H), 7.45 (m, 1H), 7.36 (m, 3H), 7.30-7.24 (m, 1H), 6.92 (d, J=2.8 Hz, 1H), 5.61 (s, 1H), 3.22 (s, 2H), 3.13 (d, J=5.3 Hz, 2H), 2.75 (d, J=13.9 Hz, 1H), 2.40-2.11 (m, 9H), 2.00 (br. s., 4H). LCMS (ESI)m/z: 496.3 (M+1).

Example 44

4-(dimethylamino)-1-(2-methoxy-5-prop-1-ynyl-3-pyridyl)-2-(1-naphthyl)-1-phenylbutan-2-ol

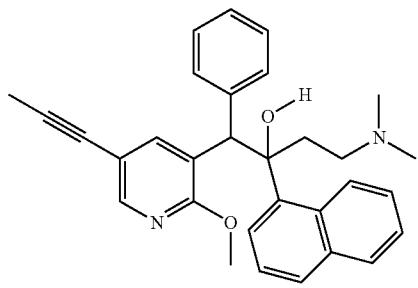

Compound 263 (A1)
Compound 264 (A2)
Compound 265 (B1)
Compound 266 (B2)

Step 1: Tributyl(prop-1-yn-1-yl)stannane

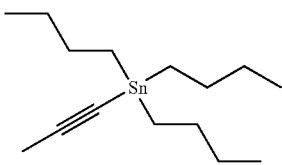 [SMILES: CC#[C][Sn]([CH2]CCC)([CH2]CCC)[CH2]CCC]

Under argon, trimethyl(prop-1-yn-1-yl)silane (2.00 g, 17.82 mmol), 1,1,1,3,3,3-hexabutyldistannoxane (5.26 g, 8.82 mmol) and 40 mL of tetrahydrofuran were charged into a dried and sealed tank. Tetrabutylammonium fluoride (360 mL, 360.00 mmol, dissolved in tetrahydrofuran, concentration of 1 mol/L) was added and the tank was sealed. The mixture was stirred at 60° C. for 2.5 h. The volatile material was removed to give tributyl(prop-1-ynyl)stannane (3.5 g, crude product) as a colorless oil which was used directly in the next step without further purification.

Step 2: 4-(dimethylamino)-1-(2-methoxy-5-prop-1-ynyl-3-pyridyl)-2-(1-naphthyl)-1-phenylbutan-2-ol

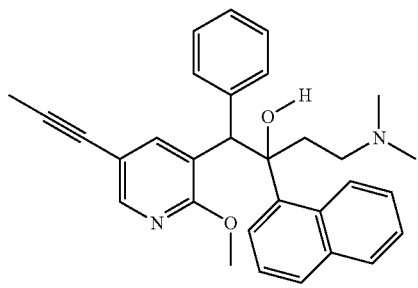

Compound 263 (A1)
Compound 264 (A2)
Compound 265 (B1)
Compound 266 (B2)

Under nitrogen, intermediate A (1.20 g, 2.37 mmol) and tributyl (prop-1-ynyl)stannane (3.5 g, crude product) were dissolved in 40 mL of N,N-dimethyl formamide and a catalytic amount of Pd(dppf)Cl$_2$ (200 mg, cat.) was added to the mixed liquid in one portion at 15-35° C. The reaction mixture was stirred at 80° C. for 10 minutes. LCMS showed the reaction was complete. The reaction mixture was cooled to 15-35° C. and the reaction was quenched with 100 mL of saturated potassium fluoride solution and stirred for 20 minutes. The aqueous phase was extracted with ethyl acetate (50 mL×3) and the combined organic phase was washed with saturated brine (50 mL×2), dried over anhydrous sodium sulfate and then filtered. The filtrate was concentrated, isolated and purified by column chromatography (eluent: petroleum ether/ethyl acetate=20/1-1/1) to give crude product which was then separated and purified by preparative HPLC (GX-G; Phenomenex Synergi C18 150*30 mm*4 um; acetonitrile 25%-55%; water (0.223% FA); 25 mL/min) to give component A and component B. Component A was separated by chiral SFC (SFC 80; AD-3 um; supercritical CO$_2$/i-PrOH (0.05% DEA)=60/40; 55 mL/min; 220 nm) to give compound 263 (A1) (41.70 mg, 3.79% yield) and compound 264 (A2) (92.80 mg, 8.43% yield) as white solid. Component B was separated by chiral SFC (SFC 80; AD-3 um; supercritical CO$_2$/i-PrOH (0.05% diethylamine)=60/40; 55 mL/min; 220 nm) to give compound 265 (B1) (62.20 mg, 5.65% yield) and compound 266 (B2) (55.20 mg, 5.02% yield) as white solid. Compound 263 (A1)/compound 264 (A2): $^1$H NMR (400 MHz, DMSO-d$_6$): δ 8.56 (d, J=8.00 Hz, 1H), 8.17 (d, J=4.00 Hz, 2H), 7.95-7.89 (m, 2H), 7.73-7.66 (m, 3H), 7.50 (t, J=8.00 Hz, 1H), 7.36 (t, J=8.00 Hz, 1H), 7.18-7.16 (m, 2H), 6.89 (br. s., 3H), 5.66 (s, 1H), 4.10 (s, 3H) 2.06 (s, 3H), 1.93-1.82 (m, 10H). Compound 265 (B1)/compound 266 (B2): $^1$H NMR (400 MHz, DMSO-d$_6$): δ 8.54 (d, J=12.0 Hz, 1H), 8.24 (d, J=4.00 Hz, 1H), 7.89 (d, J=8.00 Hz, 2H), 7.77 (d, J=8.00 Hz, 2H), 7.71-7.68 (m, 2H), 7.61 (t, J=8.00 Hz, 1H), 7.48 (t, J=8.00 Hz, 1H), 7.40-7.35 (m, 3H) 7.28 (t, J=8.00 Hz, 1H), 5.51 (s, 1H), 3.08 (s, 3H), 2.03 (s, 3H), 1.96-1.86 (m, 10H). LCMS (ESI) m/z: 465.2 (M+1).

Example 45

1-(5-(5-bromothiophen-3-yl)-2-methoxypyridin-3-yl)-4-(dimethylamino)-2-(naphthalen-1-yl)-1-phenylbutan-2-ol

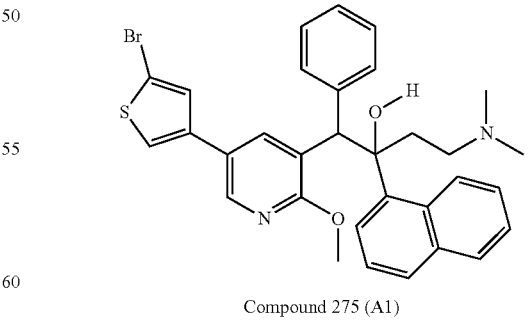

Compound 275 (A1)
Compound 276 (A2)
Compound 277 (B1)
Compound 278 (B2)

Under nitrogen, 4-(dimethylamino)-1-(2-methoxy-5-(4,4,5,5-tetramethyl-1,3,2-dioxaborolane-2-yl)pyridin-3-yl)-2-

(naphthalen-1-yl)-1-phenylbutan-2-ol(crude product, 1.0 g, 1.81 mmol) and 2,4-dibromo-thiophene (0.438 g, 1.81 mmol) were dissolved in 20 mL of 1,4-dioxane and 4 mL of water. Potassium carbonate (250 mg, 1.81 mmol) and tetrakis triphenylphosphine palladium (210 mg, 0.181 mmol) were added. The reaction mixture was stirred at 80-90° C. for 12 h. LCMS showed the reaction was complete. 20 mL of water was added to the reaction mixture. The aqueous phase was extracted with ethyl acetate (400 mL×3). The combined organic phase was washed with 20 mL of saturated brine once, dried over anhydrous sodium sulfate and concentrated to give 300 mg of crude product which was separated and purified by preparative HPLC (GX-D; Boston Symmetrix C18 ODS-R 150*30 mm*5 um; mobile phase: acetonitrile: 34%-58%; water (+0.225% formic acid); flow rate: 25 ml/min; detection wavelength: 220 nm/254 nm) to give component A and component B. Component A was separated by chiral SFC (IC-10 um; supercritical $CO_2$/MeOH (0.1% aqueous ammonia)=60/40; 70 ml/min; 220 nm) to give compound 275 (A1) (62.53 mg, 6.01% yield) and compound 276 (A2) (49.88 mg, 5.14% yield) as white solid. Component B was separated by chiral SFC (AD-10 um; supercritical $CO_2$/EtOH (0.1% aqueous ammonia)=30/70; 60 ml/min; 220 nm) to give compound 277 (B1) (53.54 mg, 5.1% yield) and compound 278 (B2) (68.19 mg, 6.55% yield) as white solid. Compound 275 (A1)/compound 276 (A2): $^1$H NMR (400 MHz, METHANOL-$d_4$): δ 8.66 (br. s., 1H), 8.47 (s, 1H), 8.39 (d, J=2.3 Hz, 1H), 7.92 (d, J=8.2 Hz, 1H), 7.83-7.65 (m, 3H), 7.59-7.50 (m, 1H), 7.43 (d, J=1.3 Hz, 1H), 7.38-7.27 (m, 2H), 7.07 (br. s., 2H), 6.95-6.85 (m, 3H), 5.84 (br. s., 1H), 4.16 (s, 3H), 3.13-2.93 (m, 1H), 2.76 (hr. s., 1H), 2.43 (s, 6H), 2.28-2.11 (m, 2H). Compound 277 (B1)/compound 278 (B2): $^1$H NMR (400 MHz, METHANOL-$d_4$): δ 8.64-8.48 (m, 1H), 8.10 (d, J=6.7 Hz, 1H), 7.90-7.72 (m, 4H), 7.69-7.59 (m, 2H), 7.45 (t, J=7.5 Hz, 1H), 7.42-7.32 (m, 5H), 7.29 (d, J=7.3 Hz, 1H), 7.12 (d, J=1.3 Hz, 1H), 5.65 (s, 1H), 3.31 (s, 3H), 2.78-2.65 (m, 1H), 2.30-2.20 (m, 2H), 2.12-2.07 (m, 6H), 2.01-1.93 (m, 1H). LCMS (ESI) m/z: 587.1 (M+1).

Example 46

4-(dimethylamino)-1-(2-methoxy-5-(4-(trifluoromethyl)phenyl)pyridin-3-yl)-2-(naphthalen-1-yl)-1-phenylbutan-2-ol

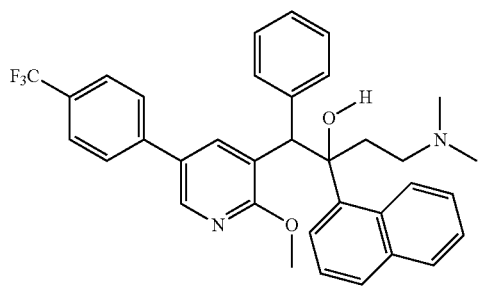

Compound 283 (A1)
Compound 284 (A2)
Compound 285 (B1)
Compound 286 (B2)

According to the method of Example 2, intermediate B and 1-bromo-4-(trifluoromethyl)benzene were used to prepare crude product which was separated by preparative HPLC (HPLC-D; SYNERGI-C 200*50 10 um; acetonitrile 25%-55%; water (0.225% formic acid); 80 mL/min) to give component A and component B. Component A was separated by chiral SFC (Chiralpak IC 250×30 mm I.D., 10 um; supercritical $CO_2$/MeOH (0.1% aqueous ammonia)=50/50; 70 ml/min; 220 nm) to give compound 283 (A1) (135.24 mg, 8.72% yield) and compound 284 (A2) (85 mg, 5.48% yield). Component B was separated by chiral SFC (Chiralpak AD 250×30 mm I.D., 5 um; supercritical $CO_2$/MeOH (0.1% aqueous ammonia)=60/40; 70 ml/min; 220 nm) to give compound 285 (B1) (39.61 mg, 2.56% yield) and compound 286 (B2) (22.15 mg, 1.43% yield). Compound 283 (A1)/compound 284 (A2): $^1$H NMR (400 MHz, CHLOROFORM-d): δ 8.60-8.54 (m, 1H), 8.51-8.45 (m, 1H), 8.17-8.12 (m, 1H), 7.93-7.87 (m, 1H), 7.84-7.80 (m, 2H), 7.71-7.63 (m, 3H), 7.61-7.51 (m, 3H), 7.50-7.30 (m, 6H), 5.67-5.63 (m, 1H), 3.31 (s, 3H), 2.78-2.71 (m, 1H), 2.65-2.54 (m, 2H), 2.40-2.29 (m, 3H), 2.22 (s, 6H), 2.01 (dd, J=5.6, 12.4 Hz, 1H). Compound 285 (B1)/compound 286 (B2): $^1$HNMR (400 MHz, METHANOL-$d_4$): δ 8.87 (s, 1H), 8.64 (d, J=6.4 Hz, 1H), 8.37 (s, 1H), 7.94 (d, J=6.4 Hz, 1H), 7.88 (d, J=6.4 Hz, 1H), 7.80-7.59 (m, 5H), 7.53 (t, J=6.4 Hz, 1H), 7.33-7.25 (m, 3H), 7.24-7.11 (m, 2H), 6.95-6.83 (m, 2H), 5.85 (m, 1H), 4.18 (s, 3H), 2.67-2.53 (m, 1H), 2.25-1.95 (m, 9H). LCMS (ESI) m/z: 571.2 (M+1).

Example 47

4-(dimethylamino)-1-(2-methoxy-5-(4-methoxyphenyl)pyridin-3-yl)-2-(naphthalen-1-yl)-1-phenylbutan-2-ol

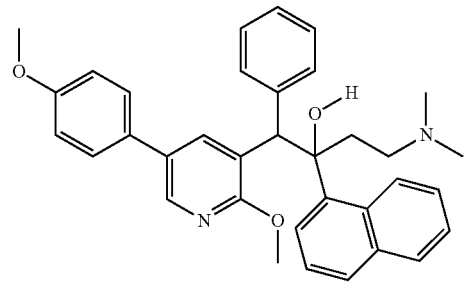

Compound 299 (A1)
Compound 300 (A2)
Compound 301 (B1)
Compound 302 (B2)

Under nitrogen, intermediate A, 2-(4-methoxyphenyl)-4,4,5,5-tetramethyl-1,3,2-dioxaborolane (278 mg, 1.19 mmol), Pd(dppf)Cl$_2$ (87 mg, 120 umol) and sodium carbonate (378 mg, 3.57 mmol) were dissolved in 8 mL of 1,4-dioxane and 1 mL of water, heated to 80° C. and stirred for 5 h. LCMS showed that the reaction was complete. 20 mL of water was added to the reaction liquid. The mixture was extracted with ethyl acetate (30 mL×3). The combined organic phase was dried over anhydrous sodium sulfate, concentrated and separated by preparative HPLC (GX-G; Phenomenex Synergi C18 150×30 mm×4 um; acetonitrile 27%-57%; water (0.225% formic acid); 25 mL/min) to give component A and component B. Component A was separated by chiral SFC (Column IC-10 um; supercritical $CO_2$/MeOH (0.2% aqueous ammonia)=50/50; 70 mL/min; 220 nm) to give compound 299 (A1) (64.64 mg, 10.22% yield) and compound 300 (A2) (76.11 mg, 12.04% yield). Component B was separated by chiral SFC (Column AD-10 um; supercritical CO$_2$/Isopropanol (0.1% aqueous ammonia) =50/50; 70 mL/min; 220 nm) to give compound 301 (B1) (70.65 mg, 11.17% yield) and compound 302 (B2) (74.00 mg, 11.70% yield). Compound 299 (A1)/compound 300 (A2): $^1$H NMR (400 MHz, DMSO-d$_6$): δ 8.63-8.53 (m, 2H), 8.35 (br. s., 1H), 7.96-7.89 (m, 2H), 7.73-7.68 (m, 2H), 7.58-7.51 (m, 3H), 7.35 (t, J=7.7 Hz, 1H), 7.19 (d, J=6.0 Hz, 2H), 7.08 (d, J=8.5 Hz, 2H), 6.92-6.84 (m, 3H), 5.74 (br. s., 1H), 4.11 (br. s., 3H), 3.81 (s, 3H), 1.99-1.80 (m, 10H). Compound 301 (B1) and compound 302 (B2): $^1$H NMR (400 MHz, DMSO-d$_6$): δ 8.61-8.48 (m, 2H), 8.18-8.10 (m, 1H), 7.88-7.83 (m, 2H), 7.77-7.72 (m, 2H), 7.71-7.64 (m, 2H), 7.43-7.33 (m, 6H), 7.27-7.23 (m, 1H), 7.07-7.02 (m, 2H), 5.58 (s, 1H), 3.81 (s, 3H), 3.29 (s, 3H), 2.13-1.88 (m, 10H). LCMS (ESI) m/z=533.3 (M+1).

Example 48

1-(5-(4-bromo-3-fluorophenyl)-2-methoxypyridin-3-yl)-4-(dimethylamino)-2-(naphthalen-1-yl)-1-phenylbutan-2-ol

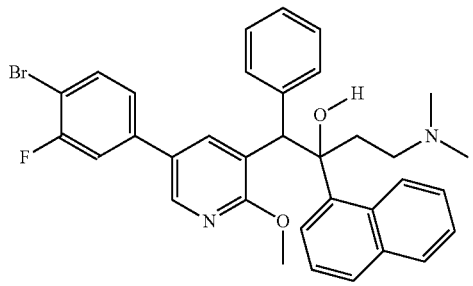

Compound 331 (A1)
Compound 332 (A2)
Compound 333 (B1)
Compound 334 (B2)

According to the method of Example 2, intermediate B and 1-bromo-2-fluoro-4-iodo-benzene were used to prepare crude product which was separated by preparative HPLC (GX-G; Phenomenex Synergi C18 150*30 mm*4 um; acetonitrile 15%-60%; water (0.225% formic acid); 25 mL/min) to give component A and component B. Component A was separated by chiral SFC (Berger MultiGram™ SFC, Mettler Toledo Co, Ltd, IC-10 um; supercritical CO$_2$/MeOH (0.05% aqueous ammonia)=60/40; 70 ml/min; 220 nm) to give compound 331 (A1) (31.07 mg, 1.91% yield) and compound 332 (A2) (31.42 mg, 1.93% yield). Component B was separated by chiral SFC (sfc 80, AD-10 um; supercritical CO$_2$/EtOH (0.05% aqueous ammonia)=60/40; 70 ml/min; 220 nm) to give compound 333 (B1) (25.57 mg, 1.57% yield) and compound 334 (B2) (56.93 mg, 3.5% yield). Compound 331 (A1)/compound 332 (A2): $^1$H NMR (400 MHz, methanol-d$_4$): δ 8.76-8.60 (m, 1H), 8.37 (d, J=2.26 Hz, 1H), 7.88 (d, J=8.28 Hz, 2H), 7.79-7.59 (m, 3H), 7.49 (d, J=10.29 Hz, 2H), 7.39 (d, J=8.03 Hz, 1H), 7.30 (t, J=7.78 Hz, 1H), 7.18 (br. s., 2H), 6.81-6.96 (m, 3H), 5.84 (br. s., 1H), 4.18 (s, 3H), 2.86-2.66 (m, 1H), 1.83-2.36 (m, 10H). Compound 333 (B1)/compound 334 (B2): $^1$H NMR (400 MHz, methanol-d$_4$): δ 8.64-8.51 (m, 2H), 8.12 (d, J=7.28 Hz, 1H), 7.93-7.55 (m, 8H), 7.51-7.10 (m, 8H), 5.69 (s, 1H), 3.34 (br. s., 3H), 2.72 (d, J=12.80 Hz, 1H), 2.38-1.91 (m, 10H). LCMS (ESI) m/z: 549.1 (M+1).

Example 49

1-(5-(4-chloro-3-fluorophenyl)-2-methoxypyridin-3-yl)-4-(dimethylamino)-2-(naphthalen-1-yl)-1-phenylbutan-2-ol

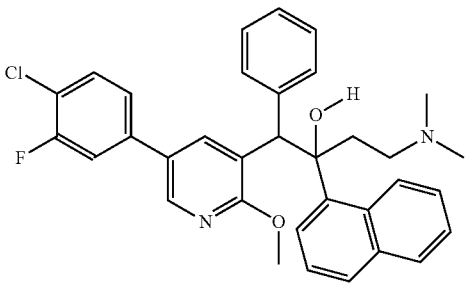

Compound 303 (A1)
Compound 304 (A2)
Compound 305 (B1)
Compound 306 (B2)

According to the method of Example 1, intermediate A and 2-(4-chloro-3-fluorophenyl)-4,4,5,5-tetramethyl-1,3,2-dioxaborolane were used to prepare crude product which was separated by preparative HPLC (GX-G; Phenomenex Synergi C18 150×30 mm×4 um; acetonitrile 30%-60%; water (0.225% formic acid); 25 mL/min) to give component A and component B. Component A was separated by chiral SFC (Column IC-10 um; supercritical CO$_2$/MeOH (0.05% aqueous ammonia)=60/40; 70 mL/min; 220 nm) to give compound 303 (A1) (61.40 mg, 5.16% yield) and compound 304 (A2) (59.83 mg, 5.45% yield). Component B was separated by chiral SFC (Column AD-10 um; supercritical CO$_2$/EtOH (0.2% aqueous ammonia)—75/25; 60 mL/min; 220 nm) to give compound 305 (B1) (56.3 mg, 5.13% yield) and compound 306 (B2) (73.17 mg, 6.66% yield). Compound 303 (A1)/compound 304 (A2): $^1$H NMR (400 MHz, METHANOL-d$_4$): δ 8.76-8.60 (m, 2H), 8.35 (d, J=2.0 Hz, 1H), 7.97-7.84 (m, 2H), 7.68-7.43 (m, 6H), 7.30 (t, J=7.8 Hz, 1H), 7.22-7.16 (m, 2H), 6.90-6.84 (m, 3H), 5.84 (br. s., 1H), 4.18 (s, 3H), 2.80-2.68 (m, 1H), 2.19-2.02 (m, 8H), 1.94-1.84 (m, 1H) 2.55-2.64 (m, 1H) 2.29 (s, 7H) 2.08-2.17 (m, 1H). Compound 305 (B1)/compound 306 (B2): $^1$H NMR (400 MHz, METHANOL-d$_4$): δ 8.61-8.54 (m, 2H), 8.15-8.09 (m, 1H), 7.87-7.77 (m, 4H), 7.68-7.54 (m, 3H), 7.46 (t, J=7.4 Hz, 1H), 7.40-7.26 (m, 6H), 5.69 (s, 1H), 3.31 (m, 3H), 2.72-2.64 (m, 1H), 2.30-2.19 (m, 2H), 2.04 (s, 6H), 1.98-1.90 (m, 1H). LCMS (ESI) m/z=555.2 (M+1).

Example 50

4-(dimethylamino)-1-[2-methoxy-5-(2-phenylethynyl)-3-pyridyl]-2-(1-naphthyl)-1-phenyl-butan-2-ol

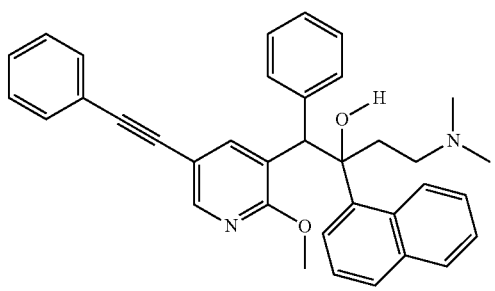

Compound 335 (A1)
Compound 336 (A2)
Compound 337 (B1)
Compound 338 (B2)

Step 1: tributyl (2-phenylethynyl)tin

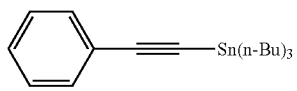

Under nitrogen, phenylacetylene (2.00 g, 19.58 mmol) was dissolved in anhydrous tetrahydrofuran (50 mL) and lithium hexamethyldisilazide (4.26 g, 25.45 mmol) was added slowly at −78° C. and stirred for another 1 hour. Tributyltin chloride (8.29 g, 25.45 mmol) was added to the reaction liquid and warmed to 20° C. and stirred for another 2 h. The reaction was quenched with 30 mL of aqueous ammonium chloride solution and the mixture was extracted with ethyl acetate (30 mL×3). The combined organic phase was washed with saturated brine (15 mL×2), dried over anhydrous sodium sulfate and concentrated to give tributyl (2-phenylethynyl)tin (7.02 g, yield: 91.65%) as a pale yellow liquid which was used directly in next step without purification.

Step 2: 4-(dimethylamino)-1-[2-methoxy-5-(2-phenylethynyl)-3-pyridyl]-2-(1-naphthyl)-1-phenyl-butan-2-ol

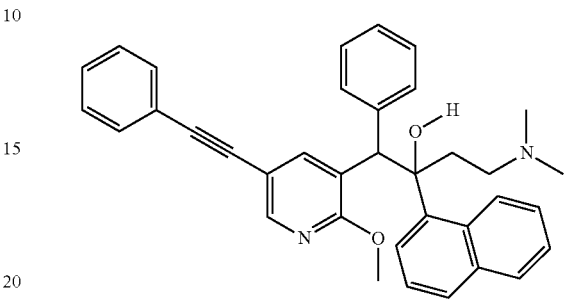

Compound 335 (A1)
Compound 336 (A2)
Compound 337 (B1)
Compound 338 (B2)

Under nitrogen, intermediate A, tributyl (2-phenylethynyl)tin (929.44 mg, 2.38 mmol) and Pd(dppf)Cl$_2$ (138.98 mg, 198.00 umol) were dissolved in 10 mL of N,N-dimethyl formamide, stirred at 15-35° C. for 10 minutes and then heated to 100° C. and stirred for 3 h. The reaction liquid was concentrated and separated by preparative HPLC (GX-D; Boston Symmetrix C18 ODS-R 150*30 mm*5 um; acetonitrile 35%-55%; water (0.225% formic acid); 25 mL/min) to give component A and component B. Component A was separated by chiral SFC (Berger MultiGram™ SFC, Mettler Toledo Co, Ltd, IC-10 um; supercritical CO$_2$/i-prOH (0.05% aqueous ammonia)=70/30; 60 g/min; 220 nm) to give compound 335 (A1) (37.69 mg, 3.8% yield) and compound 336 (A2) (35.85 mg, 3.6% yield). Component B was separated by chiral SFC (Berger MultiGram™ SFC, Mettler Toledo Co, Ltd, IC-10 um; supercritical CO$_2$/MeOH (0.05% aqueous ammonia)=50/50; 70 ml/min; 220 nm) to give compound 337 (B1) (74.95 mg, 7.5% yield) and compound 338 (B2) (21.14 mg, 2.1% yield). Compound 335 (A1)/compound 336 (A2): $^1$H NMR (400 MHz, methanol-d$_4$): δ 8.57 (d, J=9.16 Hz, 1H), 8.40 (s, 1H), 7.99 (d, J=7.03 Hz, 1H), 7.93-7.75 (m, 4H), 7.74-7.58 (m, 2H), 7.57-7.24 (m, 11H), 5.66 (s, 1H), 3.18 (s, 3H), 2.84-2.69 (m, 1H), 2.43-2.24 (m, 2H), 2.15 (br. s., 6H), 2.07-1.93 (m, 1H). Compound 337 (B1)/compound 338 (B2): $^1$H NMR (400 MHz, methanol-d$_4$): δ 8.64 (d, J=7.65 Hz, 1H), 8.54 (d, J=1.88 Hz, 1H), 8.26 (d, J=2.01 Hz, 1H), 8.01-7.78 (m, 2H), 7.67 (d, J=8.16 Hz, 2H), 7.56 (dd, J=7.47, 2.07 Hz, 2H), 7.53-7.44 (m, 1H), 7.45-7.35 (m, 3H), 7.30 (t, J=7.78 Hz, 1H), 7.17 (br. s., 2H), 6.98-6.80 (m, 3H), 5.79 (br. s., 1H), 4.17 (s, 3H), 2.81-2.62 (m, 1H), 2.15-2.01 (m, 8H), 1.89 (d, J=10.42 Hz, 1H). LCMS (ESI) m/z: 527.2 (M+1).

Example 51

1-(5-(3,4-difluorophenyl)-2-methoxypyridine-3-yl)-4-(dimethoxyamino)-2-(naphthalen-1-yl)-1-phenylbutan-2-ol)

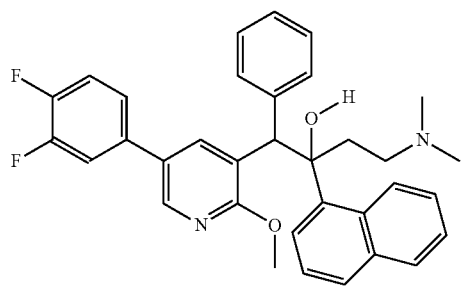

Compound 347 (A1)
Compound 348 (A2)
Compound 349 (B1)
Compound 350 (B2)

According to the method of Example 1, intermediate A and 2-(3,4-difluorophenyl)-4,4,5,5-tetramethyl-1,3,2-dioxyborate were used to prepare crude product which was separated by preparative HPLC (GX-G; Phenomenex Synergi C18 150×30 mm×4 um; acetonitrile 30%-60%; water (0.225% formic acid); 25 mL/min) to give component A and component B. Component A was separated by chiral SFC (Column IC-10 um; supercritical $CO_2$/MeOH (0.1% aqueous ammonia)=65/35; 70 mL/min; 220 nm) to give compound 347 (A1) (81.22 mg, 7.78% yield) and compound 348 (A2) (102.83 mg, 8.84% yield) as white solid. Component B was separated by chiral SFC (Column IC-10 um; supercritical $CO_2$/MeOH (0.1% aqueous ammonia)=40/60; 70 g/min; 220 nm) to give compound 349 (B1) (165.41 mg, 15.84% yield) and compound 350 (B2) (151.07 mg, 14.47% yield). Compound 347 (A1)/compound 348 (A2): $^1$H NMR (400 MHz, METHANOL-$d_4$): δ 8.67 (br. s., 2H), 8.32 (d, J=2.0 Hz, 1H), 7.97-7.85 (m, 2H), 7.71-7.62 (m, 2H), 7.56-7.47 (m, 2H), 7.43-7.36 (m, 2H), 7.30 (t, J=7.8 Hz, 1H), 7.23-7.15 (m, 2H), 6.91-6.85 (m, 3H), 5.84 (br. s., 1H), 4.18 (s, 3H), 2.82-2.70 (m, 1H), 2.26-2.17 (m, 1H), 2.12-2.03 (m, 7H), 1.96-1.87 (m, 1H). Compound 349 (B1)/compound 350 (B2): $^1$H NMR (400 MHz, METHANOL-$d_4$): δ 8.61-8.53 (m, 2H), 8.15-8.09 (m, 1H), 7.86-7.76 (m, 4H), 7.68-7.59 (m, 2H), 7.45 (t, J=7.4 Hz, 1H), 7.40-7.24 (m, 7H), 5.68 (s, 1H), 3.31 (s, 3H), 2.69-2.60 (m, 1H), 2.28-2.15 (m, 2H), 2.01 (s, 6H), 1.95-1.88 (m, 1H). LCMS (ESI) m/z=539.2 (M+1).

Example 52

4-(dimethylamino)-1-(2-methoxy-6-phenylpyridine-3-yl)-2-(naphthalen-1-yl)-1-phenylbutan-2-ol

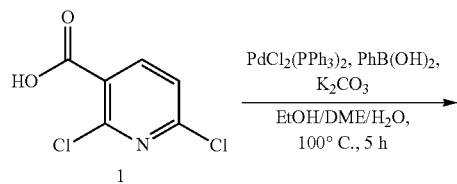

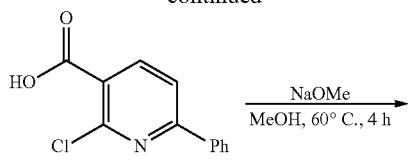

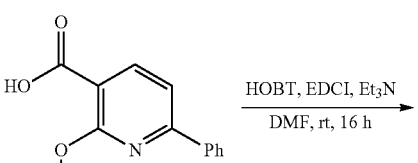

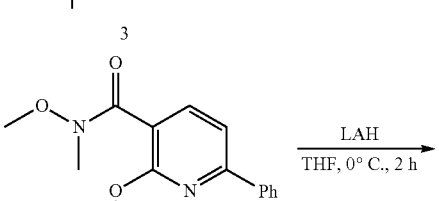

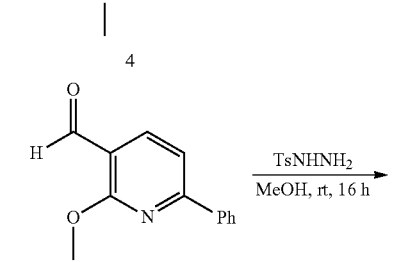

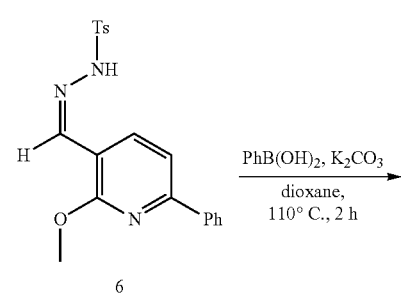

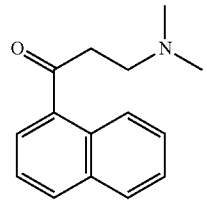

(8)

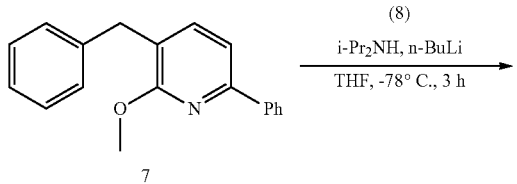

-continued

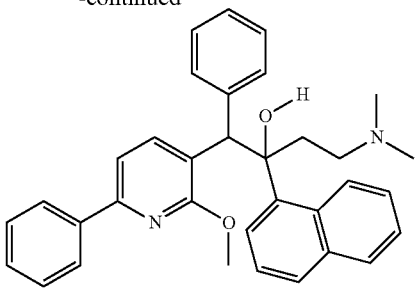

Compound 1 (A1)
Compound 2 (A2)
Compound 3 (B1)
Compound 4 (B2)

Step 1: 2-chloro-6-phenylnicotinic acid

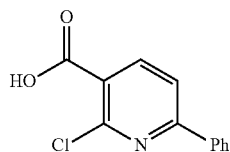 [SMILES: O=C(O)c1ccc(-c2ccccc2)nc1Cl]

2,6-dichloronicotinic acid (15.0 g, 0.0785 mol) was dissolved in 60 mL of ethanol, 20 mL of dimethyl ether and 10 mL of water. Potassium carbonate (32.0 g, 0.2355 mol), phenylboronic acid (11.5 g, 0.0942 mol), Pd(PPh$_3$)Cl$_2$ (2.75 g, 0.003925 mmol) were added and heated to 100° C. and stirred for 5 h. TLC (developing solvent:petroleum ether/ethyl acetate=1/3) showed that the reaction was complete. The reaction liquid was poured into 30 mL of water and extracted with ethyl acetate (50 mL×3). The combined organic phase was dried over anhydrous sodium sulfate, concentrated and isolated by column chromatography (eluent: petroleum ether/ethyl acetate=1/1) to give 2-chloro-6-phenylnicotinic acid (11.0 g, 60.14%) as a pale yellow solid. $^1$H NMR (400 MHz, CDCl$_3$) δ 8.44 (d, J=8.0 Hz, 1H), 8.12-8.10 (m, 2H), 7.81 (d, J=8.0 Hz, 1H), 7.56-7.52 (m, 3H). LCMS (ESI) M/Z 234 (M+1).

Step 2: 2-methoxy-6-phenylnicotinic acid

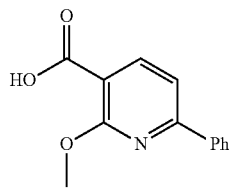 [SMILES: COc1nc(-c2ccccc2)ccc1C(=O)O]

2-chloro-6-phenylnicotinic acid (11.0 g, 47.2 mmol) was dissolved in 150 mL of methanol and sodium methoxide (25.5 g, 0.47 mol) was added. The mixture was heated to 60° C. and stirred for 12 h. TLC (developing solvent:dichloromethane/methanol=20/1) showed that the reaction was complete. The reaction liquid was quenched with 50 mL of water, and extracted with ethyl acetate (30 mL×5). The combined organic phase was washed with 50 mL of saturated brine, dried over anhydrous sodium sulfate and concentrated to give crude product which was used directly in the next step without purification. $^1$H NMR (400 MHz, CDCl$_3$) δ 8.44 (d, J=8.0 Hz, 1H), 8.12-8.10 (m, 2H), 7.69 (d, J=8.0 Hz, 1H), 7.56-7.52 (m, 3H), 4.04 (s, 3H).

Step 3: N,2-dimethoxy-N-methyl-6-phenylnicotinamide

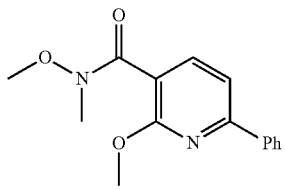 [SMILES: COc1nc(-c2ccccc2)ccc1C(=O)N(C)OC]

2-methoxy-6-phenylnicotinic acid (9.0 g, 0.0393 mol) was dissolved in 50 mL of N,N-dimethyl formamide, and 1-hydroxylbenzotriazole (6.367 g, 0.0472 mol), carbodiimide hydrochloride(6.372 g, 0.0472 mol), triethylamine(12.0 g, 0.1179 mol) and N,O-dimethylhydroxylamine hydrochloride (5.71 g, 0.0589 mol) were added and stirred at 25° C. for 12 h. TLC (developing solvent:dichloromethane/methanol=20/1) showed that the reaction was complete. The reaction liquid was poured into 30 mL of water and extracted with ethyl acetate (50 mL×3). The combined organic phase was washed with saturated brine (30 mL), dried over anhydrous sodium sulfate, concentrated and separated by silica gel column chromatography (eluent: dichloromethane/methanol=100/1) to give N,2-dimethoxy-N-methyl-6-phenylnicotinamide(10.0 g, 93.6%) as a pale yellow solid. LCMS (ESI) M/Z 278 (M+1).

Step 4: 2-methoxy-6-phenylnicotinaldehyde

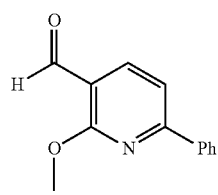

At 0° C., N,2-dimethoxy-N-methyl-6-phenylnicotinamide (500 mg, 1.83 mmol) was dissolved in 15 mL of anhydrous tetrahydrofuran and lithium aluminum tetrahydride (140 mg, 3.66 mmol) was added and warmed to 25° C. and stirred for 2 h. TLC (developing solvent:dichloromethane/methanol=20/1) showed that the reaction was complete. The reaction liquid was quenched with 10 mL of 10% aqueous sodium hydroxide solution. The aqueous phase was extracted with ethyl acetate (20 mL×3). The organic phase was washed with 20 mL of saturated brine, dried over anhydrous sodium sulfate, concentrated and isolated by column chromatography (eluent: petroleum ether/ethyl acetate=1/3) to give 2-methoxy-6-phenylnicotinaldehyde (190 mg, 48.7%) as a pale yellow solid.

Step 5: (Z)—N'-((2-methoxy-6-phenylpyridin-3-yl)methylene)-4-methyl benzene sulfonyl hydrazide

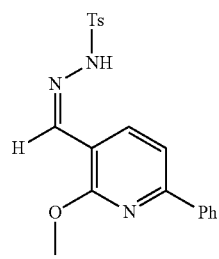 [SMILES: COc1nc(-c2ccccc2)ccc1/C=N\NS(=O)(=O)c1ccc(C)cc1]

2-methoxy-6-phenylnicotinaldehyde (50.0 mg, 0.235 mmol) was dissolved in 10 mL of ethanol and 4-methyl benzene sulfonyl hydrazide (43.0 mg, 0.282 mmol) was added and stirred at 25° C. for 2 h. TLC (developing solvent:dichloromethane/methanol=20/1) showed that the reaction was complete. The reaction liquid was poured into 10 mL of water and extracted with ethyl acetate (30 mL×3). The organic phase was washed with 20 mL of saturated brine, dried over anhydrous sodium sulfate and concentrated to give crude product which was used directly in the next step without purification.

Step 6: 3-benzyl-2-methoxy-6-phenylpyridine

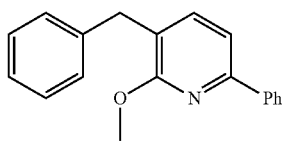 [SMILES: COc1nc(-c2ccccc2)ccc1Cc1ccccc1]

Under nitrogen, (Z)—N'-((2-methoxy-6-phenylpyridin-3-yl)methylene)-4-methyl benzene sulfonyl hydrazide (5.7 g, 45 mmol), phenylboronic acid (6.58 g, 54 mmol) and potassium carbonate (12.44 g, 45 mmol) were dissolved in 1,4-dioxane, heated to 80° C. and stirred for 2 h. The solvent was removed by rotary evaporation. The residue was isolated by column chromatography (eluent: petroleum ether/ethyl acetate=100/1-10/1) to give 3-benzyl-2-methoxy-6-phenylpyridine as a white solid.

Step 7: 4-(dimethylamino)-1-(2-methoxy-6-phenylpyridin-3-yl)-2-(naphthalen-1-yl)-1-phenylbutan-2-ol

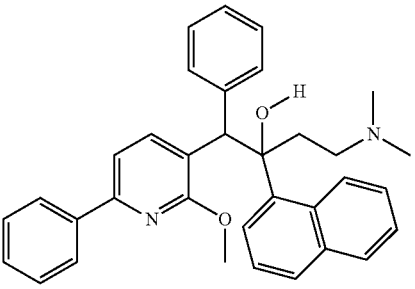

Compound 1 (A1)
Compound 2 (A2)
Compound 3 (B1)
Compound 4 (B2)

Under nitrogen, diisopropylamine (1.58 g, 15.6 mmol) was dissolved in 15 mL of tetrahydrofuran, and n-butyllithium (2.5 M n-hexane solution, 6.1 mL, 15.25 mmol) was slowly added at −70° C. and stirred for 5 minutes. A solution of 3-benzyl-2-methoxy-6-phenylpyridine (2.1 g, 7.6 mmol) in 10 mL of tetrahydrofuran was added and stirred at −70° C. for another 1 hour. 3-(dimethylamino)-1-phenylpropan-1-one (1.62 g, 9.12 mmol) was dissolved in 10 mL of tetrahydrofuran and then slowly added dropwise to the reaction liquid. Then the mixture was stirred at −70° C. for another 2 h. The reaction was quenched with saturated ammonium chloride solution (20 mL). The mixture was extracted with ethyl acetate (50 mL×3), dried over anhydrous sodium sulfate, concentrated and isolated by column chromatography (eluent: petroleum ether/ethyl acetate=30/1-5/1) to give 600 mg of crude product as a colorless liquid which was separated by preparative HPLC (GX-D; Boston Symmetrix C18 ODS-R 150*30 mm*5 um; acetonitrile 20%-54%; water (0.225% formic acid); 25 mL/min) to give component A and component B. Component A was separated by chiral SFC (Chiralpak AD 250×30 mm I.D., 5 um; supercritical CO$_2$/EtOH (0.2% NH$_3$.H$_2$O)=60/40; 80 ml/min; 220 nm) to give compound 1 (A1) (89.2 mg, 3.3% yield) and compound 2 (A2) (95.4 mg, 3.5% yield). Component B was separated by chiral SFC (Chiralpak AD 250×30 mm I.D., 5 um; supercritical CO$_2$/EtOH (0.2% NH$_3$.H$_2$O)=60/40; 80 ml/min; 220 nm) to give compound 3 (B1) (64.8 mg, 1.8% yield) and compound 4 (B2) (69.5 mg, 2.0% yield). Compound 1 (A1)/compound 2 (A2): $^1$H NMR (400 MHz, DMSO-d$_6$) δ 8.80-8.52 (m, 1H), 8.37 (d, J=7.91 Hz, 1H), 8.24-7.83 (m, 4H), 7.80-7.10 (m, 12H), 7.02-6.69 (m, 3H), 5.74 (br. s., 1H), 4.20 (s, 3H), 1.86 (br. s., 10H); compound 3 (B1)/compound 4 (B2): $^1$H NMR (400 MHz, DMSO-d$_6$) δ 8.58 (d, J=8.66 Hz, 1H), 8.46-8.24 (m, 1H), 8.03 (d, J=7.15 Hz, 1H), 7.92-7.57 (m, 6H), 7.53-7.11 (m, 7H), 5.60 (s, 1H), 3.31 (s, 3H), 2.20-1.69 (m, 10H). LCMS (ESI)m/z: 503 (M+1).

Example 53

4-(dimethylamino)-1-(2-methoxy-6-phenylpyridin-3-yl)-1,2-diphenylbutan-2-ol

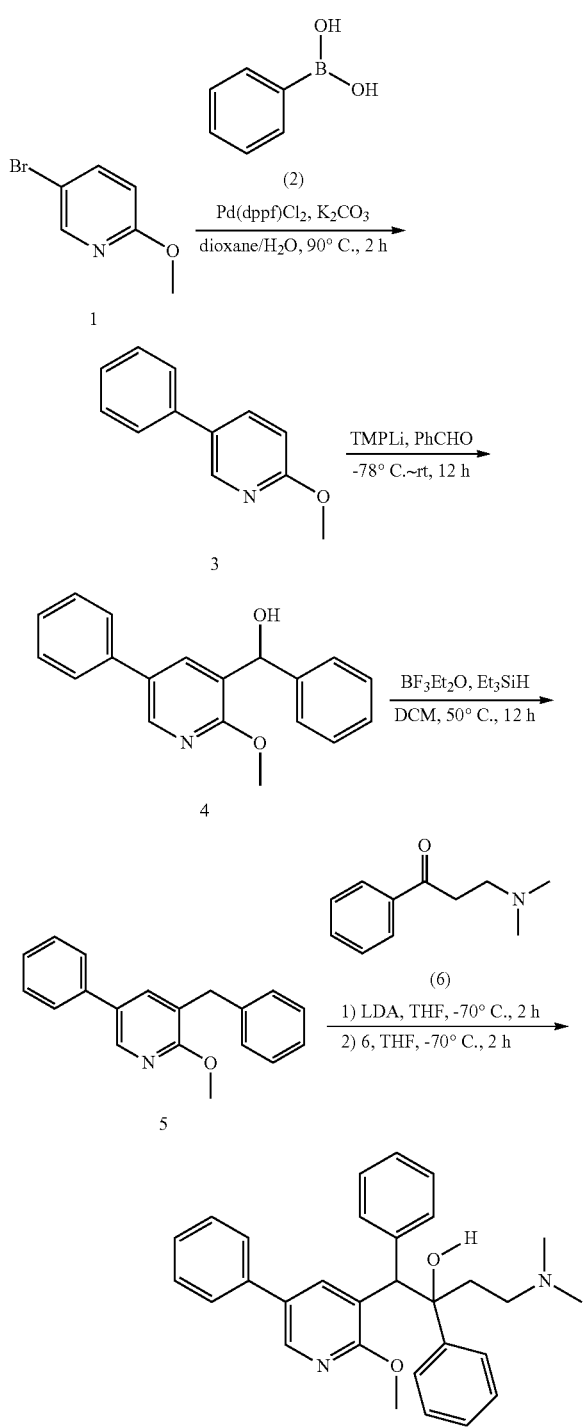

Compound 21 (A1)
Compound 22 (A2)
Compound 23 (B1)
Compound 24 (B2)

Step 1: 2-methoxy-5-phenylpyridine

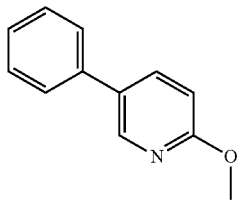

Under nitrogen, 5-bromo-2-methoxypyridine (25.0 g, 13.3 mmol), phenylboronic acid (16.8 g, 140 mmol), Pd(dppf)Cl$_2$ (4.5 g, 6.1 mmol) and potassium carbonate (55.0 g, 400 mmol) were mixed in 250 mL of 1,4-dioxane and 50 mL of water, heated to 90° C. and stirred for 12 h. TLC (developing solvent:petroleum ether/ethyl acetate=10/1) showed that the reaction was complete. The reaction liquid was concentrated and isolated by column chromatography (eluent: petroleum ether/ethyl acetate=30/1~10/1) to give 2-methoxy-5-phenylpyridine (21.0 g, 85.3%) as a yellow oil. LCMS (ESI) m/z: 186 (M+1).

Step 2: (2-methoxy-5-phenylpyridin-3-yl)(phenyl)methanol

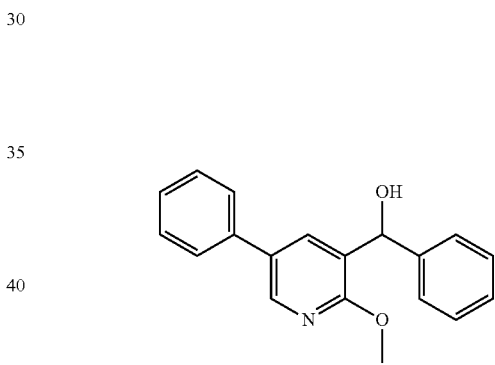

Under nitrogen, 2,2,6,6-tetramethylpyridine (22.9 g, 162 mmol) was dissolved in anhydrous tetrahydrofuran (400 mL), and n-butyllithium (2.5 M n-hexane solution, 100 mL, 37.5 mmol) was added slowly at −20° C. and stirred at room temperature for 10 minutes. 2-methoxy-5-phenylpyridine (20.0 g, 108 mmol) was dissolved in anhydrous tetrahydrofuran (100 mL) and then added to the reaction liquid and stirred for another 2 h. Benzaldehyde (13.7 g, 130 mmol) was dissolved in anhydrous tetrahydrofuran(100 mL) and then slowly added dropwise to the reaction liquid and stirred at room temperature for another 12 h. The reaction was quenched with aqueous ammonium chloride solution and the mixture was extracted with ethyl acetate (300 mL×3). The combined organic phase was dried over anhydrous sodium sulfate, concentrated and separated by silica gel column chromatography (eluent: petroleum ether/ethyl acetate=100/1-10/1) to give (2-methoxy-5-phenylpyridin-3-yl)(phenyl)methanol (20.0 g, 65%) as an off-white solid. LCMS (ESI) m/z: 292 (M+1).

Step 3: 3-benzyl-2-methoxy-5-phenylpyridine

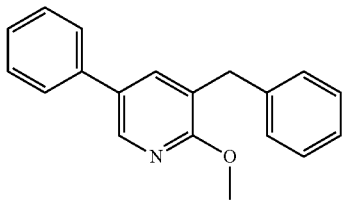 [SMILES: COc1ncc(-c2ccccc2)cc1Cc1ccccc1]

(2-methoxy-5-phenylpyridin-3-yl) (phenyl)methanol (20.0 g, 60 mmol), boron trifluoride diethyl ether (20 ml) and triethyl silicon hydride (20 ml) were dissolved in 200 mL of dichloromethane, heated to 50° C. and stirred for 12 h. TLC (developing solvent:petroleum ether/ethyl acetate=10/1) showed that the reaction was complete. The reaction liquid was cooled to room temperature, basified with potassium carbonate, and extracted with dichloromethane (200 mL×3). The combined organic phase was washed with saturated brine, dried over anhydrous sodium sulfate, concentrated and separated by silica gel column chromatography (eluent: petroleum ether/ethyl acetate=100/110/1) to give 3-benzyl-2-methoxy-5-phenylpyridine (18 g, 95%) an off-white solid. LCMS (ESI) m z: 276 (M+1).

Step 4: 4-(dimethylamino)-1-(2-methoxy-5-phenylpyridin-3-yl)-1,2-diphenylbutan-2-ol

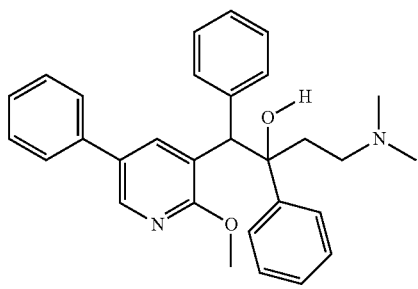

Compound 21 (A1)
Compound 22 (A2)
Compound 23 (B1)
Compound 24 (B2)

Under nitrogen, diisopropylamine (1.58 g, 15.6 mmol) was dissolved in 15 mL of tetrahydrofuran, n-butyllithium (2.5M n-hexane solution, 6.1 mL, 15.25 mmol) was added slowly at −70° C. and stirred for 5 minutes. 3-benzyl-2-methoxy-5-phenylpyridine (2.1 g, 7.6 mmol) was dissolved in 10 mL of tetrahydrofuran and added slowly dropwise to the reaction liquid. Then the mixture was stirred at −70° C. for 1 h. 3-(dimethylamino)-1-benzenepropan-1-one (2.1 g, 7.6 mmol) was dissolved in 10 mL of tetrahydrofuran and then added slowly dropwise to the reaction liquid. Then the mixture was stirred at −70° C. for another 2 h. At −70° C., the reaction was quenched with saturated ammonium chloride solution (20 mL) and the reaction mixture was extracted with ethyl acetate (50 mL×3). The combined organic phase was dried over anhydrous sodium sulfate, concentrated and isolated by column chromatography (developing solvent: petroleum ether/ethyl acetate=30/1-5/1) to give 600 mg of crude product as a colourless oil which was separated by preparative HPLC (GX-D; Boston Symmetrix C18 ODS-R 150*30 mm*5 um; acetonitrile 30%-54%; water (0.225% HCl); 25 mL/min) to give component A and component B. Component A was separated by chiral SFC (Chiralpak AD 250×30 mm I.D., 5 um; supercritical $CO_2$/EtOH (0.2% $NH_3.H_2O$)=60/40; 80 ml/min; 220 nm) to give compound 21 (A1) (64.8 mg, 1.8% yield) and compound 22 (A2) (83.3 mg, 2.4% yield). Component B was separated by chiral SFC (Chiralpak AD 250×30 mm I.D., 5 um; supercritical $CO_2$/EtOH (0.2% $NH_3.H_2O$)=60/40; 80 ml/min; 220 nm) to give compound 23 (B1) (64.4 mg, 1.8% yield) and compound 24 (B2) (69.5 mg, 2.0% yield). Compound 21 (A1)/compound 22 (A2): $^1H$ NMR (400 MHz, METHANOL-$d_4$) δ 8.67 (d, J=2.51 Hz, 1H), 8.54 (br. s., 1H), 8.28 (d, J=2.51 Hz, 1H), 7.59 (d, J=7.40 Hz, 2H), 7.53-7.42 (m, 4H), 7.41-7.33 (m, 1H), 7.32-7.19 (m, 4H), 7.17-7.07 (m, 1H), 7.05-6.90 (m, 3H), 4.97 (s, 1H), 4.06 (s, 3H), 2.53-2.38 (m, 1H), 2.18 (s, 6H), 2.14-2.05 (m, 3H); compound 23 (B1)/compound 24 (B2): $^1H$ NMR (400 MHz, METHANOL-$d_4$) δ 8.66 (d, J=2.38 Hz, 1H), 8.55 (br. s., 1H), 7.96 (d, J=2.38 Hz, 1H), 7.66 (d, J=7.28 Hz, 2H), 7.58 (d, J=7.40 Hz, 2H), 7.50-7.41 (m, 4H), 7.37-7.30 (m, 3H), 7.29-7.21 (m, 3H), 7.14-7.07 (m, 1H), 4.87 (s, 1H), 3.76 (s, 3H), 2.51-2.37 (m, 1H), 2.23-1.96 (m, 9H). LCMS (ESI) m/z: 453 (M+1).

Example 54

4-(dimethylamino)-2-(2-fluorophenyl)-1-(2-methoxy-5-phenylpyridin-3-yl)-1-phenylbutan-2-ol

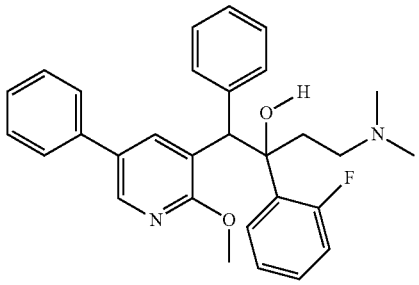

Compound 25 (A1)
Compound 26 (A2)
Compound 27 (B1)
Compound 28 (B2)

Step 1:
3-(dimethylamino)-1-(2-fluorophenyl)propan-1-one

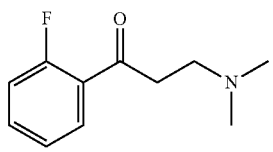

1-(2-fluorophenyl)ethanone (3.0 g, 21.7 mmol), dimethylamine hydrochloride (2.5 g, 30 mmol), paraformaldehyde (1.0 g, 32.6 mmol) and concentrated hydrochloric acid (0.1 mL) were dissolved in 20 mL of ethanol, heated to 80° C. to reflux and stirred for 12 h. The mixture was concentrated under reduced pressure, acidified with 3M hydrochloric acid, and washed with dichloromethane (15 mL×3). The aqueous phase was basified with saturated aqueous sodium carbonate solution and pH was adjusted to 10. Then the mixture was extracted with ethyl acetate (20 mL×3). The combined organic phase was dried over anhydrous sodium sulfate and concentrated to give crude product, 3-(dimethylamino)-1-(2-fluorophenyl)propan-1-one as a yellow oil which was used directly in the next step without purification.

Step 2: 4-(dimethylamino)-2-(2-fluorophenyl)-1-(2-methoxy-5-phenylpyridin-3-yl)-1-phenylbutan-2-ol

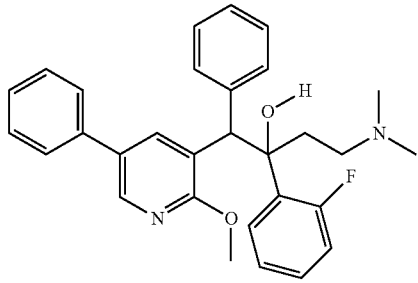

Compound 25 (A1)
Compound 26 (A2)
Compound 27 (B1)
Compound 28 (B2)

According to the method of step 4 in Example 53, 3-benzyl-2-methoxy-5-phenylpyridine and 3-(dimethylamino)-1-(2-fluorophenyl)propan-1-one were used to prepare crude product which was separated by preparative HPLC (GX-D; Phenomenex Synergi C18 150*30 mm*4 um; acetonitrile 26%-50%; water (0.225% formic acid); 25 mL/min) to give component A and component B. Component A was separated by chiral SFC (Chiralpak AD 250×30 mm I.D., 5 um; supercritical $CO_2$/EtOH (0.2% $NH_3.H_2O$) =65/35; 80 ml/min; 220 nm) to give compound 25 (A1) (58.1 mg, 1.7% yield) and compound 26 (A2) (62.8 mg, 1.8% yield). Component B was separated by chiral SFC (Chiralpak AD 250×30 mm I.D., 5 um; supercritical $CO_2$/EtOH (0.2% $NH_3.H_2O$)=65/35; 80 ml/min; 220 nm) to give compound 27 (B1) (70.3 mg, 2.0% yield) and compound 28 (B2) (74.9 mg, 2.2% yield). Compound 25 (A1)/compound 26 (A2): $^1$H NMR (400 MHz, METHANOL-$d_4$) 8.57 (m, 1H), 7.97 (d, J=2.38 Hz, 1H), 7.75 (td, J=8.03, 1.63 Hz, 1H), 7.66 (d, J=7.40 Hz, 2H), 7.52-7.41 (m, 4H), 7.34 (t, J=7.47 Hz, 3H), 7.28-7.14 (m, 2H), 7.10-7.04 (m, 1H), 6.99 (dd, J=12.36, 7.97 Hz, 1H), 5.15 (s, 1H), 3.73 (s, 3H), 2.45 (d, J=10.67 Hz, 1H), 2.32-2.01 (m, 9H); compound 27 (B1)/compound 28 (B2): $^1$H NMR (400 MHz, METHANOL-$d_4$) δ 8.67 (d, J=2.51 Hz, 1H), 8.52 (br. s., 1H), 8.29 (d, J=2.51 Hz, 1H), 7.64-7.53 (m, 3H), 7.48 (t, J=7.65 Hz, 2H), 7.427.30 (m, 3H), 7.23-7.15 (m, 1H), 7.06-6.92 (m, 5H), 5.30 (s, 1H), 4.06 (s, 3H), 2.59 (br. s., 1H), 2.51-2.18 (m, 8H), 2.15-1.98 (m, 1H). LCMS (ESI) m/z: 471 (M+1).

Example 55

2-(2,3-difluorophenyl)-4-(dimethylamino)-1-(2-methoxy-5-phenylpyridin-3-yl)-1-phenylbutan-2-ol

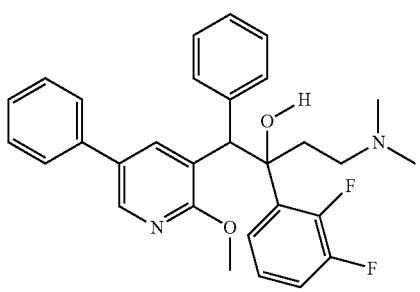

Compound 29 (A1)
Compound 30 (A2)
Compound 31 (B1)
Compound 32 (B2)

Step 1: 1-(2,3-difluorophenyl)-3-(dimethylamino)propan-1-one

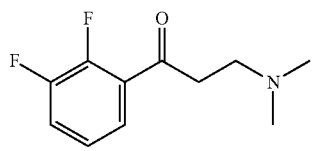

1-(2,3-difluorophenyl)ethanone (3.0 g, 19.2 mmol), dimethylamine hydrochloride (2.2 g, 27.0 mmol), paraformaldehyde (860 mg, 28.8 mmol) and concentrated hydrochloric acid (0.1 mL) were dissolved in 20 mL of ethanol, heated to 80° C. to reflux and stirred for 12 h. The mixture was concentrated under reduced pressure, acidified with 3M hydrochloric acid and washed with dichloromethane (15 mL×3). The aqueous phase was basified with saturated aqueous sodium carbonate solution and pH was adjusted to 10. Then the mixture was extracted with ethyl acetate (20 mL×3). The combined organic phase was dried over anhydrous sodium sulfate and concentrated to give crude product, 1-(2,3-difluorophenyl)-3-(dimethylamino)propan-1-one (1.6 g, 40%) as a yellow oil which was used directly in the next step without further purification.

117

Step 2: 2-(2,3-difluorophenyl)-4-(dimethylamino)-1-(2-methoxy-5-phenylpyridin-3-yl)-1-phenylbutan-2-ol

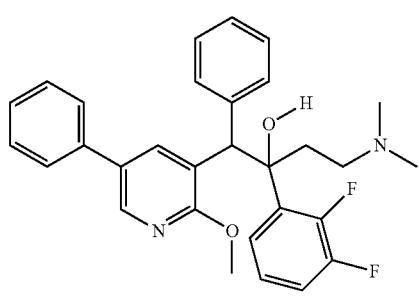

Compound 29 (A1)
Compound 30 (A2)
Compound 31 (B1)
Compound 32 (B2)

According to the method of step 4 in Example 53, 3-benzyl-2-methoxy-5-phenylpyridine was reacted with 1-(2,3-difluorophenyl)-3-(dimethylamino)propan-1-one to prepare the product which was separated by preparative HPLC (GX-D; Boston Symmetrix C18 ODS-R 150*30 mm*5 um; acetonitrile 25%-55%; water (0.225% formic acid); 25 mL/min) to give component A and component B. Component A was separated by chiral SFC (Chiralpak AD 250×30 mm I.D., 5 um; supercritical $CO_2$/EtOH (0.2% $NH_3.H_2O$)=60/40; 80 ml/min; 220 nm) to give compound 29 (A1) (40.8 mg, 1.2% yield) and compound 30 (A2) (50.6 mg, 1.5% yield). Component B was separated by chiral SFC (Chiralpak AD 250×30 mm I.D., 5 um; supercritical $CO_2$/EtOH (0.2% $NH_3.H_2O$)=65/35; 80 ml/min; 220 nm) to give compound 31 (B1) (38.9 mg, 1.1% yield) and compound 32 (B2) (37.9 mg, 1.1% yield). Compound 29 (A1)/compound 30 (A2): $^1$H NMR (400 MHz, METHANOL-$d_4$) δ 8.56 (d, J=2.51 Hz, 1H), 8.00 (d, J=2.51 Hz, 1H), 7.70 (d, J=7.15 Hz, 2H), 7.55-7.41 (m, 5H), 7.38-7.31 (m, 3H), 7.29-7.22 (m, 1H), 7.12-6.97 (m, 2H), 5.12 (s, 1H) 3.76 (s, 3H), 2.38 (d, J=12.67 Hz, 1H), 2.25-2.02 (m, 9H); compound 31 (B1)/compound 32 (B2): $^1$H NMR (400 MHz, METHANOL-$d_4$) δ 8.65 (d, J=2.26 Hz, 1H), 8.52 (br. s., 1H), 8.29 (d, J=2.38 Hz, 1H), 7.59 (d, J=7.53 Hz, 2H), 7.48 (t, J=7.59 Hz, 2H), 7.43-7.33 (m, 4H), 6.93-7.08 (m, 5H), 5.26 (s, 1H), 4.08 (s, 3H), 2.53 (br. s., 1H), 2.41-2.19 (m, 8H), 2.10-2.04 (m, 1H). LCMS (ESI) m/z: 489 (M+1).

118

Example 56

2-(3,5-difluorophenyl)-4-(dimethylamino)-1-(2-methoxy-5-phenylpyridin-3-yl)-1-phenylbutan-2-ol

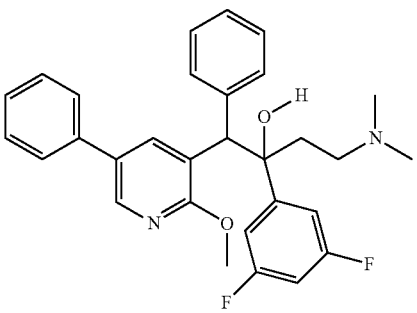

Compound 33 (A1)
Compound 34 (A2)
Compound 35 (B1)
Compound 36 (B2)

Step 1: 1-(3,5-difluorophenyl)-3-(dimethylamino)propan-1-one

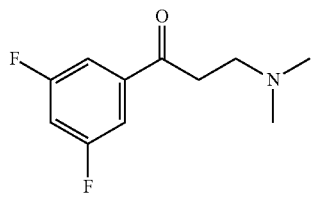

1-(3,5-difluorophenyl)ethanone (5.0 g, 32 mmol), dimethylamine hydrochloride (10.5 g, 128 mmol), paraformaldehyde (3.7 g, 123 mmol) and concentrated hydrochloric acid (0.1 mL) were dissolved in 30 mL of ethanol, heated to 80° C. to reflux and stirred for 12 h. The mixture was concentrated under reduced pressure, acidified with 3M hydrochloric acid and washed with dichloromethane (30 mL×3). The aqueous phase was basified with saturated aqueous sodium carbonate solution and pH was adjusted to 10. Then the mixture was extracted with ethyl acetate (20 mL×3). The combined organic phase was dried over anhydrous sodium sulfate and concentrated to give crude product, 1-(3,5-difluorophenyl)-3-(dimethylamino)propan-1-one (1.8 g, 26%) as a yellow oil which was used directly in the next step without further purification. LCMS (ESI) m/z: 214 (M+1).

Step 2: 2-(3,5-difluorophenyl)-4-(dimethylamino)-1-(2-methoxy-5-phenylpyridin-3-yl)-1-phenylbutan-2-ol

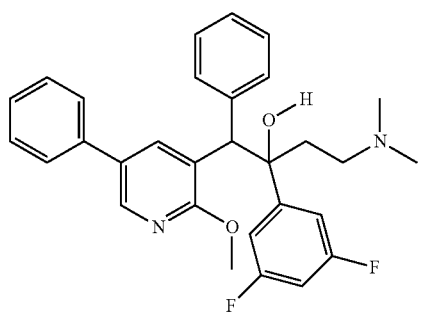

Compound 33 (A1)
Compound 34 (A2)
Compound 35 (B1)
Compound 36 (B2)

According to the method of step 4 in Example 53, 3-benzyl-2-methoxy-5-phenylpyridine was reacted with 1-(3,5-difluorophenyl)-3-(dimethylamino)propan-1-one to prepare the product which was separated by preparative HPLC (GX-D; Boston Symmetrix C18 ODS-R 150*30 mm*5 um; acetonitrile 35%-59%; water (0.225% formic acid); 25 mL/min) to give component A and component B. Component A was separated by chiral SFC (Chiralpak AD 250×30 mm I.D., 5 um; supercritical $CO_2$/EtOH (0.2% $NH_3.H_2O$)=60/40; 80 ml/min; 220 nm) to give compound 33 (A1) (22.8 mg, 0.7% yield) and compound 34 (A2) (20.1 mg, 0.6% yield). Component B was separated by chiral SFC (Chiralpak AD 250×30 mm I.D., 5 um; supercritical $CO_2$/EtOH (0.2% $NH_3.H_2O$)=60/40; 80 ml/min; 220 nm) to give compound 35 (B1) (27.5 mg, 0.8% yield) and compound 36 (B2) (35.4 mg, 1.0% yield). Compound 33 (A1)/compound 34 (A2): $^1$H NMR (400 MHz, METHANOL-$d_4$) δ 8.63 (d, J=2.38 Hz, 1H), 8.54 (br. s., 1H), 8.02 (d, J=2.51 Hz, 1H), 7.68 (d, J=7.40 Hz, 2H), 7.53-7.43 (m, 4H), 7.40-7.31 (m, 3H), 7.29-7.17 (m, 3H), 6.74-6.65 (m, 1H), 4.84 (s, 1H), 3.81 (s, 3H), 2.47 (br. s., 1H), 2.29-1.99 (m, 9H); compound 35 (B1)/compound 36 (B2): $^1$H NMR (400 MHz, METHANOL-$d_4$) δ 8.65 (d, J=2.38 Hz, 1H), 8.53 (br. s., 1H), 8.29 (d, J=2.38 Hz, 1H), 7.59 (d, J=7.65 Hz, 2H), 7.48 (t, J=7.65 Hz, 2H), 7.42-7.30 (m, 3H), 7.13-6.97 (m, 5H), 6.74-6.62 (m, 1H), 4.88 (s, 1H), 4.07 (s, 1H), 2.56-2.42 (m, 1H), 2.32-2.14 (m, 7H), 2.14-2.06 (m, 2H). LCMS (ESI) m/z: 489 (M+1).

Example 57

2-(2,5-difluorophenyl)-4-(dimethylamino)-1-(2-methoxy-5-phenylpyridin-3-yl)-1-phenylbutan-2-ol

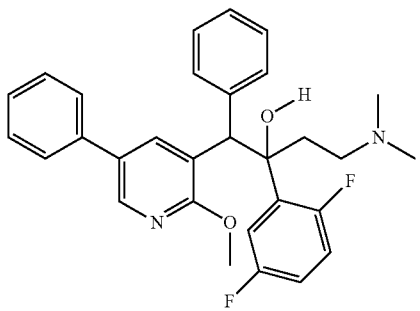

Compound 37 (A1)
Compound 38 (A2)
Compound 39 (B1)
Compound 40 (B2)

Step 1: 1-(2,5-difluorophenyl)-3-(dimethylamino)propan-1-one

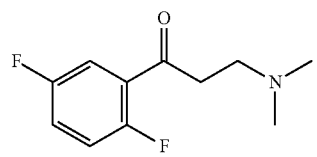

1-(2,5-difluorophenyl)ethanone (3.0 g, 19.2 mmol), dimethylamine hydrochloride (2.2 g, 27.0 mmol), paraformaldehyde (860 mg, 28.8 mmol) and concentrated hydrochloric acid (0.1 mL) were dissolved in 20 mL of ethanol, heated to 80° C. to reflux and stirred for 12 h. The mixture was concentrated under reduced pressure, acidified with 3M hydrochloric acid and washed with dichloromethane (20 mL×3). The aqueous phase was basified with saturated aqueous sodium carbonate solution and pH was adjusted to 10. Then the mixture was extracted with ethyl acetate (20 mL×3). The combined organic phase was dried over anhydrous sodium sulfate and concentrated to give 1-(2,5-difluorophenyl)-3-(dimethylamino)propan-1-one (1.8 g, 44%) crude product as a yellow oil, which was used directly in the next step without further purification. LCMS (ESI) m/z: 214 (M+1).

Step 2: 2-(2,5-difluorophenyl)-4-(dimethylamino)-1-(2-methoxy-5-phenylpyridin-3-yl)-1-phenylbutan-2-ol

Example 58

4-(dimethylamino)-1-(2-methoxy-5-phenylpyridin-3-yl)-2-(naphthalen-1-yl)-1-phenylbutan-2-ol

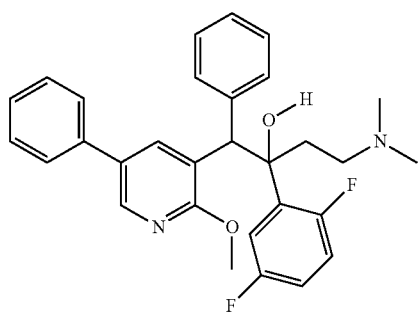

Compound 37 (A1)
Compound 38 (A2)
Compound 39 (B1)
Compound 40 (B2)

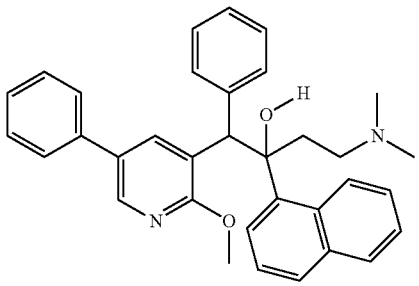

Compound 9 (A1)
Compound 10 (A2)
Compound 11 (B1)
Compound 12 (B2)

Step 1: 3-(dimethylamino)-1-(naphthalen-1-yl)propan-1-one

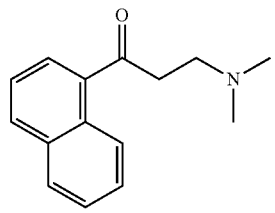 [SMILES: CN(C)CCC(=O)c1cccc2ccccc12]

According to the method of step 4 in Example 53, 3-benzyl-2-methoxy-5-phenylpyridine was reacted with 1-(2,5-difluorophenyl)-3-(dimethylamino)propan-1-one to prepare the product which was separated by preparative HPLC (GX-D; Boston Symmetrix C18 ODS-R 150*30 mm*5 um; acetonitrile 30%-60%; water (0.225% formic acid); 25 mL/min) to give component A and component B. Component A was separated by chiral SFC (Chiralpak AD 250×30 mm I.D., 5 um; supercritical $CO_2$/EtOH (0.2% $NH_3.H_2O$)=60/40; 80 ml/min; 220 nm) to give compound 37 (A1) (73.1 mg, 2.1% yield) and compound 38 (A2) (75.3 mg, 2.2% yield). Component B was separated by chiral SFC (Chiralpak AD 250×30 mm I.D., 5 um; supercritical $CO_2$/EtOH (0.2% $NH_3.H_2O$)=60/40; 80 ml/min; 220 nm) to give compound 39 (B1) (49.5 mg, 1.5% yield) and compound 40 (B2) (48.4 mg, 1.4% yield). Compound 37 (A1)/compound 38 (A2): $^1$H NMR (400 MHz, METHANOL-$d_4$) δ 8.53 (d, J=2.38 Hz, 1H), 8.50 (br. s., 1H), 8.02 (d, J=2.51 Hz, 1H), 7.65 (d, J=7.28 Hz, 2H), 7.50-7.42 (m, 5H), 7.39-7.32 (m, 3H), 7.30-7.23 (m, 1H), 7.08-6.89 (m, 2H), 5.14 (s, 1H), 3.75 (s, 3H), 2.65 (d, J=9.16 Hz, 1H), 2.35 (s, 8H), 2.18-2.04 (m, 1H); compound 39 (B1)/compound 40 (B2): $^1$H NMR (400 MHz, METHANOL-$d_4$) δ 8.69 (d, J=2.38 Hz, 1H), 8.53 (br. s., 1H), 8.28 (d, J=2.51 Hz, 1H), 7.59 (d, J=7.78 Hz, 2H), 7.48 (t, J=7.65 Hz, 2H), 7.37 (d, J=7.15 Hz, 3H), 7.30 (ddd, J=9.94, 6.37, 3.26 Hz, 1H), 7.09-6.96 (m, 4H), 6.91-6.83 (m, 1H), 5.24 (s, 1H), 4.06 (s, 3H), 2.43 (d, J=11.42 Hz, 1H), 2.36-2.27 (m, 1H), 2.19 (s, 7H), 2.10-1.98 (m, 1H). LCMS (ESI) m/z: 489 (M+1).

1-(naphthalen-1-yl)ethanone (100 g, 0.587 mol), dimethylamine hydrochloride (49.2 g, 0.61 mol), paraformaldehyde (860 mg, 28.8 mmol) and concentrated hydrochloric acid (0.75 mL) were mixed in 375 mL of ethanol and stirred at 80° C. under reflux for 12 hours. The mixture was concentrated under reduced pressure and the residue was acidified with 3M HCl solution, and washed with dichloromethane (300 mL×3). The aqueous phase was basified with saturated sodium bicarbonate and extracted with ethyl acetate (200 mL×3). The combined ethyl acetate phase was dried over anhydrous sodium sulfate, and concentrated under reduced pressure to give crude product, 3-(dimethylamino)-1-(naphthalen-1-yl)propan-1-one (80 g, crude) as a yellow oil which was used directly in the next step without further purification. $^1$H NMR (400 MHz, CHLOROFORM-d) δ 8.59 (d, J=8.53 Hz, 1H), 8.04-7.82 (m, 4H), 7.65-7.43 (m, 5H), 3.28 (t, J=7.28 Hz, 2H), 2.86 (t, J=7.28 Hz, 2H), 2.40-2.29 (m, 6H). LCMS (ESI) m/z: 228 (M+1).

123

Step 2: 4-(dimethylamino)-1-(2-methoxy-5-phe-nylpyridin-3-yl)-2-(naphthalen-1-yl)-1-phenylbutan-2-ol

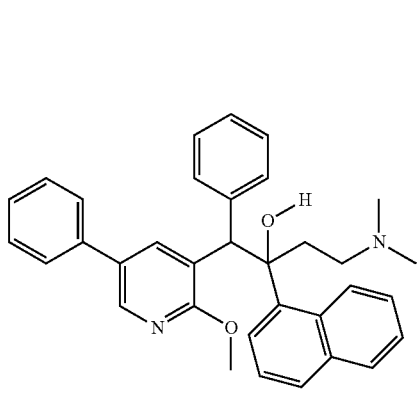

Compound 9 (A1)
Compound 10 (A2)
Compound 11 (B1)
Compound 12 (B2)

According to the method of step 4 in Example 53, 3-benzyl-2-methoxy-5-phenylpyridine was reacted with 3-(dimethylamino)-1-(naphthalen-1-yl)propan-1-one to prepare the product which was separated by preparative HPLC (GX-G; Phenomenex Synergi C18 150*30 mm*4 um; acetonitrile 27%-57%; water (0.225% formic acid); 25 mL/min) to give component A and component B. Component A was separated by chiral SFC (Chiralpak AD 250×30 mm I.D., 5 um; supercritical $CO_2$/EtOH (0.2% $NH_3.H_2O$) =60/40; 80 ml/min; 220 nm) to give compound 9 (A1) (74.6 mg, 4.1% yield) and compound 10 (A2) (55.1 mg, 3.0% yield) as white solid. Component B was separated by chiral SFC (Chiralpak AS 250×30 mm I.D., 5 um; supercritical $CO_2$/EtOH (0.2% $NH_3.H_2O$)=60/40; 80 ml/min; 220 nm) to give compound 11 (B1) (48.0 mg, 2.6% yield) and compound 12 (B2) (56.5 mg, 3.1% yield) as white product. Compound 9 (A1)/compound 10 (A2): $^1$H NMR (400 MHz, METHANOL-$d_4$) δ 8.71 (br. s., 2H), 8.52 (br. s., 1H), 8.36-8.32 (m, 1H), 7.94-7.81 (m, 2H), 7.72-7.62 (m, 4H), 7.55-7.45 (m, 3H), 7.42-7.27 (m, 2H), 7.14 (br. s., 2H), 6.91-6.87 (m, 3H), 5.87 (br. s., 1H), 4.17 (s, 3H), 2.91 (d, J=15.94 Hz, 2H), 2.50 (br. s., 1H), 2.24 (s, 6H), 2.19-1.99 (m, 2H); compound 11 (B1)/compound 12 (B2): $^1$H NMR (400 MHz, DMSO-$d_6$) δ8.68-8.48 (m, 2H), 8.26 (s, 1H), 8.14 (d, J=7.40 Hz, 1H), 7.93 (d, J=2.38 Hz, 1H), 7.86 (d, J=8.03 Hz, 1H), 7.76 (d, J=7.40 Hz, 2H), 7.71-7.58 (m, 2H), 7.52-7.21 (m, 11H), 5.59 (s, 1H) 3.29 (s, 6H), 2.17-1.82 (m, 10H). LCMS (ESI) m/z: 503 (M+1).

124

Example 59

4-(dimethylamino)-1-(2-ethoxy-5-phenylpyridin-3-yl)-2-(naphthalen-1-yl)-1-phenylbutan-2-ol

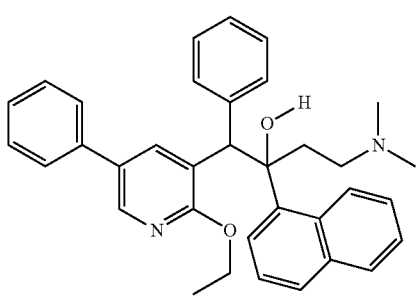

Compound 217 (A1)
Compound 218 (A2)
Compound 219 (B1)
Compound 220 (B2)

Step 1: 2-ethoxy-5-phenylpyridine

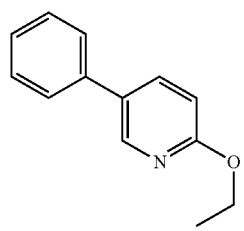

According to the method of step 1 in Example 53, 5-bromo-2-ethoxy pyridine and phenylboronic acid were used to prepare the product. Yield: 86.2%. LCMS (ESI) m/z: 200 (M+1).

Step 2: (2-ethoxy-5-phenylpyridin-3-yl)(phenyl)methanol

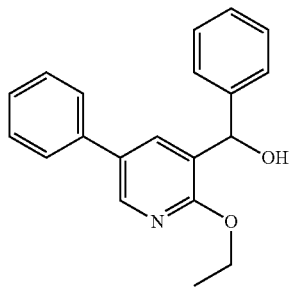 [SMILES: CCOc1ncc(-c2ccccc2)cc1C(O)c1ccccc1]

According to the method of step 2 in Example 53, 2-ethoxy-5-phenylpyridine was reacted with benzaldehyde. Yield: 53.6%. LCMS (ESI) m/z: 306 (M+1).

Step 3: 3-benzyl-2-ethoxy-5-phenylpyridine

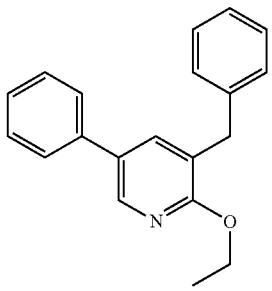 [SMILES: CCOc1ncc(-c2ccccc2)cc1Cc1ccccc1]

According to the method of step 2 in Example 53, (2-ethoxy-5-phenylpyridin-3-yl) (phenyl)methanol was used. Yield: 76.8%. LCMS (ESI) m/z: 290 (M+1).

Step 4: 4-(dimethylamino)-1-(2-ethoxy-5-phenylpyridin-3-yl)-2-(naphthalen-1-yl)-1-phenylbutan-2-ol

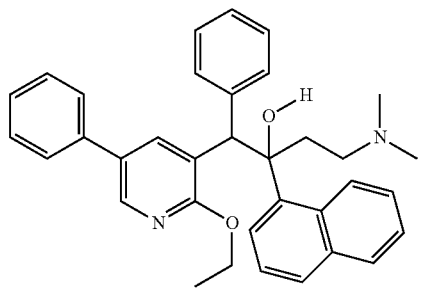

Compound 217 (A1)
Compound 218 (A2)
Compound 219 (B1)
Compound 220 (B2)

According to the method of step 4 in Example 53, 3-benzyl-2-ethoxy-5-phenylpyridine was reacted with 3-(dimethylamino)-1-(naphthalen-1-yl)propan-1-one to prepare the product which was separated by preparative HPLC (GX-D; Boston Symmetrix C18 ODS-R 150*30 mm*5 um; acetonitrile 35%-65%; water (0.225% formic acid); 25 mL/min) to give component A and component B. Component A was separated by chiral SFC (Chiralpak IC 250×30 mm I.D., 5 um; supercritical $CO_2$/EtOH (0.2% $NH_3.H_2O$) =50/50; 70 ml/min; 220 nm) to give compound 217 (A1) (40.6 mg, 0.6% yield) and compound 218 (A2) (34.6 mg, 0.5% yield) as white solid. Component B was separated by chiral SFC (Chiralpak AD 250×30 mm I.D., 5 um; supercritical $CO_2$/EtOH (0.2% $NH_3.H_2O$)—70/30; 60 ml/min; 220 nm) to give compound 219 (B1) (32.3 mg, 0.5% yield) and compound 220 (B2) (32.3 mg, 0.5% yield) as white solid. Compound 217 (A1)/compound 218 (A2): $^1$H NMR (400 MHz, METHANOL-$d_4$) δ 8.86-8.63 (m, 2H), 8.54 (s, 1H), 8.31 (d, J=2.38 Hz, 1H), 7.90 (d, J=7.65 Hz, 2H), 7.74-7.57 (m, 4H), 7.56-7.45 (m, 3H), 7.42-7.35 (m, 1H), 7.31 (t, J=7.78 Hz, 1H), 7.20 (d, J=3.51 Hz, 2H), 6.90 (dd, J=5.02, 1.76 Hz, 3H), 5.94 (br. s., 1H), 4.70-4.39 (m, 2H), 2.96-2.72 (m, 1H), 2.46-1.94 (m, 9H), 1.66 (t, J=6.84 Hz, 3H); compound 219 (B1)/compound 220 (B2): $^1$H NMR (400 MHz, METHANOL-$d_4$) δ 8.68-8.49 (m, 2H), 8.16 (d, J=7.53 Hz, 1H), 7.90-7.75 (m, 4H), 7.71-7.60 (m, 2H), 7.52-7.19 (m, 12H), 5.73 (s, 1H), 3.96 (dd, J=9.98, 6.96 Hz, 1H), 3.75 (d, J=7.03 Hz, 1H), 2.96-2.79 (m, 1H), 2.61-2.45 (m, 1H), 2.25 (br. s., 7H), 2.15-2.03 (m, 1H), 1.07 (t, J=7.03 Hz, 3H). LCMS (ESI) m/z: 517 (M+1).

Example 60

1-(4-chlorophenyl)-4-(dimethylamino)-1-(2-methoxy-5-phenylpyridin-3-yl)-2-phenylbutan-2-ol

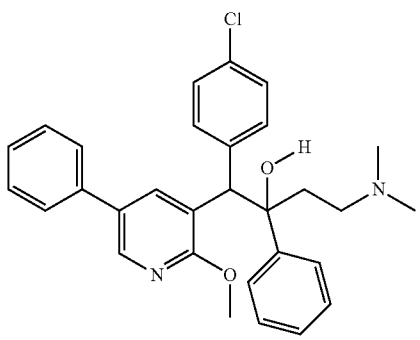

Compound 45 (A1)
Compound 46 (A2)
Compound 47 (B1)
Compound 48 (B2)

Step 1: (4-chlorophenyl) (2-methoxy-5-phenylpyridin-3-yl)methanol

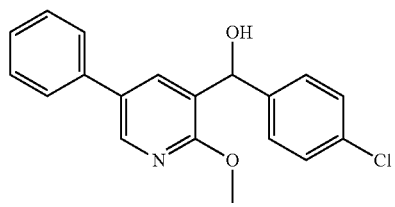 [SMILES: COc1ncc(-c2ccccc2)cc1C(O)c1ccc(Cl)cc1]

According to the method of step 2 in Example 53, the product was prepared from 2-methoxy-5-phenylpyridine and 4-chlorobenzaldehyde. Yield: 52.3%. LCMS (ESI) m/z: 326 (M+1).

Step 2: 3-(4-chlorobenzyl)-2-methoxy-5-phenylpyridine

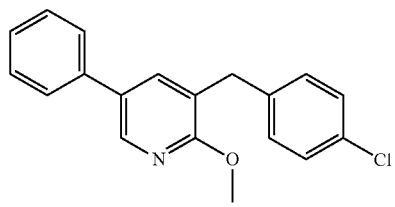 [SMILES: COc1ncc(-c2ccccc2)cc1Cc1ccc(Cl)cc1]

(4-chlorophenyl) (2-methoxy-5-phenylpyridin-3-yl) methanol (4.5 g, 13.8 mmol) was dissolved in 10 mL of triethylsilane and 10 mL of trifluoroacetic acid and stirred at 70° C. for 2 h. TLC (developing solvent:petroleum ether/ethyl acetate=20/1) showed the reaction was complete. The reaction liquid was cooled to room temperature and basified with saturated potassium carbonate solution, extracted with 30 mL of dichloromethane three times. The combined organic phase was washed with brine, dried over anhydrous sodium sulfate, concentrated and isolated by column chromatography (eluent: petroleum ether/ethyl acetate=100/1-10/1) to give 3-(4-chlorobenzyl)-2-methoxy-5-phenylpyridine (2.0 g, 46.8% yield) as a colorless oil. $^1$H NMR (400 MHz, CHLOROFORM-d) δ 8.29 (d, J=2.38 Hz, 1H), 7.56-7.41 (m, 5H), 7.37 (d, J=7.28 Hz, 1H), 7.30 (s, 1H), 7.28 (s, 1H), 7.22-7.17 (m, 2H), 4.02 (s, 3H), 3.98-3.92 (m, 2H). LCMS (ESI) m/z: 310 (M+1).

Step 3: 1-(4-chlorophenyl)-4-(dimethylamino)-1-(2-methoxy-5-phenylpyridin-3-yl)-2-phenylbutan-2-ol

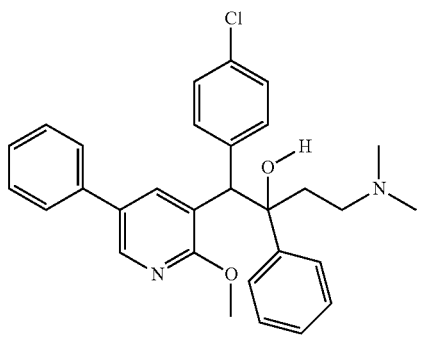

Compound 45 (A1)
Compound 46 (A2)
Compound 47 (B1)
Compound 48 (B2)

According to the method of step 4 in Example 53, the product was prepared from 3-(4-chlorobenzyl)-2-methoxy-5-phenylpyridine and 3-(dimethylamino)-1-phenylpropan-1-one, then separated and purified by preparative HPLC (GX-D; Boston Symmetrix C18 ODS-R 150*30 mm*5 um; acetonitrile 30%-60%; water (0.225% formic acid); 25 mL/min) to give component A and component B. Component A was separated by chiral SFC (Chiralpak AD 250×30 mm I.D., 5 um; supercritical CO$_2$/EtOH (0.2% NH$_3$.H$_2$O)=50/50; 70 ml/min; 220 nm) to give compound 45 (A1) (158.1 mg, 5.4% yield) and compound 46 (A2) (196.8 mg, 6.5% yield) as white solid. Component B was separated by chiral SFC (Chiralpak IC 250×30 mm I.D., 5 um; supercritical CO$_2$/EtOH (0.2% NH$_3$.H$_2$O)=70/30; 60 ml/min; 220 nm) to give compound 47 (B1) (140.6 mg, 4.7% yield) and compound 48 (B2) (82.1 mg, 2.7% yield) as white solid. Compound 45 (A1)/compound 46 (A2): $^1$H NMR (400 MHz, CHLOROFORM-d) 58.67-8.54 (m, 1H), 8.01 (d, J=2.51 Hz, 2H), 7.67 (d, J=8.53 Hz, 2H), 7.59-7.51 (m, 2H), 7.49-7.40 (m, 4H), 7.37-7.29 (m, 2H), 7.28 (s, 3H), 7.10 (s, 1H), 4.73 (s, 1H), 3.77 (s, 3H), 2.34-1.63 (m, 10H). Compound 47 (B1)/compound 48 (B2): $^1$H NMR (400 MHz, METHANOL-d$_4$) δ 8.70 (d, J=2.38 Hz, 1H), 8.57-8.52 (m, 1H), 8.30 (d, J=2.51 Hz, 1H), 7.60 (d, J=7.78 Hz, 2H), 7.52-7.43 (m, 4H), 7.38 (d, J=7.40 Hz, 1H), 7.30-7.21 (m, 4H), 7.18-7.11 (m, 1H), 6.99 (d, J=8.53 Hz, 2H), 4.93 (s, 1H), 4.05 (s, 3H), 2.52-2.35 (m, 1H), 2.18 (s, 9H). LCMS (ESI) m/z: 487 (M+1).

Example 61

1-(3-chlorophenyl)-4-(dimethylamino)-1-(2-methoxy-5-phenylpyridin-3-yl)-2-phenylbutan-2-ol

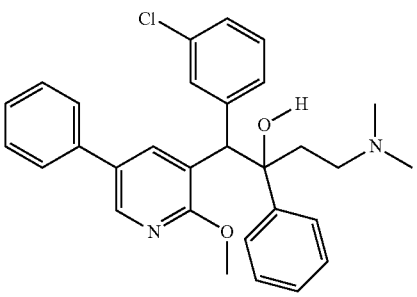

Compound 41 (A1)
Compound 42 (A2)
Compound 43 (B1)
Compound 44 (B2)

Step 1: (3-chlorophenyl)(2-methoxy-5-phenylpyridin-3-yl)methanol

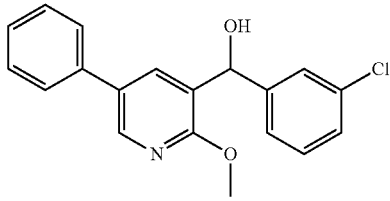 [SMILES: COc1ncc(-c2ccccc2)cc1C(O)c1cccc(Cl)c1]

According to the method of step 2 in Example 53, the product was prepared from 2-methoxy-5-phenylpyridine and 3-chlorobenzaldehyde. Yield: 64%, LCMS (ESI) m/z: 326 (M+1).

Step 2: (3-chlorophenyl)(2-methoxy-5-phenylpyridin-3-yl)methanol

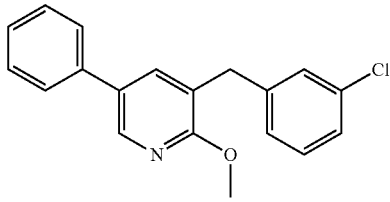 [SMILES: COc1ncc(-c2ccccc2)cc1Cc1cccc(Cl)c1]

According to the method of step 2 in Example 60, the product was prepared from (3-chlorophenyl)(2-methoxy-5-phenylpyridin-3-yl)methanol. Yield: 57%. $^1$H NMR (400 MHz, CHLOROFORM-d) δ 8.29 (d, J=2.4 Hz, 1H); 8.54 (d, J=2.4 Hz, 1H); 7.52-7.50 (m, 2H); 7.45 (t, J=7.2 Hz, 2H); 7.36 (m, 1H); 7.27-7.20 (m, 3H); 7.16-7.14 (m, 1H); 4.02 (s, 3H); 3.97 (s, 2H). LCMS (ESI) m/z: 294 (M+1).

Step 3: 1-(3-chlorophenyl)-4-(dimethylamino)-1-(2-methoxy-5-phenylpyridin-3-yl)-2-phenylbutan-2-ol

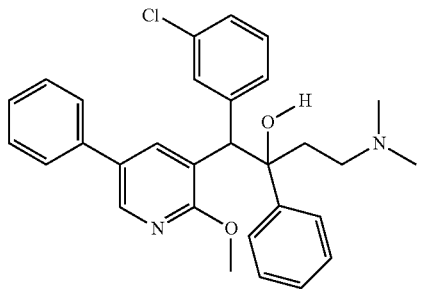

Compound 41 (A1)
Compound 42 (A2)
Compound 43 (B1)
Compound 44 (B2)

Under nitrogen, diisopropylamine (754 mg, 7.47 mmol) was dissolved in 15 mL of anhydrous tetrahydrofuran solution. At −70° C., n-butyllithium (2.5M n-hexane solution, 3.0 mL, 7.50 mmol) was added dropwise to the reaction mixture and stirred for 10 minutes. 3-(3-chlorobenzyl)-2-methoxy-5-phenylpyridine (1.50 g, 4.82 mmol) was dissolved in 5 mL of anhydrous tetrahydrofuran and slowly added dropwise to the reaction mixture at −70° C. over 2 minutes. Afterwards the reaction mixture was stirred at −75° C. for 2 h and then a solution of 3-(dimethylamino)-1-phenylpropan-1-one (896 mg, 5.06 mmol) in tetrahydrofuran was added dropwise at −70° C. Upon completion of addition, the reaction mixture was stirred at −75° C. for 2 h and the reaction was quenched with 20 mL of saturated ammonium chloride solution. The mixture was extracted with ethyl acetate (20 mL×3) and the combined organic phase was dried over anhydrous sodium sulfate and filtered. The filtrate was concentrated to give crude product which was isolated by column chromatography (developing solvent:petroleum ether/ethyl acetate=20/1-10/1) to give component A and component B. Component A was separated by chiral SFC (Chiralpak AD 250×30 mm I.D., 5 um; supercritical $CO_2$/EtOH (0.2% $NH_3.H_2O$)=60/40; 70 ml/min; 220 nm) to give compound 41 (A1) (164.0 mg, 5.5% yield) and compound 42 (A2) (173.0 mg, 5.6% yield) as white solid. Component B was separated by chiral SFC (Chiralpak IC 250×30 mm I.D., 5 um; supercritical $CO_2$/EtOH (0.2% $NH_3.H_2O$)=70/30; 60 ml/min; 220 nm) to give compound 43 (B1) (150.0 mg, 5.2% yield) and compound 44 (B2) (173.1 mg, 5.6% yield) as white solid. Compound 41 (A1)/compound 42 (A2): $^1$H NMR (400 MHz, Methanol-$d_6$): δ 8.56 (s, 1H); S 8.48 (s, 1H); 8.00 (d, J=2.4 Hz, 1H); 7.67 (s, 1H); 7.60-7.57 (m, 3H); 7.45 (d, J=4.4 Hz, 1H), 7.38-7.33 (m, 2H); 7.31-7.27 (m, 3H); 7.16-7.13 (m, 1H); 4.94 (s, 1H); 3.78 (s, 3H); 2.88-2.82 (m, 1H); 2.52 (s, 6H); 2.41-2.34 (m, 2H); 2.12-2.07 (m, 1H). Compound 43 (B1)/compound 44 (B2): $^1$H NMR (400 MHz, Methanol-$d_6$): δ 8.62 (s, 1H); δ 8.52 (s, 1H); 8.32 (d, J=2.4 Hz, 1H); 7.60 (d, J=7.2 Hz, 2H); 7.51-7.46 (m, 4H); 7.39 (t, J=4.0 Hz, 1H), 7.31-7.27 (m, 3H); 7.19-7.16 (m, 2H); 7.00-6.98 (m, 2H); 4.96 (s, 1H); 4.07 (s, 3H); 2.70 (m, 1H); 2.39 (s, 6H); 2.28 (m, 2H); 2.17-2.10 (m, 1H). LCMS (ESI) m/z: 487 (M+1).

Example 62

4-(dimethylamino)-1-(2-fluorophenyl)-1-(2-methoxy-5-phenylpyridin-3-yl)-2-phenylbutan-2-ol

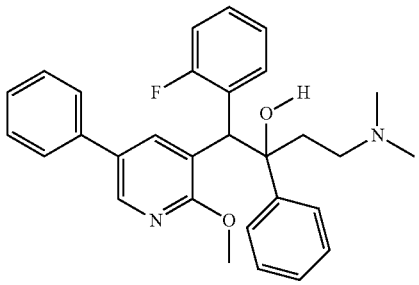

Compound 49 (A1)
Compound 50 (A2)
Compound 51 (B1)
Compound 52 (B2)

Step 1: (2-fluorophenyl)(2-methoxy-5-phenylpyridin-3-yl)methanol

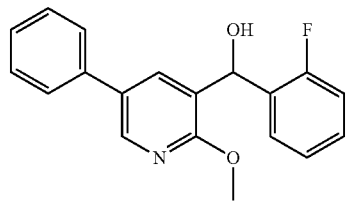 [SMILES: COc1ncc(-c2ccccc2)cc1C(O)c1ccccc1F]

According to the method of step 2 in Example 53, the product was prepared from 2-methoxy-5-phenylpyridine and 2-fluorobenzaldehyde. Yield: 56%. LCMS (ESI) m/z: 310 (M+1).

Step 2: 3-(2-fluorobenzyl)-2-methoxy-5-phenylpyridine

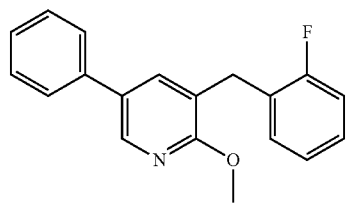 [SMILES: COc1ncc(-c2ccccc2)cc1Cc1ccccc1F]

According to the method of step 2 in Example 60, the product was prepared from (2-fluorophenyl) (2-methoxy-5-phenylpyridin-3-yl)methanol. Yield: 59%. LCMS (ESI) m/z: 294 (M+1).

Step 3: 4-(dimethylamino)-1-(2-fluorophenyl)-1-(2-methoxy-5-phenylpyridin-3-yl)-2-phenylbutan-2-ol

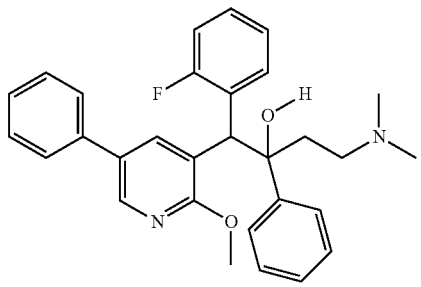

Compound 49 (A1)
Compound 50 (A2)
Compound 51 (B1)
Compound 52 (B2)

Under nitrogen, diisopropylamine (801 mg, 7.94 mmol) was dissolved in 18 mL of anhydrous tetrahydrofuran solution. At −70° C., n-butyllithium (2.5M n-hexane solution, 3.2 mL, 7.95 mmol) was added dropwise to the reaction mixture and stirred at −75° C. for 10 minutes. 3-(2-fluorobenzyl)-2-methoxy-5-phenylpyridine (1.50 g, 5.12 mmol) was dissolved in 5 mL of anhydrous tetrahydrofuran and slowly added dropwise to the reaction mixture at −70° C. over 2 minutes. Afterwards the reaction mixture was stirred at −75° C. for 2 h. 3-(dimethylamino)-1-phenylpropan-1-one (986 mg, 5.57 mmol) was dissolved in 5 mL of anhydrous tetrahydrofuran and added to the reaction liquid at −70° C. Upon completion of addition, the reaction mixture was stirred at −75° C. for another 2 h and the reaction was quenched with 20 mL of saturated ammonium chloride solution. The mixture was extracted with ethyl acetate (20 mL×3) and the combined organic phase was dried over anhydrous sodium sulfate and filtered. The filtrate was concentrated to give crude product which was separated and purified by preparative HPLC (GX-G; Boston Symmetrix C18 ODS-R 150*30 mm*5 um; acetonitrile 25%-55%; water (0.225% formic acid); 25 ml/min) to give A and component B. Component A was separated by chiral SFC (Chiralpak AD 250×30 mm I.D., 5 um; supercritical $CO_2$/EtOH (0.2% $NH_3.H_2O$)=60/40; 70 ml/min; 220 nm) to give compound 49 (A1) (160.0 mg, 5.5% yield) and compound 50 (A2) (168 mg, 5.6% yield) as white solid. Component B was separated by chiral SFC (Chiralpak IC 250×30 mm I.D., 5 um; supercritical $CO_2$/EtOH (0.2% $NH_3.H_2O$)=60/40; 60 ml/min; 220 nm) to give compound 51 (B1) (82.1 mg, 2.8% yield) and compound 52 (B2) (120.3 mg, 4.3% yield) as white solid. Compound 49 (A1)/compound 50 (A2): $^1$H NMR (400 MHz, Methanol-$d_4$): δ 8.57 (s, 1H); δ 8.45 (s, 1H); 7.99 (d, J=2.4 Hz, 1H); 7.62-7.56 (m, 3H); 7.44-7.45 (m, 4H); 7.37-7.27 (m, 4H), 7.20-7.13 (m, 3H); 5.43 (s, 1H); 3.76 (s, 3H); 2.91-2.90 (m, 1H); 2.54 (s, 6H); 2.44-2.39 (m, 2H); 2.14-2.10 (m, 1H). Compound 51 (B1)/compound 52 (B2): $^1$H NMR (400 MHz, Methanol-$d_4$): δ 8.53 (brs, 1H); δ 8.41-8.39 (m, 1H); 8.09 (d, J=2.4 Hz, 1H); 8.04-8.00 (m, 1H); 7.56-7.50 (m, 4H); 7.48-7.44 (m, 2H), 7.38-7.34 (m, 1H); 7.24 (t, J=7.2 Hz, 2H); 7.14-7.11 (m, 1H); 7.02-6.96 (m, 1H); 6.94-6.90 (m, 1H); 6.74-6.69 (m, 1H); 5.47 (s, 1H); 4.10 (s, 3H); 2.58-2.55 (m, 1H); 2.28 (s, 6H); 2.20-2.15 (m, 2H); 2.10-2.07 (m, 1H). LCMS (ESI) m/z: 471 (M+1).

Example 63

4-(dimethylamino)-1-(3-fluorophenyl)-1-(2-methoxy-5-phenylpyridin-3-yl)-2-phenylbutan-2-ol

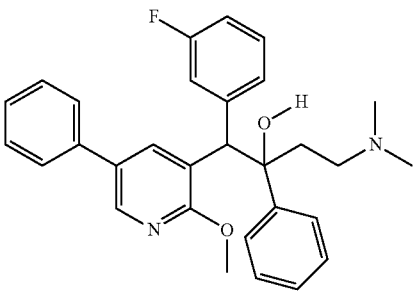

Compound 53 (A1)
Compound 54 (A2)
Compound 55 (B1)
Compound 56 (B2)

Step 1: (3-fluorophenyl)(2-methoxy-5-phenylpyridin-3-yl)methanol

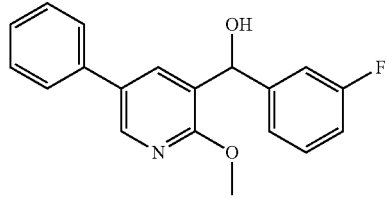 [SMILES: COc1ncc(-c2ccccc2)cc1C(O)c1cccc(F)c1]

According to the method of step 3 in Example 53, the product was prepared from 2-methoxy-5-phenylpyridine and 3-fluorobenzaldehyde. Yield: 66%, LCMS (ESI) m/z: 310 (M+1).

Step 2: 3-(3-fluorobenzyl)-2-methoxy-5-phenylpyridine

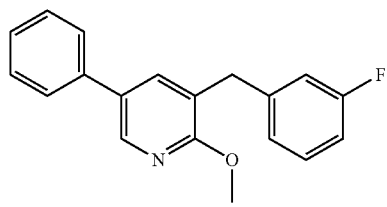 [SMILES: COc1ncc(-c2ccccc2)cc1Cc1cccc(F)c1]

According to the method of step 2 in Example 60, the product was prepared from (3-fluorophenyl)(2-methoxy-5-phenylpyridin-3-yl)methanol. Yield: 53%, LCMS (ESI) m/z: 294 (M+1).

Step 3: 4-(dimethylamino)-1-(3-fluorophenyl)-1-(2-methoxy-5-phenylpyridin-3-yl)-2-phenylbutan-2-ol

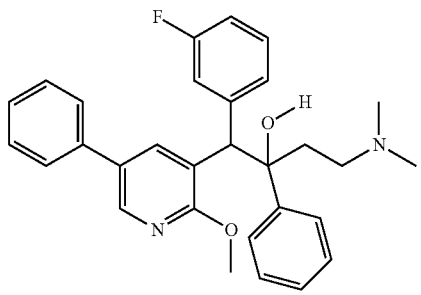

Compound 53 (A1)
Compound 54 (A2)
Compound 55 (B1)
Compound 56 (B2)

Under nitrogen, diisopropylamine (1.44 g, 14.2 mmol) was dissolved in 30 mL of anhydrous tetrahydrofuran and n-butyllithium (2.5M n-hexane solution, 3.0 mL, 7.50 mmol) was added dropwise at −70° C. The reaction mixture was stirred at −75° C. for 10 minutes. 3-(3-fluorobenzyl)-2-methoxy-5-phenylpyridine (2.70 g, 9.20 mmol) was dissolved in 10 mL of anhydrous tetrahydrofuran and added dropwise to the reaction mixture at −70° C. over 4 minutes. Afterwards the reaction mixture was stirred at −75° C. for 2 h. 3-(dimethylamino)-1-phenyl-propan-1-one (1.71 g, 9.66 mmol) was dissolved in anhydrous tetrahydrofuran and added dropwise at −70° C. to the reaction mixture. After completion of addition, the reaction mixture was stirred at −75° C. for 2 h. Then the reaction was quenched with 20 mL of saturated ammonium chloride solution and the mixture was extracted with ethyl acetate (30 mL×3). The combined organic phase was dried over anhydrous sodium sulfate and filtered. The filtrate was concentrated to give crude product which was separated by preparative HPLC (GX-G; Boston Symmetrix C18 ODS-R 150*30 mm*5 um; acetonitrile 25%-55%; water (0.225% formic acid); 25 mL/min) to give component A and component B. Component A was separated by chiral SFC (Chiralpak AD 250×30 mm I.D., 5 um; supercritical CO$_2$/EtOH (0.2% NH$_3$.H$_2$O)=60/40; 70 ml/min; 220 nm) to give compound 53 (A1) (145 mg, 3.3% yield) and compound 54 (A2) (128 mg, 2.9% yield) as white solid. Component B was separated by chiral SFC (Chiralpak IC 250×30 mm ID., 5 um; supercritical CO$_2$/EtOH (0.2% NH$_3$.H$_2$O)=60/40; 60 ml/min; 220 nm) to give compound 55 (B1) (182 mg, 4.1% yield) and compound 56 (B2) (186 mg, 4.2% yield) as white solid. Compound 53 (A1)/compound 54 (A2): $^1$H NMR (400 MHz, Methanol-d$_4$): δ 8.63 (d, J=2.4 Hz, 1H), δ 8.53 (br s, 1H), 7.98 (d, J=2.4 Hz, 1H), 7.58 (d, J=7.6 Hz, 2H), 7.48-7.41 (m, 6H), 7.37-7.31 (m, 2H), 7.26 (d, J=7.6 Hz, 2H), 7.12 (t, J=4.4 Hz, 1H), 7.01-6.96 (m, 1H), 4.96 (s, 1H), 3.77 (s, 3H), 2.54-2.47 (m, 1H), 2.23 (s, 6H), 2.16-2.05 (m, 3H). Compound 55 (B1)/compound 56 (B2): $^1$H NMR (400 MHz, Methanol-d$_4$): δ 8.60 (s, 1H), 8.31 (d, J=2.0 Hz, 1H), 7.65-7.61 (m, 2H), 7.52-7.45 (m, 4H), 7.41-7.34 (m, 1H), 7.31-7.25 (m, 2H), 7.17-7.08 (m, 2H), 7.05-6.97 (m, 2H), 6.75-6.66 (m, 1H), 5.00 (s, 1H), 4.08 (s, 3H), 2.74-2.65 (m, 2H), 2.37 (s, 6H), 2.28-2.19 (m, 1H), 2.15-2.06 (m, 1H). LCMS (ESI) m/z: 471 (M+1).

Example 64

4-(dimethylamino)-1-(4-fluorophenyl)-1-(2-methoxy-5-phenylpyridin-3-yl)-2-phenylbutan-2-ol

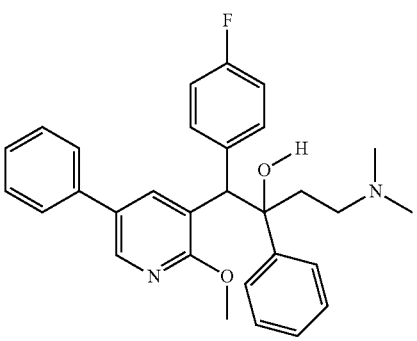

Compound 67 (A1)
Compound 68 (A2)
Compound 69 (B1)
Compound 70 (B2)

Step 1: (4-fluorophenyl)(2-methoxy-5-phenylpyridin-3-yl)methanol

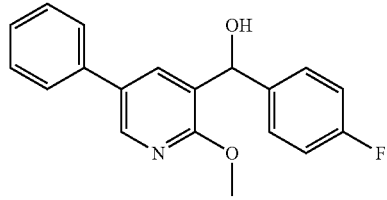 [SMILES: COc1ncc(-c2ccccc2)cc1C(O)c1ccc(F)cc1]

According to the method of step 2 in Example 53, the product was prepared from 2-methoxy-5-phenylpyridine and 4-fluorobenzaldehyde. Yield: 69%, LCMS (ESI) m/z: 310 (M+1).

Step 2: 3-(4-fluorobenzyl)-2-methoxy-5-phenylpyridine

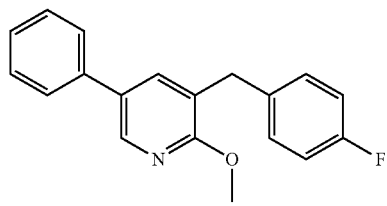 [SMILES: COc1ncc(-c2ccccc2)cc1Cc1ccc(F)cc1]

According to the method of step 2 in Example 60, the product was prepared from (4-fluorophenyl) (2-methoxy-5-phenylpyridin-3-yl)methanol. Yield: 80%. LCMS (ESI) m/z: 294 (M+1).

135

Step 3: 4-(dimethylamino)-1-(4-fluorophenyl)-1-(2-methoxy-5-phenylpyridin-3-yl)-2-phenylbutan-2-ol

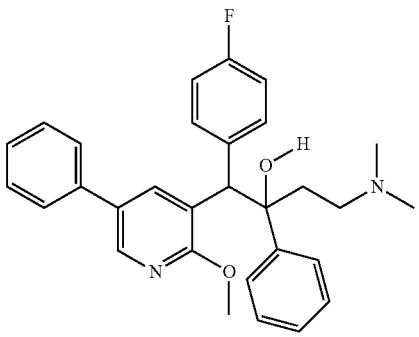

Compound 67 (A1)
Compound 68 (A2)
Compound 69 (B1)
Compound 70 (B2)

Under nitrogen, diisopropylamine (1.44 g, 14.2 mmol) was dissolved in 15 mL of anhydrous tetrahydrofuran and n-butyllithium (2.5M n-hexane solution, 6.1 mL, 15.25 mmol) was added slowly at −70° C. The reaction mixture was stirred at this temperature for 30 minutes. 3-(4-fluorobenzyl)-2-methoxy-5-phenylpyridine (2.1 g, 7.6 mmol) was dissolved in 10 mL of anhydrous tetrahydrofuran and added slowly to the reaction mixture at −70° C. Afterwards the reaction mixture was stirred at −70° C. for 1 h and then 3-(dimethylamino)-1-phenylpropan-1-one (1.62 g, 9.12 mmol) was dissolved in 10 mL of anhydrous tetrahydrofuran and added dropwise at −70° C. to the reaction mixture. Upon completion of addition, the reaction mixture was stirred at −70° C. for 2 h. The reaction was quenched with 20 mL of saturated ammonium chloride solution and the mixture was extracted with ethyl acetate (50 mL×3). The combined organic phase was dried over anhydrous sodium sulfate, concentrated and separated by preparative HPLC (GX-D; Boston Symmetrix C18 ODS-R 150*30 mm*5 um; acetonitrile 30%-54%; water (0.225% formic acid); 25 mL/min) to give component A and component B. Component A was separated by chiral SFC (Chiralpak AD 250×30 mm I.D., 5 um; supercritical $CO_2$/EtOH (0.2% $NH_3.H_2O$)=60/40; 70 ml/min; 220 nm) to give compound 67 (A1) (78.5 mg, 2.6% yield) and compound 68 (A2) (89.0 mg, 2.9% yield) as white solid. Component B was separated by chiral SFC (Chiralpak OJ 250×30 mm I.D., 5 um; supercritical $CO_2$/EtOH (0.2% $NH_3.H_2O$)=60/40; 60 ml/min; 220 nm) to give compound 69 (B1) (64.4 mg, 1.8% yield) and compound 70 (B2) (69.5 mg, 2.0% yield) as white solid. Compound 67 (A1)/compound 68 (A2): $^1$H NMR (400 MHz, METHANOL-$d_4$) 8.60 (d, J=2.5 Hz, 1H), 8.50 (s, 1H), 7.97 (d, J=2.4 Hz, 2H), 7.66-7.52 (m, 4H), 7.50-7.42 (m, 4H), 7.37-7.31 (m, 1H), 7.29-7.23 (m, 2H), 7.14-7.02 (m, 3H), 4.93 (s, 1H), 3.77 (s, 3H), 2.80-2.65 (m, 1H), 2.41 (s, 6H), 2.34-2.16 (m, 2H), 2.14-1.98 (m, 1H); compound 69 (B1)/compound 70 (B2): $^1$H NMR (400 MHz, METHANOL-$d_4$) δ 8.70 (d, J=2.4 Hz, 1H), 8.29 (d, J=2.4 Hz, 1H), 7.60 (d, J=7.8 Hz, 2H), 7.53-7.42 (m, 4H), 7.41-7.33 (m, 1H), 7.32-7.20 (m, 4H), 7.18-7.08 (m, 1H), 6.72 (t, J=8.8 Hz, 2H), 4.93 (s, 1H), 4.05 (s, 3H), 2.51-2.38 (m, 1H), 2.25-1.94 (m, 9H). LCMS (ESI) m/z: 471 (M+1).

136

Example 65

1-(2,3-dimethoxyphenyl)-4-(dimethylamino)-1-(2-methoxy-5-phenylpyridin-3-yl)-2-phenylbutan-2-ol

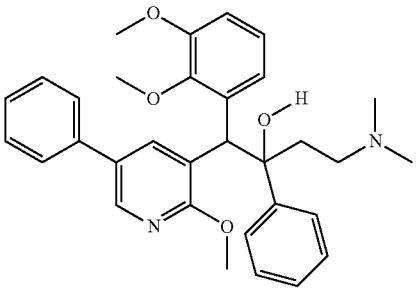

Compound 71 (A1)
Compound 72 (A2)
Compound 73 (B1)
Compound 74 (B2)

Step 1: (2,3-dimethoxyphenyl) (2-methoxy-5-phenylpyridin-3-yl)methanol

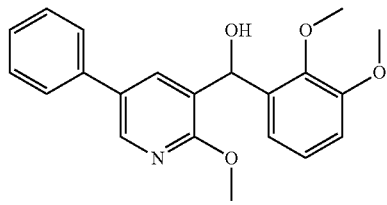 [SMILES: COc1cccc(C(O)c2cc(-c3ccccc3)cnc2OC)c1OC]

According to the method of step 2 in Example 53, the product was prepared from 2-methoxy-5-phenylpyridine and 2,3-dimethoxybenzaldehyde. Yield: 55.9%. LCMS (ESI) m/z: 352 (M+1).

Step 2: 3-(2,3-dimethoxybenzyl)-2-methoxy-5-phenylpyridine

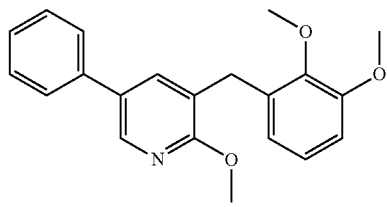 [SMILES: COc1cccc(Cc2cc(-c3ccccc3)cnc2OC)c1OC]

According to the method of step 2 in Example 60, the product was prepared from (2,3-dimethoxyphenyl)(2-methoxy-5-phenylpyridin-3-yl)methanol. Yield: 41.9%. $^1$H NMR (400 MHz, CHLOROFORM-d) δ 8.25 (d, J=2.51 Hz, 1H), 7.56-7.39 (m, 5H), 7.34 (d, J=7.28 Hz, 1H), 7.05-6.97 (m, 1H), 6.82 (ddd, J=19.70, 7.91, 1.38 Hz, 2H), 4.04 (s, 3H), 4.02 (s, 2H), 3.89 (s, 3H), 3.82 (s, 3H); LCMS (ESI) m/z: 336 (M+1).

137

Step 3: 1-(2,3-dimethoxyphenyl)-4-(dimethylamino)-1-(2-methoxy-5-phenylpyridin-3-yl)-2-phenylbutan-2-ol

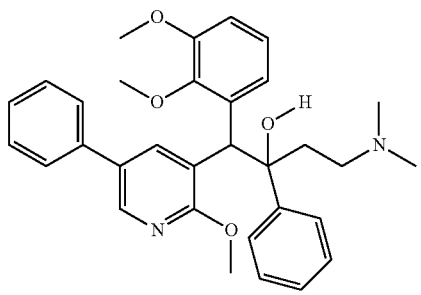

Compound 71 (A1)
Compound 72 (A2)
Compound 73 (B1)
Compound 74 (B2)

According to the method of step 4 in Example 53, 3-(2,3-dimethoxybenzyl)-2-methoxy-5-phenylpyridine and 3-(dimethylamino)-1-phenylpropan-1-one were used to prepare crude product which was separated by preparative HPLC (GX-G; Phenomenex Synergi C18 150*30 mm*4 um; acetonitrile 23%-53%; water (0.225% formic acid); 25 mL/min) to give component A and component B. Component A was separated by chiral SFC (Chiralpak IC 250×30 mm I.D., 5 um; supercritical $CO_2$/EtOH (0.05% $Et_2NH$)=60/40; 80 ml/min; 220 nm) to give compound 71 (A1) (136.9 mg, 4.8% yield) and compound (A2) (150.0 mg, 5.1% yield) as white solid. Component B was separated by chiral SFC (Chiralpak IC 250×30 mm I.D., 5 um; supercritical $CO_2$/EtOH (0.05% $Et_2NH$)=60/40; 80 ml/min; 220 nm) to give compound 73 (B1) (137.3 mg, 4.7% yield) and compound 74 (B2) (86.6 mg, 3.0% yield) as white solid. Compound 71 (A1)/compound 72 (A2): $^1$H NMR (400 MHz, METHANOL-$d_4$) δ 8.52 (s, 1H), 8.29 (d, J=2.51 Hz, 1H), 8.15 (d, J=2.38 Hz, 1H), 7.64 (d, J=8.03 Hz, 1H), 7.56-7.48 (m, 4H), 7.44 (t, J=7.59 Hz, 2H), 7.35 (d, J=7.28 Hz, 1H), 7.24 (t, J=7.78 Hz, 2H), 7.15-7.07 (m, 1H), 6.87-6.77 (m, 1H), 6.67 (d, J=8.16 Hz, 1H), 5.67 (s, 1H), 4.16 (s, 3H), 3.69 (s, 3H), 3.53 (s, 3H), 2.66 (br. s., 1H), 2.39-2.20 (m, 8H), 2.07-1.97 (m, 1H); compound 73 (B1)/compound 74 (B2): $^1$H NMR (400 MHz, METHANOL-$d_4$) δ 8.61 (d, J=2.13 Hz, 1H), 8.49 (s, 1H), 8.00 (d, J=2.38 Hz, 1H), 7.58 (d, J=7.65 Hz, 2H), 7.45 (d, J=4.27 Hz, 4H), 7.39-7.26 (m, 3H), 7.19-7.02 (m, 3H), 7.01-6.95 (m, 1H), 5.57 (br. s., 1H), 4.15-3.96 (m, 3H), 3.91 (s, 3H), 3.78 (s, 3H), 2.97-2.82 (m, 1H), 2.61-2.32 (m, 8H), 2.10-1.98 (m, 1H). LCMS (ESI) m/z: 513 (M+1).

138

Example 66

2-(3,5-difluorophenyl)-1-(2,3-dimethoxyphenyl)-4-(dimethylamino)-1-(2-methoxy-5-phenylpyridin-3-yl)butan-2-ol

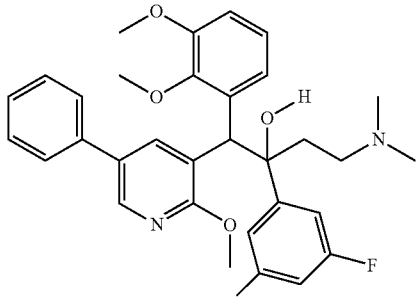

Compound 205 (A1)
Compound 206 (A2)
Compound 207 (B1)
Compound 208 (B2)

Under nitrogen, diisopropylamine (1.2 g, 12 mmol) was dissolved in 20 mL of anhydrous tetrahydrofuran and n-butyllithium (2.5M n-hexane solution, 5 mL, 12.5 mmol) was added dropwise at −78° C. After 15 minutes, 3-(2,3-dimethoxybenzyl)-2-methoxy-5-phenylpyridine (2.0 g, 5.97 mmol) dissolved in 8 mL of anhydrous tetrahydrofuran was slowly added to the reaction liquid and then stirred for 1 h. 1-(3-chlorophenyl)-3-(dimethylamino)propan-1-one (1.4 g, 6.6 mmol) was dissolved in 8 mL of anhydrous tetrahydrofuran and added slowly to the reaction system at −78° C. and then stirred for 1 h. The reaction mixture was quenched with 50 mL of ammonium chloride solution and extracted with ethyl acetate (50 mL×3). The combined organic phase was washed with brine (50 mL), dried over anhydrous sodium sulfate and filtered. The filtrate was concentrated under reduced pressure to give 300 mgcrude product as a yellow sugar which was separated and purified by preparative HPLC (GX-E; Agella Venusil ASB C18 150*21.2 mm*5 um; acetonitrile 40%-70%; water (0.225% hydrochloric acid); 25 mL/min) to give component A and component B. Component A was separated by chiral SFC (sfc-80; IC-10 um; supercritical $CO_2$/EtOH (0.1% aqueous ammonia)=40/60; 60 ml/min; 220 nm) to give compound 205 (A1) (21.45 mg, 0.86% yield) and compound 206 (A2) (27.58 mg, 0.84% yield) as white solid. Component B was separated by chiral SFC (sfc-80; AD-10 um; supercritical $CO_2$/EtOH (0.1% aqueous ammonia)=40/60; 70 ml/min; 220 nm) to give compound 207 (B1) (29.25 mg, 0.89% yield) and compound 208 (B2) (23.52 mg, 0.72% yield) as white solid. Compound 205 (A1)/compound 206 (A2): $^1$H NMR (400 MHz, METHANOL-$d_4$): δ 8.32-8.20 (m, 1H), 7.72 (dd, J=1.4, 8.0 Hz, 1H), 7.57-7.29 (m, 5H), 7.12 (d, J 7.2 Hz, 2H), 6.88 (t, J=8.1 Hz, 1H), 6.77-6.58 (m, 2H), 5.58 (s, 1H), 4.16 (s, 3H), 3.71 (s, 3H), 3.55 (s, 3H), 2.37-2.20 (m, 1H), 2.08-1.95 (m, 9H); compound 207 (B1)/compound 208 (B2): $^1$H NMR (400 MHz, METHANOL-$d_4$): δ 8.80 (br. s., 1H), 8.12 (d, J=2.1 Hz, 1H), 7.50 (d, J=4.1 Hz, 4H), 7.45-7.40 (m, 1H), 7.24 (d, J=7.0 Hz, 2H), 7.11-7.06 (m, 2H), 7.05-7.00 (m, 1H), 6.79 (t, J=8.9 Hz, 1H), 5.54 (br. s., 1H), 4.05 (d, J=7.3 Hz, 3H), 3.97 (br. s., 3H), 3.05 (dt, J=4.4, 12.1 Hz, 1H), 2.76-2.72 (m, 6H), 2.66-2.49 (m, 2H), 2.13-2.02 (m, 1H). LCMS (ESI) m/z: 548.2 (M+1).

Example 67

2-(3-chlorophenyl)-1-(2, 3-dimethoxyphenyl)-4-(dimethylamino)-1-(2-methoxy-5-phenylpyridin-3-yl)butan-2-ol

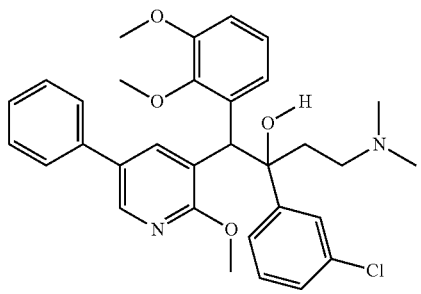

Compound 209 (A1)
Compound 210 (A2)
Compound 211 (B1)
Compound 212 (B2)

Step 1:
1-(3-chlorophenyl)-3-(dimethylamino)propan-1-one

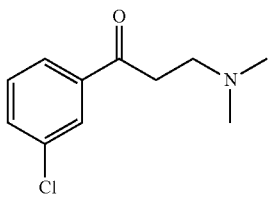

1-(3-chlorophenyl)ethanone (10.0 g, 64.7 mmol), dimethylamine hydrochloride (26.37 g, 323 mmol), paraformaldehyde (7.77 g, 258 mmol) and concentrated hydrochloric acid (1 mL) were mixed in 20 mL of ethanol and stirred at 80° C. to reflux for 16 h. The mixture was concentrated under reduced pressure and acidified with 3M hydrochloric acid solution and then washed with dichloromethane (50 mL×3). The aqueous phase was basified with saturated sodium carbonate solution (50 mL×3) and then extracted with ethyl acetate (50 ml×3). The combined ethyl acetate phase was dried over anhydrous sodium sulfate, and concentrated under reduced pressure to give crude product, 1-(3-chlorophenyl)-3-(dimethylamino)propan-1-one (6.30 g, 29.76 mmol, 46.0% yield) as a pale yellow oil which was used in the next step without further purification. $^1$H NMR (400 MHz, METHANOL-$d_4$): δ 8.07 (s, 1H), 8.01 (d, J 8.0 Hz, 1H), 7.70 (d, J=8.0 Hz, 1H), 7.57 (t, J=8.0 Hz, 2H), 3.65-3.56 (m, 4H), 2.98 (s, 6H) 2.72 (s, 1H); LCMS (ESI) m/z: 212.2 (M+1).

Step 2: 2-(3-chlorophenyl)-1-(2, 3-dimethoxyphenyl)-4-(dimethylamino-1-(2-methoxy-5-phenylpyridin-3-yl)butan-2-ol

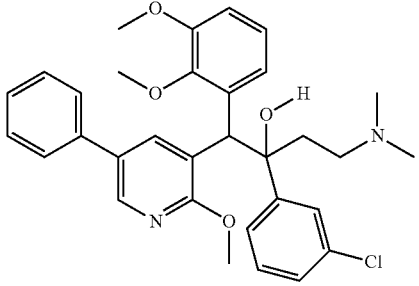

Compound 209 (A1)
Compound 210 (A2)
Compound 211 (B1)
Compound 212 (B2)

Under nitrogen, diisopropylamine (1.2 g, 12 mmol) was dissolved in 20 mL of anhydrous tetrahydrofuran and n-butyllithium (2.5M n-hexane solution, 5 mL, 12.5 mmol) was added dropwise at −78° C. After 15 minutes, 3-(2,3-dimethoxybenzyl)-2-methoxy-5-phenylpyridine (2.0 g, 5.97 mmol) dissolved in 8 mL of anhydrous tetrahydrofuran was added to the reaction liquid and then stirred for 1 h. 1-(3-chlorophenyl)-3-(dimethylamino)propan-1-one (1.4 g, 6.6 mmol) was dissolved in 8 mL of anhydrous tetrahydrofuran and added slowly to the reaction system at −78° C. and then stirred for 1 h. The reaction mixture was quenched with 50 mL of ammonium chloride solution and extracted with ethyl acetate (50 mL×3). The combined organic phase was washed with brine (50 mL), dried over anhydrous sodium sulfate and filtered. The filtrate was concentrated under reduced pressure to give 300 mg of crude product as a yellow sugar which was separated and purified by preparative HPLC (GX-E; Agella Venusil ASB C18 150*21.2 mm*5 um; acetonitrile 35%-65%; water (0.225% hydrochloric acid); 25 mL/min) to give component A and component B. Component A was separated by chiral SFC (sfc-80; IC-10 um; supercritical $CO_2$/EtOH (0.1% aqueous ammonia)=50/50; 60 ml/min; 220 nm) to give compound 209 (A1) (26.62 mg, 0.82% yield) and compound 210 (A2) (29.12 mg, 0.89% yield) as white solid. Component B was separated by chiral SFC (sfc-80; AD-10 um; supercritical $CO_2$/EtOH (0.1% aqueous ammonia)=40/60; 70 ml/min; 220 nm) to give compound 211 (B1) (21.87 mg, 0.67% yield) and compound 212 (B2) (19.92 mg, 0.61% yield) as white solid. Compound 209 (A1)/compound 210 (A2): $^1$H NMR (400 MHz, METHANOL-$d_4$): δ 8.28 (d, J=2.5 Hz, 1H), 8.20 (d, J=2.4 Hz, 1H), 7.68 (d, J=7.0 Hz, 1H), 7.57 (s, 1H), 7.54-7.49 (m, 2H), 7.43 (t, J=7.5 Hz, 3H), 7.37-7.30 (m, 1H), 7.20 (t, J=7.8 Hz, 1H), 7.10 (dd, J=1.1, 7.9 Hz, 1H), 6.85 (t, J=8.2 Hz, 1H), 6.69 (dd, J=1.1, 8.2 Hz, 1H), 5.62 (s, 1H), 4.16 (s, 3H), 3.69 (s, 3H), 3.54 (s, 3H), 2.51-2.38 (m, 1H), 2.24-1.94 (m, 9H); compound 211 (B1)/compound 212 (B2): $^1$H NMR (400 MHz, METHANOL-$d_4$): δ 8.57 (d, J=2.4 Hz, 1H), 8.43 (br. s., 1H), 8.03 (d, J=2.4 Hz, 1H), 7.69 (s, 1H), 7.46 (d, J=4.3 Hz, 5H), 7.39-7.33 (m, 1H), 7.27 (t, J=7.9 Hz, 1H), 7.17 (dd, J=1.1, 7.9 Hz, 1H), 7.13-7.03 (m, 2H), 7.01-6.96 (m, 1H), 5.54 (br. s., 1H), 4.04 (br. s., 3H), 3.91 (s, 3H), 3.81 (s, 3H), 3.04-2.90 (m, 1H), 2.65 (s, 6H), 2.58-2.40 (m, 2H), 2.08 (s, 1H). LCMS (ESI) m/z: 547.2 (M+1).

Example 68

2-(3,5-dichlorophenyl)-1-(2,3-dimethoxyphenyl)-4-(dimethylamino)-1-(2-methoxy-5-phenylpyridin-3-yl)butan-2-ol

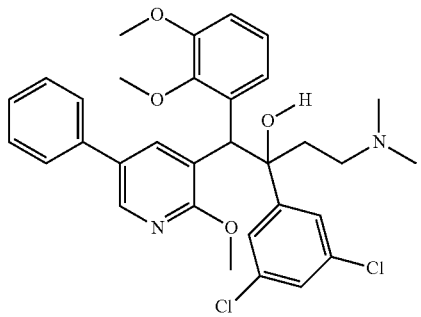

Compound 213 (A1)
Compound 214 (A2)
Compound 215 (B1)
Compound 216 (B2)

Step 1: 1-(3,5-dichlorophenyl)-3-(dimethylamino)propan-1-one

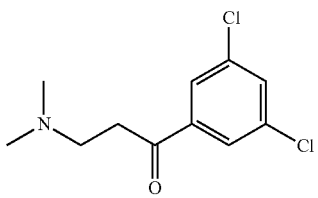

1-(3,5-dichlorophenyl)ethanone (10.0 g, 52.90 mmol) and N-methylmethylamine hydrochloride (8.63 g, 105.80 mmol) were mixed in 100 mL of ethanol and paraformaldehyde (3.18 g, 35.30 mmol) and concentrated hydrochloric acid (2 mL) were added at 25° C. The mixture was stirred at 78° C. for 72 h and concentrated under reduced pressure. The mixture was poured into 80 mL of water, and washed with dichloromethane (50 mL×2). The aqueous phase was basified with aqueous potassium carbonate solution, adjusted to pH 10, and then extracted with ethyl acetate (50 mL×3). The combined ethyl acetate phase was dried over anhydrous sodium sulfate and filtered. The filtrate was concentrated under reduced pressure to give 1-(3,5-dichlorophenyl)-3-(dimethylamino)propan-1-one (6.85 g, 52.6% yield) as a yellow oil which was used directly in the next step without further purification. LCMS (ESI) m/z: 246 (M+1).

Step 2: 2-(3,5-dichlorophenyl)-1-(2,3-dimethoxyphenyl)-4-(dimethylamino)-1-(2-methoxy-5-phenylpyridin-3-yl)butan-2-ol

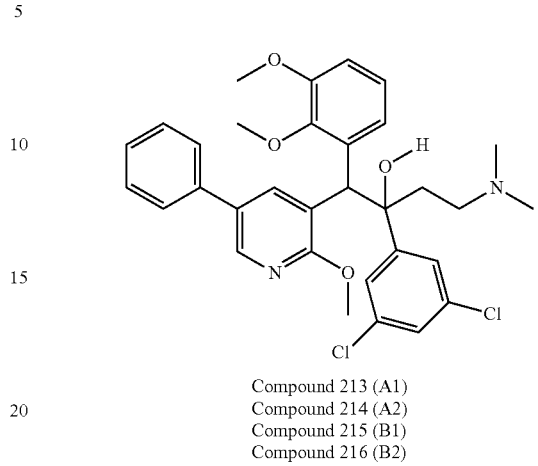

Compound 213 (A1)
Compound 214 (A2)
Compound 215 (B1)
Compound 216 (B2)

Under nitrogen, diisopropylamine (1.2 g, 12 mmol) was dissolved in 20 mL of anhydrous tetrahydrofuran and n-butyllithium (2.5M n-hexane solution, 5 mL, 12.5 mmol) was added dropwise at −78° C. After 15 minutes, 3-(2,3-dimethoxybenzyl)-2-methoxy-5-phenylpyridine (2.0 g, 5.97 mmol) dissolved in 8 mL of anhydrous tetrahydrofuran was added to the reaction liquid and stirred for 1 hour. 1-(3,5-dichlorophenyl)-3-(dimethylamino)propan-1-one (1.5 g, 6.1 mmol) dissolved in 8 mL of anhydrous tetrahydrofuran was slowly added to the reaction system at −78° C. and then stirred for 1 h. The reaction mixture was quenched with 50 mL of aqueous ammonium chloride solution and extracted with ethyl acetate (50 mL×3). The combined organic phase was washed with brine (50 mL), dried over anhydrous sodium sulfate and filtered. The filtrate was concentrated under reduced pressure to give 300 mg of crude product as a yellow sugar which was separated and purified by preparative HPLC (GX-E; Agella Venusil ASB C18 150*21.2 mm*5 um; acetonitrile 38%-68%; water (0.225% hydrochloric acid); 25 mL/min) to give component A and component B. Component A was separated by chiral SFC (sfc-80; AD-5 um; supercritical CO$_2$/EtOH (0.1% aqueous ammonia)=30/70; 55 ml/min; 220 nm) to give compound 213 (A1) (61.28 mg, 1.8% yield) and compound 214 (A2) (29.15 mg, 0.84% yield) as white solid. Component B was separated by chiral SFC (sfc-80; AD-10 um; supercritical CO$_2$/i-PrOH (0.1% aqueous ammonia)=70/30; 70 ml/min; 220 nm) to give compound 215 (B1) (46.87 mg, 0.74% yield) and compound 216 (B2) (25.72 mg, 0.61% yield) as white solid. Compound 213 (A1)/compound 214 (A2): $^1$H NMR (400 MHz, METHANOL-d$_4$): δ 8.33-8.21 (m, 2H), 7.67 (d, J=8.0 Hz, 1H), 7.54-7.38 (m, 6H), 7.32 (d, J=7.3 Hz, 1H), 7.19-7.10 (m, 1H), 6.85 (t, J=8.1 Hz, 1H), 6.75-6.64 (m, 1H), 5.55 (s, 1H), 4.14 (s, 3H), 3.68 (s, 3H), 3.55 (s, 3H), 2.24 (d, J=6.3 Hz, 1H), 2.06-1.94 (m, 9H); compound 215 (B1)/compound 216 (B2): $^1$H NMR (400 MHz, METHANOL-d$_4$): δ□ 8.16 (br. s., 1H), 7.72 (d, J=2.1 Hz, 1H), 7.64 (dd, J=1.1, 8.0 Hz, 1H), 7.58 (d, J=1.5 Hz, 2H), 7.55-7.49 (m, 2H), 7.44 (t, J=7.6 Hz, 2H), 7.38-7.30 (m, 1H), 7.22 (s, 1H), 6.93-6.85 (m, 1H), 6.77 (dd, J=1.1, 8.2 Hz, 1H), 5.26 (br. s., 1H), 3.71 (s, 3H), 3.63 (s, 3H), 3.37 (s, 3H), 3.22-3.09 (m, 1H), 2.87-2.56 (m, 8H), 2.30-2.16 (m, 1H). LCMS (ESI) m/z: 581.2 (M+1).

Example 69

4-(dimethylamino)-1-(2-fluoro-3-methoxyphenyl)-1-(2-methoxy-5-phenylpyridin-3-yl)-2-phenylbutan-2-ol

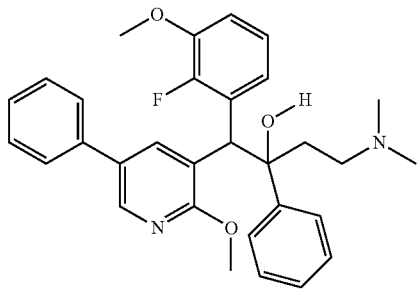

Compound 224 (A1)
Compound 225 (A2)
Compound 226 (B1)
Compound 227 (B2)

Step 1: (2-fluoro-3-methoxyphenyl) (2-methoxy-5-phenylpyridin-3-yl)methanol

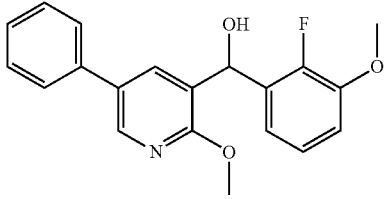 [SMILES: COc1cccc(C(O)c2cc(-c3ccccc3)cnc2OC)c1F]

According to the method of step 2 in Example 53, the product was prepared from 2-methoxy-5-phenylpyridine and 2-fluoro-3-methoxybenzaldehyde. Yield: 38.2%. LCMS (ESI) m/z: 340 (M+1).

Step 2: 3-(2-fluoro-3-methoxybenzyl)-2-methoxy-5-phenylpyridine

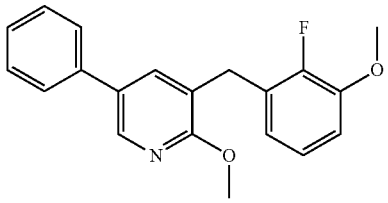 [SMILES: COc1cccc(Cc2cc(-c3ccccc3)cnc2OC)c1F]

According to the method of step 3 in Example 53, the product was prepared from (2-fluoro-3-methoxyphenyl)(2-methoxy-5-phenylpyridin-3-yl)methanol. Yield: 60.2%. LCMS (ESI) m/z: 324 (M+1).

Step 3: 4-(dimethylamino)-1-(2-fluoro-3-methoxyphenyl)-1-(2-methoxy-5-phenylpyridin-3-yl)-2-phenylbutan-2-ol

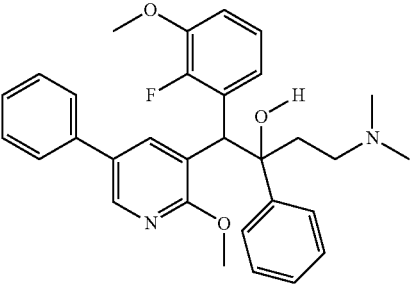

Compound 224 (A1)
Compound 225 (A2)
Compound 226 (B1)
Compound 227 (B2)

Under nitrogen, diisopropylamine (0.97 g, 9.62 mmol) was dissolved in 20 mL of anhydrous tetrahydrofuran and n-butyllithium (2.5M n-hexane solution, 2.6 mL, 6.41 mmol) was added slowly at −70° C. and stirred for 5 minutes. 3-(2-fluoro-3-methoxybenzyl)-2-methoxy-5-phenylpyridine (2.2 g, 6.4 mmol) was dissolved in 10 mL of anhydrous tetrahydrofuran and added slowly to the reaction liquid. Afterwards, the mixture was stirred at −70° C. for 1 h. Then 3-(dimethylamino)-1-phenylpropan-1-one (1.75 g, 9.6 mmol) dissolved in 10 mL of anhydrous tetrahydrofuran was added to the reaction system and then stirred at −70° C. for 2 h. The reaction mixture was quenched with 20 mL of saturated ammonium chloride solution, extracted with ethyl acetate (50 mL×3), dried over anhydrous sodium sulfate, concentrated in vacuo and isolated by column chromatography (eluent: petroleum ether/ethyl acetate=30/1-5/1) and preparative HPLC (GX-D; Boston Symmetrix C18 ODS-R 150*30 mm*5 um; acetonitrile 25%-55%; water (0.225% formic acid); 25 mL/min) to give component A and component B. Component A was separated by chiral SFC (Chiralpak IC 250×30 mm I.D., 5 um; supercritical $CO_2$/EtOH (0.2% $NH_3.H_2O$)=50/50; 70 ml/min; 220 nm) to give compound 224 (A1) (34.5 mg, 1.1% yield) and compound 225 (A2) (43.1 mg, 1.4% yield) as white solid. Component B was separated by chiral SFC (Chiralpak IC 250×30 mm I.D., 5 um; supercritical $CO_2$/EtOH (0.2% $NH_3.H_2O$)=50/50; 70 ml/min; 220 nm) to give compound 226 (B1) (34.5 mg, 1.1% yield) and compound 227 (B2) (43.1 mg, 1.4% yield) as white solid. Compound 224 (A1)/compound 225 (A2): $^1$H NMR (400 MHz, CHLOROFORM-d): δ 8.65 (d, J=2.4 Hz, 1H), 8.02 (d, J=2.5 Hz, 1H), 7.61 (br. s., 2H), 7.49-7.40 (m, 4H), 7.35-7.30 (m, 2H), 7.28-7.24 (m, 2H), 7.14-7.07 (m, 1H), 6.99 (dt, J=1.0, 8.0 Hz, 1H), 6.85 (dt, J=1.3, 8.1 Hz, 1H), 5.34 (s, 1H), 3.95 (s, 3H), 3.79 (s, 3H), 2.34-2.23 (m, 1H), 2.03 (br. s., 8H), 1.80 (d, J=14.7 Hz, 1H); compound 226 (B1)/compound 227 (B2): $^1$H NMR (400 MHz, CHLOROFORM-d): δ 8.49 (br. s., 1H), 8.31 (d, J=2.5 Hz, 1H), 7.59-7.51 (m, 5H), 7.45 (t, J=7.6 Hz, 2H), 7.36 (d, J=7.4 Hz, 1H), 7.28-7.24 (m, 2H), 7.17-7.10 (m, 1H), 6.84-6.78 (m, 1H), 6.60 (t, J=7.5 Hz, 1H), 5.45 (s, 1H), 4.11 (s, 3H), 3.70 (s, 3H), 2.43-2.24 (m, 1H), 2.13 (br. s., 7H), 1.90 (br. s., 1H), 1.66-1.53 (m, 1H). LCMS (ESI) m/z: 501 (M+1).

Example 70

4-(dimethylamino)-1-(2-methoxy-5-phenylpyridin-3-yl)-2-phenyl-1-(pyridin-2-yl)butan-2-ol Compound 228 (B)

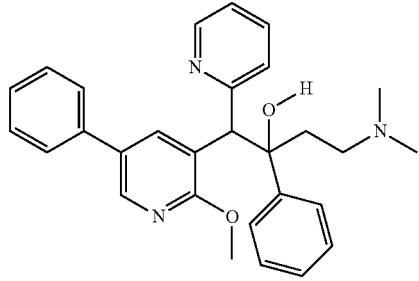

Step 1: (2-methoxy-5-phenylpyridin-3-yl) (pyridin-2-yl)methanol

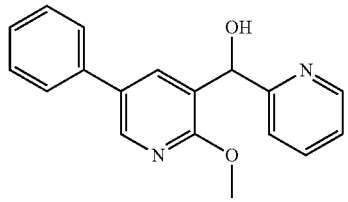

According to the method of step 2 in Example 53, the product was prepared from 2-methoxy-5-phenylpyridine and 2-pyridine carboxaldehyde. Yield: 41%. LCMS (ESI) m/z: 293 (M+1).

Step 2: O-((2-methoxy-5-phenylpyridin-3-yl) (pyridin-2-yl)methyl)thio-methyl dithiocarbonate

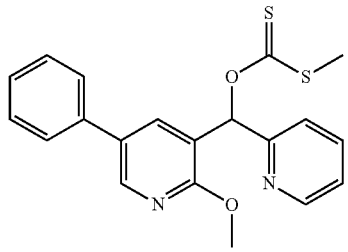 [SMILES: COc1ncc(-c2ccccc2)cc1C(OC(=S)SC)c1ccccn1]

Under nitrogen, (2-methoxy-5-phenyl-3-pyridyl)-(2-pyridyl)methanol (1.50 g, 5.13 mmol) was dissolved in 20 mL of anhydrous tetrahydrofuran. At 0° C., sodium hydride (308.00 mg, 7.70 mmol) was added in one portion and stirred for 30 minutes. Then carbon disulfide (1.17 g, 15.4 mmol) and iodomethane (2.18 g, 15.4 mmol) were added and the mixture was stirred at 25° C. for 2 h. The reaction liquid was cooled to 0° C. and added to 10 mL of iced water. The mixture was extracted with ethyl acetate (20 mL×3), dried over anhydrous sodium sulfate, concentrated in vacuo and isolated by column chromatography (eluent: petroleum ether/ethyl acetate=30/1-20/1) to give O-((2-methoxy-5-phenylpyridin-3-yl) (pyridin-2-yl)methyl)thio-methyl dithiocarbonate (1.30 g, 66.3% yield) as yellow solid.

Step 3: 2-methoxy-5-phenyl-3-(pyridin-2-ylmethyl)pyridine

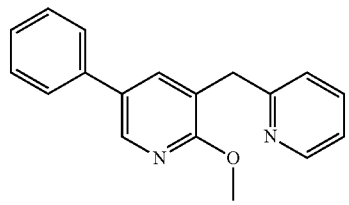

Under nitrogen, O-((2-methoxy-5-phenylpyridin-3-yl) (pyridin-2-yl)methyl)thio-methyl dithiocarbonate (1.30 g, 3.4 mmol) and tributyl stannane (2.27 g, 7.84 mmol) were mixed in 30 mL of toluene and AIBN(0.1 eq) was added at 25° C. The mixture was warmed to 80° C. and stirred for 6 h. The reaction liquid was cooled and added to 150 mL of iced water. The mixture was extracted with ethyl acetate (20 mL×3) and the combined organic phase was dried over anhydrous sodium sulfate, concentrated in vacuo and isolated by column chromatography (eluent: petroleum ether/ethyl acetate=30/1-20/1) to give 2-methoxy-5-phenyl-3-(pyridin-2-ylmethyl)pyridine as yellow solid. LCMS (ESI) m/z: 277 (M+1).

Step 4: 4-(dimethylamino)-1-(2-methoxy-5-phenylpyridin-3-yl)-2-phenyl-1-(pyridin-2-yl)butan-2-ol Compound 228 (B)

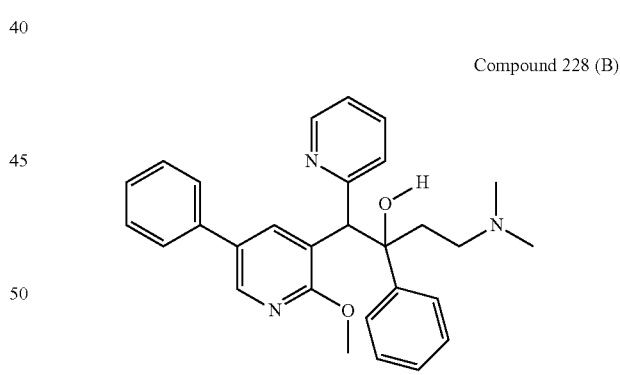

According to the method of step 4 in Example 53, the product was prepared from 2-methoxy-5-phenyl-3-(pyridin-2-ylmethyl)pyridine and 3-(dimethylamino)-1-phenylpropan-1-one. Component A was decomposed during the separation process and component B are recrystallized in methanol to give compound 228 (B). $^1$HNMR (400 MHz, DMSO-d$_6$): δ 8.40-8.34 (m, 1H), 7.58-7.52 (m, 3H), 7.52-7.46 (m, 1H), 7.43 (d, J=7.4 Hz, 1H), 7.40-7.35 (m, 1H), 7.27 (d, J=8.2 Hz, 1H), 7.22 (t, J=7.6 Hz, 2H), 7.08 (t, J=8.1 Hz, 1H), 5.16 (s, 1H), 4.05 (s, 3H), 2.17-2.11 (m, 1H), 1.98 (d, J=15.6 Hz, 1H), 1.90 (s, 6H), 1.69-1.61 (m, 2H); LCMS (ESI) m/z: 454 (M+1).

Example 71

4-(dimethylamino)-1-(2-methoxy-5-phenylpyridin-3-yl)-2-phenyl-1-(pyridin-3-yl)butan-2-ol

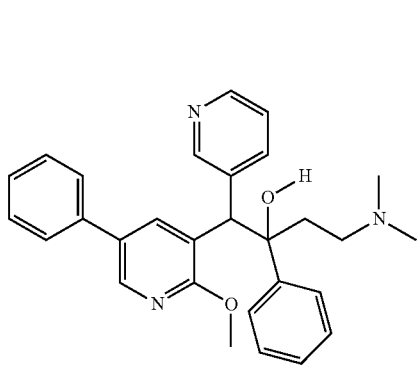

Compound 229 (A1)
Compound 230 (A2)
Compound 231 (B1)
Compound 232 (B2)

Step 1: (2-methoxy-5-phenylpyridin-3-yl) (pyridin-3-yl)methanol

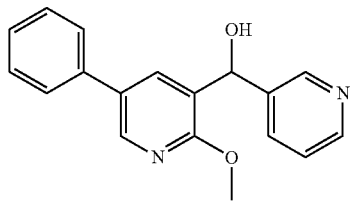 [SMILES: COc1ncc(-c2ccccc2)cc1C(O)c1cccnc1]

According to the method of step 2 in Example 53, the product was prepared from 2-methoxy-5-phenylpyridine and nicotinaldehyde. Yield: 41%. LCMS (ESI) m/z: 293 (M+1).

Step 2: O-((2-methoxy-5-phenylpyridin-3-yl) (pyridin-3-yl)methyl)thio-methyl dithiocarbonate

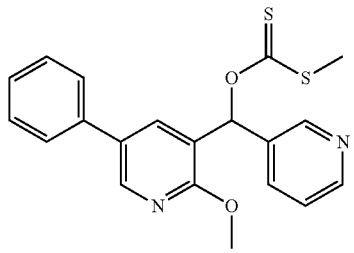 [SMILES: COc1ncc(-c2ccccc2)cc1C(OC(=S)SC)c1cccnc1]

According to the method of step 2 in Example 70, the product was prepared from (2-methoxy-5-phenylpyridin-3-yl) (pyridin-3-yl)methanol. Yield: 62%. LCMS (ESI) m/z: 383 (M+1).

Step 3: 2-methoxy-5-phenyl-3-(pyridin-3-ylmethyl)pyridine

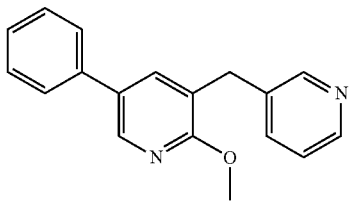 [SMILES: COc1ncc(-c2ccccc2)cc1Cc1cccnc1]

According to the method of step 3 in Example 70, the product was prepared from O-((2-methoxy-5-phenylpyridin-3-yl) (pyridin-3-yl)methyl)thio-methyl dithiocarbonate. Yield: 62%. LCMS (ESI) m/z: 277 (M+1)

Step 4: 4-(dimethylamino)-1-(2-methoxy-5-phenylpyridin-3-yl)-2-phenyl-1-(pyridin-3-yl)butan-2-ol

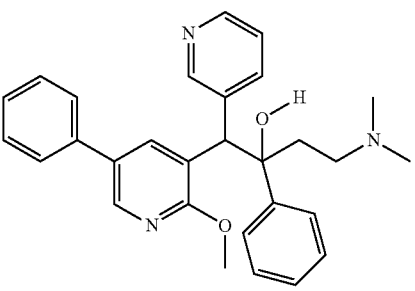

Compound 229 (A1)
Compound 230 (A2)
Compound 231 (B1)
Compound 232 (B2)

According to the method of step 4 in Example 53, 2-methoxy-5-phenyl-3-(pyridin-3-ylmethyl)pyridine and 3-(dimethylamino)-1-phenylpropan-1-one were used to prepare crude product which was isolated by column chromatography (petroleum ether/ethyl acetate=30/1-5/1) and preparative HPLC (GX-D; Boston Symmetrix C18 ODS-R 150*30 mm*5 um; acetonitrile 25%-55%; water (0.225% formic acid); 25 mL/min) to give component A and component B. Component A was separated by chiral SFC (Chiralpak AD 250×30 mm I.D., 5 um; supercritical $CO_2$/EtOH (0.2% $NH_3.H_2O$)=50/50; 70 ml/min; 220 nm) to give compound 229 (A1) (70.4 mg, 8.2% yield) and compound 230 (A2) (39.9 mg, 4.6% yield) as white solid. Component B was separated by chiral SFC (Chiralpak AD 250×30 mm I.D., 5 um; supercritical $CO_2$/EtOH (0.2% $NH_3.H_2O$)=50/50; 70 ml/min; 220 nm) to give compound 231 (B1) (26.4 mg, 2.9% yield) and compound 232 (B2) (23.2 mg, 2.7% yield) as white solid. Compound 229 (A1)/compound 230 (A2): $^1$H NMR (400 MHz, CHLOROFORM-d): δ 8.89 (d, J=1.9 Hz, 1H), 8.61 (d, J=2.5 Hz, 1H), 8.49 (dd, J=1.6, 4.8 Hz, 1H), 8.09 (td, J=1.9, 8.0 Hz, 1H), 8.02 (d, J=2.5 Hz, 1H), 7.57 (d, J=5.8 Hz, 2H), 7.48-7.40 (m, 5H), 7.37-7.31 (m, 1H), 7.29-7.21 (m, 4H), 7.14-7.09 (m, 1H), 4.77 (s, 1H), 3.80 (s, 3H), 2.33-2.24 (m, 1H), 2.06-1.95 (m, 8H), 1.69 (br. s., 1H); compound 231 (B1)/compound 232 (B2): $^1$H NMR (400 MHz, CHLOROFORM-d): δ 8.70 (br. s., 1H), 8.33 (d, J=2.4 Hz, 2H), 8.21 (br. s., 1H), 7.85 (d, J=8.0 Hz, 1H), 7.62-7.58 (m, 2H), 7.50-7.42 (m, 4H), 7.39-7.35 (m, 1H), 7.28-7.22 (m, 2H), 7.17-7.11 (m, 1H), 7.03-6.97 (m, 1H), 4.89 (s, 1H), 4.07 (s, 3H), 2.45 (br. s., 1H), 2.21-2.13 (m, 8H), 1.99-1.92 (m, 1H). LCMS (ESI) m/z: 454 (M+1).

Example 72

4-(dimethylamino)-1-(2-methoxy-5-phenylpyridin-3-yl)-1-(3-methoxyphenyl)-2-phenylbutan-2-ol

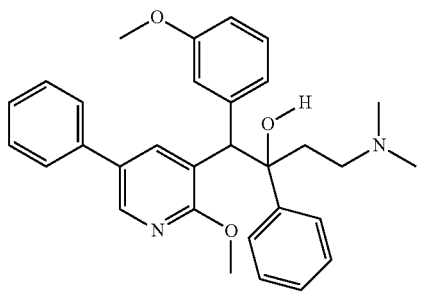

Compound 233 (A1)
Compound 234 (A2)
Compound 235 (B1)
Compound 236 (B2)

Step 1: (2-methoxy-5-phenylpyridin-3-yl)(3-methoxyphenyl)methanol

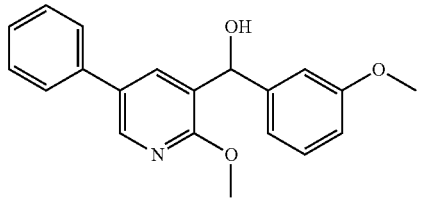 [SMILES: COc1cccc(C(O)c2cc(-c3ccccc3)cnc2OC)c1]

According to the method of step 2 in Example 53, the product was prepared from 2-methoxy-5-phenylpyridine and 4-methoxybenzaldehyde. Yield: 61%. $^1$H NMR (400 MHz, CHLOROFORM-d): δ 8.36-8.31 (m, 1H), 7.85-7.80 (m, 1H), 7.54-7.50 (m, 2H), 7.45 (t, J=7.5 Hz, 2H), 7.37 (s, 1H), 7.31 (br. s., 1H), 7.04-6.96 (m, 2H), 6.88-6.83 (m, 1H), 6.04 (s, 1H), 4.03 (s, 3H), 3.89-3.81 (m, 4H). LCMS (ESI) m/z: 322 (M+1).

Step 2: 2-methoxy-3-(3-methoxybenzyl)-5-phenylpyridine

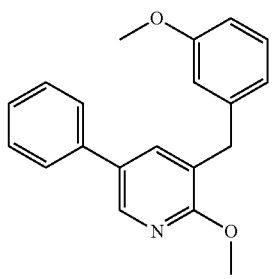 [SMILES: COc1cccc(Cc2cc(-c3ccccc3)cnc2OC)c1]

According to the method of step 2 in Example 60, the product was prepared from (2-methoxy-5-phenylpyridin-3-yl)(3-methoxyphenyl)methanol. Yield: 62%. $^1$H NMR (400 MHz, CHLOROFORM-d): δ 8.29-8.27 (m, 1H), 7.57-7.52 (m, 1H), 7.52-7.47 (m, 2H), 7.46-7.41 (m, 2H), 7.38-7.32 (m, 1H), 7.27-7.22 (m, 1H), 6.89-6.77 (m, 3H), 4.04 (s, 3H), 3.98 (s, 2H), 3.81 (s, 3H). LCMS (ESI) m/z: 306.1 (M+1).

Step 3: 4-(dimethylamino)-1-(2-methoxy-5-phenylpyridin-3-yl)-1-(3-methoxyphenyl)-2-phenylbutan-2-ol

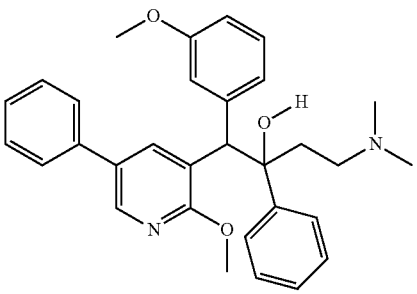

Compound 233 (A1)
Compound 234 (A2)
Compound 235 (B1)
Compound 236 (B2)

According to the method of step 4 in Example 53, 2-methoxy-3-(3-methoxybenzyl)-5-phenylpyridine and 3-(dimethylamino)-1-phenylpropan-1-one were used to prepare crude product which was separated by preparative HPLC (GX-E; Agella Venusil ASB C18 150*21.2 mm*5 um; acetonitrile 28%-58%; water (0.225% hydrochloric acid); 80 mL/min) to give component A and component B. Component A was separated by chiral SFC (Chiralpak IC 250×30 mm I.D., 10 um; supercritical CO$_2$/MeOH (0.1% aqueous ammonia)=50/50; 70 ml/min; 220 nm) to give compound 233 (A1) (6.65 mg, 0.14% yield) and compound 234 (A2) (6.67 mg, 0.14% yield) as white solid. Component B was separated by chiral SFC (Chiralpak IC 250×30 mm I.D., 10 um; supercritical CO$_2$/MeOH (0.1% aqueous ammonia)=60/40; 70 mL/min; 220 nm) to give compound 235 (B1) (6.65 mg, 0.14% yield) and compound 236 (B2) (6.67 mg, 0.14% yield) as white solid. Compound 233 (A1)/compound 234 (A2): $^1$H NMR (400 MHz, METHANOL-d$_4$): δ 8.59 (d, J=2.3 Hz, 1H), 8.56-8.41 (m, 1H), 7.97 (d, J=2.3 Hz, 1H), 7.57 (d, J=7.5 Hz, 2H), 7.49-7.41 (m, 4H), 7.38-7.32 (m, 1H), 7.30-7.27 (m, 1H), 7.26-7.20 (m, 3H), 7.15-7.09 (m, 1H), 6.88-6.82 (m, 1H), 4.79-4.52 (m, 1H), 3.80 (s, 3H), 3.77 (s, 3H), 2.85-2.72 (m, 1H), 2.46 (s, 6H), 2.38-2.26 (m, 2H), 2.22-2.11 (m, 1H); compound 235 (B1)/compound 236 (B2): $^1$HNMR (400 MHz, METHANOL-d$_4$): δ 8.61 (d, J=2.26 Hz, 1H), 8.30 (d, J=2.26 Hz, 1H), 7.60 (d, J=7.53 Hz, 2H), 7.48 (dt, J=7.47, 3.67 Hz, 4H), 7.37 (s, 1H), 7.28 (t, J=7.65 Hz, 2H), 7.18 (d, J=7.28 Hz, 1H), 6.93 (d, J=8.03 Hz, 1H), 6.89-6.79 (m, 2H), 6.56 (dd, J=8.16, 1.88 Hz, 1H), 4.64 (br. s., 2H), 4.07 (s, 3H), 3.61 (s, 3H), 2.67 (d, J=9.29 Hz, 1H), 2.36 (s, 6H), 2.24 (dd, J=18.57, 8.28 Hz, 2H), 2.16-2.00 (m, 1H). LCMS (ESI) m/z: 483.2 (M+1).

Example 73

4-(dimethylamino)-1-(2-methoxy-5-phenylpyridin-3-yl)-1-(4-methoxyphenyl)-2-phenylbutan-2-ol

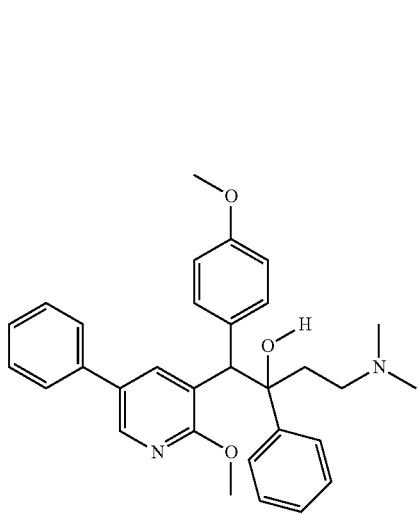

Compound 237 (A)
Compound 238 (B)

Step 1: (2-methoxy-5-phenylpyridin-3-yl)(4-methoxyphenyl)methanol

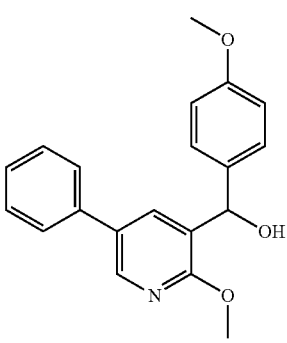 [SMILES: COc1ccc(C(O)c2cc(-c3ccccc3)cnc2OC)cc1]

According to the method of step 2 in Example 53, the product was prepared from 2-methoxy-5-phenylpyridine and 4-methoxybenzaldehyde. Yield: 29%. $^1$H NMR (400 MHz, CDCl$_3$): δ 8.31 (d, J=2.3 Hz, 1H), 7.86 (d, J=2.3 Hz, 1H), 7.55-7.51 (m, 2H), 7.48-7.43 (m, 2H), 7.39-7.30 (m, 5H), 6.01 (br. s., 1H), 4.01 (s, 3H), 3.83 (s, 3H); LCMS (ESI) m/z: 322 (M+1).

Step 2: 2-methoxy-3-(4-methoxybenzyl)-5-phenylpyridine

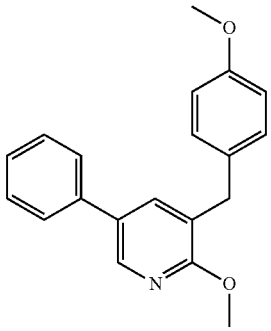 [SMILES: COc1ccc(Cc2cc(-c3ccccc3)cnc2OC)cc1]

According to the method of step 2 in Example 60, the product was prepared from (2-methoxy-5-phenylpyridin-3-yl) (4-methoxyphenyl)methanol. Yield: 68%. LCMS (ESI) m/z: 306 (M+1).

Step 3: 4-(dimethylamino)-1-(2-methoxy-5-phenylpyridin-3-yl)-1-(4-methoxyphenyl)-2-phenylbutan-2-ol

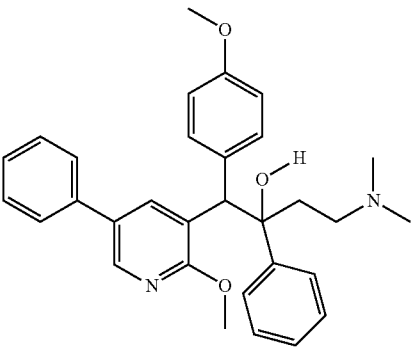

Compound 237 (A)
Compound 238 (B)

According to the method of step 4 in Example 53, 2-methoxy-3-(4-methoxybenzyl)-5-phenylpyridine and 3-(dimethylamino)-1-phenylpropan-1-one were used to prepare crude product which was purified by preparative HPLC (GX-G; Phenomenex Synergi C18 150×30 mm×4 um; acetonitrile 25%-55%; water (0.225% formic acid); 25 mL/min) to give compound 237 (A) (13.57 mg, 0.53% yield) and compound 238 (B) (4.96 mg, 0.2% yield) as white solid. Compound 237 (A): $^1$H NMR (400 MHz, METHANOL-d$_4$): δ 8.64 (d, J=2.3 Hz, 1H), 8.28 (d, J=2.3 Hz, 1H), 7.60 (d, J=7.5 Hz, 2H), 7.50-7.43 (m, 4H), 7.40-7.35 (m, 1H), 7.26 (t, J=7.5 Hz, 2H), 7.16 (d, J=8.8 Hz, 3H), 6.58 (d, J=8.8 Hz, 2H), 4.90-4.88 (m, 1H), 4.05 (s, 3H), 3.64 (s, 3H), 2.57-2.49 (m, 1H), 2.25 (br. s., 6H), 2.20-2.09 (m, 3H); compound 238 (B): $^1$H NMR (400 MHz, METHANOL-d$_4$): δ 8.62 (d, J=2.3 Hz, 1H), 7.95 (d, J=2.3 Hz, 1H), 7.59-7.53 (m, 4H), 7.49-7.43 (m, 4H), 7.36-7.32 (m, 1H), 7.25 (t, J=7.7 Hz, 2H), 7.12-7.08 (m, 1H), 6.90 (d, J=8.5 Hz, 2H), 4.82 (s, 1H), 3.83-3.75 (m, 6H), 2.48-2.40 (m, 1H), 2.19 (s, 6H), 2.12-1.97 (m, 3H). LCMS (ESI) m/z: 483.2 (M+1).

Example 74

4-(dimethylamino)-1-(2-methoxy-5-phenylpyridin-3-yl)-2-phenyl-1-(2-(trifluoromethyl)phenyl)butan-2-ol

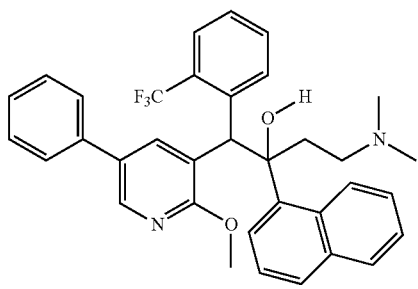

Compound 239 (B1)
Compound 240 (B2)

Step 1: (2-methoxy-5-phenylpyridin-3-yl) (2-trifluoromethyl)phenyl)methanol

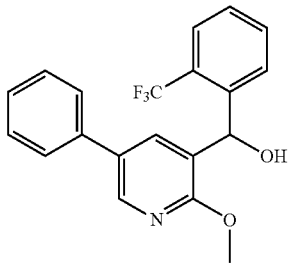 [SMILES: COc1ncc(-c2ccccc2)cc1C(O)c1ccccc1C(F)(F)F]

According to the method of step 2 in Example 53, the product was prepared from 2-methoxy-5-phenylpyridine and 2-(trifluoromethyl)benzaldehyde. Yield: 38%. LCMS (ESI) m/z: 360 (M+1).

Step 2: 2-methoxy-5-phenyl-3-(2-(trifluoromethyl)phenyl)pyridine

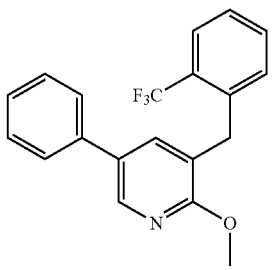 [SMILES: COc1ncc(-c2ccccc2)cc1Cc1ccccc1C(F)(F)F]

According to the method of step 2 in Example 60, the product was prepared from (2-methoxy-5-phenylpyridin-3-yl) (4-methoxyphenyl)methanol. Yield: 60%. $^1$H NMR (400 MHz, DMSO-$d_6$): δ 8.40 (s, 1H), 7.78 (d, J=8.0 Hz, 1H), 7.61 (t, J=8.0 Hz, 1H), 7.56-7.52 (m, 3H), 7.49-7.42 (m, 3H), 7.35 (t, J=8.0 Hz, 1H), 7.27 (d, J=8.0 Hz, 1H), 4.16 (s, 2H), 3.91 (s, 3H); LCMS (ESI) m/z: 344 (M+1).

Step 3: 4-(dimethylamino)-1-(2-methoxy-5-phenylpyridin-3-yl)-2-phenyl-1-(2-(trifluoromethyl)phenyl)butan-2-ol

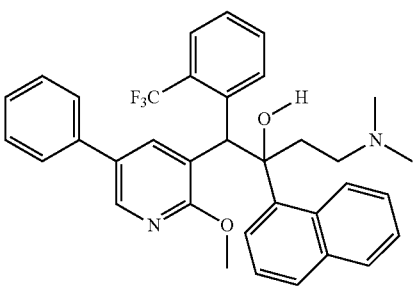

Compound 239 (B1)
Compound 240 (B2)

Under nitrogen, diisopropylamine (973 mg, 9.62 mmol) was dissolved in 20 mL of anhydrous tetrahydrofuran and n-butyllithium (2.5 M n-hexane solution, 2.56 mL, 6.41 mmol) was added slowly at −78° C. and stirred at this temperature for 0.5 h. 2-methoxy-5-phenyl-3-[[2-(trifluoromethyl)phenyl]methyl]pyridine (2.19 g, 6.41 mmol) dissolved in 10 mL of anhydrous tetrahydrofuran slowly added and stirred at −70° C. for 1 hour. 3-(dimethylamino)-1-(naphthalen-1-yl)propan-1-one(1.75 g, 7.69 mmol) dissolved in 10 mL of anhydrous tetrahydrofuran was added slowly at −70° C. and stirred at −70° C. for 2 h. The reaction was quenched with water (10 mL). The mixture was extracted with ethyl acetate (20 mL×3). The combined organic phase was washed with brine (20 mL×2), dried over anhydrous sodium sulfate, filtered and concentrated in vacuo, and isolated by column chromatography (petroleum ether/ethyl acetate=20/1-1/1) and preparative HPLC (GX-D; Phenomenex Synergi C18 150×30 mm×4 um; acetonitrile 25%-55%; water (0.225% formic acid); 25 mL/min) to give component A and component B. Component B was separated by chiral SFC (Chiralpak IC 250×30 mm I.D., 5 um; supercritical CO$_2$/EtOH (0.2% NH$_3$.H$_2$O)=50/50; 70 ml/min; 220 nm) to give compound 239 (B1) (8.9 mg, 2.4% yield) and compound 240 (B2) (7.0 mg, 1.9% yield) as white solid. Compound 239 (B1)/compound 240 (B2): 1H NMR (400 MHz, METHANOL-d$_4$): δ 9.13 (d, J=8.0 Hz, 1H), 8.58 (d, J=8.0 Hz, 1H), 8.31 (s, 1H), 7.94 (d, J=8.0 Hz, 1H), 7.82-7.72 (m, 5H), 7.61 (t, J=8.0 Hz, 1H), 7.55-7.43 (m, 7H), 7.34 (t, J=8.0 Hz, 1H), 7.27 (t, J=8.0 Hz, 1H), 6.12 (s., 1H), 2.73-2.67 (m, 4H), 2.25 (t, J=12 Hz, 1H), 2.05-1.96 (m, 8H). LCMS (ESI) m/z: 571 (M+1).

Example 75

4-(dimethylamino)-1-(2-methoxy-5-phenylpyridin-3-yl)-2-(naphthalen-1-yl)-1-(3-trifluoromethyl)phenyl)butan-2-ol

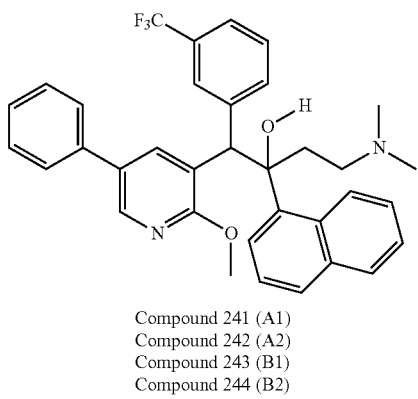 [SMILES: COc1ncc(-c2ccccc2)cc1C(c1cccc(C(F)(F)F)c1)C(O)(CCN(C)C)c1cccc2ccccc12]

Compound 241 (A1)
Compound 242 (A2)
Compound 243 (B1)
Compound 244 (B2)

Step 1: (2-methoxy-5-phenylpyridin-3-yl) (3-(trifluoromethyl)phenyl)methanol

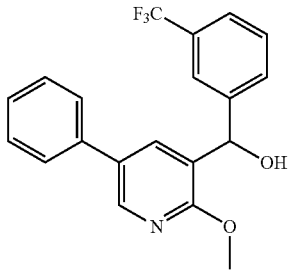 [SMILES: COc1ncc(-c2ccccc2)cc1C(O)c1cccc(C(F)(F)F)c1]

According to the method of step 2 in Example 53, the product was prepared from 2-methoxy-5-phenylpyridine and 3-(trifluoromethyl)benzaldehyde. Yield: 62%. LCMS (ESI) m/z: 360 (M+1).

Step 2: 2-methoxy-5-phenyl-3-(3-(trifluoromethyl)benzyl)pyridine

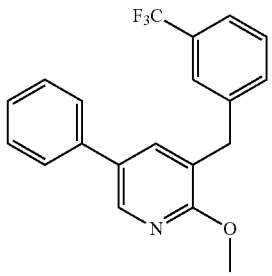 [SMILES: COc1ncc(-c2ccccc2)cc1Cc1cccc(C(F)(F)F)c1]

According to the method of step 3 in Example 53, the product was prepared from (2-methoxy-5-phenylpyridin-3-yl) (3-(trifluoromethyl)phenyl)methanol. Yield: 42%. $^1$H NMR (400 MHz, CDCl$_3$): δ 8.32 (d, J=2.3 Hz, 1H), 7.59-7.55 (m, 2H), 7.53-7.38 (m, 8H), 4.06 (s, 2H), 4.03 (s, 3H). LCMS (ESI) m/z: 344.1 (M+1).

Step 3: 4-(dimethylamino)-1-(2-methoxy-5-phenylpyridin-3-yl)-2-(naphthalen-1-yl)-1-(3-(trifluoromethyl)phenyl)butan-2-ol

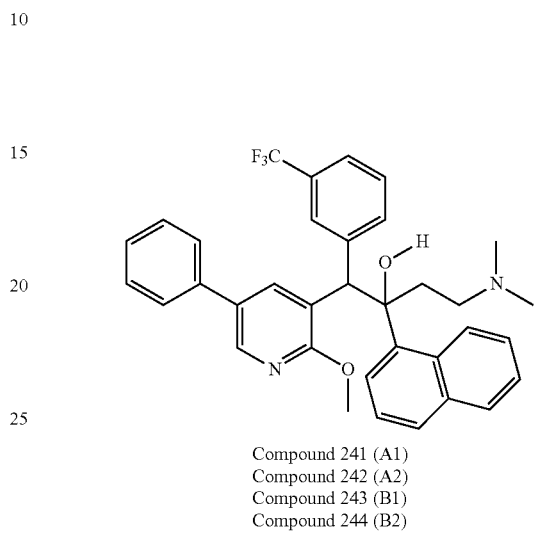

Compound 241 (A1)
Compound 242 (A2)
Compound 243 (B1)
Compound 244 (B2)

According to the method of step 4 in Example 53, the product was prepared from 2-methoxy-5-phenyl-3-(3-(trifluoromethyl)benzyl)pyridine and 3-(dimethylamino)-1-(naphthalen-1-yl)propan-1-one. The crude product which was separated by preparative HPLC (GX-G; Phenomenex Synergi C18 150×30 mm×4 um; acetonitrile 33%-63%; water (0.225% formic acid); 25 mL/min) to give component A and component B. Component A was separated by chiral SFC (Column AD-10 um; supercritical CO$_2$/Isopropanol (0.2% aqueous ammonia)=80/20; 55 mL/min; 220 nm) to give compound 241 (A1) (33.04 mg, 0.99% yield) and compound 242 (A2) (26.54 mg, 0.74% yield) as white solid. Component B was separated by chiral SFC (Column AD-10 um; supercritical CO$_2$/Isopropanol (0.2% aqueous ammonia)=70/30; 60 g/min; 220 nm) to give compound 243 (B1) (57.35 mg, 1.6%) and compound 244 (B2) (81.39 mg, 2.45%) as white solid. Compound 241 (A1)/compound 242 (A2): $^1$H NMR (400 MHz, METHANOL-d$_4$): δ 8.75 (d, J=2.3 Hz, 1H), 8.70-8.60 (m, 1H), 8.36 (d, J=2.0 Hz, 1H), 7.99-7.84 (m, 2H), 7.72-7.60 (m, 4H), 7.58-7.47 (m, 4H), 7.42-7.37 (m, 1H), 7.35-7.27 (m, 2H), 7.17 (d, J=7.8 Hz, 1H), 7.07-7.01 (m, 1H), 5.91 (br. s., 1H), 4.19 (s, 3H), 2.80-2.70 (m, 1H), 2.23-2.13 (m, 2H), 2.05 (s, 6H), 1.99-1.90 (m, 1H); compound 243 (B1)/compound 244 (B2): $^1$H NMR (400 MHz, METHANOL-d$_4$): δ 8.62-8.57 (m, 2H), 8.21-8.14 (m, 2H), 8.05 (d, J=7.0 Hz, 1H), 7.86-7.82 (m, 2H), 7.69-7.56 (m, 4H), 7.47-7.33 (m, 7H), 5.78 (s, 1H), 3.36 (s, 3H), 2.73-2.64 (m, 1H), 2.22-2.14 (m, 2H), 2.03 (s, 6H), 1.98-1.92 (m, 1H). LCMS (ESI) m/z: 571.2 (M+1).

Example 76

1-(5-(4-chlorophenyl)-2-methoxypyridin-3-yl)-2-(3,5-dichlorophenyl)-4-(dimethylamino)-1-phenylbutan-2-ol

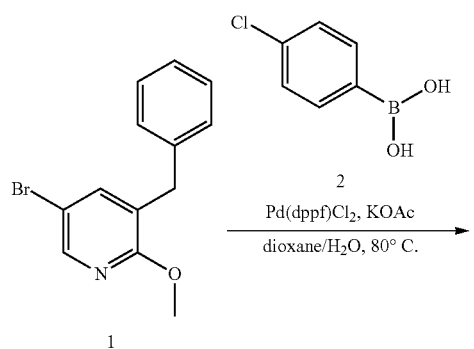

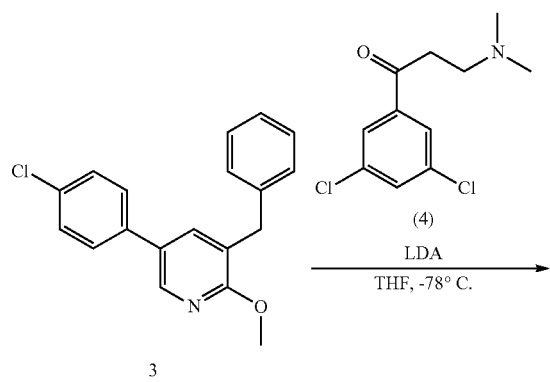

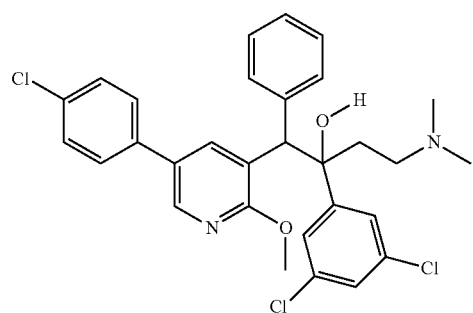

Compound 339 (A1)
Compound 340 (A2)
Compound 341 (B1)
Compound 342 (B2)

Step 1: 3-benzyl-5-(4-chlorophenyl)-2-methoxypyridine

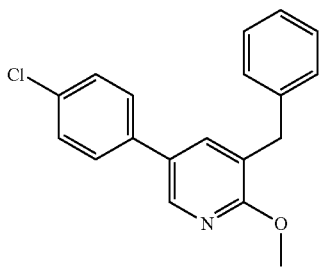 [SMILES: COc1ncc(-c2ccc(Cl)cc2)cc1Cc1ccccc1]

Under nitrogen, 3-benzyl-5-bromo-2-methoxy-pyridine (10.00 g, 35.95 mmol), (4-chlorophenyl)boronic acid (5.90 g, 37.75 mmol), Pd(dppf)Cl$_2$ (1.32 g, 1.80 mmol) and potassium acetate (10.58 g, 107.85 mmol) were dissolved in 100 mL of 1,4-dioxane and 20 mL of water, heated to 80-90° C. and stirred for 12 h. The mixture was cooled and filtered. The filtrate was poured into water, extracted with ethyl acetate (50 mL×3). The combined organic phase was washed with saturated brine, dried over anhydrous sodium sulfate, dried by rotation evaporation in vacuo and isolated by column chromatography (eluent: petroleum ether/ethyl acetate=100/130/1) to give 3-benzyl-5-(4-chlorophenyl)-2-methoxypyridine (10.0 g, 89.8% yield) as an off-white solid. LCMS (ESI) m/z: 310 (M+1).

Step 2: 1-(5-(4-chlorophenyl)-2-methoxypyridin-3-yl)-2-(3,5-dichlorophenyl)-4-(dimethylamino)-1-phenylbutan-2-ol

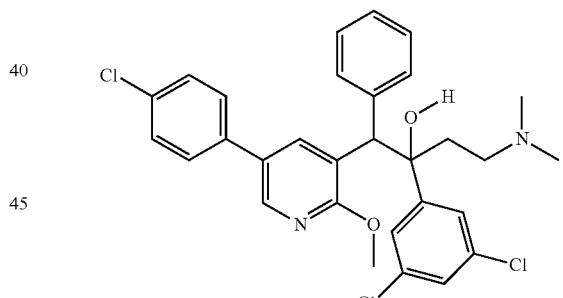

Compound 339 (A1)
Compound 340 (A2)
Compound 341 (B1)
Compound 342 (B2)

Under nitrogen, diisopropylamine (0.6 g, 5.9 mmol) was dissolved in 10 mL of anhydrous tetrahydrofuran and n-butyllithium (2.5M n-hexane solution, 2.4 mL, 5.9 mmol) was added slowly at −78° C. Then the mixture was stirred for 30 minutes. 3-benzyl-5-(4-chlorophenyl)-2-methoxypyridine (0.59 g, 1.9 mmol) dissolved in 10 mL of anhydrous tetrahydrofuran was added slowly dropwise to the reaction liquid at −78° C. and stirred for 1.5 h. Then 1-(3,5-dichlorophenyl)-3-(dimethylamino)propan-1-one (0.7 g, 2.85 mmol) was dissolved in 10 mL of anhydrous tetrahydrofuran and added slowly dropwise to the reaction system at −78° C. and stirred at −78° C. for another 1.5 h. The reaction was quenched with 10 mL of saturated aqueous ammonium chloride. The mixture was extracted with ethyl acetate (10 mL×3). The combined organic phase was dried over anhydrous sodium sulfate, dried by rotation evaporation in vacuo and isolated by column chromatography (eluent: petroleum ether/ethyl acetate=100/15/1) to give component A and component B. Component A was separated by chiral SFC (Chiralpak AD 250×30 mm I.D., 10 um; supercritical $CO_2$/EtOH (0.1% aqueous ammonia)=70/30; 60 g/min; 220 nm) to give compound 339 (A1) (96.84 mg, 9.14% yield) and compound 340 (A2) (110.63 mg, 10.44% yield). Component B was separated by chiral SFC (Chiralpak IC 250×30 mm I.D., 10 um; supercritical $CO_2$/MeOH (0.1% aqueous ammonia)=65/35; 70 mL/min; 220 nm) to give compound 341 (B1) (62.8 mg, 5.92% yield) and compound 342 (B2) (42.62 mg, 4.02% yield) as white solid. Compound 339 (A1)/compound 340 (A2): $^1$H NMR (400 MHz, CHLOROFORM-d): δ 8.52-8.47 (m, 1H), 8.03-7.98 (m, 1H), 7.77-7.69 (m, 2H), 7.40 (s, 6H), 7.37-7.31 (m, 2H), 7.27-7.20 (m, 1H), 7.14-7.08 (m, 1H), 4.70-4.65 (m, 1H), 3.82 (s, 3H), 2.34-2.23 (m, 1H), 2.18-2.04 (m, 8H), 1.70-1.60 (m, 1H); compound 341 (B1)/compound 342 (B2): $^1$H NMR (400 MHz, CHLOROFORM-d): δ 8.71-8.64 (m, 1H), 8.29-8.23 (m, 1H), 7.53-7.48 (m, 2H), 7.46-7.41 (m, 2H), 7.40-7.29 (m, 4H), 7.15-6.98 (m, 4H), 4.80-4.74 (m, 1H), 4.07 (s, 3H), 2.33-2.23 (m, 1H), 2.08 (s, 8H), 1.76-1.71 (m, 1H). LCMS (ESI) m/z: 555.1 (M+1).

Example 77

1-(5-(4-chlorophenyl)-2-methoxypyridin-3-yl)-2-(2,5-difluorophenyl)-4-(dimethylamino)-1-phenylbutan-2-ol

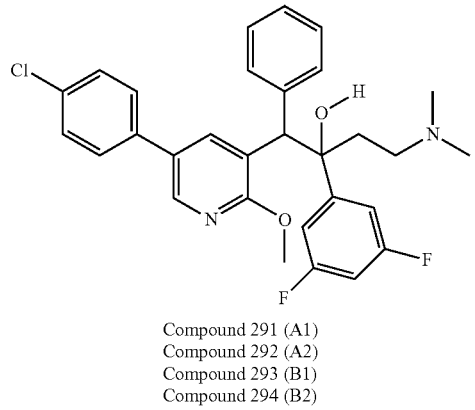 [SMILES: COc1ncc(-c2ccc(Cl)cc2)cc1C(c1ccccc1)C(O)(CCN(C)C)c1cc(F)cc(F)c1]

Compound 291 (A1)
Compound 292 (A2)
Compound 293 (B1)
Compound 294 (B2)

According to the method of step 2 in Example 76, the product was prepared from 3-benzyl-5-(4-chlorophenyl)-2-methoxypyridine and 1-(2,5-difluorophenyl)-3-(dimethylamino)propan-1-one. The crude product was separated by preparative HPLC (GX-D; Boston Symmetrix C18 ODS-R 150*30 mm*5 um; acetonitrile 32%-62%; water (0.225% formic acid); 80 mL/min) to give component A and component B. Component A was separated by chiral SFC (Chiralpak IC 250×30 mm I.D., 10 um; supercritical $CO_2$/i-PrOH (0.1% aqueous ammonia)=75/25; 60 g/min; 220 nm) to give compound 291 (A1) (40.2 mg, 1.59% yield) and compound 292 (A2) (49.5 mg, 1.96% yield) as white solid. Component B was separated by chiral SFC (Chiralpak IC 250×30 mm I.D., 10 um; supercritical $CO_2$/MeOH (0.1% aqueous ammonia)=75/25; 60 ml/min; 220 nm) to give compound 293 (B1) (13.14 mg, 0.52% yield) and compound 294 (B2) (21.96 mg, 0.87% yield) as white solid. Compound 291 (A1)/compound 292 (A2): $^1$H NMR (400 MHz, CHLOROFORM-d): δ 8.51-8.46 (m, 1H), 8.02-7.97 (m, 1H), 7.79-7.72 (m, 2H), 7.41 (s, 5H), 7.36-7.31 (m, 2H), 7.28-7.23 (m, 1H), 6.94-6.86 (m, 1H), 6.84-6.77 (m, 1H), 5.10-5.05 (m, 1H), 3.75 (s, 3H), 2.32-2.24 (m, 1H), 2.16-2.10 (m, 1H), 2.05 (s, 7H), 1.31-1.21 (m, 1H); compound 293 (B1)/compound 294 (B2): $^1$H NMR (400 MHz, CHLOROFORM-d): δ 8.79-8.74 (m, 1H), 8.29-8.23 (m, 1H), 7.51 (s, 2H), 7.44 (s, 2H), 7.40-7.36 (m, 2H), 7.35-7.30 (m, 1H), 7.06 (s, 3H), 6.95-6.87 (m, 1H), 6.82-6.76 (m, 1H), 5.23-5.19 (m, 1H), 4.05 (s, 3H), 2.34-2.26 (m, 1H), 2.16 (d, J=14.1 Hz, 2H), 2.08 (s, 6H), 2.05-1.96 (m, 1H). LCMS (ESI) m/z: 523.2 (M+1).

Example 78

1-(5-(4-chlorophenyl)-2-methoxypyridin-3-yl)-4-(dimethylamino-2-(3-fluorophenyl)-1-phenylbutan-2-ol

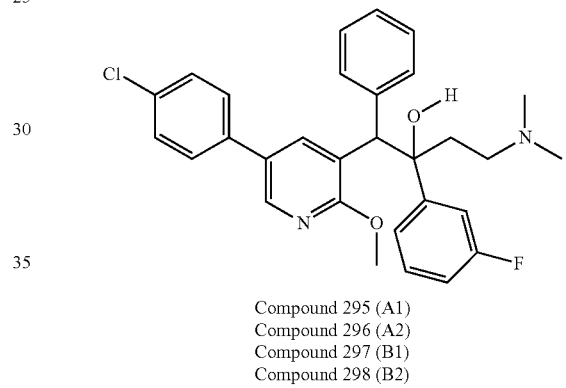

Compound 295 (A1)
Compound 296 (A2)
Compound 297 (B1)
Compound 298 (B2)

According to the method of step 2 in Example 76, the product was prepared from 3-benzyl-5-(4-chlorophenyl)-2-methoxypyridine and 3-(dimethylamino)-1-(3-fluorophenyl)propan-1-one. The crude product was isolated by column chromatography (eluent: petroleum ether/ethyl acetate=10/1-1/1) to give component A and component B. Component A was separated by chiral SFC (Chiralpak AD 250×30 mm I.D., 10 um; supercritical $CO_2$/EtOH (0.1% aqueous ammonia)=70/30; 60 ml/min; 220 nm) to give compound 295 (A1) (62.2 mg, 3.82% yield) and compound 296 (A2) (47.1 mg, 2.89% yield) as white solid. Component B was separated by chiral SFC (Chiralpak IC 250×30 mm I.D., 10 um; supercritical $CO_2$/MeOH (0.1% aqueous ammonia)=75/25; 60 ml/min; 220 nm) to give compound 297 (B1) (68.6 mg, 4.21% yield) and compound 298 (B2) (70.3 mg, 4.31% yield) as white solid. Compound 295 (A1)/compound 296 (A2): $^1$H NMR (400 MHz, CHLOROFORM-d): δ 8.62-8.55 (m, 1H), 8.13 (s, 1H), 8.02-7.96 (m, 1H), 7.68-7.60 (m, 2H), 7.40 (d, J=3.0 Hz, 8H), 7.24-7.16 (m, 1H), 6.84-6.77 (m, 1H), 6.56-6.05 (m, 2H), 4.79-4.73 (m, 1H), 3.80 (s, 3H), 2.82-2.72 (m, 1H), 2.31 (s, 6H), 2.20-2.07 (m, 2H), 2.02-1.93 (m, 1H); compound 297 (B1)/compound 298 (B2): $^1$H NMR (400 MHz, CHLOROFORM-d): δ 8.77-8.69 (m, 1H), 8.30-8.23 (m, 1H), 7.57-7.48 (m, 2H), 7.47-7.39 (m, 2H), 7.34-7.29 (m, 2H), 7.26-7.16 (m, 3H), 7.04 (d, J=7.5 Hz, 3H), 6.86-6.78 (m, 1H), 4.87-4.83 (m, 1H), 4.06 (s, 3H), 2.40-2.28 (m, 1H), 2.10 (s, 8H), 1.84-1.77 (m, 1H). LCMS (ESI) m/z: 505.2 (M+1).

Example 79

2-(3-chlorophenyl)-1-(5-(4-chlorophenyl)-2-methoxypyridin-3-yl)-4-(dimethylamino)-1-phenylbutan-2-ol

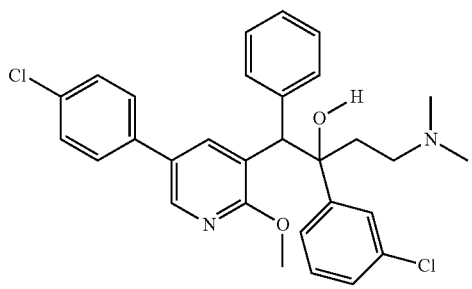

Compound 351 (A1)
Compound 352 (A2)
Compound 353 (B1)
Compound 354 (B2)

Under nitrogen, diisopropylamine (980 mg, 9.69 mmol) was dissolved in 20 mL of anhydrous tetrahydrofuran and n-butyllithium (2.5 M n-hexane solution, 3.88 mL, 9.7 mmol) was added slowly at −70° C. Then the mixture was stirred at −70° C. for 0.5 h. 3-benzyl-5-(4-chlorophenyl)-2-methoxy-pyridine (1.0 g, 3.23 mmil) was dissolved in 10 mL of anhydrous tetrahydrofuran and slowly added to the reaction liquid and stirred at −70° C. for 1.5 h. Then 1-(3-chlorophenyl)-3-(dimethylamino)propan-1-one (820.51 mg, 3.88 mmol) was dissolved in 10 mL of anhydrous tetrahydrofuran and added to the reaction system and stirred at −70° C. for 2 h. The reaction was quenched with 20 mL of saturated aqueous ammonium chloride. The mixture was extracted with ethyl acetate (20 mL×3) and the combined organic phase was dried over anhydrous sodium sulfate, dried by rotation evaporation in vacuo and isolated by column chromatography (eluent: petroleum ether/ethyl acetate=20/1-1/1) and preparative HPLC (GX-D; Boston Symmetrix C18 ODS-R 150*30 mm*5 um; acetonitrile 33%-63%; water (0.225% formic acid); 80 mL/min) to give component A and component B. Component A was separated by chiral SFC (Chiralpak OJ 100×4.6 mm I.D., 3 um; supercritical CO$_2$/i-PrOH (0.05% i-Pr$_2$NH)=60/40; 60 g/min; 220 nm) to give compound 351 (A1) (79.1 mg, 4.7% yield) and compound 352 (A2) (54.7 mg, 3.3% yield) as white solid. Component B was separated by chiral SFC (Chiralpak AD 100×4.6 mm I.D., 3 um; supercritical CO$_2$/Methanol (0.05% i-Pr$_2$NH)=60/40; 60 ml/min; 220 nm) to give compound 353 (B1) (97.6 mg, 5.8% yield) and compound 354 (B2) (105.0 mg, 6.2% yield) as white solid. Compound 351 (A1)/compound 352 (A2): $^1$H NMR (400 MHz, DMSO-d$_6$): δ 8.68 (s, 1H), 8.38 (d, J=4.0, 1H), 7.66-7.64 (m, 2H), 7.58-7.56 (m, 2H), 7.40 (t, J=8.0, 2H) 7.29-7.24 (m, 3H), 7.16-7.14 (m, 1H), 7.04-7.01 (t, J=8.0, 2 H), 6.96 (t, J=4.0, 1H), 4.76 (s, 1H), 3.99 (s, 3H), 2.14-2.10 (m, 1H), 1.98 (s, 6H), 1.97-1.90 (m, 3H); compound 353 (B1)/compound 354 (B2): $^1$H NMR (400 MHz, DMSO-d$_6$): δ 8.61 (s, 1H), 8.09 (d, J=4.0, 1H), 7.65-7.64 (m, 3H), 7.54 (s, 4H), 7.51 (d, J=8.0, 1H), 7.31 (t, J=8.0, 2 H), 7.27-7.20 (m, 2H), 7.14 (d, J=8.00, 1H), 4.75 (s, 1H), 3.70 (s, 3H), 2.10 (t, J=8.00, 1H), 1.94 (s, 6H), 1.90-1.80 (m, 3H). LCMS (ESI) m/z: 521 (M+1).

Example 80

1-(5-(4-chlorophenyl)-2-methoxypyridin-3-yl)-2-(2,3-dichlorophenyl)-4-(dimethylamino)-1-phenylbutan-2-ol

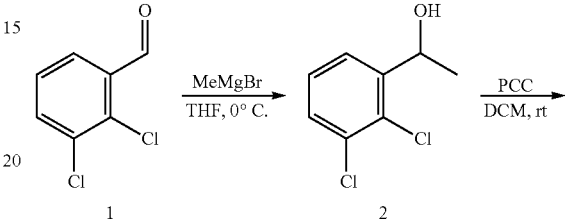

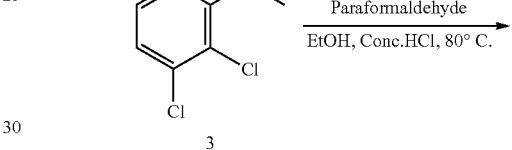

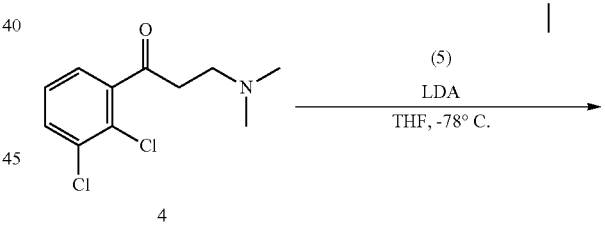

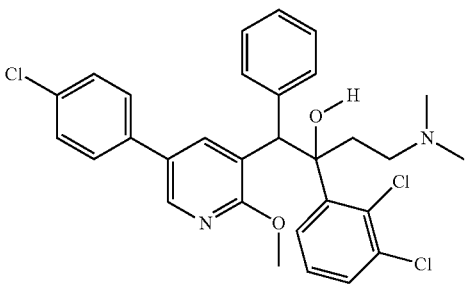

Compound 359 (A1)
Compound 360 (A2)
Compound 361 (B1)
Compound 362 (B2)

Step 1: 1-(2,3-dichlorophenyl)ethanol

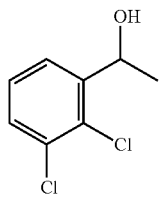

Under nitrogen, 2,3-dichlorobenzaldehyde (8.00 g, 15.71 mmol) was dissolved in 80 mL of anhydrous tetrahydrofuran and methyl magnesium bromide (3M in tetrahydrofuran, 45.71 mL, 137.1 mmol) was slowly added dropwise at 0° C. Then the mixture was stirred at 10-35° C. for 3 h. The reaction was quenched with saturated aqueous ammonium chloride solution. The mixture was extracted with ethyl acetate (40 mL×3) and the combined organic phase was washed with saturated brine, dried over anhydrous sodium sulfate, and concentrated in vacuo to give 1-(2,3-dichlorophenyl)ethanol (7.00 g, crude product) which was used directly in the next step without further purification. LCMS (ESI) m/z: 191 (M+1).

Step 2: 1-(2,3-dichlorophenyl)ethanone

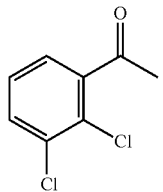

Under nitrogen, 1-1-(2,3-dichlorophenyl)ethanol(7.00 g, 36.64 mmol) was dissolved in 80 mL of dichloromethane and pyridinium chlorochromate (15.80 g, 73.28 mmol) was added at 10-35° C. in one portion and stirred at 10-35° C. for 3 h. The mixture was concentrated in vacuo and isolated by column chromatography (eluent: petroleum ether/ethyl acetate=50/1-20/1) to give 1-(2,3-dichlorophenyl)ethanone (6.00 g, 86.62% yield) as a yellow oil. LCMS (ESI) m/z: 189 (M+1).

Step 3: 1-(2,3-dichlorophenyl)-3-(dimethylamino)propan-1-one

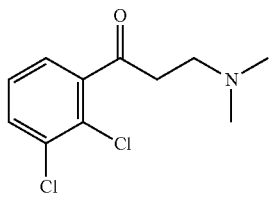

1-(2,3-dichlorophenyl)ethanone (5.50 g, 29.09 mmol), dimethylamine hydrochloride (9.49 g, 116.38 mmol), paraformaldehyde (3.41 g, 37.82 mmol) and 1 mL of concentrated hydrochloric acid were mixed in 60 mL of ethanol, heated to 80° C. and stirred for 16 h. The reaction liquid was concentrated, added with 20 mL of 3N diluted hydrochloric acid, and washed with dichloromethane three times. The aqueous phase was adjusted with 10% aqueous potassium carbonate solution to pH 10 and extracted with ethyl acetate (30 mL×3). The combined ethyl acetate phase was dried over anhydrous sodium sulfate and concentrated in vacuo to give 1-(2,3-dichlorophenyl)-3-(dimethylamino)propan-1-one (2.40 g, 33.52% yield) as a yellow oil. LCMS (ESI) m/z: 246 (M+1).

Step 4: 1-(5-(4-chlorophenyl)-2-methoxypyridin-3-yl)-2-(2,3-dichlorophenyl)-4-(dimethylamino)-1-phenylbutan-2-ol

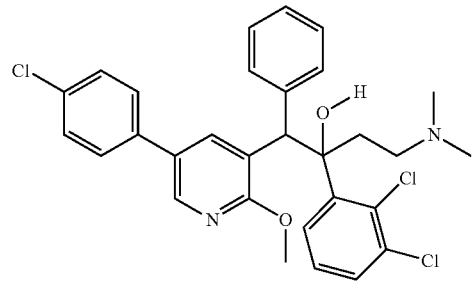

Compound 359 (A1)
Compound 360 (A2)
Compound 361 (B1)
Compound 362 (B2)

Under nitrogen, diisopropylamine (1.49 g, 14.77 mmol) was dissolved in 20 mL of anhydrous tetrahydrofuran and n-butyllithium (2.5M n-hexane solution, 5.81 mL, 14.53 mmol) was added slowly at −78° C. and stirred for 30 minutes. 3-benzyl-5-(4-chlorophenyl)-2-methoxy-pyridine (1.50 g, 4.84 mmol) dissolved in 10 mL of anhydrous tetrahydrofuran was added to the reaction liquid at −78° C. and stirred at −78° C. for 1.5 h. Then 1-(2,3-dichlorophenyl)-3-(dimethylamino)propan-1-one (1.31 g, 5.32 mmol) was dissolved in 10 mL of anhydrous tetrahydrofuran and added slowly to the reaction system at −78° C. and stirred for another 1.5 h. The reaction was quenched with saturated aqueous ammonium chloride solution. The mixture was extracted with ethyl acetate (20 mL×3) and the combined organic phase was dried over anhydrous sodium sulfate, concentrated in vacuo and isolated by column chromatography (eluent: petroleum ether/ethyl acetate=30/1-5/1) to give component A and component B. Component A separated by preparative HPLC (GX-D; Boston Symmetrix C18 ODS-R 150*30 mm*5 um; acetonitrile 30%-60%; water (0.225% formic acid); 25 mL/min) and chiral SFC (sfc-80; AD-10 um; supercritical $CO_2$/EtOH (0.1% aqueous ammonia)=70/30; 60 g/min; 220 nm) to give compound 359 (A1) (69.33 mg, 2.38% yield) and compound 360 (A2) (53.83 mg, 1.85% yield) as white solid. Component B separated by preparative HPLC (GX-D; Boston Symmetrix C18 ODS-R 150*30 mm*5 um; acetonitrile 33%-63%; water (0.225% formic acid); 25 mL/min) and chiral SFC (sfc-80; IC-10 um; supercritical $CO_2$/MeOH (0.1% aqueous ammonia)—60/40; 70 g/min; 220 nm) to give compound 361 (B1) (69.33 mg, 2.38% yield) and compound 362 (B2) (53.83 mg, 1.85% yield) as white solid. Compound 359 (A1)/compound 360 (A2): $^1$H NMR (400 MHz, $CDCl_3$): δ 8.42 (d, J=2.51 Hz, 1H), 7.99 (d, J=2.51 Hz, 1H), 7.83 (dd, J=8.16, 1.51 Hz, 1H), 7.78 (d, J=7.28 Hz, 2H), 7.40 (s, 4H), 7.38-7.33 (m, 2H), 7.32-7.29 (m, 1H), 7.28-7.24 (m, 1H), 7.05 (t, J=7.97 Hz, 1H), 5.61 (s, 1H), 3.71 (s, 3H), 2.69-2.80 (m, 1H), 2.34-2.27 (m, 1H), 2.03-2.15 (m, 8H); compound 361 (B1)/compound 362 (B2): $^1$H NMR (400 MHz, CDCl$_3$): δ □8.72 (d, J=2.38 Hz, 1H), 8.26 (d, J=2.38 Hz, 1H), 7.78 (dd, J=8.03, 1.38 Hz, 1H), 7.56-7.50 (m, 2H), 7.46-7.41 (m, 2H), 7.38 (d, J=7.15 Hz, 2H), 7.30 (d, J=1.51 Hz, 1H), 7.28 (s, 1H), 7.08-6.96 (m, 4H), 5.83 (s, 1H), 4.06 (s, 3H), 2.78 (d, J=15.06 Hz, 1H), 2.32-2.25 (m, 1H), 2.07-2.16 (m, 7H), 2.00-1.92 (m, 1H). LCMS (ESI) m/z: 557.1 (M+1).

Example 81

1-(5-(4-chlorophenyl)-2-methoxypyridin-3-yl)-2-(2,5-dichlorophenyl)-4-(dimethylamino)-1-phenylbutan-2-ol

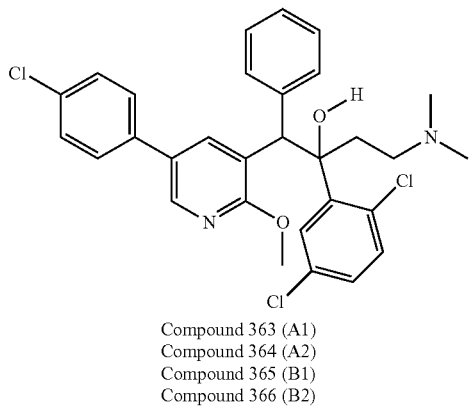 [SMILES: COc1ncc(-c2ccc(Cl)cc2)cc1C(c1ccccc1)C(O)(CCN(C)C)c1cc(Cl)ccc1Cl]

Compound 363 (A1)
Compound 364 (A2)
Compound 365 (B1)
Compound 366 (B2)

Step 1: 1-(2,5-dichlorophenyl)-3-(dimethylamino)propan-1-one

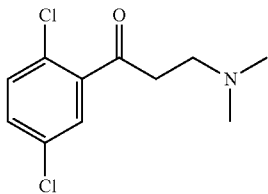

1-(2,5-dichlorophenyl)ethanone (5.00 g, 26.45 mmol), dimethylamine hydrochloride (8.63 g, 105.80 mmol), paraformaldehyde (3.10 g, 34.39 mmol) and 1 mL of concentrated hydrochloric acid were mixed in 60 mL of ethanol, heated to 80° C. and stirred for 16 h. The mixture was concentrated in vacuo, added with 20 mL of 3N aqueous hydrochloric acid solution, and washed with 30 mL of dichloromethane three times. The aqueous phase was adjusted with 10% aqueous potassium carbonate solution to pH 10 and extracted with dichloromethane (50 mL×3). The combined organic phase was dried over anhydrous sodium sulfate and concentrated in vacuo to give 1-(2,5-dichlorophenyl)-3-(dimethylamino)propan-1-one (900.0 mg, crude product) which was used directly in the next step without any further purification. LCMS (ESI) m/z: 247.1 (M+1).

Step 2: 1-(5-(4-chlorophenyl)-2-methoxypyridin-3-yl)-2-(2,5-dichlorophenyl)-4-(dimethylamino)-1-phenylbutan-2-ol

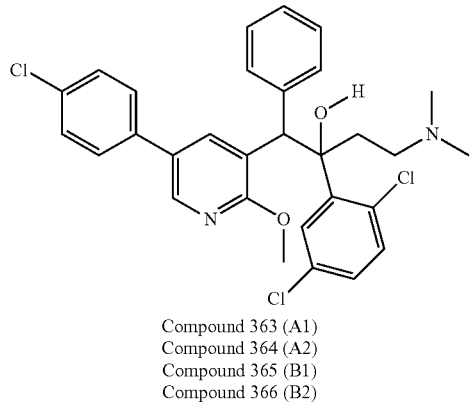 [SMILES: COc1ncc(-c2ccc(Cl)cc2)cc1C(c1ccccc1)C(O)(CCN(C)C)c1cc(Cl)ccc1Cl]

Compound 363 (A1)
Compound 364 (A2)
Compound 365 (B1)
Compound 366 (B2)

Under nitrogen, diisopropylamine (1.49 g, 14.77 mmol) was dissolved in 20 mL of anhydrous tetrahydrofuran and n-butyllithium (2.5 M n-hexane solution, 5.81 mL, 14.53 mmol) was added and stirred for 30 minutes. 3-benzyl-5-(4-chlorophenyl)-2-methoxy-pyridine (1.50 g, 4.84 mmol) was dissolved in 10 mL of anhydrous tetrahydrofuran and added to the reaction liquid at −78° C. and stirred at −78° C. for 1.5 h. Then 1-(2,5-dichlorophenyl)-3-(dimethylamino)propan-1-one (1.31 g, 5.32 mmol) was dissolved in 10 mL of anhydrous tetrahydrofuran and slowly added to the reaction system at −78° C. and stirred for another 1.5 h. The reaction was quenched with saturated aqueous ammonium chloride solution. The mixture was extracted with ethyl acetate (20 mL×3) and the combined organic phase was dried over anhydrous sodium sulfate, concentrated in vacuo and isolated by column chromatography (eluent: petroleum ether/ethyl acetate=30/1-5/1) and preparative HPLC (GX-D; Boston Symmetrix C18 ODS-R 150*30 mm*5 um; acetonitrile 34%-64%; water (0.225% formic acid); 25 mL/min) to give component A and component B. Component A was separated by chiral SFC (sfc-80; AD-10 um; supercritical CO$_2$/Isopropanol (0.1% aqueous ammonia)=70/30; 60 g/min; 220 nm) to give compound 363 (A1) (12.81 mg, 0.48% yield) and compound 364 (A2) (14.13 mg, 0.53% yield) as white solid. Component B was separated by chiral SFC (sfc-80; AD-5 um; supercritical CO$_2$/Isopropanol (0.1% aqueous ammonia)=75/25; 60 g/min; 220 nm) to give compound 365 (B1) (18.56 mg, 0.64% yield) and compound 366 (B2) (13.30 mg, 0.46% yield) as white solid. Compound 363 (A1)/compound 364 (A2): $^1$H NMR (400 MHz, CDCl$_3$): δ 0.8.70 (br. s., 1H), 8.26 (d, J=2.51 Hz, 1H), 7.88 (d, J=2.51 Hz, 1H), 7.55-7.48 (m, 2H), 7.47-7.37 (m, 4H), 7.20 (d, J=8.41 Hz, 1H), 7.09-6.98 (m, 4H), 5.78 (s, 1H), 4.06 (s, 3H), 2.61 (d, J=15.69 Hz, 1H), 2.20-2.00 (m, 8H), 1.96-1.88 (m, 1H); compound 365 (B1)/compound 366 (B2): $^1$H NMR (400 MHz, CDCl$_3$): δ 8.47 (d, J=2.38 Hz, 1H), 8.09 (d, J=2.64 Hz, 1H), 7.98 (d, J=2.51 Hz, 1H), 7.69 (d, J=7.15 Hz, 2H), 7.44-7.36 (m, 4H), 7.35-7.30 (m, 2H), 7.28-7.22 (m, 1H), 7.19 (d, J=8.41 Hz, 1H), 7.06 (dd, J=8.41, 2.64 Hz, 1H), 5.53 (s, 1H), 3.76 (s, 3H), 2.62-2.53 (m, 1H), 2.26 (d, J=12.55 Hz, 1H), 2.13-2.10 (m, 1H), 2.05 (s, 6H), 2.02-1.97 (m, 1H). LCMS (ESI) m/z: 557.1 (M+1).

Example 82

1-(5-(4-chlorophenyl)-2-methoxypyridin-3-yl)-2-(3,4-dichlorophenyl)-4-(dimethylamino)-1-phenylbutan-2-ol

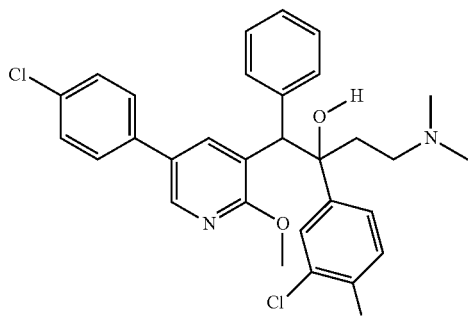

Compound 367 (A1)
Compound 368 (A2)
Compound 369 (B1)
Compound 370 (B2)

Step 1: 1-(3,4-dichlorophenyl)-3-(dimethylamino)propan-1-one

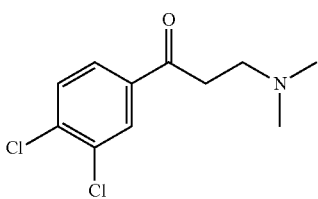

1-(3,4-dichlorophenyl)ethanone (5.00 g, 26.45 mmol), dimethylamine hydrochloride (8.63 g, 105.80 mmol), paraformaldehyde (3.10 g, 34.39 mmol) and 1 mL of concentrated hydrochloric acid were mixed in 60 mL of ethanol, heated to 80° C. and stirred for 16 h. The reaction liquid was concentrated in vacuo, added with 20 mL of 3N hydrochloric acid solution, and washed with 30 mL of dichloromethane three times. The aqueous phase was basified with 10% aqueous potassium carbonate solution to pH 10, and extracted with ethyl acetate (30 mL×3). The combined organic phase was dried over anhydrous sodium sulfate, and concentrated in vacuo to give 1-(3,4-dichlorophenyl)-3-(dimethylamino)propan-1-one (3.0 g, 46.1% yield) as yellow solid. The crude product was used directly without further purification in the next step. LCMS (ESI) m/z: 247.1 (M+1).

Step 2: 1-(5-(4-chlorophenyl)-2-methoxypyridin-3-yl)-2-(3,4-dichlorophenyl)-4-(dimethylamino)-1-phenylbutan-2-ol

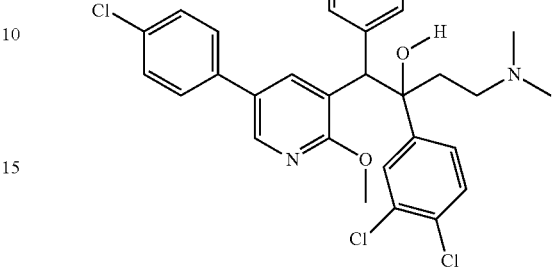

Compound 367 (A1)
Compound 368 (A2)
Compound 369 (B1)
Compound 370 (B2)

Under nitrogen, diisopropylamine (1.30 g, 12.81 mmol) was dissolved in 20 mL of anhydrous tetrahydrofuran and n-butyllithium (2.5M n-hexane solution, 5.04 mL, 12.6 mmol) was added slowly at −78° C. and stirred at −78° C. for 30 minutes. 3-benzyl-5-(4-chlorophenyl)-2-methoxypyridine (1.30 g, 4.20 mmol) was dissolved in 10 mL of anhydrous tetrahydrofuran and slowly added to the reaction liquid at −78° C. and stirred at this temperature for 1.5 h. Then 1-(3,4-dichlorophenyl)-3-(dimethylamino)propan-1-one (1.14 g, 4.62 mmol) was dissolved in 10 mL of anhydrous tetrahydrofuran and slowly added to the reaction liquid at −78° C. and stirred for another 1.5 h. The reaction was quenched with 10 mL of aqueous saturated ammonium chloride solution. The mixture was extracted with ethyl acetate (20 mL×3) and the combined organic phase was dried over anhydrous sodium sulfate, dried by rotation evaporation in vacuo and isolated by column chromatography (eluent: petroleum ether/ethyl acetate=30/1-5/1) preparative HPLC (GX-D; Boston Symmetrix C18 ODS-R 150*30 mm*5 um; acetonitrile 32%-52%; water (0.225% formic acid); 25 mL/min) to give component A and component B. Component A was separated by chiral SFC (sfc-80; IC-10 um; supercritical $CO_2$/MeOH (0.1% aqueous ammonia)=70/30; 60 g/min; 220 nm) to give compound 367 (A1) (33.16 mg, 1.31% yield) and compound 368 (A2) (28.11 mg, 1.11% yield) as white solid. Component B was separated by chiral SFC (sfc-80; IC-10 um; supercritical $CO_2$/MeOH (0.1% aqueous ammonia)=65/35; 70 g/min; 220 nm) to give compound 369 (B1) (24.26 mg, 0.96% yield) and compound 370 (B2) (43.36 mg, 1.72% yield) as white solid. Compound 367 (A1)/compound 368 (A2): $^1$H NMR (400 MHz, CDCl$_3$): δ 8.64 (d, J=2.38 Hz, 1H), 8.26 (d, J=2.51 Hz, 1H), 7.59 (s, 1H), 7.54-7.48 (m, 2H), 7.46-7.40 (m, 2H), 7.36-7.29 (m, 4H), 7.11-6.98 (m, 3H), 4.81 (s, 1H), 4.07 (s, 3H), 2.41-2.32 (m, 1H), 2.15-2.05 (m, 8H), 1.83-1.77 (m, 1H); compound 369 (B1)/compound 370 (B2): $^1$H NMR (400 MHz, CDCl$_3$): δ 8.53 (d, J=2.51 Hz, 1H), 8.01 (d, J=2.51 Hz, 1H), 7.72 (d, J=7.28 Hz, 3H), 7.40 (s, 4H), 7.37-7.31 (m, 3H), 7.28-7.23 (m, 2H), 4.70 (s, 1H), 3.79 (s, 3H), 2.41-2.33 (m, 1H), 2.16-2.08 (m, 8H), 1.74-1.68 (m, 1H). LCMS (ESI) m/z: 555.1 (M+1).

Example 83

1-(5-(4-bromophenyl)-2-methoxypyridin-3-yl)-2-(2,5-difluorophenyl)-4-(dimethylamino)-1-phenylbutan-2-ol

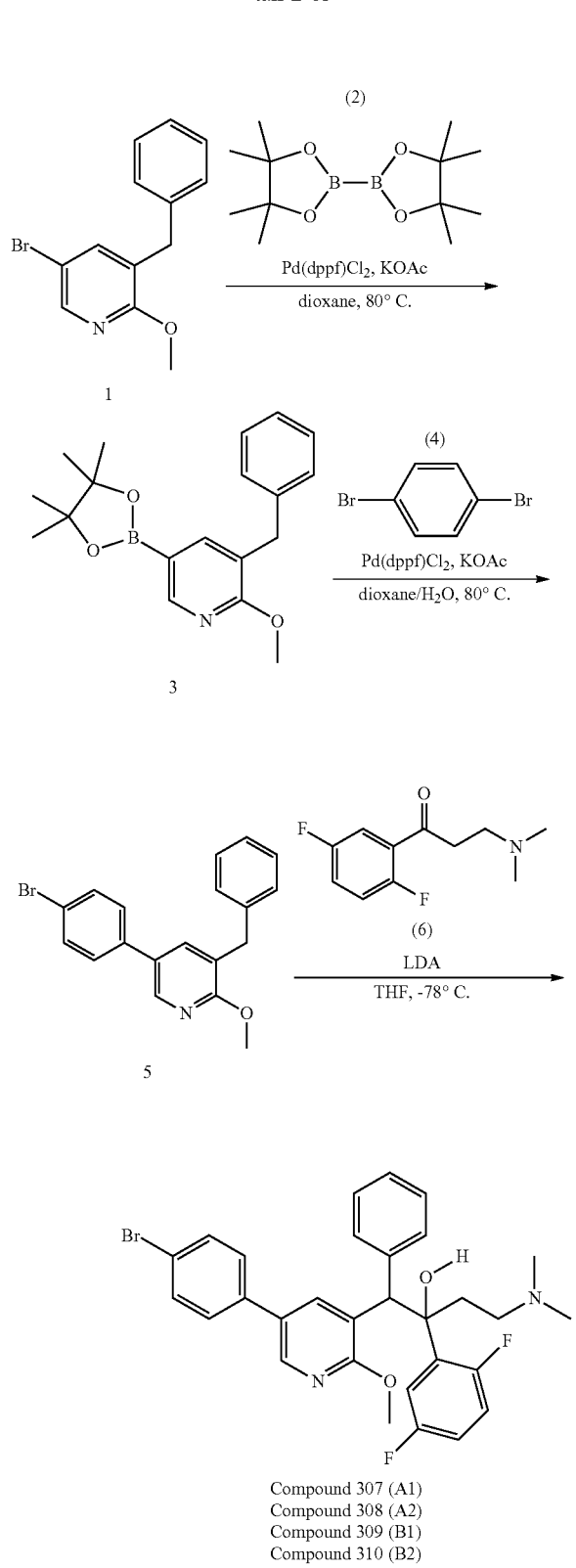

Compound 307 (A1)
Compound 308 (A2)
Compound 309 (B1)
Compound 310 (B2)

Step 1: 3-benzyl-2-methoxy-5-(4,4,5,5-tetramethyl-1,3,2-dioxaborolan-2-yl)pyridine

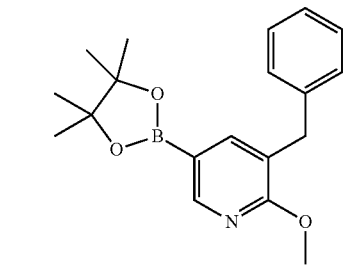 [SMILES: COc1ncc(B2OC(C)(C)C(C)(C)O2)cc1Cc1ccccc1]

Under nitrogen, 3-benzyl-5-bromo-2-methoxypyridine (4.00 g, 14.38 mmol), 4,4,5,5-tetramethyl-2-(4,4,5,5-tetramethyl-1,3,2-dioxaborolan-2-yl)-1,3,2-dioxaborolane (4.38 g, 17.26 mmol), Pd(dppf)Cl₂ (1.05 g, 1.44 mmol) and potassium acetate (4.23 g, 43.14 mmol) were dissolved in 1,4-dioxane (40 mL) and degassed. Then the mixture was heated to 80° C. and stirred for 16 h. The reaction mixture was cooled to tepidity and filtered. The filtrate was poured into water (100 mL) and the mixture was extracted with ethyl acetate (100 mL×2). The combined organic phase was washed with saturated brine (200 mL), dried over anhydrous sodium sulfate, concentrated in vacuo and purified by column chromatography (petroleum ether/ethyl acetate: 100/1-20/1) to give 3-benzyl-2-methoxy-5-(4,4,5,5-tetramethyl-1,3,2-dioxaborolan-2-yl)pyridine (3.10 g, 66.3% yield) as white solid. LCMS (ESI) m/z: 326 (M+1).

Step 2: 3-benzyl-5-(4-bromophenyl)-2-methoxypyridine

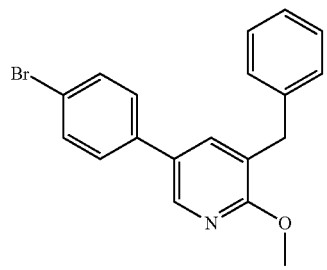

Under nitrogen, 3-benzyl-2-methoxy-5-(4,4,5,5-tetramethyl-1,3,2-dioxaborolan-2-yl)pyridine (5.00 g, 15.37 mmol), 1,4-dibromobenzene (4.35 g, 18.45 mmol), potassium acetate (4.53 g, 46.12 mmol) and Pd(dppf)Cl₂ (1.12 g, 1.54 mmol) were dissolved in 50 mL of 1,4-dioxane and 20 mL of water, heated to 80° C. and stirred for 16 h. The reaction mixture was filtered and the filtrate was poured into water (20 mL). The mixture was extracted with ethyl acetate (20 mL×3). The combined organic phase was washed with saturated brine (20 mL), dried over anhydrous sodium sulfate, concentrated in vacuo and purified by column chromatography (petroleum ether/ethyl acetate: 100/1-20/1) to give pure 3-benzyl-5-(4-bromophenyl)-2-methoxypyridine (3.20 g, 58.77% yield) as an off-white solid. LCMS (ESI) m/z: 355 (M+1).

Step 3: 1-(5-(4-bromophenyl)-2-methoxypyridin-3-yl)-2-(2,5-difluorophenyl)-4-(dimethylamino)-1-phenylbutan-2-ol

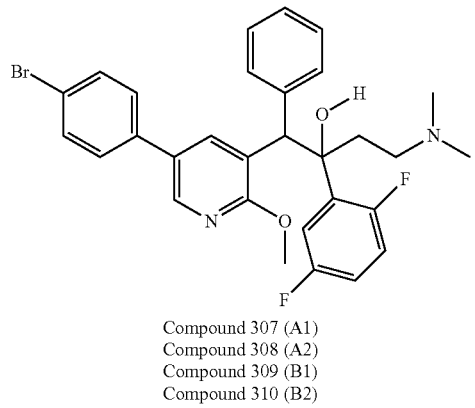 [SMILES: COc1ncc(-c2ccc(Br)cc2)cc1C(c1ccccc1)C(O)(CCN(C)C)c1cc(F)ccc1F]

Compound 307 (A1)
Compound 308 (A2)
Compound 309 (B1)
Compound 310 (B2)

Under nitrogen, diisopropylamine (959.8 mg, 9.49 mmol) was dissolved in 20 mL of anhydrous tetrahydrofuran and n-butyllithium (2.5M n-hexane solution, 3.73 mL, 9.33 mmol) was added slowly at −78° C. The mixture was stirred at −78° C. for 30 minutes. 3-benzyl-5-(4-bromophenyl)-2methoxypyridine (1.10 g, 3.11 mmol) was dissolved in 10 mL of anhydrous tetrahydrofuran and added dropwise to the reaction liquid at −78° C. The mixture was stirred at −78° C. for 1.5 h. 1-(2,5-difluorophenyl)-3-(dimethylamino)propan-1-one (722.81 mg, 3.39 mmol) was dissolved in 10 mL of anhydrous tetrahydrofuran and added dropwise to the reaction system. Afterwards, the reaction mixture was stirred at −78° C. for 1.5 h. The reaction was quenched with 10 mL of saturated ammonium chloride solution and extracted with ethyl acetate (20 mL×3). The combined organic phase was dried over anhydrous sodium sulfate, concentrated in vacuo and purified by column chromatography (petroleum ether/ethyl acetate: 30/1-5/1) and preparative HPLC (GX-D; Boston Symmetrix C18 ODS-R 150*30 mm*5 um; acetonitrile 32%-62%; water (0.225% formic acid); 25 mL/min) to give component A and component B. Component A was separated by chiral SFC (sfc-80; AD-10 um; supercritical $CO_2$/EtOH (0.1% aqueous ammonia)=75/25; 60 ml/min; 220 nm) to give compound 307 (A1) (13.10 mg, 0.69% yield) and compound 308 (A2) (17.80 mg, 0.93% yield) as white solid. Component B was separated by chiral SFC (sfc-80; AD-10 um; supercritical $CO_2$/EtOH (0.1% aqueous ammonia)=70/30; 60 ml/min; 220 nm) to give compound 309 (B1) (27.60 mg, 1.45% yield) and compound 310 (B2) (34.20 mg, 1.79% yield) as white solid. Compound 307 (A1)/compound 308 (A2): $^1$H NMR (400 MHz, $CDCl_3$): δ 8.73 (d, J=2.38 Hz, 1H), 8.26 (d, J=2.51 Hz, 1H), 7.59 (d, J=8.41 Hz, 2H), 7.47 (d, J=8.53 Hz, 2H), 7.41-7.30 (m, 3H), 7.11-6.97 (m, 3H), 6.95-6.86 (m, 1H), 6.84-6.75 (m, 1H), 5.20 (s, 1H), 4.05 (s, 3H), 2.42-2.34 (m, 1H), 2.20-2.09 (m, 8H), 2.08-1.97 (m, 1H); compound 309 (B1)/compound 310 (B2): $^1$H NMR (400 MHz, $CDCl_3$): δ 8.49 (d, J=2.38 Hz, 1H), 8.00 (d, J=2.38 Hz, 1H), 7.73 (d, J=7.28 Hz, 2H), 7.56 (d, J=8.28 Hz, 2H), 7.46 (ddd, J=9.76, 6.37, 3.20 Hz, 1H), 7.38-7.31 (m, 4H), 7.28-7.23 (m, 1H), 6.94-6.86 (m, 1H), 6.84-6.76 (m, 1H), 5.07 (s, 1H), 3.75 (s, 3H), 2.44-2.36 (m, 1H), 2.18-2.05 (m, 9H). LCMS (ESI) m/z: 568.9 (M+1).

Example 84

1-(5-(4-bromophenyl)-2-methoxypyridin-3-yl)-4-(dimethylamino-2-(3-fluorophenyl)-1-phenylbutan-2-ol

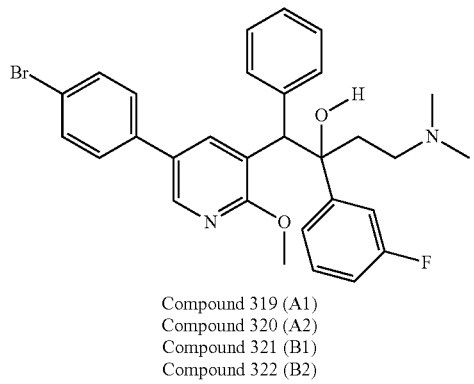

Compound 319 (A1)
Compound 320 (A2)
Compound 321 (B1)
Compound 322 (B2)

Under nitrogen, diisopropylamine (1.29 g, 9.95 mmol) was dissolved in 20 mL of anhydrous tetrahydrofuran and n-butyllithium (2.5M n-hexane solution, 3.7 mL, 9.25 mmol) was added at −78° C. After 15 minutes, 3-benzyl-5-(4-bromophenyl)-2-methoxypyridine (1.10 g, 3.11 mmol) was dissolved in 8 mL of anhydrous tetrahydrofuran and added to the reaction system at −78° C. The mixture was stirred at this temperature for 1 hour. 3-(dimethylamino)-1-(3-fluorophenyl)propan-1-one (728.6 mg, 3.73 mmol) was dissolved in 8 mL of anhydrous tetrahydrofuran and added to the reaction liquid. The resulted mixture was stirred at −78° C. for 1 hour. The reaction was quenched with 50 mL of saturated aqueous ammonium chloride solution and extracted with ethyl acetate (50 mL×3). The combined organic phase was washed with brine (50 mL), dried over anhydrous sodium sulfate, and concentrated in vacuo to give the crude product (300 mg) as a yellow syrup which was separated and purified by preparative HPLC (GX-G; Phenomenex Synergi C18 150*30 mm*4 um; acetonitrile 30%-60%; water (0.225% formic acid); 25 mL/min) to give component A and component B. Component A was separated by chiral SFC (sfc-80; IC-10 um; supercritical $CO_2$/EtOH (0.1% aqueous ammonia)=70/30; 60 ml/min; 220 nm) to give compound 319 (A1) (56.0 mg, 3.3% yield) and compound 320 (A2) (51.6 mg, 3.0% yield) as white solid. Component B was separated by chiral SFC (sfc-80; AD-10 um; supercritical $CO_2$/EtOH (0.1% aqueous ammonia)=65/35; 70 ml/min; 220 nm) to give compound 321 (B1) (45.0 mg, 2.6% yield) and compound 322 (B2) (57.8 mg, 3.4% yield) as white solid. Compound 319 (A1)/compound 320 (A2): $^1$H NMR (400 MHz, METHANOL-$d_4$): δ 8.65 (d, J=2.38 Hz, 1H), 8.29 (d, J=2.51 Hz, 1H), 7.63 (d, J=8.53 Hz, 2H), 7.52 (d, J=8.53 Hz, 2H), 7.35-7.15 (m, 5H), 7.07-6.93 (m, 3H), 6.84 (br. s., 1H), 4.91 (s, 1H), 4.06 (s, 2H), 2.50-2.33 (m, 1H), 2.24-2.00 (m, 9H); compound 321 (B1)/compound 322 (B2): $^1$H NMR (400 MHz, METHANOL-$d_4$): δ 8.65 (d, J=2.38 Hz, 1H), 7.99 (d, J=2.38 Hz, 1H), 7.67 (d, J=7.28 Hz, 2H), 7.61 (d, J=8.53 Hz, 2H), 7.46-7.19 (m, 8H), 6.87-6.76 (m, 1H), 4.82 (s, 1H), 3.77 (s, 3H), 2.36-2.21 (m, 1H), 2.13-1.83 (m, 9H). LCMS (ESI) m/z: 549.1 (M+1).

Example 85

1-(5-(4-bromophenyl)-2-methoxypyridin-3-yl)-2-(3,5-dichlorophenyl)-4-(dimethylamino)-1-phenylbutan-2-ol

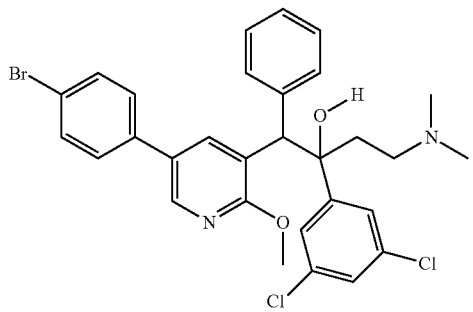

Compound 343 (A1)
Compound 344 (A2)
Compound 345 (B1)
Compound 346 (B2)

According to the method of step 3 in Example 83, 3-benzyl-5-(4-bromophenyl)-2-methoxypyridine and 1-(3,5-dichlorophenyl)-3-(dimethylamino)propan-1-one were used to prepare the crude product which was separated and purified by preparative HPLC (GX-F; Phenomenex Synergi C18 150*30 mm*4 um; acetonitrile 30%-60%; water (0.225% formic acid); 25 mL/min) to give component A and component B. Component A was separated by chiral SFC (Chiralpak AD 250×30 mm I.D., 10 um; supercritical $CO_2$/EtOH (0.1% aqueous ammonia)=70/30; 60 mL/min; 220 nm) to give compound 343 (A1) (38.74 mg, 2.83% yield) and compound 344 (A2) (62.93 mg, 4.60% yield) as white solid. Component B was separated by chiral SFC (Chiralpak AD 250×30 mm I.D., 5 um; supercritical $CO_2$/EtOH (0.1% aqueous ammonia)=70/30; 55 mL/min; 220 nm) to give compound 345 (B1) (51.38 mg, 3.75% yield) and compound 346 (B2) (57.87 mg, 4.23% yield) as white solid. Compound 343 (A1)/compound 344 (A2): $^1$HNMR (400 MHz, CHLOROFORM-d): δ 8.52-8.46 (m, 1H), 8.03-7.97 (m, 1H), 7.77-7.70 (m, 2H), 7.61-7.53 (m, 2H), 7.52-7.38 (m, 2H), 7.37-7.31 (m, 4H), 7.27-7.20 (m, 1H), 7.12 (s, 1H), 4.70-4.65 (m, 1H), 3.81 (s, 3H), 2.33-2.23 (m, 1H), 2.06 (s, 8H), 1.67-1.60 (m, 1H); compound 345 (B1)/compound 346 (B2): $^1$H NMR (400 MHz, CHLOROFORM-d): δ 8.70-8.64 (m, 1H), 8.29-8.24 (m, 1H), 7.62-7.56 (m, 2H), 7.48-7.41 (m, 2H), 7.40-7.29 (m, 4H), 7.15-7.01 (m, 4H), 4.79-4.75 (m, 1H), 4.07 (s, 3H), 2.32-2.24 (m, 1H), 2.08 (s, 8H), 1.76-1.72 (m, 1H). LCMS (ESI) m/z: 601.1 (M+1).

Example 86

1-(5-(4-bromophenyl)-2-methoxypyridin-3-yl)-2-(3-chlorophenyl)-4-(dimethylamino)-1-phenylbutan-2-ol

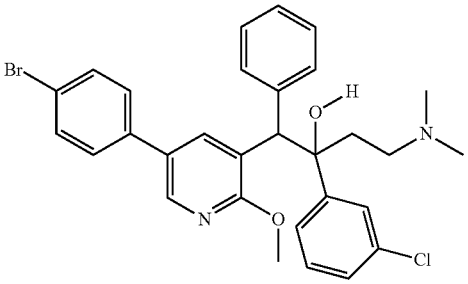

Compound 355 (A1)
Compound 356 (A2)
Compound 357 (B1)
Compound 358 (B2)

Under nitrogen, diisopropylamine (1.03 g, 10.2 mmol) was dissolved in 20 mL of anhydrous tetrahydrofuran and n-butyllithium (2.5M hexane solution, 4.1 mL, 10.2 mmol) was added slowly at −70° C. The mixture was stirred at this temperature for 0.5 h. Then 3-benzyl-5-(4-bromophenyl)-2-methoxypyridine (1.20 g, 3.39 mmol) was dissolved in 10 mL of anhydrous tetrahydrofuran and added to the reaction system and stirred at −70° C. for 1.5 h. 1-(3-chlorophenyl)-3-(dimethylamino)propan-1-one (861.2 mg, 4.07 mmol) was dissolved in 10 mL of anhydrous tetrahydrofuran and added slowly at −70° C. and stirred at −70° C. for 2 h. The reaction was quenched with 20 mL of saturated ammonium chloride solution. The mixture was extracted with ethyl acetate (20 mL×3) and the combined organic phase was washed with brine (20.0 mL×2), dried over anhydrous sodium sulfate, concentrated in vacuo and isolated by column chromatography (eluent: petroleum ether/ethyl acetate=20/1-1/1) and preparative HPLC (GX-D; Boston Symmetrix C18 ODS-R 150*30 mm*5 um; acetonitrile 33%-63%; water (0.225% formic acid); 25 mL/min) to give component A and component B. Component A was separated by chiral SFC (Chiralpak IC-3 100×4.6 mm I.D., 3 um; supercritical $CO_2$/Methanol (0.05% i-$Pr_2$NH)=95/5-60/40; 60 mL/min; 220 nm) to give compound 355 (A1) (54.3 mg, 2.8% yield) and compound 356 (A2) (48.3 mg, 2.5% yield) as white solid. Component B was separated by chiral SFC (Chiralpak IC-3 100×4.6 mm I.D., 3 um; supercritical $CO_2$/Methanol (0.05% i-$Pr_2$NH)=95/5-60/40; 60 mL/min; 220 nm) to give compound 357 (B1) (67.7 mg, 3.5% yield) and compound 358 (B2) (72.1 mg, 3.7% yield) as white solid. Compound 355 (A1)/compound 356 (A2): $^1$H NMR (400 MHz, DMSO-$d_6$): δ 8.68 (s, 1H), 8.39 (s, 1H) 7.76-7.71 (m, 2H), 7.59-7.56 (m, 2H), 7.40 (t, J=8.0, 2H) 7.29-7.24 (m, 3H), 7.16-7.14 (m, 1H), 7.03 (t, J=8.0, 2H), 6.96 (t, J=4.0, 1H), 4.76 (s, 1H), 3.99 (s, 3H), 2.14 (s, 1H), 1.99 (s, 6H), 1.97-1.90 (m, 3H); compound 357 (B1)/compound 358 (B2): $^1$H NMR (400 MHz, DMSO-$d_6$): δ 8.61 (s, 1H), 8.10 (s, 1H) 7.69-7.64 (m, 5H), 7.51-7.47 (m, 3H), 7.32 (t, J=8.0, 3H), 7.32 (t, J=8.0, 2H), 7.28-7.20 (m, 2H), 7.14 (d, J=8.0, 1H), 4.76 (s, 1H) 3.71 (s, 3H) 2.19-2.05 (m, 1H) 1.95 (s, 6H) 1.91-1.80 (m, 3H). LCMS (ESI) m/z: 565.1 (M+1).

Example 87

4-(dimethyl amino)-1-(2-methoxy-5-thiomorpholin-pyridin-3-yl)-2-(naphthalen-1-yl)-1-phenylbutan-2-ol

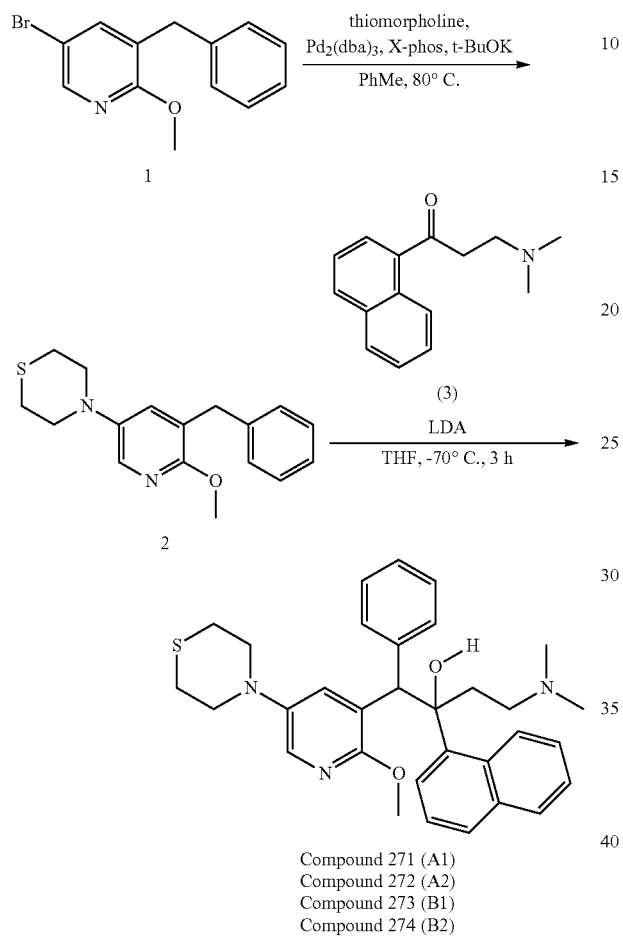

Compound 271 (A1)
Compound 272 (A2)
Compound 273 (B1)
Compound 274 (B2)

Step 1:
4-(5-benzyl-6-methoxypyridin-3-yl)thiomorpholin 3-benzyl-5-bromo-2-methoxy-pyridine (3.00 g, 10.79 mmol), thiomorpholin (1.34 g, 12.95 mmol), tris(dibenzylideneacetone) dipalladium (0) (1.98 g, 2.16 mmol), 2-(dicyclohexylphosphino)-2',4',6'-trisisopropyl biphenyl (1.54 g, 3.24 mmol) and potassium t-butoxide (2.42 g, 21.58 mmol) were mixed in toluene (30 mL) and degassed, heated to 100° C. and stirred for 16 h under nitrogen. The reaction mixture was cooled, poured into water (60 mL) and extracted with ethyl acetate (50 mL×3). The combined organic phase was washed with 100 mL of saturated brine, dried over anhydrous sodium sulfate, concentrated in vacuo and purified by column chromatography (petroleum ether/ethyl acetate: 100/1-5/1) to give 4-(5-benzyl-6-methoxy-pyridin-3-yl)thiomorpholin (2.50 g, 77.11% yield) as white solid. LCMS (ESI) m/z: 301.4 (M+1).

Step 2: 4-(dimethylamino)-1-(2-methoxy-5-thiomorpholinpyridin-3-yl)-2-(naphthalen-1-yl)-1-phenylbutan-2-ol

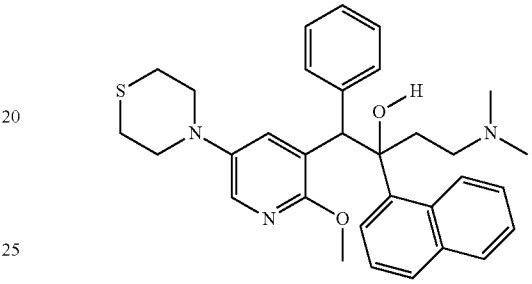

Compound 271 (A1)
Compound 272 (A2)
Compound 273 (B1)
Compound 274 (B2)

Under nitrogen, diisopropylamine (1.01 g, 9.99 mmol) was dissolved in 20 mL of anhydrous tetrahydrofuran and n-butyllithium (2.5M n-hexane solution, 4.0 mL, 10.0 mmol) was added at −78° C. he mixture was stirred at this temperature for 0.5 h. 4-(5-benzyl-6-methoxypyridin-3-yl)thiomorpholin (2.0 g, 6.66 mmol) was dissolved in 10 mL of anhydrous tetrahydrofuran and added slowly to the reaction liquid and stirred for 1 hour. Then 3-(dimethylamino)-1-(naphthalen-1-yl)propan-1-one (1.67 g, 7.33 mmol) was dissolved in 10 mL, of anhydrous tetrahydrofuran and added dropwise. Afterwards the reaction liquid was stirred at −70° C. for 2 h. The reaction was quenched with 20 mL, of saturated ammonium chloride solution. The mixture was extracted with ethyl acetate (20 mL×3) and the combined organic phase was dried over anhydrous sodium sulfate, concentrated in vacuo, and isolated by column chromatography (petroleum ether/ethyl acetate=30/1-5/1) and preparative HPLC (GX-D; Boston Symmetrix C18 ODS-R 150*30 mm*5 um; acetonitrile 30%-60%; water (0.225% formic acid); 25 mL/min) to give component A and component B. Component A was separated by chiral SFC((sfc-80; AD-10 um; supercritical $CO_2$/EtOH (0.1% aqueous ammonia)=75/25; 60 ml/min; 220 nm) to give compound 271 (A1) (30.73 mg, 0.88% yield) and compound 272 (A2) (24.68 mg, 0.70% yield) as white solid. Component B was separated by chiral SFC (sfc-80; IC-10 um; supercritical $CO_2$/MeOH (0.1% aqueous ammonia)—60/40; 60 ml/min; 220 nm) to give compound 273 (B1) (13.94 mg, 0.40% yield) and compound 274 (B2) (15.99 mg, 4.5% yield) as white solid. Compound 271 (A1)/compound 272 (A2): $^1$H NMR (400 MHz, METHANOL-$d_4$): δ 8.54 (d, J=8.91 Hz, 1H), 8.12-8.00 (m, 2H), 7.83 (d, J=8.0 Hz, 1H), 7.74 (d, J=7.40 Hz, 2H), 7.68 (d, J=8.16 Hz, 1H) 7.63-7.50 (m, 1H), 7.49-7.32 (m, 4H), 7.31-7.22 (m, 2H), 5.61 (s, 1H), 3.30-3.11 (m, 6H), 2.82-2.66 (m, 5H), 2.61-1.91 (m, 10H); compound 273 (B1)/compound 274 (B2): $^1$H NMR (400 MHz, METHANOL-d$_4$): δ 8.78-8.46 (m, 1H), 8.20 (br. s., 1H), 7.87 (d, J=8.16 Hz, 2H), 7.78-7.58 (m, 3H), 7.55-7.43 (m, 1H), 7.30 (t, J=7.72 Hz, 1H), 7.13 (br. s., 2H), 6.94-6.83 (m, 3H), 5.76 (br. s., 1H), 4.08 (s, 3H), 3.42 (d, J=5.02 Hz, 4H), 2.86-2.78 (m, 4H), 2.71 (br. s., 1H), 2.34-1.89 (m, 9H). LCMS (ESI) m/z: 528.2 (M+1).

Example 88

4-(dimethylamino)-1-(2-methoxy-5-morpholinopyridin-3-yl)-2-(naphthalen-1-yl)-1-phenylbutan-2-ol

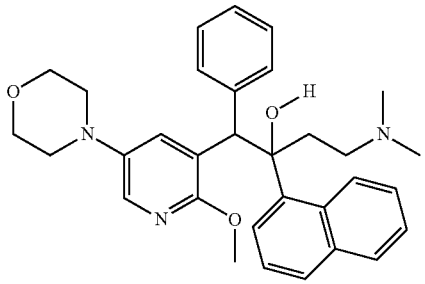

Compound 267 (A1)
Compound 268 (A2)
Compound 269 (B1)
Compound 270 (B2)

Step 1:
4-(5-benzyl-6-methoxypyridin-3-yl)morpholine

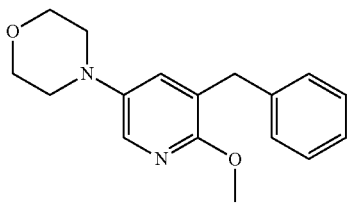 [SMILES: COc1ncc(N2CCOCC2)cc1Cc1ccccc1]

According to the method of step 1 in Example 87, the product was prepared from 3-benzyl-5-bromo-2-methoxypyridine and morpholine. Yield: 52.2%. LCMS (ESI) m/z: 285 (M+1).

Step 2: 4-(dimethylamino)-1-(2-methoxy-5-morpholinopyridin-3-yl)-2-(naphthalen-1-yl)-1-phenylbutan-2-ol

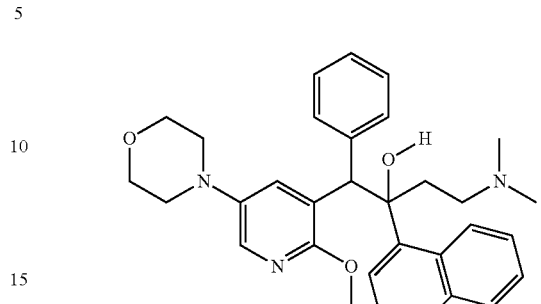

Compound 267 (A1)
Compound 268 (A2)
Compound 269 (B1)
Compound 270 (B2)

Under nitrogen, diisopropylamine (554.9 mg, 5.48 mmol) was dissolved in 10 mL of anhydrous tetrahydrofuran and n-butyllithium (2.5M n-hexane solution, 2.0 mL, 5.0 mmol) was added at −78° C. The mixture was at this temperature stirred for 0.5 h. 4-(5-benzyl-6-methoxypyridin-3-yl)morpholine (1.30 g, 4.57 mmol) was dissolved in 5 mL of anhydrous tetrahydrofuran and added slowly to the reaction liquid and stirred for 1 hour. Then 3-(dimethylamino)-1-(naphthalen-1-yl)propan-1-one (1.25 g, 5.48 mmol) was dissolved in 5 mL of anhydrous tetrahydrofuran and added slowly dropwise. Then the reaction liquid was stirred at −70° C. for 2 h. The reaction was quenched with 10 mL of water. The mixture was extracted with ethyl acetate (20 ml×3) and the combined organic phase was washed with saturated brine (20 mL×2), dried over anhydrous sodium sulfate, concentrated in vacuo and isolated by column chromatography (petroleum ether/ethyl acetate=20/1-1/1) and preparative HPLC (GX-G; Phenomenex Synergi C18 150*30 mm*4 um; acetonitrile 25%-55%; water (0.225% formic acid); 25 mL/min) to give component A and component B. Component A was separated by chiral SFC (sfc-80; IC-3 um; supercritical CO$_2$/EtOH (0.1% aqueous ammonia)=60/40; 60 ml/min; 220 nm) to give compound 267 (A1) (55.59 mg, 2.4% yield) and compound 268 (A2) (57.43 mg, 2.5% yield) as white solid. Component B was separated by chiral SFC (sfc-80; AD-3 um; supercritical CO$_2$/i-PrOH (0.05% Et$_2$NH) =60/40; 60 ml/min; 220 nm) to give compound 269 (B1) (49.41 mg, 2.1% yield) and compound 270 (B2) (51.34 mg, 2.2% yield) as white solid. Compound 267 (A1)/compound 268 (A2): $^1$H NMR (400 MHz, DMSO-d$_6$): δ 8.53 (d, J=8.0 Hz, 1H), 8.06 (s, 2H), 7.84 (d, J=8.0 Hz, 1H), 7.70 (d, J=4.0 Hz, 3H), 7.58 (t, J=4.0 Hz, 1H), 7.42-7.33 (m, 5H), 7.37-7.24 (m, 2H), 5.49 (s., 1H), 3.73 (s, 4H), 3.22 (s, 3H), 2.92-2.76 (m, 4H), 2.68 (m, 1H), 2.08-2.19 (m, 9H); compound 269 (B)/compound 270 (B2): $^1$H NMR (400 MHz, DMSO-d$_6$): δ 8.58 (d, J=8.0 Hz, 1H), 8.31 (s, 1H), 8.11 (d, J=4.0 Hz, 1H), 7.93-7.86 (m, 1H), 7.75-7.69 (m, 3H), 7.51 (t, J=8.0 Hz, 1H), 7.34 (t, J=8.0 Hz, 1H), 7.12 (d, J=4.0 Hz, 2H), 6.90-6.85 (m, 3H): 5.66 (s., 1H), 4.01 (s, 3H), 3.78 (t, J=4.0 Hz, 4H), 3.08-3.00 (m, 4H), 2.50-2.44 (m, 2H), 1.93 (s, 8H). LCMS (ESI) m/z: 528.2 (M+1).

Example 89

1-(5-tert-butyl-2-methoxypyridin-3-yl)-4-dimethyl-amino-2-(naphthalen-1-yl)-1-phenylbutan-2-ol

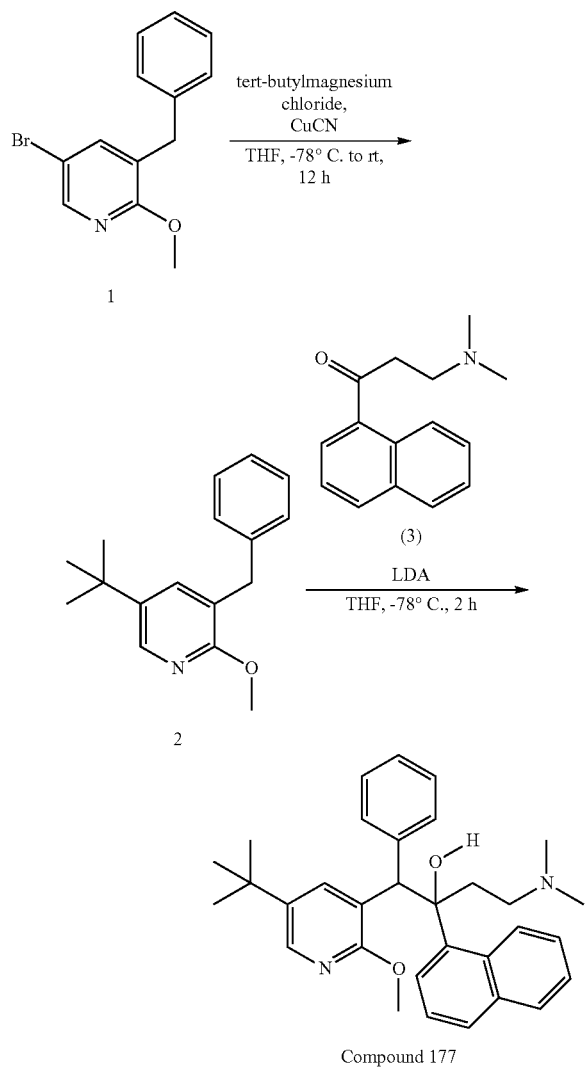

Step 1: 3-benzyl-5-tert-butyl-2-methoxypyridine

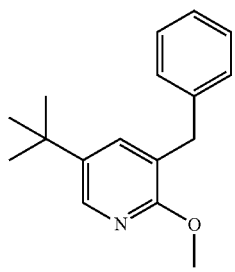 [SMILES: COc1ncc(C(C)(C)C)cc1Cc1ccccc1]

Under nitrogen, cuprous cyanide (4.44 g, 48.3 mmol) was suspended in 40 mL of anhydrous tetrahydrofuran, and tert-butylmagnesium chloride (1M in tetrahydrofuran, 96.6 mL, 96.6 mmol) was added slowly at −78 CC. Afterwards, the mixture was stirred at −78° C. for 30 minutes. 3-benzyl-5-bromo-2-methoxypyridine (1.68 g, 6.0 mmol) was dissolved in 3 mL of anhydrous tetrahydrofuran, added to the reaction system at −78° C., warmed to room temperature and stirred for 12 h. The reaction was quenched with saturated ammonium chloride solution. The mixture was extracted with ethyl acetate (100 mL×3). The combined organic phase was washed with saturated brine, dried over anhydrous sodium sulfate, dried by rotation evaporation in vacuo and isolated by column chromatography (developing solvent: petroleum ether/ethyl acetate=100/1-10/1) to give 3-benzyl-5-tert-butyl-2-methoxypyridine (2.0 g, crude product) as a yellow oil. The crude product was used directly in the next step.

Step 2: 1-(5-tert-butyl-2-methoxypyridin-3-yl)-4-dimethylamino-2-(naphthalen-1-yl)-1-phenylbutan-2-ol

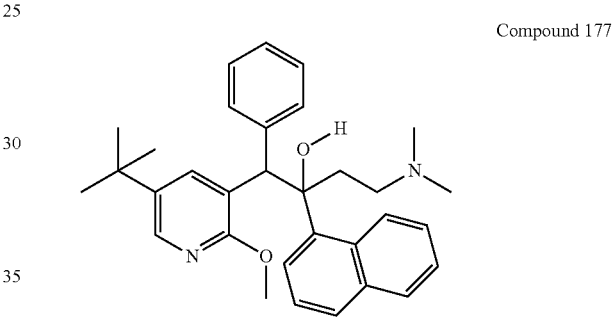

Compound 177

Under nitrogen, diisopropylamine (1.83 g, 18.0 mmol) was dissolved in 40 mL of anhydrous tetrahydrofuran and n-butyllithium (2.5M n-hexane solution, 4.53 mL, 11.3 mmol) was added slowly at −70° C. Afterwards, the mixture was stirred for 30 minutes. 3-benzyl-5-tert-butyl-2-methoxypyridine (2.2 g, 8.6 mmol) was dissolved in 8 mL of anhydrous tetrahydrofuran at −70° C., slowly added to the reaction liquid and stirred for another 1 hour. 3-dimethylamino-1-(naphthalen-1-yl)propan-I-one (2.74 g, 12.0 mmol) was dissolved in 10 mL of anhydrous tetrahydrofuran, slowly added to the reaction liquid and stirred at −78° C. for 2 h. The reaction was quenched with saturated ammonium chloride solution at −70° C. The mixture was extracted with ethyl acetate (50 mL×3). The combined organic phase was dried over anhydrous sodium sulfate, concentrated in vacuo, and isolated by column chromatography (developing solvent:petroleum ether/ethyl acetate=30/1-5/1) to give 300 mg of crude product which was separated by preparative HPLC (GX-G; Phenomenex Synergi C18 150*30 mm*4 um; MeCN: 18%-48%; $H_2O$ (+0.225 HCOOH); 25 mL/min; 220 nm/254 nm) to give compound 177 (the mixture of A and B) (10 mg, 2.4% yield) as white solid. $^1$H NMR (400 MHz, METHANOL-$d_4$): δ 8.68 (br. s., 2H), 8.06 (d, J=2.4 Hz, 1H), 7.89 (d, J=8.2 Hz, 2H), 7.72-7.58 (m, 2H), 7.50 (d, J=7.4 Hz, 1H), 7.29 (t, J=7.8 Hz, 1H), 7.09 (br. s., 2H), 6.91-6.79 (m, 3H), 5.78 (br. s., 1H), 4.09 (s, 3H), 2.77-2.54 (m, 1H), 2.07 (s, 9H), 1.40 (s, 9H). LCMS (ESI) m/z: 483.3 (M+1).

Example 90

1-(6-chloro-5-(4-chlorophenyl)-2-methoxypyridin-3-yl)-4-dimethylamino-2-(naphthalen-1-yl)-1-phenylbutan-2-ol

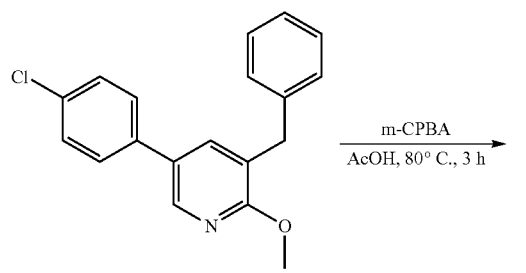

1

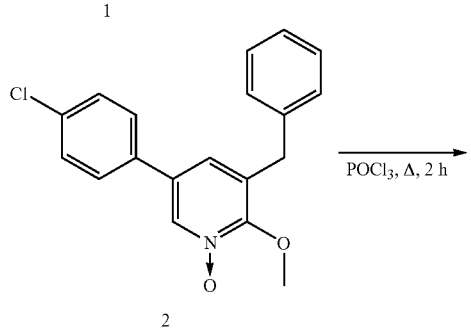

2

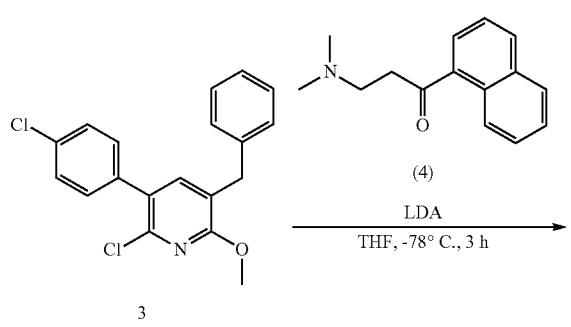

3

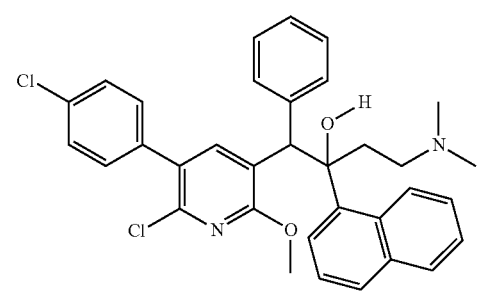

Compound 221 (A1)
Compound 371 (A2)
Compound 222 (B1)
Compound 223 (B2)

Step 1: 3-benzyl-5-(4-chlorophenyl)-2-methoxypyridine1-oxide

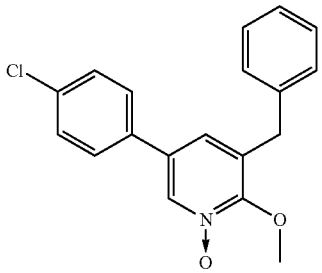 [SMILES: COc1c(Cc2ccccc2)cc(-c2ccc(Cl)cc2)c[n+]1[O-]]

3-benzyl-5-(4-chlorophenyl)-2-methoxy-pyridine (6.0 g, 19.4 mmol) and m-chloroperbenzoic acid (19.66 g, 96.85 mmol) were mixed in 100 mL of acetic acid, stirred at 80° C. for 2 hours. The reaction was quenched with 300 mL of saturated potassium carbonate solution. The reaction mixture was extracted with dichloromethane (100 mL×3) and the combined organic phase was dried over anhydrous sodium sulfate, and concentrated in vacuo to give 3-benzyl-5-(4-chlorophenyl)-2-methoxypyridine-oxide (6.31 g, crude product) as a yellow oil. The crude product was used directly in the next step. LCMS (ESI) m/z: 326.1 (M+1).

Step 2: 3-benzyl-6-chloro-5-(4-chlorophenyl)-2-methoxypyridine

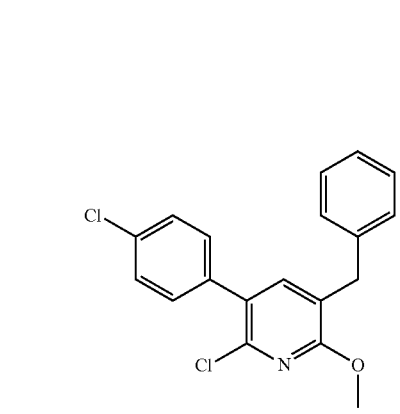 [SMILES: COc1nc(Cl)c(-c2ccc(Cl)cc2)cc1Cc1ccccc1]

3-benzyl-5-(4-chlorophenyl)-2-methoxypyridine1-oxide (6.25 g, crude product) and 100 mL of phosphorus oxychloride were mixed and stirred at 110° C. for 2 h. The mixture was cooled, poured into iced water and stirred for 10 minutes. The mixture was extracted with ethyl acetate (100 mL×2) and the combined organic phase was dried over anhydrous sodium sulfate, concentrated in vacuo and isolated by column chromatography (developing solvent:petroleum ether) to give 3-benzyl-6-chloro-5-(4-chlorophenyl)-2-methoxypyridine (800 mg, 12.1% yield) as a yellow oil. LCMS (ESI) m/z: 344.1 (M+1).

183

Step 3: 1-(6-chloro-5-(4-chlorophenyl)-2-methoxy-pyridin-3-yl)-4-dimethylamino-2-(naphthalen-1-yl)-1-phenylbutan-2-ol

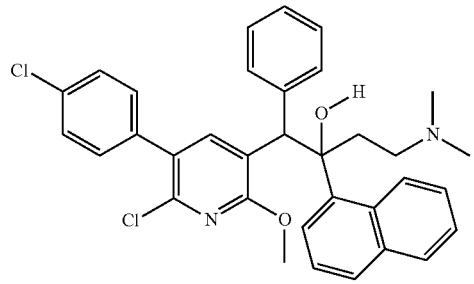

Compound 221 (A1)
Compound 371 (A2)
Compound 222 (B1)
Compound 223 (B2)

Under nitrogen, diisopropylamine (469.5 mg, 4.6 mmol) was dissolved in 5 mL of anhydrous tetrahydrofuran and n-butyllithium (2.5M n-hexane solution, 1.86 mL, 4.65 mmol) was added at −78° C. The reaction mixture was stirred at −78° C. for 10 minutes. 3-benzyl-6-chloro-5-(4-chlorophenyl)-2-methoxypyridine (800 mg, 2.32 mmol) was dissolved in 3 mL of anhydrous tetrahydrofuran and slowly added to the reaction liquid at −78° C. Afterwards, the mixture was stirred for 1 hour. 3-(dimethylamino)-1-(1-naphthyl)propan-1-one (632.8 mg, 2.78 mmol) was dissolved in 2 mL of anhydrous tetrahydrofuran and slowly added to the reaction liquid at −78° C. Afterwards, the mixture was stirred for 1 hour. The reaction was quenched with 20 mL of saturated ammonium chloride solution. The mixture was extracted with ethyl acetate (50 mL×2) and the combined organic phase was dried over anhydrous sodium sulfate and concentrated in vacuo to give a crude product which was separated by preparative HPLC (GX-G; Phenomenex Synergi C18 150*30 mm*4 um; acetonitrile 38%-68%; water (0.225% formic acid); 25 mL/min) to give component A and component B. Component A was separated by chiral SFC (SFC 80, IC-5 um; supercritical $CO_2$/methanol (0.05% $NH_3.H_2O$)=60/40; 70 g/min; 220 nm) to give compound 221 (A1) (24.55 mg, 1.85% yield) and compound 371 (A2) (23.43 mg, 1.77% yield) as white solid. Component B was separated by chiral SFC (SFC 80, IC-10 um; supercritical $CO_2$/methanol (0.05% $NH_3.H_2O$)=50/50; 70 g/min; 220 nm) to give compound 222 (B1) (25.00 mg, 1.89% yield) and compound 223 (B2) (30.76 mg, 2.32% yield) as white solid. Compound 221 (A1)/compound 371 (A2): $^1$H NMR (400 MHz, $CDCl_3$): δ 8.61-8.53 (m, 2H), 7.89 (t, J=7.40 Hz, 2H), 7.68-7.59 (m, 2H), 7.53-7.47 (m, 1H), 7.45 (s, 4H), 7.34-7.29 (m, 1H), 7.15-7.10 (m, 2H), 6.92-6.87 (m, 3H), 5.75 (s, 1H), 4.17 (s, 3H), 2.57 (m, 1H), 2.10 (m, 2H), 2.04 (s, 6H), 2.01 (m, 1H). Compound 222 (B1)/compound 223 (B2): $^1$H NMR (400 MHz, $CDCl_3$): δ 8.45 (d, J=8.66 Hz, 1H), 8.33 (s, 1H), 8.08 (dd, J=7.40, 1.00 Hz, 1H), 7.86 (d, J=7.15 Hz, 1H), 7.79 (d, J=7.40 Hz, 2H), 7.70 (d, J=8.16 Hz, 1H), 7.56 (d, J=7.15 Hz, 1H), 7.49-7.45 (m, 1H), 7.43-7.36 (m, 6H), 7.33-7.29 (m, 1H), 7.25 (d, J=8.41 Hz, 2H), 5.57 (s, 1H), 3.29 (s, 3H), 2.51 (d, J=13.18 Hz, 1H), 2.26 (m, 1H), 2.03 (m, 8H). LCMS (ESI) m/z: 571.2 (M+1).

184

Example 91

2-cyclohexyl-4-dimethylamino-1-(2-methoxy-5-phenylpyridin-3-yl)-1-phenylbutan-2-ol

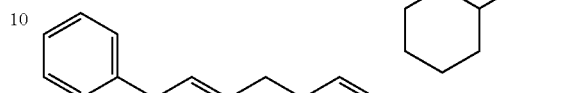

1

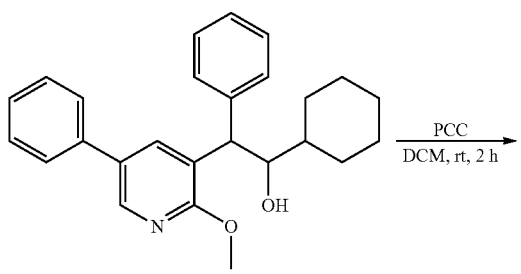

2

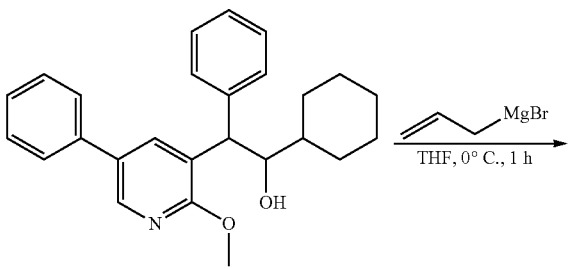

3

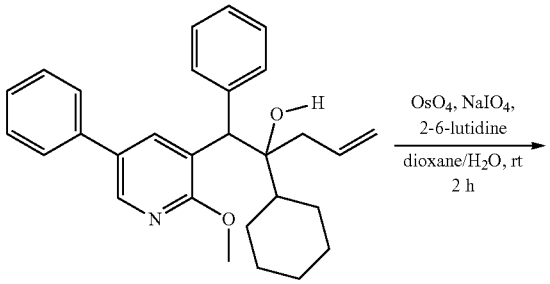

4

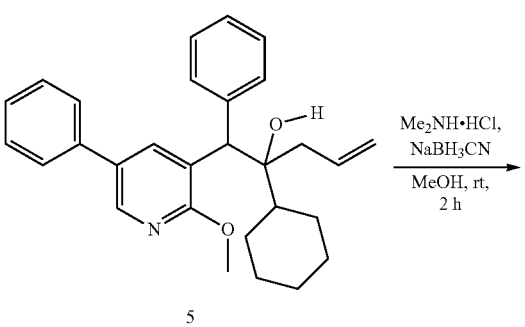

5

-continued

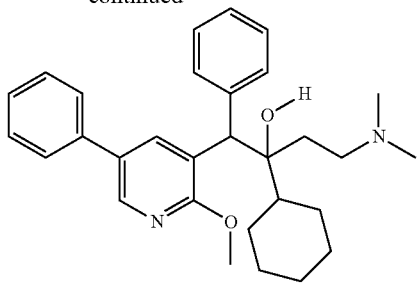

Compound 186 (A1)
Compound 187 (A2)
Compound 188 (B1)
Compound 189 (B2)

Step 1: 1-cyclohexyl-2-(2-methoxy-5-phenylpyridin-3-yl)-2-benzeneethanol

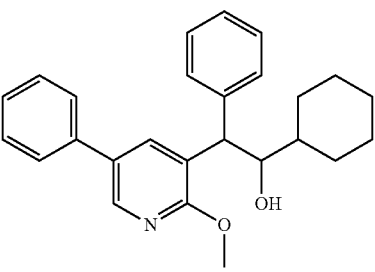 [SMILES: COc1ncc(-c2ccccc2)cc1C(c1ccccc1)C(O)C1CCCCC1]

Under nitrogen, diisopropylamine (1.25 g, 12.35 mmol) was dissolved in 30 mL of tetrahydrofuran and n-butyllithium (2.5M n-hexane solution, 3.9 mL, 9.69 mmol) was added slowly at −70° C. The mixture was stirred at −70° C. for 10 minutes. 3-benzyl-2-methoxy-5-phenylpyridine (2.0 g, 6.46 mmol) was dissolved in 30 mL of tetrahydrofuran, slowly added to the reaction liquid and stirred for another 1 hour. Cyclohexyl carbaldehyde (0.87 g, 7.75 mmol) was dissolved in 30 mL of tetrahydrofuran, and added to the reaction system to react for another 1 h. The reaction was quenched with saturated ammonium chloride solution. The mixture was extracted with ethyl acetate (30 mL×3) and the combined organic phase was washed with 50 mL of saturated brine, dried over anhydrous sodium sulfate, dried by rotation evaporation, and isolated by column chromatography (developing solvent:petroleum ether/ethyl acetate: 100/1-20/1) to give 1-cyclohexyl-2-(2-methoxy-5-phenylpyridin-3-yl)-2-benzeneethanol (1.1 g, 37.7% yield) as yellow solid.

Step 2: 1-cyclohexyl-2-(2-methoxy-5-phenylpyridin-3-yl)-2-benzeneethanone

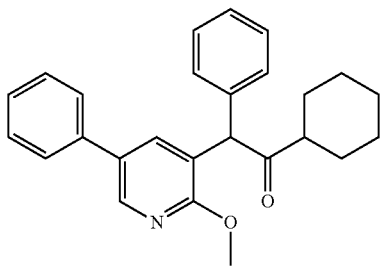 [SMILES: COc1ncc(-c2ccccc2)cc1C(C(=O)C1CCCCC1)c1ccccc1]

1-cyclohexyl-2-(2-methoxy-5-phenylpyridin-3-yl)-2-benzeneethanol (900 mg, 1.99 mmol) was dissolved in 20 mL of dichloromethane and pyridinium chlorochromate (1.29 g, 5.97 mmol) and silica (1.29 g, 21.47 mmol) were added in one portion at 25° C. The mixture was stirred at 25° C. for 2 h. The reaction liquid was concentrated and isolated by column chromatography (developing solvent:petroleum ether/ethyl acetate: 30/1-20/1) to give 1-cyclohexyl-2-(2-methoxy-5-phenylpyridin-3-yl)-2-benzeneethanone (800 mg, 89.4% yield) as yellow solid. LCMS (ESI) m/z: 386 (M+1).

Step 3: 2-cyclohexyl-1-(2-methoxy-5-phenylpyridin-3-yl)-1-phenylpent-4-en-ol

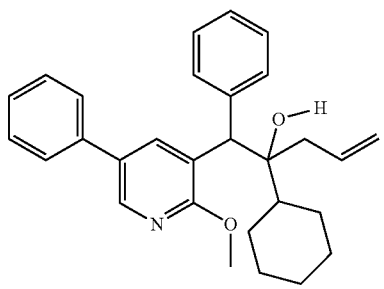 [SMILES: C=CCC(O)(C1CCCCC1)C(c1ccccc1)c1cc(-c2ccccc2)cnc1OC]

Under nitrogen, 1-cyclohexyl-2-(2-methoxy-5-phenylpyridin-3-yl)-2-acetophenone (647.82 mg, 1.44 mmol) was dissolved in 10 mL of tetrahydrofuran and allyl magnesium bromide (1M solution in tetrahydrofuran, 2.88 mL, 2.88 mmol) was added slowly at 0° C. Afterwards, the mixture was stirred at 25° C. for 1 hour. The reaction liquid was poured into 50 mL of saturated ammonium chloride solution and extracted with ethyl acetate (50 mL×3). The combined organic phase was washed with saturated brine, dried over anhydrous sodium sulfate, concentrated in vacuo and isolated and purified by column chromatography (developing solvent:petroleum ether/ethyl acetate: 50/1-20/1) to give 2-cyclohexyl-1-(2-methoxy-5-phenylpyridin-3-yl)-1-phenylpent-4-en-ol (580 mg, 81.9% yield) as yellow solid. LCMS (ESI) m/z: 428 (M+1).

Step 4: 3-cyclohexyl-3-hydroxyl-4-(2-methoxy-5-phenylpyridin-3-yl)-4-phenylbutanal

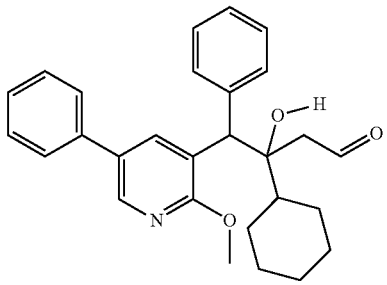 [SMILES: COc1ncc(-c2ccccc2)cc1C(c1ccccc1)C(O)(CC=O)C1CCCCC1]

2-cyclohexyl-1-(2-methoxy-5-phenylpyridin-3-yl)-1-phenylpent-4-en-ol (850 mg, 2.0 mmol) was dissolved in 10 mL of 1,4-dioxane and 3 mL of water. Osmium tetroxide (2.59 mg, 10.2 umol), 2,6-lutidine (420 mg, 4.0 mmol), and sodium periodate (1.72 g, 8.0 mmol) were added and stirred at 20° C. for 2 h. The reaction liquid was diluted with 30 mL of water, and extracted with dichloromethane (20 mL×3). The combined organic phase was washed with 20 mL of saturated brine, dried over anhydrous sodium sulfate, concentrated in vacuo to give 3-cyclohexyl-3-hydroxyl-4-(2-methoxy-5-phenylpyridin-3-yl)-4-phenylbutanal (750 mg, crude product) as yellow solid. The crude product was used directly in the next step. LCMS (ESI) m/z: 430 (M+1).

Step 5: 2-cyclohexyl-4-dimethylamino-1-(2-methoxy-5-phenylpyridin-3-yl)-1-phenylbutan-2-ol

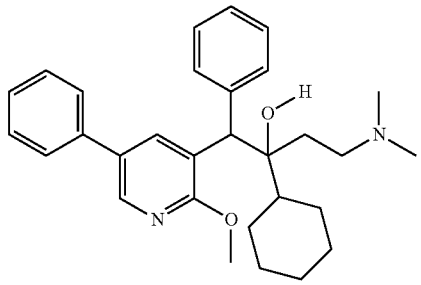

Compound 186 (A1)
Compound 187 (A2)
Compound 188 (B1)
Compound 189 (B2)

3-cyclohexyl-3-hydroxyl-4-(2-methoxy-5-phenylpyridin-3-yl)-4-phenylbutanal (750 mg, 1.6 mmol) was dissolved in 10 mL of methanol and dimethylamine hydrochloride (650 mg, 8.0 mmol) and sodium cyanoborohydride (190 mg, 3.2 mmol) were added and stirred at 20° C. for 2 h. The reaction liquid was diluted with water. The mixture was extracted with ethyl acetate (20 mL×3) and the combined organic phase was washed with 20 mL of saturated brine, dried over anhydrous sodium sulfate, concentrated in vacuo and separated by preparative HPLC (GX-D; Boston Symmetrix C18 ODS-R 150*30 mm*5 um; acetonitrile 15%-45%; water (0.225% formic acid); 25 mL/min) to give component A and component B. Component A was separated by chiral SFC (Chiralpak AD 250×30 mm I.D., 5 um; supercritical $CO_2$/i-PrOH (0.2% $NH_3.H_2O$)=80/20; 55 ml/min; 220 nm) to give compound 186 (A1) (67.8 mg, 3.5% yield) and compound 187 (A2) (60.2 mg, 3.3% yield) as white solid. Component B was separated by chiral SFC (Chiralpak AD 250×30 mm I.D., 5 um; supercritical $CO_2$/EtOH (0.2% $NH_3.H_2O$)=70/30; 60 ml/min; 220 nm) to give compound 188 (B1) (35.6 mg, 2.1% yield) and compound 189 (B2) (38.7 mg, 2.4% yield) as white solid. Compound 186 (A1)/compound 187 (A2): $^1$H NMR (400 MHz, METHANOL-$d_4$): δ 8.85 (s, 1H), 8.22 (d, J=2.4 Hz, 1H), 7.67-7.61 (m, 4H), 7.51-7.42 (m, 2H), 7.40-7.35 (m, 1H), 7.30-7.15 (m, 3H), 4.48 (s, 1H), 3.96 (s, 3H), 2.45-2.30 (m, 1H), 2.06 (s, 6H), 1.93-1.52 (m, 8H), 1.24-0.71 (m, 6H); compound 188 (B1)/Compound 187 (A2): $^1$H NMR (400 MHz, METHANOL-$d_4$): δ 8.58 (d, J=2.38 Hz, 1H), 8.22 (d, J=2.38 Hz, 1H), 7.66 (d, J=7.40 Hz, 2H), 7.58-7.50 (m, 2H), 7.45 (t, J=7.65 Hz, 2H), 7.41-7.31 (m, 1H), 7.31-7.23 (m, 2H), 7.18 (d, J=7.40 Hz, 1H), 4.72 (s, 1H), 3.33 (s, 3H), 2.16-2.02 (m, 1H), 2.01 (s, 6H), 1.96-1.51 (m, 7H), 1.20-0.79 (m, 6H). LCMS (ESI) m/z: 459 (M+1).

Example 92

2-cyclopentyl-4-(dimethylamino)-1-(2-methoxy-5-phenylpyridin-3-yl)-1-phenylbutan-2-ol Compound 190

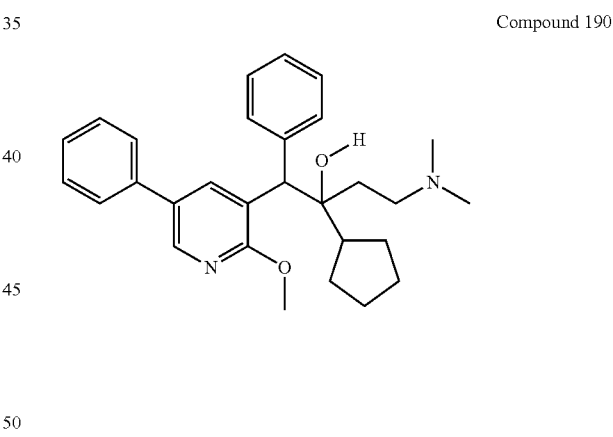

According to the method of Example 91 and the order of Step 1, 2, 3, 4, 5, cyclohexanecarboxaldehyde was replaced by cyclopentanecarbaldehyde in the first step. The crude product was separated by preparative HPLC (GX-G; Phenomenex Synergi C18 150*30 mm*4 um; acetonitrile 30%-55%; water (0.225% formic acid); 25 mL/min) to give compound 190 (the mixture of A and B). $^1$H NMR (400 MHz, METHANOL-$d_4$): δ 8.59 (d, J=2.38 Hz, 1H), 8.22 (d, J=2.38 Hz, 1H), 7.66 (d, J=7.28 Hz, 2H), 7.59-7.51 (m, 2H), 7.46 (t, J=7.65 Hz, 2H), 7.40-7.32 (m, 1H), 7.32-7.22 (m, 2H), 7.22-7.11 (m, 1H), 4.04 (s, 3H), 2.51-2.35 (m, 1H), 2.11-1.97 (m, 6H), 1.96-1.83 (m, 2H), 1.79 (d, J=10.79 Hz, 1H), 1.72-1.44 (m, 4H), 1.22-0.97 (m, 4H). LCMS (ESI) m/z: 445 (M+1).

Example 93

2-benzyl-4-dimethylamino-1-(2-methoxy-5-phenylpyridin-3-yl)-1-phenylbutan-2-ol

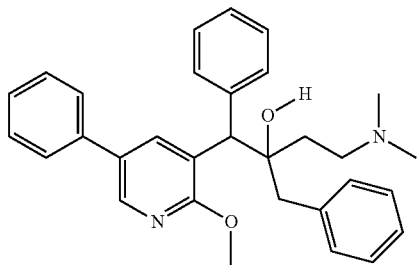

Compound 191 (A1)
Compound 192 (A2)
Compound 193 (B)

Step 1: 1-(2-methoxy-5-phenylpyridin-3-yl)-1,3-diphenylpropan-2-ol

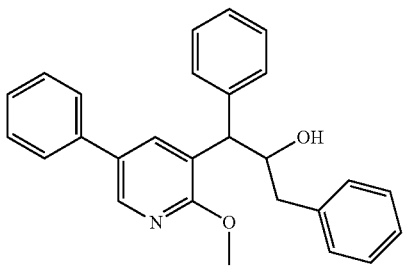 [SMILES: COc1ncc(-c2ccccc2)cc1C(c1ccccc1)C(O)Cc1ccccc1]

According to the method of step 1 in Example 91, the product was prepared from 3-benzyl-2-methoxy-5-phenylpyridine and 2-phenylacetaldehyde. Yield: 36%. LCMS (ESI) m/z: 396 (M+1).

Step 2: 1-(2-methoxy-5-phenylpyridin-3-yl)-1, 3-diphenylpropan-2-one

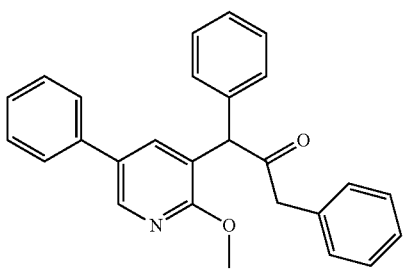 [SMILES: COc1ncc(-c2ccccc2)cc1C(C(=O)Cc1ccccc1)c1ccccc1]

According to the method of step 2 in Example 91, the product was prepared from 1-(2-methoxy-5-phenylpyridin-3-yl)-1,3-diphenylpropan-2-ol. Yield: 50%. $^1$H NMR (400 MHz, CDCl$_3$): δ 8.27 (d, J=2.3 Hz, 1H), 7.40-7.29 (m, 14H), 7.19 (d, J=6.8 Hz, 2H), 5.48 (s, 1H), 3.92 (s, 3H), 3.87 (d, J=7.0 Hz, 2H). LCMS (ESI) m/z: 394 (M+1).

Step 3: 2-benzyl-1-(2-methoxy-5-phenylpyridin-3-yl)-1-phenylpent-4-en-2-ol

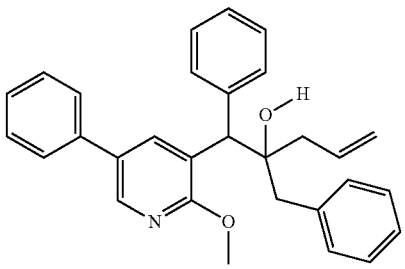 [SMILES: C=CCC(O)(Cc1ccccc1)C(c1ccccc1)c1cc(-c2ccccc2)cnc1OC]

According to the method of step 3 in Example 91, the product was prepared from 1-(2-methoxy-5-phenylpyridin-3-yl)-1, 3-diphenylpropan-2-one and allylmagnesium bromide. Yield: 45%. LCMS (ESI) m/z: 436 (M+1).

Step 4: 3-benzyl-3-hydroxyl-4-(2-methoxy-5-phenylpyridin-3-yl)-4-phenylbutanal

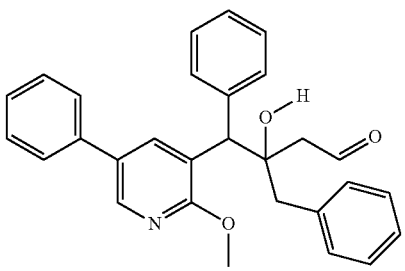 [SMILES: COc1ncc(-c2ccccc2)cc1C(c1ccccc1)C(O)(CC=O)Cc1ccccc1]

According to the method of step 4 in Example 91, 2-benzyl-1-(2-methoxy-5-phenylpyridin-3-yl)-1-phenylpent-4-en-2-ol was used to prepare the crude product which was used directly in the next step. LCMS (ESI) m/z: 438 (M+1).

Step 5: 2-benzyl-4-(dimethylamino)-1-(2-methoxy-5-phenylpyridin-3-yl)-1-phenylbutan-2-ol

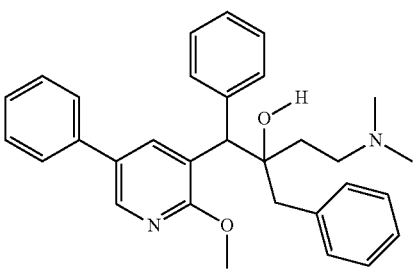

Compound 191 (A1)
Compound 192 (A2)
Compound 193 (B)

3-benzyl-3-hydroxyl-4-(2-methoxy-5-phenylpyridin-3-yl)-4-phenylbutanal (1.0 g, 2.3 mmol) and dimethylamine hydrochloride (563 mg, 6.9 mmol) were dissolved in 10 mL of methanol and added with sodium cyanoborohydride (217 mg, 3.45 mmol), and the mixture was stirred at 16° C. for 16 h. The reaction mixture was poured into 20 mL of water, and extracted with ethyl acetate (30 mL×3). The combined organic phase was dried over anhydrous sodium sulfate, concentrated in vacuo and separated by preparative HPLC (GX-G; Phenomenex Synergi C18 150*30 mm*4 um; acetonitrile 30%-60%; water (0.225% formic acid); 25 mL/min) to give component A and compound 193 (B) (283.7 mg, 24.16% yield). Component A was separated by chiral SFC (Column OD-5 um; supercritical $CO_2$/MeOH (0.2% aqueous ammonia)=80/20; 55 mL/min; 220 nm) to give compound 191 (A1) (26.91 mg, 2.5% yield) and compound 192 (A2) (20.0 mg, 1.9% yield). Compound 191 (A1)/compound 192 (A2): $^1$H NMR (400 MHz, METHANOL-$d_4$) δ 8.71 (d, J=2.3 Hz, 1H), 8.23 (d, J=2.3 Hz, 1H), 7.70 (d, J=7.5 Hz, 2H), 7.57 (d, J=7.5 Hz, 2H), 7.46 (t, J=7.5 Hz, 2H), 7.35 (q, J=7.7 Hz, 3H), 7.28-7.20 (m, 6H), 4.49 (s, 1H), 3.98 (s, 3H), 2.90-2.81 (m, 2H), 2.57-2.49 (m, 1H), 2.35-2.28 (m, 1H), 2.02 (s, 6H), 1.73-1.61 (m, 2H); compound 193 (B): $^1$H NMR (400 MHz, METHANOL-$d_4$) δ 8.85 (d, J=2.0 Hz, 1H), 8.51 (s, 1H), 8.29 (d, J=2.3 Hz, 1H), 7.65 (d, J=7.3 Hz, 2H), 7.59 (d, J=7.5 Hz, 2H), 7.50 (t, J=7.5 Hz, 2H), 7.41-7.37 (m, 1H), 7.29 (s, 6H), 7.15-7.11 (m, 2H), 4.32 (s, 1H), 3.95 (s, 3H), 3.04-2.92 (m, 2H), 2.89-2.79 (m, 2H), 2.44 (s, 6H), 1.91-1.83 (m, 1H), 1.81-1.72 (m, 1H). LCMS (ESI) m/z: 467.2 (M+1).

Example 94

4-((2-hydroxylethyl)(methylamino)-1-(2-methoxy-5-phenylpyridin-3-yl)-2-(naphthalen-1-yl)-1-phenylbutan-2-ol

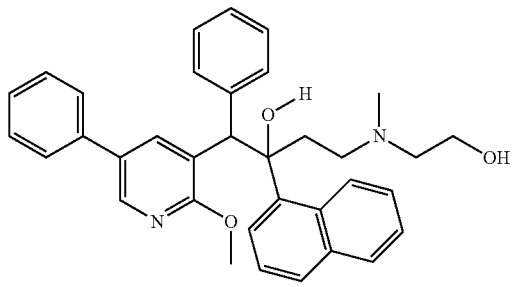

Compound 198 (A1)
Compound 199 (A2)
Compound 200 (B1)
Compound 201 (B2)

Step 1: 2-(2-methoxy-5-phenylpyridin-3-yl)-1-(naphthalen-1-yl)-2-phenylethanol

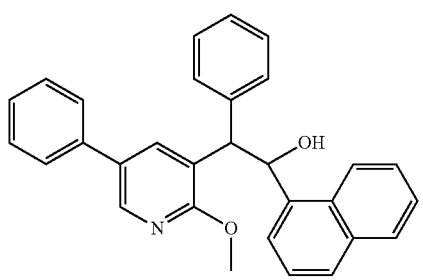 [SMILES: COc1ncc(-c2ccccc2)cc1C(c1ccccc1)C(O)c1cccc2ccccc12]

According to the method of step 1 in Example 91, the product was prepared from 3-benzyl-2-methoxy-5-phenylpyridine and 1-naphthaldehyde. Yield: 43.4%. LCMS (ESI) m/z: 432 (M+1).

Step 2: 2-(2-methoxy-5-phenylpyridin-3-yl)-1-(naphthalen-1-yl)-2-phenylethanone

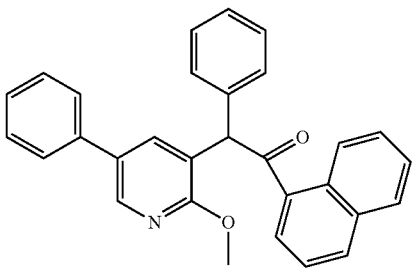 [SMILES: COc1ncc(-c2ccccc2)cc1C(C(=O)c1cccc2ccccc12)c1ccccc1]

According to the method of step 2 in Example 91, the product was prepared from 2-(2-methoxy-5-phenylpyridin-3-yl)-1-(naphthalen-1-yl)-2-phenylethanol. Yield: 47%. LCMS (ESI) m/z: 430 (M+1).

Step 3: 1-(2-methoxy-5-phenylpyridin-3-yl)-2-(naphthalen-1-yl)-1-phenylpent-4-en-2-ol

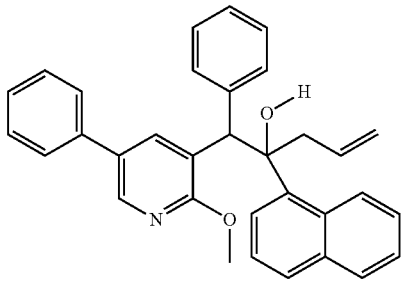 [SMILES: C=CCC(O)(c1cccc2ccccc12)C(c1ccccc1)c1cc(-c2ccccc2)cnc1OC]

According to the method of step 3 in Example 91, the product was prepared from 2-(2-methoxy-5-phenylpyridin-3-yl)-1-(naphthalen-1-yl)-2-phenylethanone and allylmagnesium bromide. Yield: 79.4%. LCMS (ESI) m/z: 472 (M+1).

Step 4: 3-hydroxyl-4-(2-methoxy-5-phenylpyridin-3-yl)-3-(naphthalen-1-yl)-4-phenylbutanal

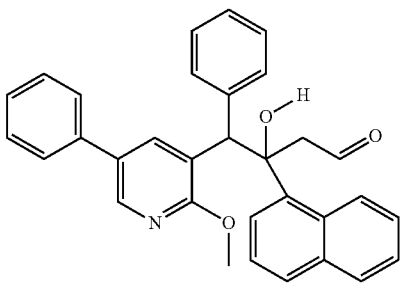 [SMILES: COc1ncc(-c2ccccc2)cc1C(c1ccccc1)C(O)(CC=O)c1cccc2ccccc12]

According to the method of step 4 in Example 91, 1-(2-methoxy-5-phenylpyridin-3-yl)-2-(naphthalen-1-yl)-1-phenylpent-4-en-2-ol was used to prepare the crude product which was used directly in the next step. LCMS (ESI) m/z: 474 (M+1).

Step 5: 4-((2-hydroxylethyl)(methyl)amino)-1-(2-methoxy-5-phenylpyridin-3-yl)-2-(naphthalen-1-yl)-1-phenylbutan-2-ol

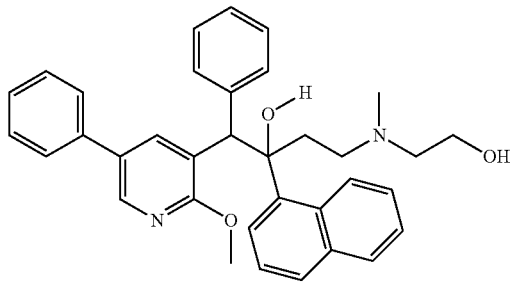

Compound 198 (A1)
Compound 199 (A2)
Compound 200 (B1)
Compound 201 (B2)

3-hydroxyl-4-(2-methoxy-5-phenylpyridin-3-yl)-3-(naphthalen-1-yl)-4-phenylbutanal (0.8 g, 1.69 mmol) was dissolved in 1,2-dichloroethane (10 mL) and added with 2-(methylamino)ethanol (634 mg, 8.45 mmol). Acetic acid was added to adjust pH to 5. The mixture was stirred at 15° C. for 0.5 h. Then sodium cyanoborohydride (159 mg, 2.53 mmol) was added and the mixture was stirred at 15° C. for 2 h. The reaction mixture was poured into 30 mL of water. The mixture was extracted with ethyl acetate (20 mL×3) and the combined organic phase was dried over anhydrous sodium sulfate, concentrated in vacuo and separated by preparative HPLC (GX-G; Phenomenex Synergi C18 150*30 mm*4 um; acetonitrile 25%-55%; water (0.225% formic acid); 25 mL/min) to give component A and component B. Component A was separated by chiral SFC (Chiralpak AD 250×30 mm I.D., 5 um; supercritical CO$_2$/EtOH (0.1% aqueous ammonia)=60/40; 45 g/min; 220 nm) to give compound 198 (A1) (28.14 mg, 3.13% yield) and compound 199 (A2) (27.29 mg, 3.03% yield) as white solid. Component B was separated by chiral SFC (Chiralpak AD 250×30 mm I.D., 10 um; supercritical CO$_2$/i-PrOH (0.2% aqueous ammonia)=75/25; 60 g/min; 220 nm) to give compound 200 (B1) (44.9 mg, 4.99% yield) and compound 201 (B2) (40.14 mg, 4.46% yield) as white solid. Compound 198 (A1)/compound 199 (A2): $^1$H NMR (400 MHz, CHLOROFORM-d): δ 8.56-8.44 (m, 2H), 8.16-8.10 (m, 1H), 7.89 (d, J=2.26 Hz, 1H), 7.85 (d, J=7.28 Hz, 3H), 7.69-7.64 (m, 1H), 7.62-7.55 (m, 1H), 7.50-7.30 (m, 10H), 5.65-5.62 (m, 1H), 3.54-3.35 (m, 2H), 3.30-3.21 (m, 3H), 2.69-2.59 (m, 1H), 2.53-2.45 (m, 1H), 2.41-2.30 (m, 3H), 2.16 (s, 4H); compound 200 (B1)/compound 201 (B2): $^1$H NMR (400 MHz, CHLOROFORM-d): δ 8.73-8.67 (m, 1H), 8.65-8.58 (m, 1H), 8.40-8.31 (m, 2H), 7.91 (s, 2H), 7.71-7.63 (m, 4H), 7.50 (t, J=7.65 Hz, 4H), 7.40-7.32 (m, 2H), 7.18 (br. s., 2H), 6.94-6.90 (m, 3H), 5.85-5.81 (m, 1H), 4.18 (s, 4H), 3.59-3.51 (m, 2H), 2.83-2.78 (m, 1H), 2.61-2.56 (m, 1H), 2.50-2.43 (m, 1H), 2.25 (s, 5H), 2.17-2.08 (m, 1H). LCMS (ESI) m/z: 533.3 (M+1).

Example 95

1-(3-hydroxyl-4-(2-methoxy-5-phenylpyridin-3-yl)-3-(naphthalen-1-yl)-4-phenylbutyl)azetidin-3-ol

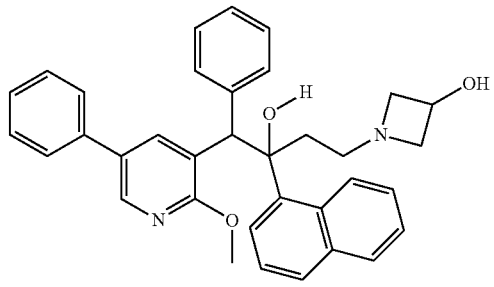

Compound 202 (A)
Compound 203 (B1)
Compound 204 (B2)

2,2,2-trifluoroacetic acid (5 mL) was added to the solution of tert-butyl tert-butyl-3-hydroxylazetidine-1-carboxylate (1.5 g, 8.66 mmol) in dichloromethane (40 ml) and stirred at 15° C. for 1 hour. The mixture was concentrated in vacuo to give azetidin-3-ol (617 mg). The obtained azetidin-3-ol (617 mg, 8.45 mmol) was dissolved in 1,2-dichloroethane (10 mL) and added with triethylamine (2 mL). pH was adjusted to 5-6. 3-hydroxyl-4-(2-methoxy-5-phenylpyridin-3-yl)-3-(naphthalen-1-yl)-4-phenylbutanal (0.8 g, 1.69 mmol) was added. After 0.5 h, sodium cyanoborohydride (159 mg, 2.53 mmol) was added and stirred at 15° C. for 2 h. The reaction mixture was poured into 30 mL of water and extracted with ethyl acetate (30 mL×3). The combined organic phase was dried over anhydrous sodium sulfate, concentrated in vacuo and separated by preparative HPLC (GX-E; Agella Venusil ASB C18 150*21.2 mm*5 um; acetonitrile 39%-69%; water (0.225% hydrochloric acid); 25 mL/min) to give compound 202 (A) (68.22 mg, 7.61% yield) as white solid and component B. Component B was separated by chiral SFC (Chiralpak AD 250×30 mm I.D., 10 um; supercritical CO$_2$/EtOH (0.1% aqueous ammonia)=70/30; 60 mL/min; 220 nm) to give compound 203 (B1) (11.44 mg, 1.28% yield) and compound 204 (82) (8.45 mg, 0.94% yield) as white solid. Compound 202 (A): $^1$H NMR (400 MHz, METHANOL-d$_4$): δ 8.63-8.55 (m, 1H), 8.53-8.44 (m, 2H), 8.14-8.07 (m, 1H), 7.88-0.80 (m, 2H), 7.78-7.62 (m, 4H), 7.41 (t, J=6.40 Hz, 10H), 5.75-5.68 (m, 1H), 4.42-4.32 (m, 1H), 3.88 (d, J=9.54 Hz, 2H), 3.38 (s, 3H), 3.28-3.18 (m, 1H), 2.97-2.81 (m, 2H), 2.42-2.31 (m, 1H), 2.22-2.10 (m, 1H). Compound 203 (B1)/compound 204 (B2): $^1$H NMR (400 MHz, CHLOROFORM-d): δ 8.80-8.68 (m, 1H), 8.64-8.52 (m, 1H), 8.40-8.31 (m, 1H), 7.95-7.78 (m, 2H), 7.75-7.57 (m, 4H), 7.51 (t, J=7.15 Hz, 3H), 7.44-7.36 (m, 1H), 7.35-7.30 (m, 1H), 7.10 (br. s., 2H), 6.93 (br. s., 3H), 5.83 (br. s., 1H), 4.41-4.29 (m, 1H), 4.15 (s, 3H), 3.68-3.57 (m, 1H), 3.53-3.41 (m, 1H), 2.96-2.81 (m, 2H), 2.72-2.57 (m, 2H), 2.45-2.32 (m, 2H), 2.26-2.17 (m, 2H), 2.06-1.92 (m, 3H). LCMS (ESI) m/z: 531.2 (M+1).

Example 96

1-(5-(4-bromophenyl)-2-methoxypyridin-3-yl)-2-(2,3-difluorophenyl)-4-(dimethylamino)-1-phenylbutan-2-ol

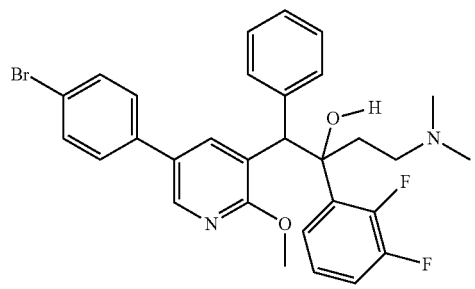

Compound 311 (A1)
Compound 312 (A2)
Compound 313 (B1)
Compound 314 (B2)

Step 1: 2-(5-(4-bromophenyl)-2-methoxypyridin-3-yl)-1-(2,3-difluorophenyl)-2-phenylethanol

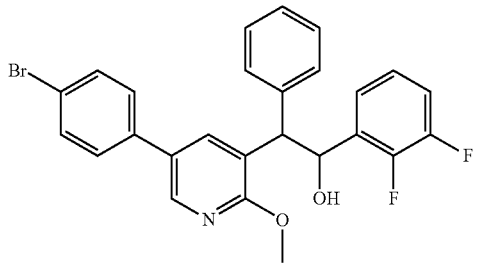 [SMILES: COc1ncc(-c2ccc(Br)cc2)cc1C(c1ccccc1)C(O)c1cccc(F)c1F]

Under nitrogen, diisopropylamine (2.18 g, 21.5 mmol) was dissolved in 30 mL of THF and n-butyllithium (2.5 M n-hexane solution, 8.4 mL, 21 mmol) was added slowly at −78° C. with stirring. The mixture was stirred at −78° C. for 30 minutes. Then 3-benzyl-5-(4-bromophenyl)-2-methoxypyridine (2.5 g, 7.06 mmol) was dissolved in 20 mL of tetrahydrofuran and added dropwise to the reaction liquid and stirred at −78° C. for 1 hour. Then 2,3-difluorobenzaldehyde (1.10 g, 7.77 mmol) was dissolved in 20 mL of tetrahydrofuran and added dropwise over 5 minutes. The reaction mixture was stirred at −78° C. for 1.5 h. The reaction was quenched with 10 mL of saturated ammonium chloride solution and extracted with ethyl acetate (20 mL×3). The combined organic phase was dried over anhydrous sodium sulfate, dried by rotary evaporation, isolated by column chromatography (petroleum ether/ethyl acetate: 50/1-5/1) to give 2-[5-(4-bromophenyl)-2-methoxy-3-pyridyl]-1-(2,3-difluorophenyl)-2-phenyl-ethanol (1.10 g, 31.39% yield) as an off-white solid. LCMS (ESI) m/z: 497.3 (M+1).

Step 2: 2-(5-(4-bromophenyl)-2-methoxypyridin-3-yl)-1-(2,3-difluorophenyl)-2-phenylethanone

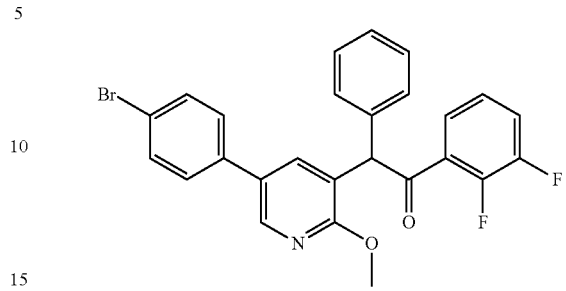

Under nitrogen, 2-[5-(4-bromophenyl)-2-methoxy-3-pyridyl]-1-(2,3-difluorophenyl)-2-phenyl-ethanol (1.10 g, 2.22 mmol) and pyridinium chlorochromate (1.44 g, 6.66 mmol) were dissolved in 20 mL of dichloromethane. The mixture was stirred at 20-30° C. under nitrogen for 12 h. The reaction liquid was dried by rotary evaporation and isolated by column chromatography (petroleum ether/ethyl acetate: 50/1-10/1) to give 2-(5-(4-bromophenyl)-2-methoxypyridin-3-yl)-1-(2,3-difluorophenyl)-2-phenylethanone (0.8 g, 72.90% yield) as yellow solid. LCMS (ESI) m/z: 495.3 (M+1).

Step 3: 1-(5-(4-bromophenyl)-2-methoxypyridin-3-yl)-2-(2,3-difluorophenyl)-1-phenylpent-4-en-2-ol

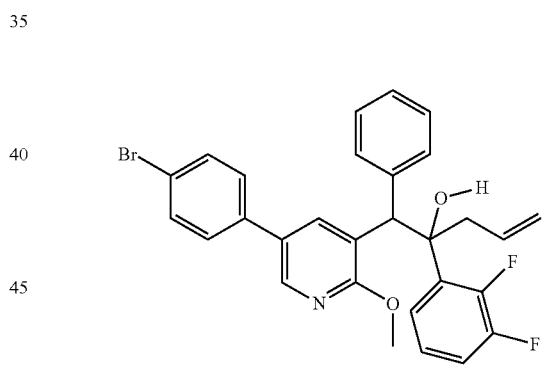

Under nitrogen, allylmagnesium bromide (1M in tetrahydrofuran, 8.10 mL, 8.1 mmol) was added to the solution of 2-(5-(4-bromophenyl)-2-methoxypyridin-3-yl)-1-(2,3-difluorophenyl)-2-phenylethanone (0.8 g, 1.62 mmol) in 15 mL of tetrahydrofuran at 0° C. The mixture was stirred at 0° C. for 2 h. The reaction was quenched with 10 mL of saturated ammonium chloride solution and extracted with ethyl acetate (10 mL×3). The combined organic phase was washed with brine, dried over anhydrous sodium sulfate and concentrated in vacuo to give 1-(5-(4-bromophenyl)-2-methoxypyridin-3-yl)-2-(2,3-difluorophenyl)-1-phenylpent-4-en-2-ol (800 mg, crude product) as yellow solid which was used without further purification in the next step. LCMS (ESI) m/z: 537.4 (M+1).

Step 4: 4-(5-(4-bromophenyl)-2-methoxypyridin-3-yl)-3-(2,3-difluorophenyl)-3-hydroxyl-4-phenylbutanal

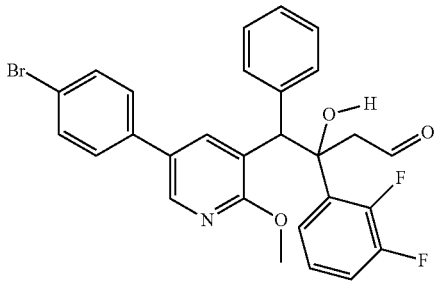 [SMILES: COc1ncc(-c2ccc(Br)cc2)cc1C(c1ccccc1)C(O)(CC=O)c1cccc(F)c1F]

Under nitrogen, 1-(5-(4-bromophenyl)-2-methoxypyridin-3-yl)-2-(2,3-difluorophenyl)-1-phenylpent-4-en-2-ol (800.00 mg, 1.49 mmol) and 2,6-lutidine (319.61 mg, 2.98 mmol) were dissolved in 1,4-dioxane (15 mL) and 3 mL of water and added with sodium periodate (1.28 g, 5.97 mmol) and osmium tetroxide (37.92 mg, 149.14 mmol) and stirred at 20° C. for 2 h. The reaction liquid was diluted with 10 mL of water and extracted with ethyl acetate (10 mL×3). The combined organic phase was washed with 20 mL of saturated brine, dried over anhydrous sodium sulfate, filtered and concentrated in vacuo to give 4-(5-(4-bromophenyl)-2-methoxypyridin-3-yl)-3-(2,3-difluorophenyl)-3-hydroxyl-4-phenylbutanal (800 mg, crude product) as a yellow oil, which was used without further purification in the next step. LCMS (ESI) m/z: 539.4 (M+1).

Step 5: 1-(5-(4-bromophenyl)-2-methoxypyridin-3-yl)-2-(2,3-difluorophenyl)-4-(dimethylamino)-1-phenylbutan-2-ol

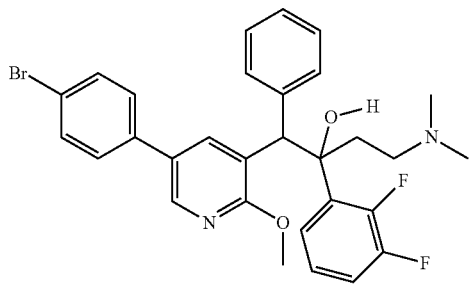

Compound 311 (A1)
Compound 312 (A2)
Compound 313 (B1)
Compound 314 (B2)

4-(5-(4-bromophenyl)-2-methoxypyridin-3-yl)-3-(2,3-difluorophenyl)-3-hydroxyl-4-phenylbutanal (800 mg, 1.49 mmol) and dimethylamine hydrochloride (605.8 mg, 7.43 mmol) were dissolved in 10 mL of methanol and added with sodium cyanoborohydride (112 mg, 1.78 mol) and 0.1 mL of concentrated hydrochloric acid. The reaction mixture was stirred at 10-35° C. for 2 h, diluted with 10 mL of water and extracted with dichloromethane (10 mL×3). The combined organic phase was dried over anhydrous sodium sulfate, dried by rotary evaporation and purified by preparative HPLC (GX-D; Boston Symmetrix C18 ODS-R 150*30 mm*5 um; acetonitrile 31%-61%; water (0.225% formic acid); 25 mL/min) to give component A and component B. Component A was separated by chiral SFC (sfc-80; AD-10 um; supercritical $CO_2$/Isopropanol (0.1% aqueous ammonia)=70/30; 60 g/min; 220 nm) to give compound 311 (A1) (31.19 mg, 3.41% yield) and compound 312 (A2) (28.76 mg, 3.15% yield) as white solid. Component B was separated by chiral SFC (sfc-80; AD-10 um; supercritical $CO_2$/Isopropanol (0.1% aqueous ammonia)=55/45; 70 ml/min; 220 nm) to give compound 313 (B1) (28.76 mg, 3.15% yield) and compound 314 (B2) (18.40 mg, 2.01% yield) as white solid. Compound 311 (A1)/compound 312 (A2): $^1$H NMR (400 MHz, METHANOL-$d_4$): δ 8.63 (s, 1H), 8.52 (br. s., 1H), 8.30 (d, J=1.76 Hz, 1H), 7.64 (d, J=8.28 Hz, 2H), 7.52 (d, J=8.28 Hz, 2H), 7.38 (d, J=7.28 Hz, 3H), 7.08-6.94 (m, 5H), 5.26 (s, 1H), 4.08 (s, 3H), 2.51 (br. s., 1H), 2.39-2.15 (m, 8H), 2.11-1.99 (m, 1H); compound 313 (B1)/compound 314 (B2): $^1$H NMR (400 MHz, METHANOL-$d_4$): δ 8.53 (d, J=2.38 Hz, 1H), 8.01 (d, J=2.38 Hz, 1H), 7.68 (d, J=7.28 Hz, 2H), 7.61 (d, J=8.41 Hz, 2H), 7.49 (t, J=7.28 Hz, 1H), 7.41 (d, J=8.53 Hz, 2H), 7.38-7.31 (m, 2H), 7.30-7.23 (m, 1H), 7.13-6.98 (m, 2H), 5.12 (s, 1H), 3.76 (s, 3H), 2.48 (br. s., 1H), 2.30-2.02 (m, 9H). LCMS (ESI) m/z: 568.9 (M+1).

Example 97

1-(5-(4-chlorophenyl)-2-methoxy-3-pyridyl)-2-(2,3-difluorophenyl)-4-dimethylamino-1-phenylbutan-2-ol

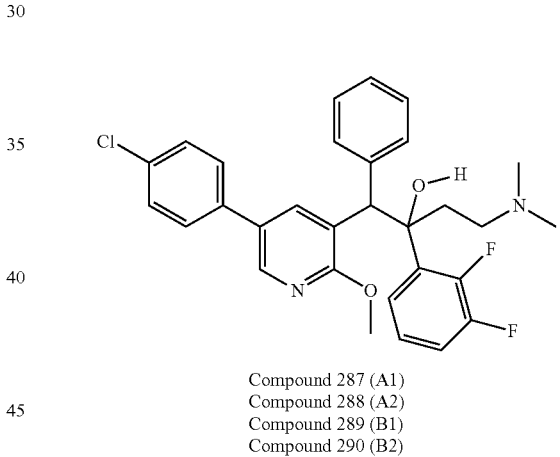

Compound 287 (A1)
Compound 288 (A2)
Compound 289 (B1)
Compound 290 (B2)

The title compound was prepared according to the method of Example 96 and the order of step 1,2,3,4, and 5, wherein 3-benzyl-5-(4-chlorophenyl)-2-methoxypyridine was used to replace 3-benzyl-5-(4-bromophenyl)-2-methoxypyridine in the first step. The crude product was separated by preparative HPLC (GX-D; Boston Symmetrix C18 ODS-R 150*30 mm*5 um; acetonitrile: 25%-55%; $H_2O$ (+0.0023 HCOOH); 25 ml/min; 220 nm/254 nm) to give component A and component B. Component A was separated by chiral SFC (Column: IC-10 um; Condition: 30% MeOH (aqueous ammonia) 60 ML/MIN; detection wavelength: 220 nm) to give compound 287 (A1) (19.79 mg, 2.6% yield) and compound 288 (A2) (67.04 mg, 2.9% yield) as white solid. Component B was separated by chiral SFC (Column: IC-10 um; Condition: 25% MeOH (aqueous ammonia) 60 ML/MIN; detection wavelength: 220 nm) to give compound 289 (B1) (67.04 mg, 2.9% yield) and compound 290 (B2) (68.91 mg, 2.0% yield) as white solid. Compound 287 (A1)/compound 288 (A2): $^1$H NMR (400 MHz, METHA- NOL-d₄): δ 8.65 (s, 1H), 8.29 (d, J=2.51 Hz, 1H), 7.63-7.55 (m, 2H), 7.53-7.45 (m, 2H), 7.39-7.38 (d, J=7.65 Hz, 3H), 7.11-6.92 (m, 4H), 5.25 (s, 1H), 4.08 (s, 3H), 2.80-2.77 (m, 1H), 2.56-2.38 (m, 8H), 2.11-2.07 (m, 1H); compound 289 (B1)/compound 290 (B2): ¹H NMR (400 MHz, METHANOL-d₄): δ 8.49 (s, 1H), 8.03 (s, 1H), 7.67 (d, J=7.40 Hz, 3H), 7.57-7.22 (m, 13H), 7.17-6.92 (m, 3H), 5.16 (s, 1H), 3.77 (s, 3H), 3.05 (m, J=4.89 Hz, 1H), 2.44-2.30 (s, 8H), 2.17-2.14 (m, 1H). LCMS (ESI) m/z: 523.2 (M+1).

Example 98

1-(5-(4-bromophenyl)-2-methoxypyridin-3-yl)-2-(3,5-difluorophenyl)-4-dimethylamino-1-phenylbutan-2-ol

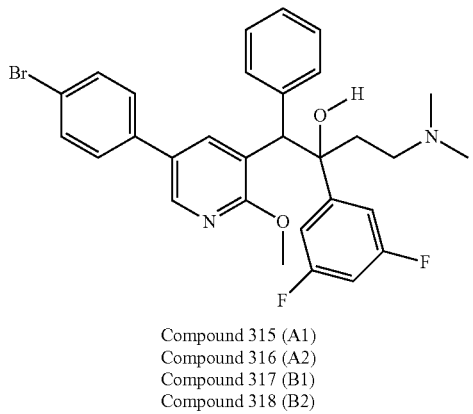

Compound 315 (A1)
Compound 316 (A2)
Compound 317 (B1)
Compound 318 (B2)

Step 1: 2-(5-(4-bromophenyl)-2-methoxypyridin-3-yl)-1-(3,5-difluorophenyl)-2-phenylethanol

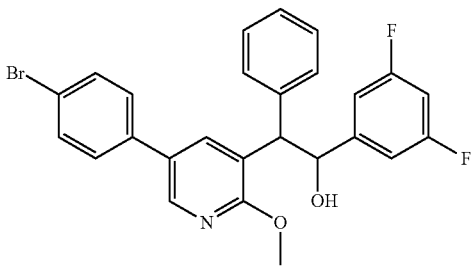 [SMILES: COc1ncc(-c2ccc(Br)cc2)cc1C(c1ccccc1)C(O)c1cc(F)cc(F)c1]

According to the method of step 1 in Example 96, the product was prepared from 3-benzyl-5-(4-bromophenyl)-2-methoxypyridine and 3,5-difluorobenzaldehyde. Yield: 22.8%. LCMS (ESI) m/z: 496 (M+1).

Step 2: 2-(5-(4-bromophenyl)-2-methoxypyridin-3-yl)-1-(3,5-difluorophenyl)-2-phenylethanone

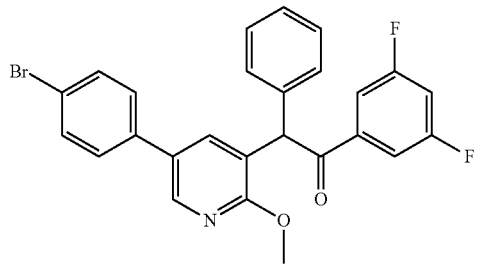 [SMILES: COc1ncc(-c2ccc(Br)cc2)cc1C(C(=O)c1cc(F)cc(F)c1)c1ccccc1]

According to the method of step 2 in Example 96, the product was prepared from 2-(5-(4-bromophenyl)-2-methoxypyridin-3-yl)-1-(3,5-difluorophenyl)-2-phenylethanol. Yield: 94%. LCMS (ESI) m/z: 494 (M+1).

Step 3: 1-(5-(4-bromophenyl)-2-methoxypyridin-3-yl)-2-(3,5-difluorophenyl)-1-benzenepent-4-en-2-ol

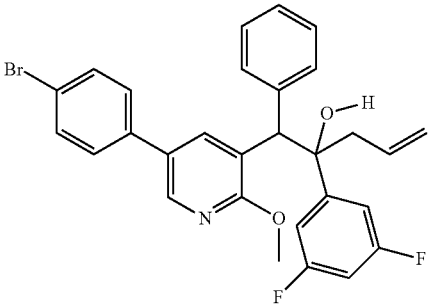 [SMILES: C=CCC(O)(c1cc(F)cc(F)c1)C(c1ccccc1)c1cc(-c2ccc(Br)cc2)cnc1OC]

According to the method of step 3 in Example 96, 2-(5-(4-bromophenyl)-2-methoxypyridin-3-yl)-1-(3,5-difluorophenyl)-2-phenylethanone and allylmagnesium bromide was used to prepare the crude product which was used directly in the next step. LCMS (ESI) m/z: 536/538 (M+1).

Step 4: 4-(5-(4-bromophenyl)-2-methoxypyridin-3-yl)-3-(3,5-difluorophenyl)-3-hydroxyl-4-phenylbutanal

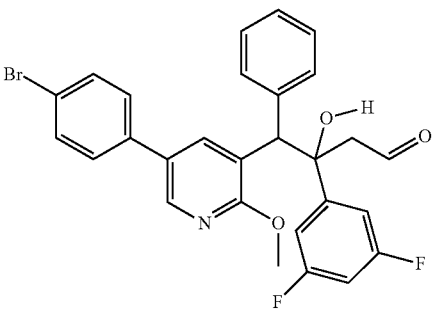 [SMILES: COc1ncc(-c2ccc(Br)cc2)cc1C(c1ccccc1)C(O)(CC=O)c1cc(F)cc(F)c1]

According to the method of step 4 in Example 96, 1-(5-(4-bromophenyl)-2-methoxypyridin-3-yl)-2-(3,5-difluorophenyl)-1-benzenepent-4-en-2-ol was used to prepare the crude product which was used directly in the next step. LCMS (ESI) m/z: 538/540 (M+1).

Step 5: 1-(5-(4-bromophenyl)-2-methoxypyridin-3-yl)-2-(3,5-difluorophenyl)-4-dimethylamino-1-phenylbutan-2-ol

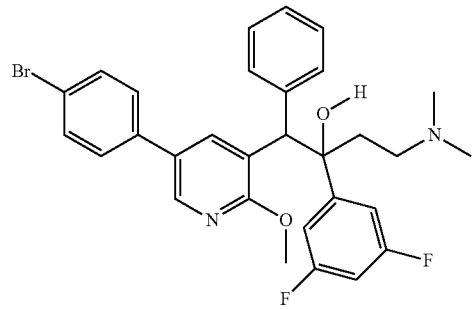

Compound 315 (A1)
Compound 316 (A2)
Compound 317 (B1)
Compound 318 (B2)

Under nitrogen, 4-(5-(4-bromophenyl)-2-methoxypyridin-3-yl)-3-(3,5-difluorophenyl)-3-hydroxyl-4-phenylbutanal (500.00 mg, 928.71 umol) and dimethylamine hydrochloride (378.64 mg, 4.64 mmol) were dissolved in 10 mL of methanol and sodium cyanoborohydride (87.54 mg, 1.39 mmol) and 0.1 mL of concentrated hydrochloric acid were added in one portion at 0° C. The mixture was stirred at 10-35° C. for 2 h. The reaction liquid was diluted with 20 mL of water and extracted with dichloromethane (10 mL×3). The combined organic phase was dried over anhydrous sodium sulfate and concentrated to give a crude product which was separated by preparative HPLC (GX-D; Boston Symmetrix C18 ODS-R 150*30 mm*5 um; acetonitrile 33%-63%; water (0.225% formic acid); 25 mL/min) to give component A and component B. Component A was separated by chiral SFC (sfc-80; AD-10 um; supercritical $CO_2$/Isopropanol (0.1% aqueous ammonia)=75/25; 60 g/min; 220 nm) to give compound 315 (A1) (9.83 mg, 1.73% yield) and compound 316 (A2) (14.89 mg, 2.61% yield) as white solid. Component B was separated by chiral SFC (sfc-80; AD-10 um; supercritical $CO_2$/Isopropanol (0.1% aqueous ammonia)-65/35; 65 mL/min; 220 nm) to give compound 317 (B1) (27.33 mg, 4.8% yield) and compound 318 (B2) (30.72 mg, 5.39% yield) as white solid. Compound 315 (A1)/compound 316 (A2): $^1$H NMR (400 MHz, METHANOL-$d_4$): δ 8.66 (d, J=2.01 Hz, 1H), 8.29 (d, J=2.26 Hz, 1H), 7.64 (d, J=8.53 Hz, 2H), 7.52 (d, J=8.53 Hz, 2H), 7.34 (d, J=7.53 Hz, 2H), 7.11-6.97 (m, 5H), 6.67 (t, J=8.91 Hz, 1H), 4.86 (s, 1H), 4.07 (s, 3H), 2.39 (br. s., 1H), 2.18-2.02 (m, 9H); compound 317 (B1)/compound 318 (B2): $^1$H NMR (400 MHz, METHANOL-$d_4$): δ 8.63 (d, J=2.26 Hz, 1H), 8.03 (d, J=2.26 Hz, 1H), 7.69 (d, J=7.28 Hz, 2H), 7.62 (d, J=8.28 Hz, 2H), 7.42 (d, J=8.53 Hz, 2H), 7.37-7.29 (m, 2H), 7.28-7.16 (m, 3H), 6.68 (t, J=8.78 Hz, 1H), 4.81 (s, 1H), 3.80 (s, 3H), 2.34 (d, J=9.03 Hz, 1H), 2.20-1.88 (m, 9H). LCMS (ESI) m/z: 568.9 (M+1).

Example 99

1-(5-(4-chlorophenyl)-2-methoxypyridin-3-yl)-2-(3,5-difluorophenyl)-4-dimethylamino-1-phenylbutan-2-ol

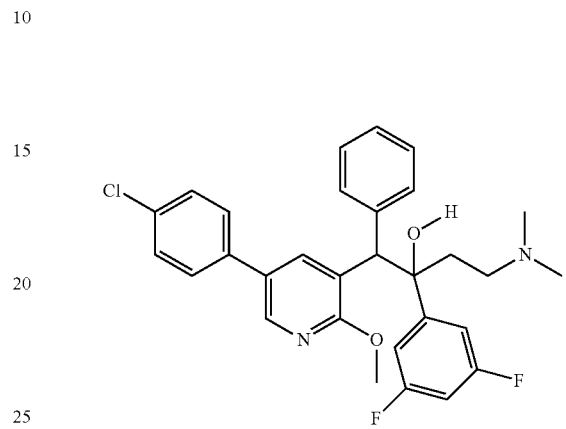

Compound 279 (A1)
Compound 280 (A2)
Compound 281 (B1)
Compound 282 (B2)

The title compound was prepared according to the method of Example 98 and the order of step 1,2,3,4, and 5, wherein 3-benzyl-5-(4-chlorophenyl)-2-methoxypyridine was used to replace 3-benzyl-5-(4-bromophenyl)-2-methoxypyridine in the first step. The crude product was separated by preparative HPLC (GX-G; Phenomenex Synergi C18 150*30 mm*4 um; acetonitrile 22%-52%; water (0.225% formic acid); 25 mL/min) to give component A(145.8 mg) and component B(220.1 mg). Component A was separated by chiral SFC (IC-10 um; 25% MeOH (0.1% aqueous ammonia) 60 mL/MIN; 220 nm) to give compound 279 (A1) (12.63 mg, 2.7%) and compound 280 (A2) (10.10 mg, 2.6%) as white solid. Component B was separated by chiral SFC (AD-10 um, 5 um; 30% i-PrOH (0.1% aqueous ammonia) 60 g/min; 220 nm) to give compound 281 (B1) (65.57 mg, 6.8%) and compound 282 (B2) (95.54 mg, 7.9%) as white solid. Compound 279 (A1)/compound 280 (A2): $^1$H NMR (400 MHz, METHANO L-$d_4$): δ 8.66 (d, J=2.38 Hz, 1H), 8.29 (d, J=2.51 Hz, 1H), 7.72-7.26 (m, 6H), 7.18-6.92 (m, 5H), 6.67-6.65 (t, J=8.85 Hz, 1H), 4.86 (s, 1H), 4.07 (s, 3H), 2.18-1.96 (m, 10H); compound 281 (B1)/compound 282 (B2): $^1$H NMR (400 MHz, METHANOL-$d_4$): δ 8.64 (d, J=2.38 Hz, 1H), 8.02 (d, J=2.51 Hz, 1H), 7.69 (d, J=7.28 Hz, 2H), 7.55-7.43 (m, 4H), 7.40-7.08 (m, 5H), 6.68 (t, J=8.91 Hz, 1H), 4.80 (s, 1H), 3.80 (s, 3H), 2.41-2.21 (m, 1H), 2.17-1.96 (m, 8H), 1.95-1.77 (m, 1H). LCMS (ESI) m/z: 523 (M+1).

Example 100

1-(4-chlorophenyl)-1-(5-(4-chlorophenyl)-2-methoxypyridin-3-yl)-4-dimethylamino-2-naphthalen-1-yl)butan-2-ol

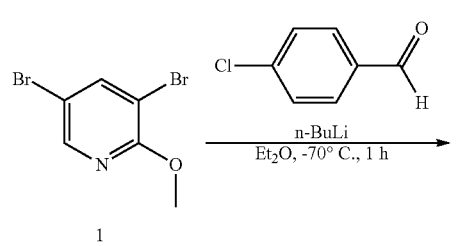

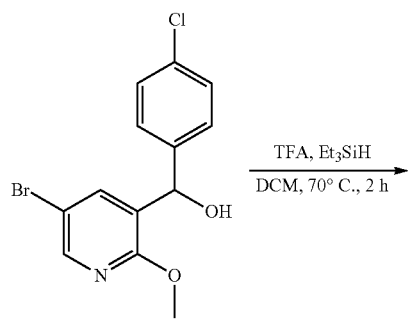

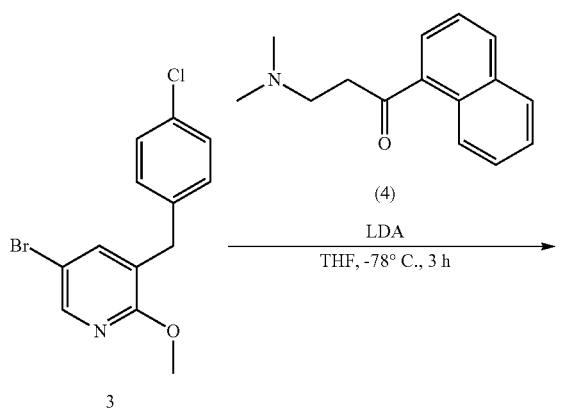

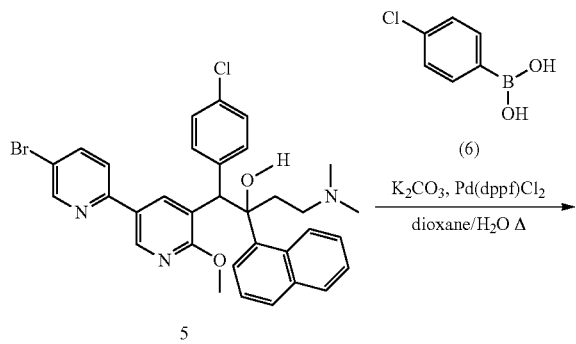

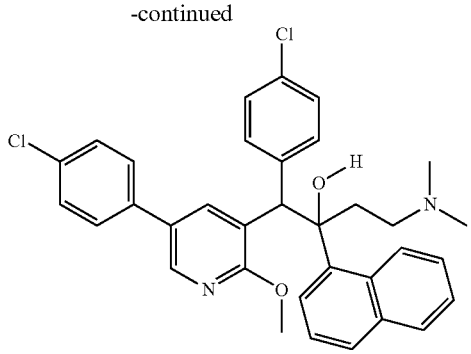

Compound 327 (A1)
Compound 328 (A2)
Compound 329 (B1)
Compound 330 (B2)

Step 1: (5-bromo-2-methoxypyridin-3-yl)(4-chlorophenyl)methanol

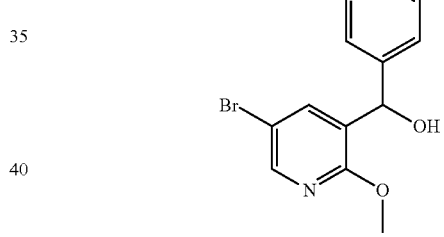

Under nitrogen, 3,5-dibromo-2-methoxypyridine (10.0 g, 37.4 mmol) was dissolved in anhydrous ethyl ether (50 mL) and n-butyllithium (100 mL, 37.5 mmol) was added slowly at −78° C. and stirred for another 30 minutes. 4-chlorobenzaldehyde (6.32 g, 44.9 mmol) dissolved 20 mL of anhydrous ethyl ether (20 mL) and slowly added dropwise to the reaction liquid. Afterwards, the mixture was stirred at −78° C. for 1 hour. The reaction was quenched with 100 mL of aqueous ammonium chloride solution and the mixture was extracted with ethyl acetate (50 mL×2). The combined organic phase was dried over anhydrous sodium sulfate and concentrated to give (5-bromo-2-methoxypyridin-3-yl)(4-chlorophenyl)methanol (6.20 g, yield: 50.37%) as white solid. $^1$H NMR (400 MHz, CDCl$_3$): δ 8.05 (d, J=2.38 Hz, 1H), 7.83 (d, J=2.38 Hz, 1H), 7.30-7.23 (m, 4H), 5.85 (s, 1H), 3.85 (s, 3H).

Step 2: 5-bromo-3-(4-chlorophenyl)-2-methoxypyridine

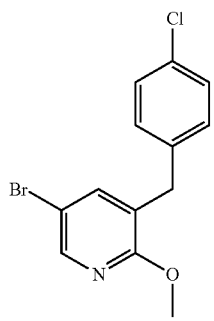 [SMILES: COc1ncc(Br)cc1Cc1ccc(Cl)cc1]

(5-bromo-2-methoxypyridin-3-yl) (4-chlorophenyl) methanol (6.2 g, 18.8 mmol) was dissolved in 20 mL of dichloromethane and 10 mL of trifluoroacetic acid, and 10 mL of triethylsilane was added and stirred at 70° C. for 2 h. TLC (petroleum ether/ethyl acetate=10/1) showed the reaction was complete. The reaction liquid was concentrated and 100 mL of sodium carbonate solution was added. The mixture was extracted with dichloromethane (30 mL×2) and the combined organic phase was washed with brine, dried over anhydrous sodium sulfate, concentrated and isolated by column chromatography (developing solvent:petroleum ether/ethyl acetate=100/1) to give 5-bromo-3-(4-chlorophenyl)-2-methoxypyridine (5.0 g, 84%) as a colorless oil.

Step 3: 1-(5-bromo-2-methoxypyridin-3-yl)-1-(4-chlorophenyl)-4-dimethylamino-2-(naphthalen-1-yl)butan-2-ol

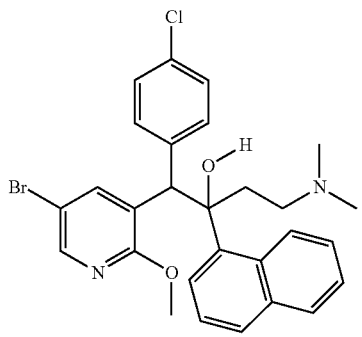 [SMILES: COc1ncc(Br)cc1C(c1ccc(Cl)cc1)C(O)(CCN(C)C)c1cccc2ccccc12]

Under nitrogen, diisopropylamine (4.86 g, 48.00 mmol) was dissolved in 50 mL of tetrahydrofuran and n-butyllithium (2.5M n-hexane solution, 19 mL, 48.0 mmol) was added slowly at −78° C. The mixture was stirred at −78° C. for another 1 hour. 5-bromo-3-(4-chlorophenyl)-2-methoxypyridine (5.00 g, 16.00 mmol) was dissolved in 50 mL of tetrahydrofuran and added slowly dropwise to the reaction liquid. Afterwards, the mixture was stirred at −78° C. for another 1 hour. 3-(dimethylamino)-1-(1-naphthyl)propan-1-ol (4.00 g, 17.60 mmol) was dissolved in 50 mL of tetrahydrofuran and slowly added to the reaction liquid. Afterwards, the mixture was stirred at −78° C. for another 1 hour. The reaction was quenched with saturated ammonium chloride solution and the mixture was extracted with ethyl acetate (100 mL×2). The combined organic phase was dried over anhydrous sodium sulfate, concentrated and isolated by column chromatography (developing solvent:petroleum ether/ethyl acetate=100/1-10/1-5/1) to give 1-(5-bromo-2-methoxypyridin-3-yl)-1-(4-chlorophenyl)-4-dimethylamino-2-(naphthalen-1-yl)butan-2-ol (5.0 g, 57.8% yield) as white solid. LCMS (ESI) m/z: 539, 541.1 (M+1).

Step 4: 1-(5-(4-bromophenyl)-2-methoxypyridin-3-yl)-2-(3,5-difluorophenyl)-4-dimethylamino-1-phenylbutan-2-ol

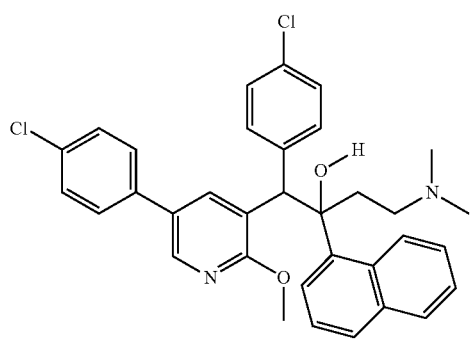

Compound 327 (A1)
Compound 328 (A2)
Compound 329 (B1)
Compound 330 (B2)

Under nitrogen, 1-(5-bromo-2-methoxypyridin-3-yl)-1-(4-chlorophenyl)-4-dimethylamino-2-(naphthalen-1-yl)butan-2-ol (1.90 g, 3.52 mmol), 4-chlorophenylboronic acid (660 mg, 4.22 mmol), potassium carbonate (972 mg, 7.04 mmol) and Pd(dppf)Cl$_2$ (127 mg, 0.176 mmol) were mixed in 20 mL of 1,4-dioxane and 4 mL of water, heated to 80° C. and stirred for 5 h. The reaction liquid was poured into 50 mL of water, and extracted with ethyl acetate (30 mL×3). The combined organic phase was dried over anhydrous sodium sulfate, concentrated and isolated by column chromatography (developing solvent:petroleum ether/ethyl acetate=50/1-5/1) to give component A and component B. Component A was separated by chiral SFC (sfc 80; IC-10 um; supercritical CO$_2$/MeOH (0.05% aqueous ammonia) =50/50; 70 ml/min; 220 nm) to give compound 327 (A1) (230 mg, 11.44% yield) and compound 328 (A2) (177 mg, 8.80% yield) as white solid. Component B was separated by chiral SFC (sfc 80, IC-10 um; supercritical CO$_2$/MeOH (0.05% aqueous ammonia)=60/40; 70 ml/min; 220 nm) to give compound 329 (B1) (170 mg, 8.45% yield) and compound 330 (B2) (156 mg, 7.75% yield) as white solid. Compound 327 (A1)/compound 328 (A2): $^1$HNMR (400 MHz, CDCl$_3$): δ 8.49 (d, J=2.38 Hz, 1H), 8.44 (d, J=8.66 Hz, 1H), 8.13 (d, J=6.65 Hz, 1H), 7.87-7.78 (m, 4H), 7.65 (d, J=7.91 Hz, 1H), 7.57 (t, J=7.22 Hz, 1H), 7.48-7.33 (m, 8H), 5.61 (s, 1H), 3.28 (s, 3H), 2.56-2.47 (m, 1H), 2.23 (br. s., 1H), 2.11-2.04 (m, 7H), 2.02-1.97 (m, 1H); compound 329 (B1)/compound 330 (B2): $^1$H NMR (400 MHz, CDCl$_3$): δ 8.72 (d, J=2.26 Hz, 1H), 8.58 (d, J=8.91 Hz, 1H), 8.32 (d, J=2.38 Hz, 1H), 7.92 (m, 2H), 7.70 (d, J=8.03 Hz, 1H), 7.63 (t, J=7.28 Hz, 1H), 7.58-7.49 (m, 3H), 7.48-7.42 (m, 2H), 7.36 (t, J=7.72 Hz, 1H), 7.14 (d, J=8.53 Hz, 2H), 6.88 (d, J=8.53 Hz, 2H), 5.81 (s, 1H), 4.17 (s, 3H), 2.56 (d, J=8.66 Hz, 1H), 2.11 (d, J=10.2 Hz, 2H), 2.04 (s, 6H), 2.00-1.95 (m, 1H). LCMS (ESI) m/z: 571.2 (M+1).

Example 101

1-(5-(4-bromophenyl)-2-methoxypyridin-3-yl)-1-(4-chlorophenyl)-4-dimethylamino-2-(naphthalen-1-yl)butan-2-ol

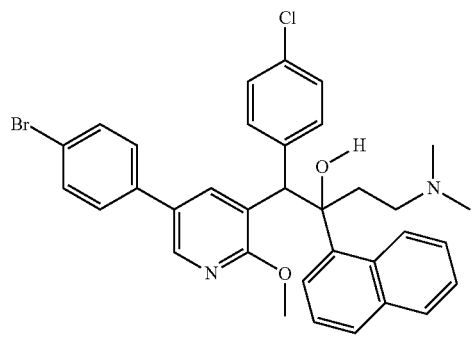

Compound 323 (A1)
Compound 324 (A2)
Compound 325 (B1)
Compound 326 (B2)

Step 1: 1-(4-chlorophenyl)-4-dimethylamino-1-(2-methoxy-5-boronic acid pinacol ester)pyridin-3-yl)-2-(naphthalen-1-yl)butan-2-ol

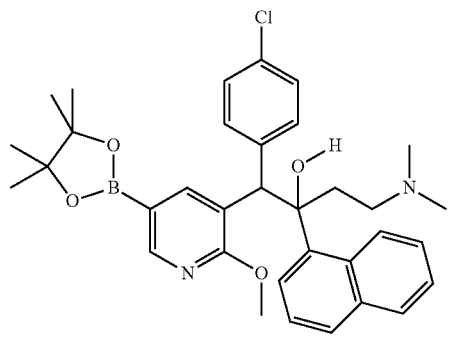

Under nitrogen, 1-(5-bromo-2-methoxypyridin-3-yl)-1-(4-chlorophenyl)-4-dimethylamino-2-(naphthalen-1-yl)butan-2-ol (1.6 g, 2.96 mmol), bis(pinacolato)diboron (1.5 g, 5.9 mmol), Pd(dppf)Cl$_2$ (107 mg, 148 umol) and potassium acetate (409.2 mg, 5.9 mmol) were dissolved in 20 mL of 1,4-dioxane, heated to 80° C. and stirred for 16 h. 60 mL of water was added to the reaction liquid and the mixture was extracted with ethyl acetate (20 mL×3). The combined organic phase was dried over anhydrous sodium sulfate, concentrated and isolated by column chromatography (developing solvent:petroleum ether/ethyl acetate=100/1-10/1) to give 1-(4-chlorophenyl)-4-dimethylamino-1-(2-methoxy-5-boronic acid pinacol ester)pyridin-3-yl)-2-(naphthalen-1-yl)butan-2-ol (1.4 g, 80.5% yield) as a yellow oil. LCMS (ESI) m/z: 587.3 (M+1).

Step 2: 1-(5-(4-bromophenyl)-2-methoxypyridin-3-yl)-1-(4-chlorophenyl)-4-dimethylamino-2-(naphthalen-1-yl)butan-2-ol

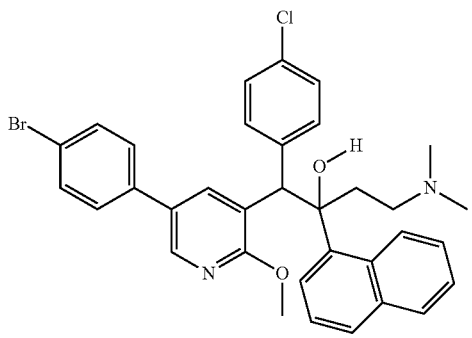

Compound 323 (A1)
Compound 324 (A2)
Compound 325 (B1)
Compound 326 (B2)

Under nitrogen, 1-(4-chlorophenyl)-4-dimethylamino-1-(2-methoxy-5-boronic acid pinacol ester)pyridin-3-yl)-2-(naphthalen-1-yl)butan-2-ol (1.4 g, 2.39 mmol), 1,4-dibromobenzene (0.675 g, 2.86 mmol), potassium carbonate (659 mg, 4.77 mmol) and Pd(dppf)Cl$_2$ (86 mg, 0.119 mmol) were dissolved in 20 mL of 1,4-dioxane and 4 mL of water, heated to 80° C. and stirred for 16 h. The reaction liquid was poured into 60 mL of water and extracted with ethyl acetate (30 mL×3). The combined organic phase was dried over anhydrous sodium sulfate, concentrated and isolated by column chromatography (developing solvent:petroleum ether/ethyl acetate=50/1-5/1) to give component A and component B. Component A was separated by chiral SFC (sfc 80, IC-10 um; supercritical CO$_2$/MeOH (0.05% aqueous ammonia) =50/50; 70 ml/min; 220 nm) to give compound 323 (A1) (48.40 mg, 3.29% yield) and compound 324 (A2) (50.10 mg, 3.41% yield). Component B was separated by chiral SFC (sfc 80, AD-10 um; supercritical CO$_2$/EtOH (0.05% aqueous ammonia)—70/30; 60 ml/min; 220 nm) to give compound 325 (B1) (10.90 mg, 0.74% yield) and compound 326 (B2) (24.70 mg, 1.68% yield). Compound 323 (A1)/compound 324 (A2): $^1$H NMR (400 MHz, CDCl$_3$): δ 8.47 (d, J=2.01 Hz, 1H), 8.42 (d, J=8.66 Hz, 1H), 8.25 (br. s., 1H), 8.14 (d, J=7.28 Hz, 1H), 7.87-7.81 (m, 2H), 7.76 (d, J=8.41 Hz, 2H), 7.65 (d, J=8.16 Hz, 1H), 7.53-7.60 (m, 3H), 7.48-7.44 (m, 1H), 7.38-7.34 (m, 3H), 7.29 (m, 2H), 5.59 (s, 1H) 3.30 (s, 3H), 2.72-2.62 (m, 1H), 2.55-2.46 (m, 1H) 2.32-2.26 (m, 1H), 2.19 (s, 6H) 2.04-1.97 (m, 1H). Compound 325 (B1)/compound 326 (B2): $^1$H NMR (400 MHz, CDCl$_3$): δ 8.71 (br. s., 1H), 8.58 (d, J=9.03 Hz, 1H), 8.32 (d, J=2.26 Hz, 1H), 7.92 (dd, J=17.07, 7.78 Hz, 2H), 7.70 (d, J=7.91 Hz, 1H), 7.61 (d, J=8.53 Hz, 3H), 7.53-7.47 (m, 3H), 7.35 (t, J=7.72 Hz, 1H), 7.13 (d, J=8.41 Hz, 2H), 6.87 (d, J=8.41 Hz, 2H), 5.81 (s, 1H), 4.16 (s, 3H), 2.57 (m, 1H), 2.12 (m, 2H), 2.05 (s, 6H), 2.01-1.95 (m, 1H). LCMS (ESI) m/z: 617.1 (M+1).

Example 102

4-(dimethylamino)-1-(2-methoxy-5-(p-tolyl)pyridin-3-yl)-2-(naphthalen-1-yl)-1-phenylbutan-2-ol

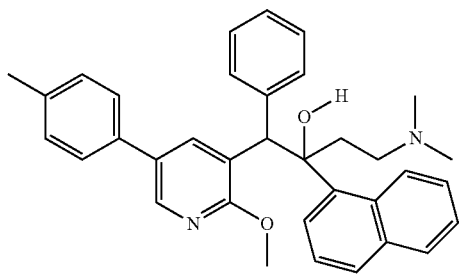

Compound 371 (A1)
Compound 372 (A2)
Compound 373 (B1)
Compound 374 (B2)

Intermediate A (1.50 g, 2.97 mmol), p-tolylboronic acid (485 mg, 3.56 mmol), potassium acetate (583 mg, 5.94 mmol) and Pd(dppf)Cl$_2$ (109 mg, 148.97 mmol) were dissolved in the mixed solvent of 1,4-dioxane/H$_2$O (16 mL×4 mL) and purged with nitrogen three times. Then the mixture was heated to 80° C. and reacted under nitrogen for 16 h. The reaction mixture was poured into water (30 mL) and the mixture was extracted with ethyl acetate (30 mL×3). The combined organic phase was dried over anhydrous sodium sulfate, and concentrated in vacuo to give a residue which was purified by silica gel column chromatography (developing solvent:petroleum ether/ethyl acetate=30/1-5/1) and then purified by preparative HPLC (GX-G; Phenomenex Synergi C18 150*30 mm*4 um; acetonitrile 30%-60%; water (0.225% formic acid); 25 mL/min); 25 mL/minutes) to give component A and component B. Component A was separated by chiral SFC (Chiralpak IC 250×30 mm I.D., 10 um; supercritical CO$_2$/MeOH (0.1% NH$_3$.H$_2$O)=50/50; 70 g/min; 220 nm) to give compound 371 (A1) (95.16 mg, 6.20% yield) and compound 372 (A2) (124.42 mg, 8.11% yield) as white solid. Component B was separated by chiral SFC (Chiralpak IC 250×30 mm I.D., 10 um; supercritical CO$_2$/EtOH (0.1% NH$_3$.H$_2$O)—60/40; 70 g/min; 220 nm) to give compound 373 (B1) (73.94 mg, 4.82% yield) and compound 374 (B2) (86.76 mg, 5.65% yield) as white solid. Compound 371 (A1)/compound 372 (A2): $^1$H NMR (400 MHz, CDCl$_3$) δ: 8.92-8.71 (m, 1H), 8.68-8.55 (m, 1H), 8.36-8.28 (m, 1H), 7.96-7.79 (m, 2H), 7.72-7.58 (m, 2H), 7.56-7.46 (m, 3H), 7.35-7.27 (m, 3H), 7.17-7.08 (m, 2H), 6.92-6.85 (m, 3H), 5.86-5.80 (m, 1H), 4.14 (s, 3H), 2.64-2.55 (m, 1H), 2.42 (s, 3H), 2.06 (br. s., 9H). Compound 373 (B1)/compound 374 (B2): $^1$H NMR (400 MHz, CDCl$_3$) δ: 8.50-8.44 (m, 1H), 8.43-8.34 (m, 1H), 8.11-8.04 (m, 1H), 7.92-7.74 (m, 4H), 7.65-7.55 (m, 2H), 7.48-7.34 (m, 4H), 7.30 (br. s., 3H), 7.25-7.18 (m, 1H), 5.63 (s, 1H), 3.38-3.23 (m, 3H), 2.74-2.65 (m, 1H), 2.39 (s, 6H), 2.29-2.11 (m, 6H). LCMS (ESI) m/z: 517.3 (M+1).

Example 103

4-(dimethylamino)-1 (2-methoxy-5-(4-(trifluoromethoxy)phenyl)pyridin-3-yl)-2-(naphthalen-1-yl)-1-phenylbutan-2-ol

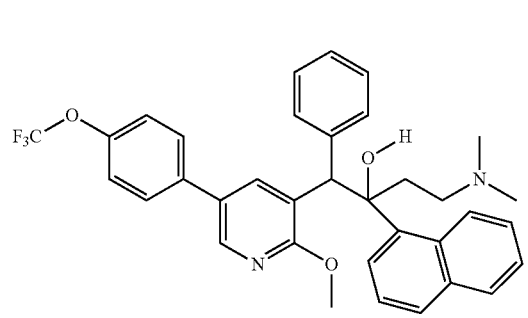

Compound 375 (A1)
Compound 376 (A2)
Compound 377 (B1)
Compound 378 (B2)

According to the method of Example 102, the title compound was prepared from intermediate A and (4-(trifluoromethoxy)phenyl)boronic acid. The crude product was purified by silica gel column chromatography (developing solvent:petroleum ether/ethyl acetate=30/1-5/1), and separated and purified by preparative HPLC (GX-G; Phenomenex Synergi C18 150*30 mm*4 um; acetonitrile 30%-60%; water (0.225% formic acid); 25 mL/min) to give component A and component B. Component A was separated by chiral SFC (Chiralpak IC 250×30 mm I.D., 10 um; supercritical CO$_2$/MeOH (0.1% NH$_3$.H$_2$O)=70/30; 60 g/min; 220 nm) to give compound 375 (A1) (80.17 mg, 4.60% yield) and compound 376 (A2) (64.19 mg, 3.68% yield) as white solid. Component B was separated by chiral SFC (Chiralpak IC 250×30 mm I.D., 10 um; supercritical CO$_2$/MeOH (0.1% NH$_3$.H$_2$O)=65/35; 70 g/min; 220 nm) to give compound 377 (B1) (121.62 mg, 6.98% yield) and compound 378 (12) (115.28 mg, 6.62% yield) as while solid. Compound 375 (A1)/compound 376 (A2): $^1$H NMR (400 MHz, CDCl$_3$) δ: 8.83-8.77 (m, 1H), 8.66-8.59 (m, 1H), 8.35-8.27 (m, 1H), 7.97-7.85 (m, 2H), 7.68-7.60 (m, 4H), 7.52-7.47 (m, 1H), 7.35-7.30 (m, 3H), 7.18 (d, J=3.3 Hz, 2H), 6.93-6.88 (m, 3H), 5.87-5.82 (m, 1H), 4.17 (s, 3H), 2.62-2.53 (m, 1H), 2.11 (d, J=10.3 Hz, 2H), 2.03 (s, 7H); compound 377 (B1)/compound 378 (B2): $^1$H NMR (400 MHz, CDCl$_3$) δ: 8.52-8.38 (m, 2H), 8.10-8.04 (m, 1H), 7.86-7.76 (m, 4H), 7.64 (d, J=8.0 Hz, 1H), 7.57 (s, 1H), 7.48-7.28 (m, 8H), 7.25 (br. s., 1H), 5.64 (s, 1H), 3.27 (s, 3H), 2.66-2.53 (m, 1H), 2.37-2.24 (m, 2H), 2.11 (br. s., 7H); LCMS (ESI) m/z: 587.2 (M+1).

Example 104

1-5-(4-chloro-3-methoxyphenyl)-2-methoxypyridin-3-yl)-4-(dimethylamino)-2-(naphthalen-1-yl)-1-phenylbutan-2-ol

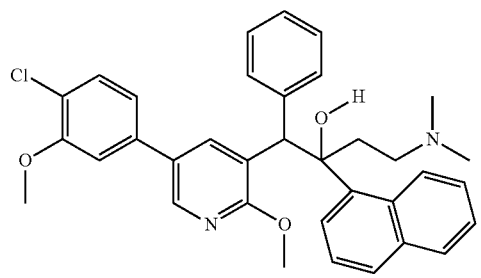

Compound 379 (A1)
Compound 380 (A2)
Compound 381 (B1)
Compound 382 (B2)

According to the method of Example 102, the title compound was prepared from intermediate A and (4-chloro-3-methoxyphenyl)boronic acid. The crude product was separated and purified by silica gel column chromatography (developing solvent:petroleum ether/ethyl acetate=30/1-5/1) and preparative HPLC (GX-G; Phenomenex Synergi C18 150*30 mm*4 um; acetonitrile 30%-60%; water (0.225% formic acid); 25 mL/min) to give component A and component B. Component A was separated by chiral SFC (Chiralpak IC 250×30 mm I.D., 10 um; supercritical $CO_2$/MeOH (0.1% $NH_3.H_2O$)=55/45; 70 g/min; 220 nm) to give compound 379 (A1) (15.06 mg, 2.13% yield) and compound 380 (A2) (23.37 mg, 3.31% yield) as white solid. Component B was separated by chiral SFC (Chiralpak IC 250×30 mm I.D., 10 um; supercritical $CO_2$/MeOH (0.1% $NH_3.H_2O$)=40/60; 70 g/min; 220 nm) to give compound 381 (B1) (14.96 mg, 2.12% yield) and compound 382 (B2) (24.83 mg, 3.51% yield) as white solid. Compound 379 (A1)/compound 380 (A2): $^1$H NMR (400 MHz, $CDCl_3$) δ: 8.76-8.69 (m, 1H), 8.68-8.63 (m, 1H), 8.25-8.20 (m, 1H), 7.93-7.84 (m, 2H), 7.68-7.58 (m, 2H), 7.52-7.45 (m, 1H), 7.33-7.28 (m, 2H), 7.17 (br. s., 2H), 7.07-7.03 (m, 1H), 6.99 (s, 1H), 6.92-6.88 (m, 3H), 5.83 (s, 1H), 4.15 (s, 3H), 3.81 (s, 3H), 2.58-2.51 (m, 1H), 1.98 (s, 9H); compound 381 (B1)/compound 382 (B2): $^1$H NMR (400 MHz, $CDCl_3$) δ: 8.55-8.48 (m, 1H), 8.46-8.41 (m, 1H), 8.06-8.00 (m, 1H), 7.83 (s, 4H), 7.67-7.63 (m, 1H), 7.61-7.55 (m, 1H), 7.49-7.43 (m, 1H), 7.41-7.30 (m, 4H), 7.15-7.08 (m, 1H), 7.04-6.99 (m, 1H), 6.96-6.91 (m, 1H), 5.65 (s, 1H), 3.78 (s, 3H), 3.18 (s, 3H), 2.58-2.51 (m, 1H), 2.03 (br. s., 9H); LCMS (ESI) m/z: 567.2 (M+1).

Example 105

2-(2-bromophenyl)-1-(5-(4-chlorophenyl)-2-methoxypyridin-3-yl)-4-(dimethylamino)-1-phenylbutan-2-ol

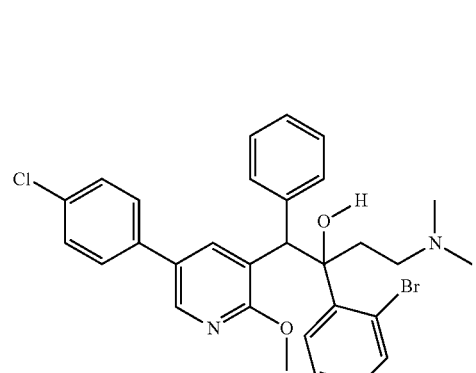

Compound 383 (A1)
Compound 384 (A2)
Compound 385 (B1)

Step 1:
1-(2-bromophenyl)-3-(dimethylamino)propan-1-one

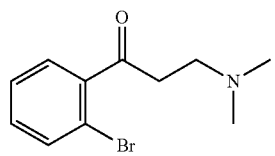

Under nitrogen, paraformaldehyde (2.94 g, 32.66 mmol) and concentrated hydrochloric acid (12 M, 0.1 mL) were added in one portion to the mixture of 1-(2-bromophenyl)ethanone (5.00, 25.12 mmol) and dimethylamine hydrochloride (8.19 g, 100.48 mmol) in EtOH (100 mL) at 20° C. The mixture was warmed to 80-90° C. and stirred for 16 h. Then the reaction mixture was concentrated in vacuo and the residue was dissolved in water and extracted with dichloromethane (15 mL×3). The aqueous phase was basified with sodium carbonate to pH 10 and then extracted with dichloromethane/methanol (10:1, 30 mL×3). The organic phases obtained in the second extraction were combined and washed with saturated brine, dried over anhydrous sodium sulfate, filtered and concentrated in vacuo to give 1-(2-bromophenyl)-3-(dimethylamino)propan-1-one (1.60 g, 24.87%) as a yellow oil. LCMS (ESI) m/z: 256.1/258.1 (M+1).

Step 2: 2-(2-bromophenyl)-1-(5-(4-chlorophenyl)-2-methoxypyridin-3-yl)-4-(dimethylamino)-1-phenylbutan-2-ol

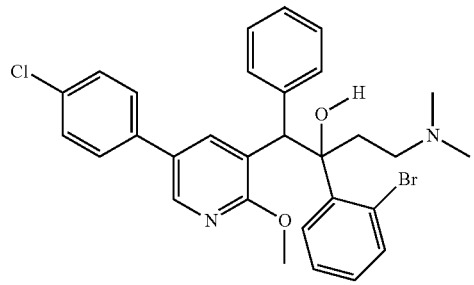

Compound 383 (A1)
Compound 384 (A2)
Compound 385 (B1)

Cooled in dry ice bath, n-butyllithium (2.5 M, 5.81 mL, 14.53 mmol) was added dropwise to diisopropylamine (1.49 g, 14.76 mmol) in THF (20 mL) under nitrogen. The reaction mixture was stirred at −78° C. for 1.5 h. Then a solution of 3-benzyl-5-(4-chlorophenyl)-2-methoxypyridine (1.50 g, 4.84 mmol) in THF (10 mL) was added dropwise to the reaction liquid at −78° C. under nitrogen over 5 minutes. The mixture was stirred at −78° C. for 1.5 h. Then a solution of 1-(2-bromophenyl)-3-(dimethylamino)propan-1-one (1.24 g, 4.84 mmol) in THF (10 mL) was added dropwise to the reaction liquid at −78° C. over 10 minutes. The final reaction mixture was stirred at −78° C. for another 1.5 h. The reaction was quenched with saturated aqueous ammonium chloride solution (40 mL) and the mixture was extracted with ethyl acetate (20 mL×3). The combined organic layers were dried over sodium sulfate and concentrated in vacuo. The residue was purified by silica gel column chromatography (developing solvent:petroleum ether/ethyl acetate=20:1-5:1) to give component A and component B. Component A was separated by chiral SFC (sfc-80; AD-10 um; supercritical CO$_2$/EtOH(0.1% NH$_3$.H$_2$O)=70/30; 60 g/min; 220 nm) to give compound (A1) (13.10 mg, 0.48%) and compound 384 (A2) (17.80 mg, 0.65%) as white solid. Component B was separated by chiral SFC (sfc-80; IC-10 um; supercritical CO$_2$/MeOH (0.1% NH$_3$.H$_2$O)=60/40/70 g/min; 220 nm) to give compound 385 (B1) (27.60 mg, 1.01%) as white solid. Compound (A1)/compound 384 (A2): $^1$H NMR (400 MHz, CDCl$_3$) δ: 8.51 (s, 1H), 8.29 (s, 1H), 8.02-7.94 (m, 2H), 7.75 (d, J=7.5 Hz, 2H), 7.50 (d, J=8.0 Hz, 1H), 7.40 (s, 4H), 7.37-7.31 (m, 2H), 7.28-7.22 (m, 1H), 7.18 (t, J=7.4 Hz, 1H), 6.97 (t, J=7.5 Hz, 1H), 5.70 (s, 1H), 3.73 (s, 3H), 2.95-2.84 (m, 1H), 2.45-2.32 (m, 1H), 2.13-2.08 (m, 7H), 1.99-1.88 (m, 1H); compound 385 (B1): $^1$H NMR (400 MHz, CDCl$_3$) δ: 8.72 (d, J=2.3 Hz, 1H), 8.26 (d, J=2.5 Hz, 1H), 8.17 (s, 1H), 7.87 (d, J=7.9 Hz, 1H), 7.57-7.49 (m, 3H), 7.47-7.38 (m, 4H), 7.14 (t, J=7.1 Hz, 1H), 7.08-6.93 (m, 4H), 5.92 (s, 1H), 4.07 (s, 3H), 2.98-2.89 (m, 1H), 2.45-2.32 (m, 1H), 2.15-2.10 (m, 7H), 1.93-1.89 (m, 1H).

Example 106

2-(3-bromophenyl)-1-(5-(4-chlorothen)-2-methoxypyridin-3-yl)-4-(dimethylamino)-1-phenylbutan-2-ol

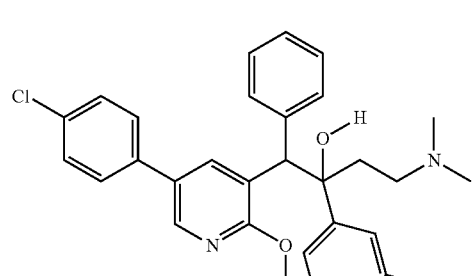

Compound 386 (A1)
Compound 387 (A2)
Compound 388 (B1)
Compound 389 (B2)

Step 1: 1-(3-bromophenyl)-3-(dimethylamino)propan-1-one

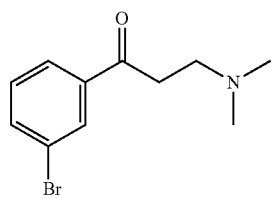

According to the method of step 1 in Example 105, the product was prepared from 1-(3-bromophenyl)ethanone. Yield: 62.2%. LCMS (ESI) m/z: 256.1/258.1 (M+1).

Step 2: 2-(3-bromophenyl)-1-(5-(4-chlorophenyl)-2-methoxypyridin-3-yl)-4-(dimethylamino)-1-phenylbutan-2-ol

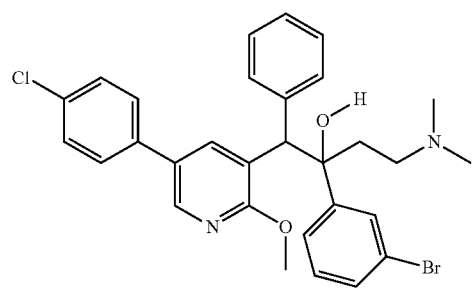

Compound 386 (A1)
Compound 387 (A2)
Compound 388 (B1)
Compound 389 (B2)

According to the method of step 2 in Example 105, 3-benzyl-5-(4-chlorophenyl)-2-methoxypyridine (1.50 g, 4.84 mmol) and 1-(3-bromophenyl)-3-(dimethylamino)propan-1-one were used to prepare crude product which was separated by silica gel column chromatography (developing solvent:petroleum ether/ethyl acetate=20/1-5/1) to give component A and component B. Component A was separated by chiral SFC (sfc-80; AD-10 um; supercritical CO$_2$/EtOH (0.1% NH$_3$.H$_2$O)=70/30; 60 g/min; 220 nm) to give compound (A1) (68.92 mg, 2.52% yield) and compound 387 (A2) (75.43 mg, 2.75%) as white solid. Component B was separated by chiral SFC (sfc-80; IC-10 um; supercritical CO$_2$/EtOH (0.1% NH$_3$.H$_2$O)=60/40; 70 g/min; 220 nm) to give compound 388 (B1) (27.47 mg, 1.00% yield) and compound 389 (B2) (30.04 mg, 1.10% yield) as white solid. Compound (A1)/compound 387 (A2): $^1$H NMR (400 MHz, CDCl$_3$) δ: 8.54 (d, J=2.5 Hz, 1H), 8.13 (s, 1H), 7.98 (d, J=2.5 Hz, 1H), 7.79 (br. s., 1H), 7.69 (d, J=7.2 Hz, 2H), 7.45-7.29 (m, 7H), 7.28-7.22 (m, 2H), 7.12-7.05 (m, 1H), 4.72 (s, 1H), 3.79 (s, 3H), 2.48-2.42 (m, 1H), 2.17-2.04 (m, 8H), 1.80-1.73 (m, 1H); compound 388 (B1)/compound 389 (B2): $^1$H NMR (400 MHz, CDCl$_3$) δ: 8.62 (s, 1H), 8.26 (s, 1H), 8.05 (s, 1H), 7.64 (s, 1H), 7.53 (d, J=8.2 Hz, 2H), 7.47-7.36 (m, 3H), 7.33 (d, J=7.4 Hz, 2H), 7.26 (d, J=7.8 Hz, 1H), 7.15-6.97 (m, 4H), 4.84 (s, 1H), 4.07 (s, 3H), 2.55-2.41 (m, 1H), 2.17-2.06 (m, 8H), 1.92-1.83 (m, 1H); LCMS (ESI) m/z: 565.2/567.1 (M+1).

Example 107

2-(4-bromophenyl)-1-(5-(4-chlorophenyl)-2-methoxypyridin-3-yl)-4-(dimethylamino)-1-phenylbutan-2-ol

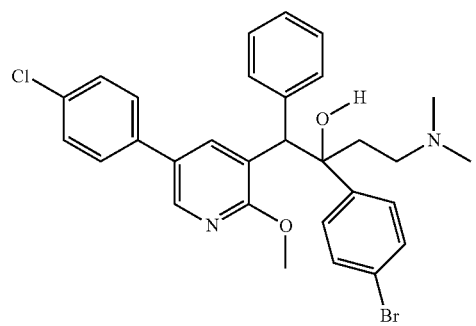

Compound 390 (A1)
Compound 391 (A2)
Compound 392 (B1)
Compound 393 (B2)

Step 1:
1-(4-bromophenyl)-3-(dimethylamino)propan-1-one

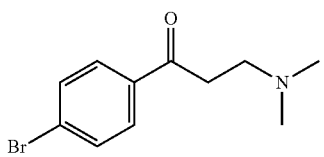

According to the method of step 1 in Example 105, the product was prepared from 1-(4-bromophenyl)ethanone. Yield: 37.3%.

Step 2: 2-(4-bromophenyl)-1-(5-(4-chlorophenyl)-2-methoxypyridin-3-yl)-4-(dimethylamino)-1-phenylbutan-2-ol

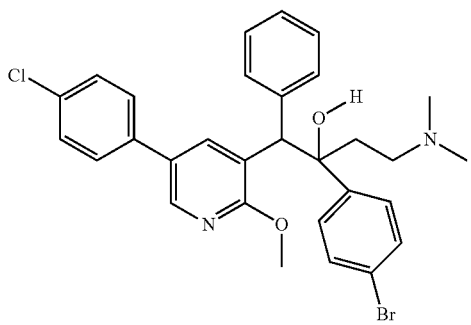

Compound 390 (A1)
Compound 391 (A2)
Compound 392 (B1)
Compound 393 (B2)

According to the method of step 2 in Example 105, 3-benzyl-5-(4-chlorophenyl)-2-methoxypyridine (1.0 g, 3.23 mmol) and 1-(4-bromophenyl)-3-(dimethylamino)propan-1-one were used to prepare crude product which was separated by silica gel column chromatography (developing solvent:petroleum ether/ethyl acetate=100/1-10/1-1/1) to give component A and component B. Component A was separated by chiral SFC (Chiralpak IC 250×30 mm I.D., 10 um; supercritical CO$_2$/EtOH (0.1% NH$_3$.H$_2$O)=70/30; 65 g/min; 220 nm) to give compound 390 (A1) (81.52 mg, 7.41% yield) and compound 391 (A2) (51.96 mg, 4.72% yield) as white solid. Component A was separated by chiral SFC (Chiralpak IC 250×30 mm A.D., 10 um; supercritical CO$_2$/EtOH (0.1% NH$_3$.H$_2$O)=60/40; 70 g/min; 220 nm) to give compound 392 (B1) (42.66 mg, 3.88% yield) and compound 393 (B2) (44.17 mg, 4.02% yield) as white solid. Compound 390 (A1)/compound 391 (A2): $^1$H NMR (400 MHz, CDCl$_3$) δ: 8.74-8.68 (m, 1H), 8.26-8.22 (m, 1H), 7.52-7.47 (m, 2H), 7.44-7.39 (m, 2H), 7.34 (s, 4H), 7.29 (s, 2H), 7.06-6.98 (m, 3H), 4.81 (s, 1H), 4.74-4.67 (m, 1H), 4.04 (s, 3H), 2.29-2.22 (m, 1H), 2.04 (s, 8H), 1.77-1.73 (m, 1H); compound 392 (B1)/compound 393 (B2): $^1$H NMR (400 MHz, CDCl$_3$) δ: 8.57-8.53 (m, 1H), 8.01-7.95 (m, 1H), 7.71 (d, J=7.5 Hz, 2H), 7.39 (s, 6H), 7.35-7.29 (m, 4H), 7.26-7.21 (m, 1H), 4.85-4.73 (m, 1H), 4.70 (s, 1H), 3.75 (s, 3H), 2.28-2.20 (m, 1H), 2.10-2.00 (m, 8H), 1.74-1.69 (m, 1H); LCMS (ESI) m/z: 565.2/567.1 (M+1).

Example 108

1-(5-(4-chlorophenyl)-2-methoxypyridin-3-yl)-2-(3,5-dichlorophenyl)-1-(2,3-dimethoxyphenyl)-4-(dimethylamino)butan-2-ol

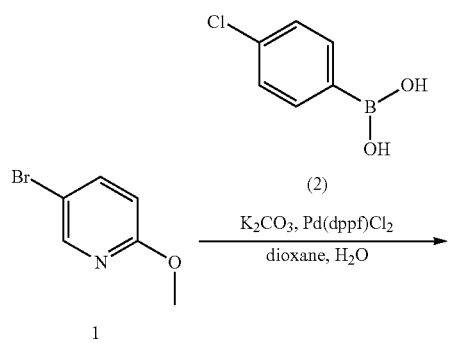

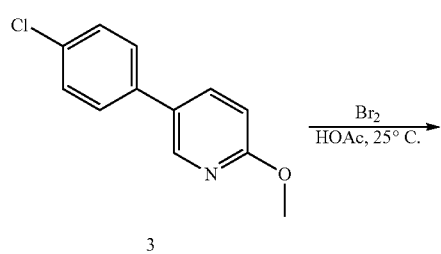

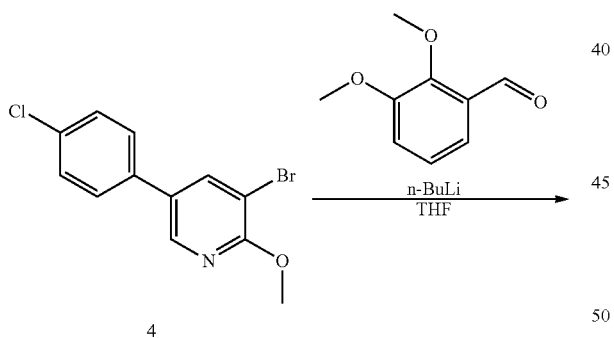

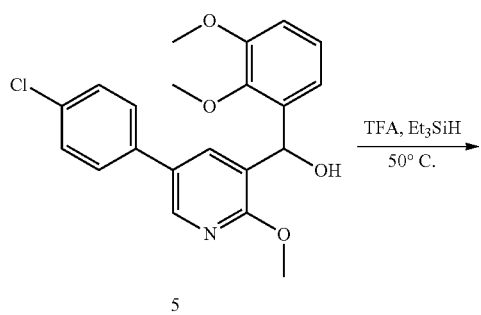

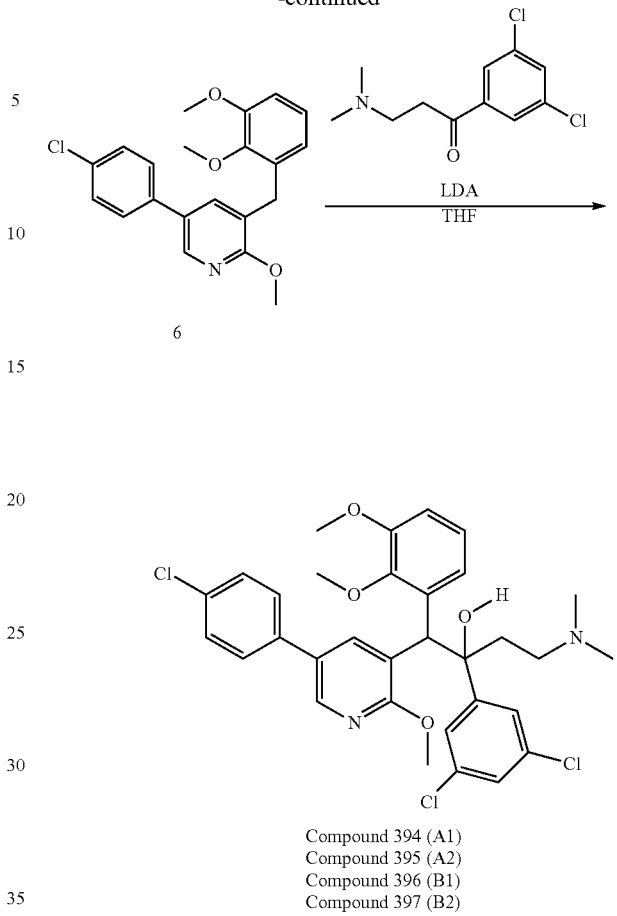

Compound 394 (A1)
Compound 395 (A2)
Compound 396 (B1)
Compound 397 (B2)

Step 1: 5-(4-chloro phenyl)-2-methoxypyridine

Under nitrogen, potassium carbonate (11.03 g, 79.78 mmol) and Pd(dppf)Cl$_2$ (3.88 g, 5.31 mmol) were added in sequence to the solution of 5-bromo-2-methoxypyridine (10.00 g, 53.19 mmol) and (4-chlorophenyl) boronic acid (9.15 g, 58.5 mmol) in 1,4-dioxane/water (50 mL×10 mL). The reaction mixture was heated to 90-95° C. and stirred for 4 h, then cooled to 25° C. and concentrated under reduced pressure. The residue was extracted with ethyl acetate (100 mL×2). The combined organic phase was washed with saturated brine (100 mL), dried over anhydrous sodium sulfate and concentrated under reduced pressure to give 5-(4-chlorophenyl)-2-methoxypyridine (13 g. crude product) as a dark brown solid (after cooled). The crude product was used directly without further purification in the next step.

Step 2: 3-bromo-5-(4-chlorophenyl)-2-methoxy

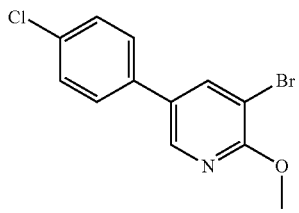 [SMILES: COc1ncc(-c2ccc(Cl)cc2)cc1Br]

Bromine (21.83 g, 136.57 mmol) was dissolved in acetic acid (50 mL) and added slowly to the solution of 5-(4-chlorophenyl)-2-methoxypyridine (12.00 g, 54.63 mmol) in DMF (50 mL) at 25° C. under nitrogen over 4 h. The mixture was stirred at 25° C. for 24 h. The reaction solution was poured into aqueous sodium bisulfite solution (0.4 M, 1 L) and a large amount of solid was separated out. The precipitate was filtered and washed with water (100 mL×2) and MeOH (100 mL), filtered and dried to give 3-bromo-5-(4-chlorophenyl)-2-methoxypyridine (11.00 g, 67.44% yield) as white solid. The crude product was used directly in the next step without purification.

Step 3: (5-(4-chlorophenyl)-2-methoxypyridin-3-yl) (2,3-dimethoxyphenyl)methanol

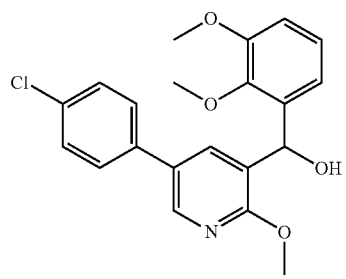 [SMILES: COc1cccc(C(O)c2cc(-c3ccc(Cl)cc3)cnc2OC)c1OC]

Under nitrogen, n-butyllithium (2.5 M, 8.71 mL, 21.77 mmol) was added to the solution of 3-bromo-5-(4-chlorophenyl)-2-methoxypyridine (5.00 g, 16.75 mmol) in THF (60 mL) at −78° C. The mixture was stirred at this temperature for 1 hour. Then the solution of 2,3-dimethoxybenzaldehyde (3.34 g, 20.10 mmol) in THF (60 mL) was added to the mixture. The resulted mixture was stirred at −70--60° C. for another 1 hour. The reaction was quenched with saturated aqueous ammonium chloride solution (20 mL) and the mixture was poured into water (50 mL). The aqueous phase was extracted with ethyl acetate (40 mL×3). The combined organic phase was dried over anhydrous sodium sulfate, filtered and concentrated in vacuo to give a residue which was purified by silica gel column chromatography (developing solvent:petroleum ether/ethyl acetate=100:1, 10/1-1/1) to give [5-(4-chlorophenyl)-2-methoxy-3-pyridyl]-(2,3-dimethoxyphenyl)methanol (2.92 g, 45.2% yield) as yellow solid.

Step 4: 5-(4-chlorophenyl)-3-(2,3-dimethoxybenzyl)-2-methoxypyridine

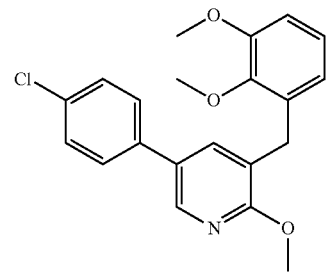 [SMILES: COc1cccc(Cc2cc(-c3ccc(Cl)cc3)cnc2OC)c1OC]

[5-(4-chlorophenyl)-2-methoxy-3-pyridyl]-(2,3-dimethoxyphenyl)methanol (2.70 g, 7.00 mmol) was dissolved in trifluoroacetic acid (0.8 g, 7.0 mmol) and triethylsilane (5.11 g, 43.95 mmol) was added slowly at 25° C. The mixture was heated to 60° C., stirred for 5 h, and then concentrated in vacuo to give a residue which was poured into saturated aqueous sodium carbonate (30 mL) and stirred at 25° C. for 10 minutes. The mixture was extracted with ethyl acetate (30 mL×2). The combined organic phase was dried over anhydrous sodium sulfate, filtered and concentrated in vacuo to give a residue which was purified by silica gel column chromatography (developing solvent:petroleum ether/ethyl acetate=100/1-50/1) to give 5-(4-chlorophenyl)-3-[(2,3-dimethoxyphenyl)methyl]-2-methoxypyridine (850.00 mg, 32.83% yield) as yellow solid.

Step 5: 1-(5-(4-chlorophenyl)-2-methoxypyridin-3-yl)-2-(3,5-dichlorophenyl)-1-(2,3-dimethoxyphenyl)-4-(dimethylamino)butan-2-ol

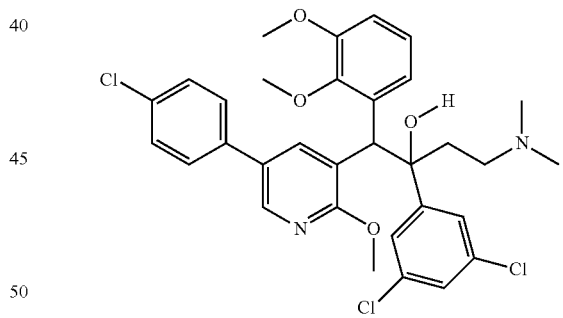

Compound 394 (A1)
Compound 395 (A2)
Compound 396 (B1)
Compound 397 (B2)

Under nitrogen, n-butyllithium (2.5 M in hexane, 1.84 mL, 4.60 mmol) was added slowly dropwise to diisopropylamine (465.47 mg, 4.60 mmol) solution in THF(5 mL). The mixture was stirred at −78° C. for 1 hour. Then the solution of 5-(4-chlorophenyl)-3-[(2,3-dimethoxyphenyl) methyl]-2-methoxy-pyridine (850.00 ing, 2.30 mmol) in THF (15.00 mL) was added slowly. The mixture was stirred at −60--70° C. for another 1 hour. Then the solution of 1-(3,5-dichlorophenyl)-3-(dimethylamino)propan-1-one (679.32 mg, 2.76 mmol) in THF (15.00 mL) was slowly added dropwise. The final mixture was stirred at −60--70°

C. for 1 hour. The reaction was quenched with saturated aqueous ammonium chloride solution (10 mL) and then the mixture was poured into water (30 mL) and extracted with EtOAc (30 mL×3). The combined organic phase was dried over anhydrous sodium sulfate, filtered, and concentrated under reduced pressure to give a residue which was purified by silica gel column chromatography (developing solvent: petroleum ether/ethyl acetate:50/1-10/1) and preparative HPLC (GX-G: Phenomenex Synergi C18 150*30 mm*4 um; acetonitrile 30%-60%; water (0.225% formic acid): 25 mL/min) to give component A and component B. Component A was separated by chiral SFC (Chiralpak AD 250×30 mm I.D., 10 um; supercritical $CO_2$/EtOH (0.1% $NH_3.H_2O$) =70/30; 60 g/min; 220 nm) to give compound 394 (A1) (83.86 mg, 5.80% yield) and compound 395 (A2) (85.70 mg, 5.94% yield) as white solid. Component B was separated by chiral SFC (Chiralpak IC 250×30 mm I.D., 10 um; supercritical $CO_2$/EtOH (0.1% $NH_3$—$H_2O$)=50/50; 70 g/min; 220 nm) to give compound 396 (B1) (30.46 mg, 1.97% yield) and compound 397 (B2) (68.76 mg, 4.80% yield) as white solid. Compound 394 (A1)/compound 395 (A2): $^1$H NMR (400 MHz, $CDCl_3$) δ: 8.23 (s, 1H), 8.19-8.15 (m, 1H), 7.60-7.53 (m, 1H), 7.41 (d, J=12.0 Hz, 6H), 7.12-7.07 (m, 1H), 6.88-6.81 (m, 1H), 6.65-6.59 (m, 1H), 5.50-5.46 (m, 1H), 4.13 (s, 3H), 3.72 (s, 3H), 3.59 (s, 3H), 2.43-2.36 (m, 1H), 2.19-2.07 (m, 8H), 1.99 (br. s, 1H); compound 396 (B1)/compound 397 (B2): $^1$H NMR (400 MHz, $CDCl_3$) δ: 8.53 (d, J=2.3 Hz, 1H), 8.01 (d, J=2.5 Hz, 1H), 7.54-7.34 (m, 7H), 7.10 (s, 1H), 7.01 (t, J=8.2 Hz, 1H), 6.83 (d, J=7.5 Hz, 1H), 5.42-5.40 (m, 1H), 3.98 (s, 3H), 3.90 (s, 3H), 3.80 (s, 3H), 2.24-2.18 (m, 1H), 2.07-1.97 (m, 8H), 1.73 (d, J=14.1 Hz, 1H). LCMS (ESI) m/z: 615.2 (M+1).

Example 109

2-(3-chlorphenyl)-1-5-(4-chlorophenyl)-2-methoxypyridin-3-yl)-1-(2,3-dimethoxyphenyl)-4-(dimethylamino) butan-2-ol

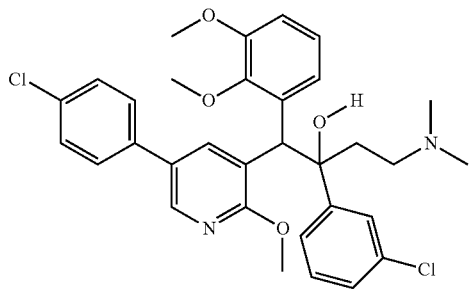

Compound 398 (A1)
Compound 399 (A2)
Compound 400 (B2)

According to the method of step 5 in Example 108, 5-(4-chlorophenyl)-3-[(2,3-dimethoxyphenyl)methyl]-2-methoxypyridine (610.00 mg, 1.65 mmol) and 1-(3-chlorophenyl)-3-(dimethylamino)propan-1-one (419.15 mg, 1.98 mmol) were used to prepare crude product which was purified by preparative HPLC (GX-D; Boston Symmetrix C18 ODS-R 150*30 mm*5 um; acetonitrile 30%-60%; water (0.225% formic acid); 25 mL/min) to give component A and component B. Component A was separated by chiral SFC (Chiralpak AD 250×30 mm I.D., 10 um; supercritical $CO_2$/EtOH (0.1% $NH_3.H_2O$)=70/30; 60 g/min; 220 nm) to give compound 398 (A1) (14.10 mg, 1.46% yield) and compound 399 (A2) (15.22 mg, 1.59% yield) as white solid. Component B was separated by chiral SFC (Chiralpak AD 250×30 mm I.D., 5 um; supercritical $CO_2$/EtOH (0.1% $NH_3.H_2O$)=70/30; 60 g/min; 220 nm) to give compound 400 (B2) (25.90 mg, 2.67% yield) as white solid. Compound 398 (A1)/compound 399 (A2): $^1$H NMR (400 MHz, $CDCl_3$) δ: 8.27-8.18 (m, 2H), 8.03-7.99 (m, 1H), 7.70-7.64 (m, 1H), 7.62-7.56 (m, 1H), 7.51-7.35 (m, 5H), 7.20-7.14 (m, 1H), 7.10-7.05 (m, 1H), 6.83 (s, 1H), 6.63-6.57 (m, 1H), 5.60-5.55 (m, 1H), 4.15 (s, 3H), 3.71 (s, 3H), 3.59 (s, 3H), 2.42-2.33 (m, 2H), 2.15-2.06 (m, 7H), 2.04-2.01 (m, 1H); compound 400 (B2): $^1$H NMR (400 MHz, $CDCl_3$) δ: 8.62-8.57 (m, 1H), 7.98 (d, J=2.3 Hz, 1H), 7.68-7.57 (m, 1H), 7.43-7.35 (m, 6H), 7.17-7.11 (m, 1H), 7.09-7.04 (m, 1H), 7.03-6.98 (m, 1H), 6.84-6.80 (m, 1H), 5.46-5.42 (m, 1H), 4.01 (s, 3H), 3.91 (s, 3H), 3.77 (s, 3H), 2.25-2.19 (m, 1H), 2.00 (s, 7H), 1.80 (br. s., 2H). LCMS (ESI) m/z: 581.2 (M+1).

Example 110

1-(5-(4-chlorophenyl)-2,6-dimethoxypyridin-3-yl)-4-(dimethylamino)-2-(naphthalen-1-yl)-1-phenylbutan-2-ol

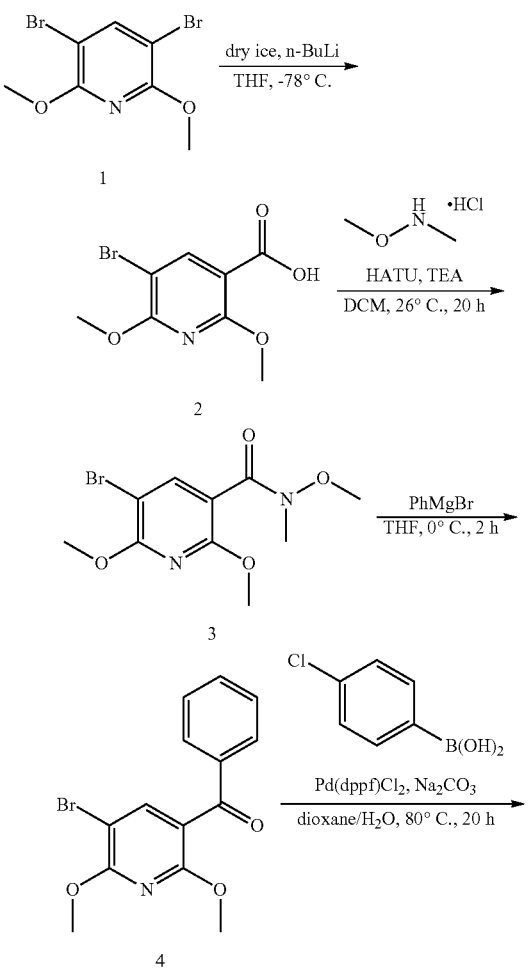

223
-continued

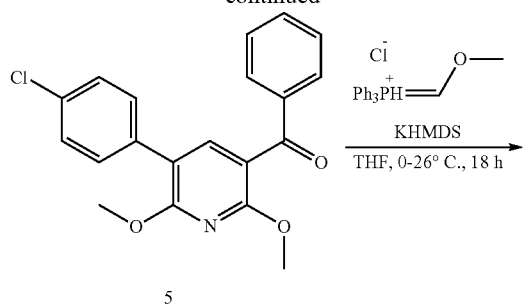

5

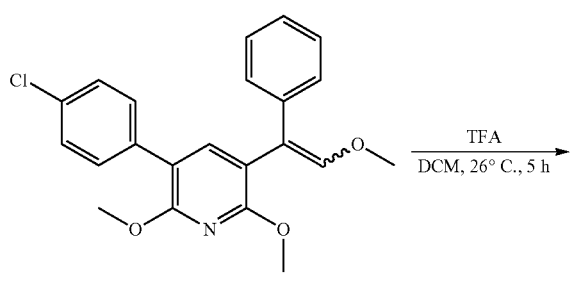

6

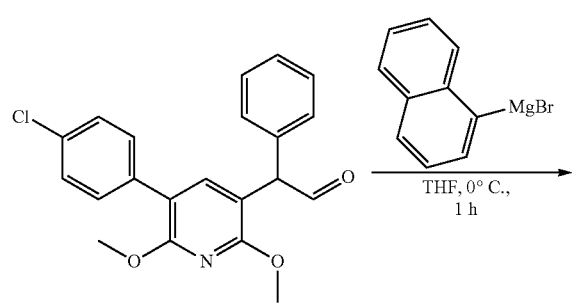

7

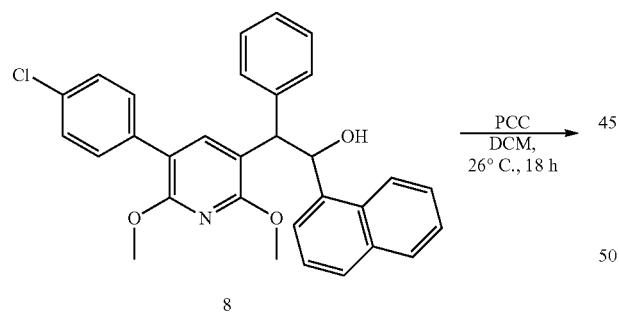

8

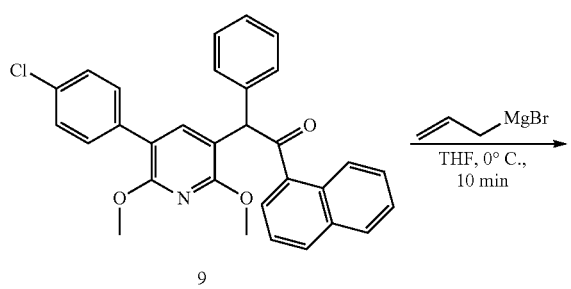

9

224
-continued

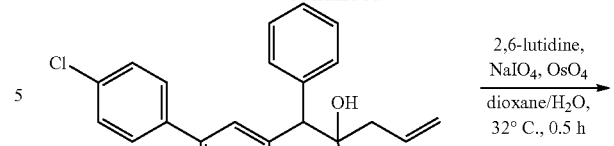

10

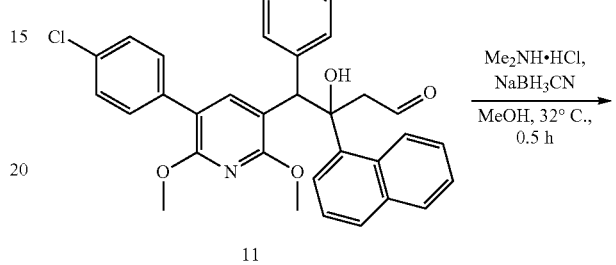

11

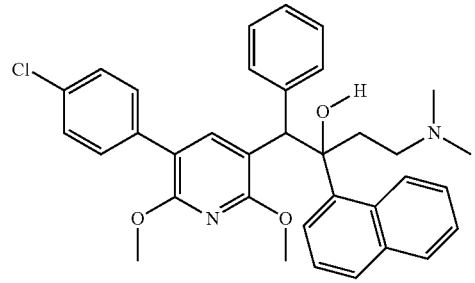

Compound 401 (A1)
Compound 402 (A2)
Compound 403 (B1)
Compound 404 (B2)

Step 1:
5-bromo-2,6-dimethoxy-pyridine-3-carboxylic acid

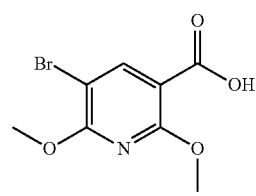

Under nitrogen, n-butyllithium (2.5 M, 13.5 mL, 33.75 mmol) was added slowly dropwise to the mixed solution of 3,5-dibromo-2,6-dimethoxypyridine (10.0 g, 33.7 mmol) in isopropyl ether (100 mL) at −70−−60° C. After the addition was complete, the mixture was stirred at −70−−60° C. for 10 minutes. Dry ice (7.41 g, 168 mmol) was added portionwise to the reaction system and stirred at −70-60° C. for 10 minutes. The reaction mixture was quenched with saturated ammonium chloride solution (50 mL) and extracted with ethyl acetate (100 mL×10). The combined organic phase was dried over anhydrous sodium sulfate, filtered and concentrated to give crude product which was suspended in 20 mL of petroleum ether and stirred at 25° C. for 10 minutes.

The precipitate was filtered and dried to give 5-bromo-2,6-dimethoxypyridine-3-carboxylic acid (6.70 g, 75.91% yield) as a pale yellow solid. ¹H NMR (400 MHz, DMSO-d): 8.24 (s, 1H), 4.01 (s, 3H), 3.96 (s, 3H).

Step 2: 5-bromo-N,2,6-trimethoxy-N-methylpyridine-3-carboxamide

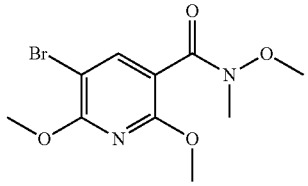

5-bromo-2,6-dimethoxypyridine-3-carboxylic acid (5.00 g, 19.1 mmol) was dissolved in dichloromethane (30 mL), and HATU (8.71 g, 22.9 mmol) and triethylamine (5.43 g, 53.6 mmol) were added. After the mixture was stirred at 26° C. for 0.5 h, N-methoxymethylamine hydrochloride (2.23 g, 22.9 mmol) was added to the mixture and stirred at 26° C. for 48 h. Then water (100 mL) was added to the mixture and extracted with dichloromethane (50 mL×3). The combined organic phase was dried over anhydrous sodium sulfate and concentrated to give crude product which was purified by silica gel column chromatography (developing solvent:petroleum ether/ethyl acetate=10/1-5/1) to give 5-bromo-N,2,6-trimethoxy-N-methylpyridine-3-carboxamide (3.5 g, 60.1% yield) as a pale yellow solid. LCMS (ESI) m/z: 305.0/307.0 (M+1).

Step 3: (5-bromo-2,6-dimethoxypyridin-3-yl)(phenyl)methanone

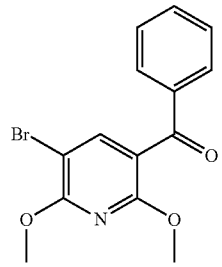

Phenylmagnesium bromide (2.8 M, 8.19 mL, 22.93 mmol) was added to the solution of 5-bromo-N,2,6-trimethoxy-N-methylpyridine-3-carboxamide (3.50 g, 11.47 mmol) in anhydrous tetrahydrofuran (35 mL) under nitrogen at 0° C. Afterwards, the mixture was stirred for 1 hour. Then the reaction was quenched with saturated aqueous ammonium chloride solution (25 mL) and the reaction mixture was extracted with ethyl acetate (50 mL×3). The combined organic phase was dried over anhydrous sodium sulfate, filtered and was concentrated to give a residue which was purified by silica gel column chromatography (developing solvent:petroleum ether/ethyl acetate=1/0-10/1) to give (5-bromo-2,6-dimethoxy-3-pyridyl)-phenylmethanone (3.20 g, 86.60% yield) as a pale yellow solid. ¹H NMR (400 MHz, CDCl₃) δ: 7.97 (s, 1H), 7.77 (d, J=7.3 Hz, 2H), 7.61-7.57 (m, 1H), 7.49-7.45 (m, 2H), 4.10 (s, 3H), 3.90 (s, 3H).

Step 4: [5-(4-chlorophenyl)-2,6-dimethoxy-3-pyridyl]-phenylmethanone

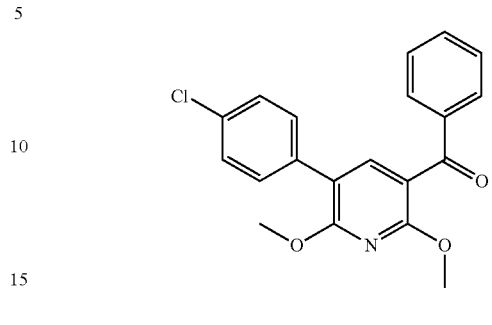

(5-bromo-2,6-dimethoxy-3-pyridyl)-phenylmethanone (3.20 g, 9.9.3 mmol), (4-chlorophenyl)boronic acid (2.33 g, 14.9 mmol) and sodium carbonate (2.11 g, 19.9 mmol) were mixed in the solution of 1,4-dioxane/water (8 mL×2 mL). Under nitrogen, Pd(dppf)Cl₂ (726 mg, 993 mmol) was added at 28° C. Afterwards, the reaction mixture was heated to 80° C., stirred for 20 h under nitrogen, and then cooled to 28° C. Water (50 mL) was added and the mixture was extracted with ethyl acetate (50 mL×3). The combined organic phase was dried over anhydrous sodium sulfate, filtered and concentrated to give crude product which was purified by silica gel column chromatography (developing solvent:petroleum ether/ethyl acetate=50/1-10/1) to give [5-(4-chlorophenyl)-2,6-dimethoxy-3-pyridyl]-phenylmethanone (3.30 g, 93.93% yield) as a pale yellow solid. ¹H NMR (400 MHz, CDCl₃): 7.87-7.79 (m, 3H), 7.60-7.56 (m, 1H), 7.51-7.45 (m, 4H), 7.39 (d, J=8.5 Hz, 2H), 4.07 (s, 3H), 3.95 (s, 3H).

Step 5: 3-(4-chlorophenyl)-2,6-dimethoxy-5-(2-methoxy-1-phenylvinyl)pyridine

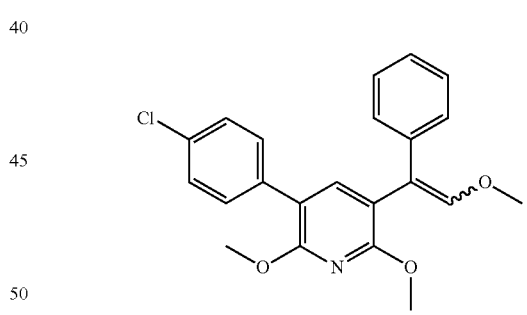

Under nitrogen, KHMDS (8.19 g, 41.0 mmol) was added to the solution of (methoxymethylene)triphenylphosphoranyl chloride (15.0 g, 43.8 mmol) in anhydrous THF (100 mL) at 0° C. and stirred at this temperature for 30 minutes. Then the solution of [5-(4-chlorophenyl)-2,6-dimethoxy-3-pyridyl]-phenylmethanone (3.30 g, 9.33 mmol) in anhydrous tetrahydrofuran (20 mL) was added at 0° C. Afterwards, the reaction mixture was stirred at 28° C. for 18 h. The reaction mixture was quenched with saturated aqueous ammonium chloride solution (50 mL) and extracted with ethyl acetate (50 mL×3). The combined organic layers was dried over anhydrous sodium sulfate, filtered and concentrated to give crude product which was purified by silica gel column chromatography (developing solvent:petroleum ether/ethyl acetate=1/0-10/1) to give 3-(4-chlorophenyl)-2, 6-dimethoxy-5-(2-methoxy-1-phenylvinyl)pyridine (3.90 g, crude product) as a pale yellow solid. LCMS (ESI) m/z: 382.1 (M+1).

Step 6: 2-(5-(4-chlorophenyl)-2,6-dimethoxypyridin-3-yl)-2-phenylacetaldehyde

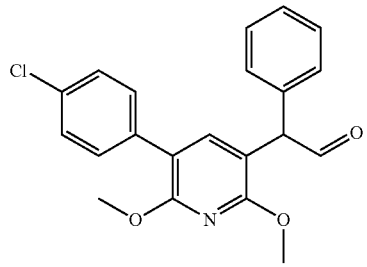 [SMILES: COc1nc(OC)c(C(C=O)c2ccccc2)cc1-c1ccc(Cl)cc1]

At 32° C., trifluoroacetic acid (5.82 g, 51.1 mmol) was added to the solution of 3-(4-chlorophenyl)-2,6-dimethoxy-5-(2-methoxy-1-phenylvinyl)pyridine (3.90 g, 10.2 mmol) in DCM (40 mL) and stirred at this temperature for 20 h. The reaction liquid was poured into saturated aqueous sodium hydrogencarbonate solution (30 ml) and extracted with ethyl acetate (50 mL×3). The combined organic phase was dried over anhydrous sodium sulfate, filtered and concentrated to give 2-[5-(4-chlorophenyl)-2,6-dimethoxy-3-pyridyl]-2-phenylacetaldehyde (3.30 g, crude product) as a yellow oil. The crude product was used directly in the next step without further purification. LCMS (ESI) m/z: 368.0 (M+1).

Step 7: 2-[5-(4-chlorophenyl)-2,6-dimethoxy-3-pyridyl]-1-(1-naphthyl)-2-phenylethanol

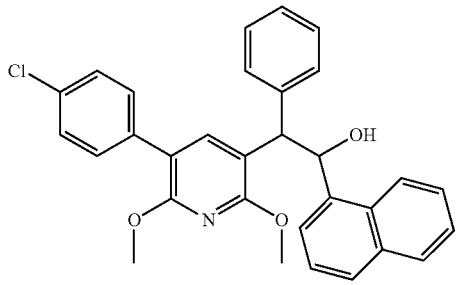 [SMILES: COc1nc(OC)c(C(c2ccccc2)C(O)c2cccc3ccccc23)cc1-c1ccc(Cl)cc1]

Magnesium chips (2.18 g, 89.7 mmol) and iodine (22.8 mg, 89.7 mol) was suspended in anhydrous tetrahydrofuran (30.00 mL) and 2-bromonaphthalene (1.5 g, 7.25 mmol) was added at 28° C. under nitrogen. The mixture was heated until the color disappeared. Then a solution of 2-bromonaphthalene (7.79 g, 37.65 mmol) in anhydrous tetrahydrofuran (10 mL) was added dropwise. Afterwards, the reaction liquid was stirred at 30° C. for 1 hour. The above freshly prepared 1-naphthylmagnesium bromide solution in tetrahydrofuran (1 M, mL) was added dropwise to a solution of 2-[5-(4-chlorophenyl)-2,6-dimethoxy-3-pyridyl]-2-phenylacetaldehyde (3.30 g, 8.97 mmol) in anhydrous tetrahydrofuran (20.00 mL) at 0° C. under nitrogen and stirred at room temperature for 1.5 hours. The reaction liquid was quenched with saturated aqueous ammonium chloride solution (30 mL) and extracted with ethyl acetate (50 mL×3). The combined organic phase was dried over anhydrous sodium sulfate, filtered and concentrated to give crude product which was purified by silica gel column chromatography (developing solvent:petroleum ether/ethyl acetate=50/1-20/1) to give 2-[5-(4-chlorophenyl)-2,6-dimethoxy-3-pyridyl]-1-(1-naphthyl)-2-phenylethanol(2.00 g. crude product) as a yellow oil. LCMS (ESI) m/z: 496.2 (M+1).

Step 8: 2-[5-(4-chlorophenyl)-2,6-dimethoxy-3-pyridyl]-1-(1-naphthyl)-2-phenylethanone

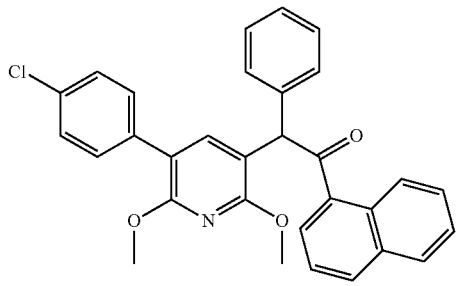 [SMILES: COc1nc(OC)c(C(C(=O)c2cccc3ccccc23)c2ccccc2)cc1-c1ccc(Cl)cc1]

2-[5-(4-chlorophenyl)-2,6-dimethoxy-3-pyridyl]-1-(1-naphthyl)-2-phenylethanol (1.80 g, 3.63 mmol) was dissolved in dichloromethane (20 mL) and Dess-Martin Oxidant (3.08 g, 7.26 mmol) was added at 32° C. and stirred for 30 minutes. The reaction mixture was concentrated to give crude product which was purified by silica gel column chromatography (developing solvent:petroleum ether/ethyl acetate=100/1-80/1) to give 2-[5-(4-chlorophenyl)-2,6-dimethoxy-3-pyridyl]-1-(1-naphthyl)-2-phenylethanone (1.10 g, 61.34% yield) as a pale yellow solid. $^1$H NMR (400 MHz, CDCl$_3$) δ: 8.58 (d, J=8.5 Hz, 1H), 8.04 (d, J=7.3 Hz, 1H), 7.97 (d, J=8.0 Hz, 1H), 7.87 (d, J=7.8 Hz, 1H), 7.60-7.52 (m, 2H), 7.48-7.30 (m, 11H), 6.21 (s, 1H), 3.99-3.94 (m, 6H).

Step 9: 1-[5-(4-chlorophenyl)-2,6-dimethoxy-3-pyridyl]-2-(1-naphthyl)-1-phenylpent-4-en-2-ol

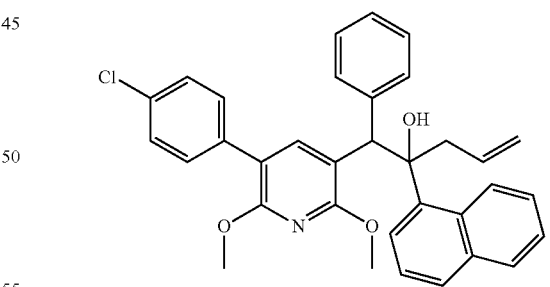

Under nitrogen, a solution of allylmagnesium bromide (I M, 4.46 mL, 4.46 mmol) in diethyl ether was slowly added dropwise to the solution of 2-[5-(4-chlorophenyl)-2,6-dimethoxy-3-pyridyl]-1-(1-naphthyl)-2-phenylethanone (1.10 g, 2.23 mmol) in anhydrous tetrahydrofuran (10.0 mL) at 0° C. The mixture was stirred at 0° C. for 30 minutes and then quenched with saturated aqueous ammonium chloride solution (30 mL) and extracted with ethyl acetate (30 mL×3). The combined organic phase was dried over anhydrous sodium sulfate, filtered and concentrated to give 1-[5-(4-chlorophenyl)-2,6-dimethoxy-3-pyridyl]-2-(1-naphthyl)-1- phenylpent-4-en-2-ol (1.20 g, crude product) as a yellow oil. The crude product was used directly in the next step without further purification.

Step 10: 4-[5-(4-chlorophenyl)-2,6-dimethoxy-3-pyridyl]-3-hydroxyl-3-(1-naphthyl)-4-phenylbutanal

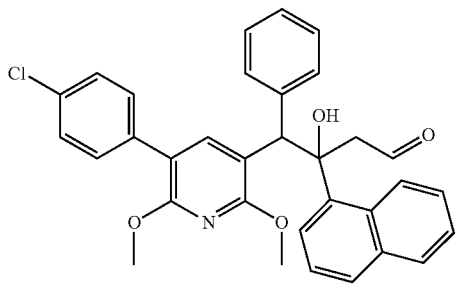 [SMILES: COc1nc(OC)c(C(c2ccccc2)C(O)(CC=O)c2cccc3ccccc23)cc1-c1ccc(Cl)cc1]

1-[5-(4-chlorophenyl)-2,6-dimethoxy-3-pyridyl]-2-(1-naphthyl)-1-phenyl-pent-4-en-2-ol (1.20 g, 2.24 mmol) was dissolved in the mixed solvent of 1,4-dioxane/water (15.0 mL×5.0 mL), and sodium periodate (1.92 g, 8.95 mmol), 2,6-lutidine(480 mg, 4.48 mmol) and osmium tetroxide(5.69 mg, 22.39 umol) were added at 32° C. Afterwards, the reaction mixture was stirred for 0.5 h. Water (30 mL) was added to the reaction liquid and the mixture was extracted with dichloromethane (30 mL×3). The combined organic layer was dried over anhydrous sodium sulfate, filtered and concentrated to give 4-[5-(4-chlorophenyl)-2,6-dimethoxy-3-pyridyl]-3-hydroxyl-3-(1-naphthyl)-4-phenylbutanal (1.80 g, crude product) as a yellow oil. The crude product was used directly in the next step without further purification. LCMS (ESI) m/z: 538.2 (M+1).

Step 11: 1-(5-(4-chlorophenyl)-2,6-dimethoxypyridin-3-yl)-4-(dimethylamino)-2-(naphthalen-1-yl)-1-phenylbutan-2-ol

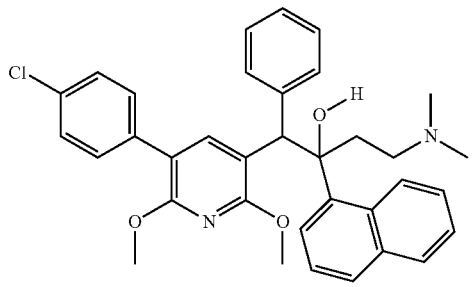

Compound 401 (A1)
Compound 402 (A2)
Compound 403 (B1)
Compound 404 (B2)

4-[5-(4-chlorophenyl)-2,6-dimethoxy-3-pyridyl]-3-hydroxyl-3-(1-naphthyl)-4-phenylbutanal (1.20 g, 2.23 mmol) was dissolved in methanol (10.0 mL), and dimethylamine hydrochloride (546 mg, 6.69 mmol) and sodium cyanoborohydride (210) mg, 3.35 mmol) were added at 28° C. Afterwards, the reaction liquid was stirred at 28° C. for another 18 h. Water (10 mL) was added to the reaction mixture which was then extracted with ethyl acetate (10 mL×3). The combined organic layers was dried over anhydrous sodium sulfate, filtered and concentrated to give crude product which was purified by preparative HPLC (GX-B; Phenomenex Synergi C18 150*30 mm*4 um; acetonitrile 50-80%; water (0.225% trifluoroacetic acid); 25 mL/min) to give component A and component B. Component A was separated by chiral SFC (SFC 80, IC-10 um; supercritical $CO_2$/MeOH (0.05% $NH_3.H_2O$)=60/40; 70 mL/min; 220 nm) to give compound 401 (A1) (16.07 mg, 1.18% yield) and compound 402 (A2) (19.75 mg, 1.44% yield) as white solid. Component B was separated by chiral SFC (SFC 80, IC-10 um; supercritical $CO_2$/MeOH (0.05% $NH_3.H_2O$)=60/40; 70 g/min; 220 nm) to give compound 403 (B1) (21.39 mg, 1.69% yield) as a pale yellow solid and compound 404 (B2) (20.65 mg, 1.63% yield) as white solid. Compound 401 (A1)/compound 402 (A2): $^1$H NMR (400 MHz, CDCl$_3$) δ: 8.66 (br. s., 1H), 8.45 (br. s., 1H), 7.87 (d, J=7.0 Hz, 2H), 7.46-7.70 (m, 6H), 7.41 (d, J=8.5 Hz, 2H), 7.29 (t, J=7.8 Hz, 1H), 7.10-7.17 (m, 2H), 6.82-6.90 (m, 3H), 5.73 (br. s., 1H), 4.19 (s, 3H), 4.02 (s, 3H), 2.68-2.75 (m, 1H), 2.17 (br. s., 2H), 2.06 (s, 6H), 1.88-1.95 (m, 1H); compound 403 (B1)/compound 404 (B2): $^1$H NMR (400 MHz, CD$_3$OD) δ: 8.47-8.70 (m, 2H), 8.27 (s, 1H), 8.09 (d, J=7.3 Hz, 1H), 7.86 (d, J=7.8 Hz, 1H), 7.67-7.78 (m, 3H), 7.59-7.63 (m, 1H), 7.32-7.51 (m, 8H), 7.24-7.28 (m, 1H), 5.59 (s, 1H), 3.67 (s, 3H), 3.29-3.32 (m, 3H), 2.76 (br. s., 1H), 2.25-2.37 (m, 2H), 2.13 (br. s., 6H), 2.00 (br. s., 1H); LCMS (ESI) m/z: 567.2 (M+1).

PHARMACOLOGY SECTION

Part I: In Vitro Efficacy Test of Anti-*M. Tuberculosis* Compound Using *Mycobacterium smegmatis* Strain ATCC19420

On the day of the test, the compound was dissolved in pure DMSO (Sigma 276855-2 L) to a concentration of 12.8 mg/ml as a stock solution of the compound. 30 μl DMSO was added to all wells of v-bottom 96-well plate (Axygen-wipp02280). 30 μl of the stock solution of the compound was added to the well in the first column and mixed by pipetting, and then 30 μl from the well in the first column was added to the well in the second column and mixed by pipetting. Such operation was conducted to the 11$^{th}$ column. The 12$^{th}$ column did not contain drug and contained only 30 μl of DMSO. This plate was the "mother plate" of the compound. From the first column to the 12$^{th}$ column, the concentration of compound was 6.4, 3.2, 1.6, 0.8, 0.4, 0.2, 0.1, 0.05, 0.025, 0.0125, 0.00625, and 0 mg/ml, respectively. For the compound having a relatively good efficacy, the test concentration was reduced appropriately. The u-bottom 96-well plate (Costar 3788) was used as a "child plate". 98 μl of CA-MHB (BD-212322) medium containing 0.02% Tween 80 was added to the wells of all child plates. 2 μl of the compound from the mother plate was added to the corresponding position of the child plate.

The bacteria were inoculated on Roche modified slant medium (Difco-244420) two days ahead and cultured in a 37° C. incubator for 48 h. On the day of the test, the bacteria colonies were collected from the slants of the culture medium and suspended in a sterile physiological saline containing 0.02% Tween 80, 7-10 sterile glass beads of 3 mm in diameter were added to the bacteria solution and the bacteria were disrupted using a vortex instrument at the maximum speed. Turbidity was adjusted to 0.10 with a Siemens MicroScan turbidity meter and the corresponding bacteria concentration was ~1.5×108 cfu/mL The bacteria solution was diluted with CA-MHB+0.02% Tween 80 medium for 20 times, and then 25 times (totally 500 times). The diluted bacteria solution were to be used to inoculate the child plate.

100 μl of the bacterial solution was added to each well of the child plate. Each well contained ~3.0×10$^4$ cfu bacteria, 1% DMSO and a gradient diluted compound in 200 μl of CA-MHB+0.02% Tween 80 medium. Then the child plate was placed in a 30° C. incubator. The minimum inhibitory concentration (MIC) was read after 72 hours.

MIC was read by reference to CLSI Method M7-A7, and defined as the minimum concentration of a drug that completely or significantly inhibits bacterial growth. The test results of the compounds were shown in Table 1.

Part II: In Vitro Efficacy Test of Anti-*M. Tuberculosis* Compound Using the H37Rv Strain On the day of the test, the compound was dissolved in pure DMSO (Sigma 276855-2 L) to a concentration of 10 mg/ml as the stock solution of the compound. 30 μl DMSO was added to the wells in the 2$^{nd}$ to 11$^{th}$ columns of a v-bottom 96-well plate (Axygen-wipp02280). 30 μl of the stock solution of the compound was added to the well in the second column and mixed by pipetting, and then 30 μl from the well in the second column was added to the well in the third column and mixed by pipetting. Such operation was conducted to the 10$^{th}$ column. The 11$^{th}$ column did not contain drug and contained only 30 μl of DMSO. This plate was the "mother plate" of the compound. From the 2$^{nd}$ column to the 11' column, the concentration of the compound was 5, 2.5, 1.25, 0.625, 0.3125, 0.156, 0.078, 0.039, 0.02, and 0 mg/ml, respectively. For the compound having a relatively good efficacy, the test concentration was reduced appropriately. A flat-bottom 96-well plate (Greiner 655090) was used as the "child plate". 98 μl of 7H9 (Sigma M0178) medium was added to the wells of all child plates. 2 μl of the compound from the mother plate was added to the corresponding position of the child plate. The wells in row A, row H, column 1 and column 12 only contained 7H9 medium.

The H37Rv strain in glycerol cryovials was inoculated into 7H9 medium containing 0.05% Tween 80 and incubated for 4 weeks at 37° C. in a shaker at 200 rpm. The bacteria solution was washed twice with 7H9 medium containing 0.05% Tween 80 and resuspended in the same culture medium. The absorbance of the bacterial solution was adjusted to OD$_{550}$=0.4-0.5 using the same medium. The bacteria solution was subpackaged in microcentrifuge tubes and store at −80° C. The storage time was no more than 1 month. On the day of the test, the subpackaged bacteria solution was thawed. The thawed bacteria solution was diluted 20 times with 7H9 medium and then diluted 50 times (a total of 1000 times). The diluted bacteria solution was used to inoculate the child plate. 100 μl of the bacteria solution was inoculated into each well of the child plate. 100 μl of 7H9 medium was added to the wells in the 12$^1$ column and no bacteria solution was added.

The test child plates were incubated in a 37° C. incubator and the humidity was maintained more than 80%. One week later, 12.5 μl of 7H9 medium containing 20% Tween 80 and 20 μl of Alamar Blue (Invitrogen DAL 1100) was added daily to one well containing bacteria in the first column and one well without bacteria in the 12$^1$ column and cultured for another 24 h before observation. When the bacteria solution in the first column can reduce the added Alamar Blue to pink within 24 hours, 7H9 medium containing 20% Tween 80 and Alamar Blue was added to all wells in the test plate and cultured at 37° C. for another 24 h before the fluorescence values were measured.

The minimum inhibitory concentration (MIC) is defined as the minimum concentration of the drug which can completely suppress Alamar blue discoloration as determined by visual observation, or the minimum concentration of the drug which can suppress the generation of more than 90% of the reduced Alamar blue as determined by a fluorometer. The detection results of the compounds were shown in Table 1.

TABLE 1

In vitro screening results

| Compound number | *M. smegmatis* ATCC19420 MIC (ug/mL) | *M. tuberculosis* H37Rv MABA (MIC) (ug/mL) | *M. tuberculosis* H37R LORA (MIC) (ug/mL) | Vero Cell (IC50) (ug/mL) | CC50_Hela (ug/mL) |
|---|---|---|---|---|---|
| Bedaquiline | 0.039 | 0.03 | 0.2 | >32 | >64 |
| 341 | ≤0.0625 | 0.031 | 0.23 | >32 | >64 |
| 375 | 0.015625 | 0.031 | 0.61 | >32 | >64 |
| 395 | 0.039 | 0.031 | <0.125 | >32 | >64 |
| 280 | 0.015625 | 0.04 | 0.16 | >32 | 35 |
| 287 | 0.03125 | 0.04 | 0.16 | >32 | >64 |
| 312 | 0.015625 | 0.04 | 0.19 | >32 | 31.3 |
| 316 | 0.015625 | 0.04 | 2.97 | >32 | >64 |
| 325 | 0.03125 | 0.04 | 0.125 | >32 | >64 |
| 331 | 0.0625 | 0.04 | 4.07 | >32 | >64 |
| 401 | 0.03125 | 0.05 | 0.19 | >32 | >64 |
| 385 | 0.03125 | 0.062 | <0.125 | >32 | 37.02 |
| 388 | 0.015625 | 0.062 | <0.125 | >32 | 26.16 |
| 115 | 0.015625 | 0.08 | 0.56 | >50 | >64 |
| 329 | 0.03125 | 0.08 | 2.02 | >32 | >64 |
| 390 | 0.0625 | 0.087 | <0.125 | >32 | 24.14 |
| 319 | 0.03125 | 0.09 | 0.22 | >32 | 49.19 |
| 308 | 0.03125 | 0.09 | 0.19 | >32 | >64 |
| 371 | 0.03125 | 0.09 | 0.259375 | >32 | 30.51 |
| 297 | 0.03125 | 0.1 | 0.74 | >32 | 39.12 |
| 351 | 0.015625 | 0.11 | 0.16 | >32 | 25.52 |
| 213 | ≤0.0625 | 0.125 | 0.46 | 25.2 | >64 |
| 337 | 0.25 | 0.14 | 1.51 | >32 | >64 |
| 293 | 0.015625 | 0.16 | 0.33 | >32 | >64 |
| 355 | 0.015625 | 0.17 | 0.21 | >32 | 53.23 |
| 303 | 0.03125 | 0.19 | 0.52 | >32 | >64 |
| 133 | 0.015625 | 0.22 | 0.22 | >32 | >64 |

TABLE 1-continued

| | In vitro screening results | | | | |
|---|---|---|---|---|---|
| Compound number | M. smegmatis ATCC19420 MIC (ug/mL) | M. tuberculosis H37Rv MABA (MIC) (ug/mL) | M. tuberculosis H37R LORA (MIC) (ug/mL) | Vero Cell (IC50) (ug/mL) | CC50_Hela (ug/mL) |
| 347 | 0.0625 | 0.23 | 0.51 | >32 | >64 |
| 259 | 0.125 | 0.32 | 4.33 | >32 | >64 |
| 299 | 0.125 | 0.33 | 0.19 | >32 | >64 |
| 91 | 0.03125 | 0.34 | 0.71 | >50 | >64 |
| 136 | 0.03125 | 0.35 | 0.79 | >50 | >64 |
| 275 | 0.125 | 0.41 | 0.67 | >32 | >64 |
| 217 | ≤0.0625 | 0.41 | 1.66 | >32 | >64 |
| 226 | 0.125 | 0.44 | 0.97 | 25.49 | 13.1 |
| 157 | 0.03125 | 0.44 | 0.77 | >32 | >64 |
| 87 | ≤0.0625 | 0.48 | 1.18 | >50 | 62.78 |
| 255 | 0.25 | 0.48 | 8.33 | >32 | >64 |
| 183 | ≤0.0625 | 0.5 | 1.33 | 24.51 | >64 |
| 31 | 0.25 | 0.58 | 0.46 | >50 | 28.1 |
| 251 | 0.25 | 0.64 | 1.39 | >32 | >64 |
| 39 | 0.125 | 0.68 | 0.71 | >50 | ND |
| 35 | ≤0.0625 | 0.73 | 0.37 | >50 | 28.85 |
| 63 | <0.0625 | 0.75 | 1.41 | >50 | 52.85 |
| 103 | 0.125 | 0.76 | 1.48 | 32.32 | 57.72 |
| 178 | 0.03125 | 0.78 | 0.88 | 25.51 | 25.77 |
| 245 | ≤0.0625 | 0.86 | 1.39 | >32 | >64 |
| 209 | 0.03125 | 0.89 | 0.84 | 27.32 | 13.29 |
| 141 | ≤0.0625 | 0.93 | 1.44 | 24.38 | >64 |
| 153 | 0.25 | 0.96 | 2.54 | >32 | >64 |
| 207 | ≤0.0625 | 0.96 | 0.99 | 25.69 | 10.26 |
| 285 | 0.015625 | 0.96 | 0.63 | >32 | >64 |
| 145 | 0.0625 | 0.97 | 1.57 | 25.1 | 12.65 |
| 9 | 0.03125 | 1.08 | 0.72 | >50 | 30.36 |
| 55 | 0.125 | 1.15 | 2.06 | >50 | ND |
| 107 | 0.5 | 1.17 | 3.03 | >50 | >64 |
| 43 | 0.125 | 1.18 | 1.42 | >50 | ND |
| 51 | ≤0.0625 | 1.2 | 1.77 | >50 | ND |
| 47 | 0.125 | 1.25 | 0.75 | >50 | ND |
| 75 | 0.125 | 1.32 | 2.73 | >50 | 22.49 |
| 263 | 0.5 | 1.38 | 2.08 | >32 | >64 |
| 71 | ≤0.0625 | 1.4 | 1.47 | >50 | ND |
| 83 | 0.125 | 1.41 | 0.57 | >50 | ND |
| 175 | 0.25 | 1.42 | 2.83 | >50 | 27.63 |
| 104 | 0.5 | 1.45 | 1.52 | >50 | 19.18 |
| 22 | 0.125 | 1.48 | 1.15 | >50 | 11.96 |
| 70 | 0.125 | 1.49 | 1.33 | >50 | 13.68 |
| 161 | 0.125 | 1.6 | 4.24 | 25.05 | 14.4 |
| 171 | 0.125 | 1.7 | 2.86 | 25.35 | 14.35 |
| 169 | 0.25 | 1.73 | 4.95 | 25.86 | 19.26 |
| 177 | 0.125 | 1.74 | 1.81 | 27.6 | >64 |
| 125 | 0.5 | 1.84 | 1.89 | >32 | >64 |
| 129 | 0.5 | 1.88 | 2.57 | >32 | >64 |
| 237 | 0.5 | 1.89 | 3.07 | 24.3 | 15.62 |
| 165 | 0.25 | 1.98 | 3.94 | 26.29 | 28.81 |
| 13 | 0.25 | 2.1 | 0.94 | >50 | 9.611 |
| 64 | 0.5 | 2.33 | 3.06 | >50 | 28.75 |
| 111 | 0.5 | 2.73 | 1.36 | >50 | ND |
| 19 | 0.5 | 2.85 | 3.11 | >50 | 10.29 |
| 269 | 0.25 | 5.64 | 6.3 | >32 | 17.43 |
| 379 | 0.125 | ND | ND | ND | 61.8 |
| 399 | ≤0.0625 | ND | ND | ND | >64 |

Note:
ATCC—American Type Culture Collection;
MABA—Microplate Alma Blue Assay;
LORA—Low oxygen recovery assay;
Vero Cell—African green monkey kidney cells;
IC50—Half inhibition concentration;
Hela—human cervical cancer cells;
CC50—Half of the toxic concentration.

Analysis of the results: Most of the compounds developed in the present invention have excellent inhibitory activity against M. smegmatis, wherein many compounds have inhibitory activity against M. tuberculosis that are superior to or equivalent to Bedaquiline (a marketed anti-TB drug) under both aerobic (MABA) and anaerobic (LORA) conditions. Furthermore, these compounds did not exhibit obvious cytotoxicity to any one of Vero and Hela cells.

Part III: In Vitro Efficacy Evaluation of the Compounds on Drug-Resistant Mycobacterium tuberculosis We tested the activity of some compounds developed in the present invention using drug-sensitive and drug-resistant Mycobacterium tuberculosis strains using the same procedure as described in Part II. The results are shown in Table 2.

TABLE 2

The activity of some of the test compounds on drug-sensitive and drug-resistant Mycobacterium tuberculosis strains MIC (uM)

| Compound number | Molecular weight | Storage Concentration (mg/ml) | MABA MIC (uM) | | | | | |
|---|---|---|---|---|---|---|---|---|
| | | | vs. H37Rv | | vs. rRMP | | vs. rINH | |
| Compound 115 | 537.1 | 0.8 | 0.06 | 0.06 | 0.18 | 0.18 | 0.11 | 0.12 |
| Compound 133 | 581.6 | 0.8 | 0.12 | 0.10 | 0.24 | 0.34 | 0.22 | 0.12 |
| compound9 | 502.7 | 0.8 | 0.46 | 0.36 | 0.90 | 0.91 | 0.47 | 0.44 |
| Bedaquiline | 555.50 | 0.8 | 0.06 | 0.05 | 0.12 | 0.13 | 0.07 | 0.09 |
| rifampin | | | 0.12 | 0.24 | >4 | >4 | <0.016 | <0.016 |
| isoniazide | | | 0.37 | 0.53 | 0.83 | 0.65 | >8 | >8 |

Note:
MIC—minimum inhibition concentration; MABA—Microplate Alma Blue Assay; vs—versus; H37Rv—wild-type H37Rv strain; rRMP—rifampicin-resistant M. tuberculosis strain; rINH—isoniazide-resistant Mycobacterium tuberculosisstrains.

Analysis of the results: The compounds developed in the present invention have excellent inhibitory activity not only against wild-type Mycobacterium tuberculosis H37Rv, but only against rifampin-resistant and isoniazid-resistant strains, in which the inhibitory activities of compounds 115 and 133 on all the three tested strains were comparable to that of the marketed anti-TB drug, Bedaquiline.

Part IV: In Vivo Evaluation of the Efficacy of the Compound in a Mice Model Infected with M. tuberculosis by Spray Mycobacterium tuberculosis culture: the medium used for culturing Mycobacterium tuberculosis (ATCC35801) was Middlebrook 7H9, on which basis 0.2% glycerol, 0.05% Tween-80 and 10% oleic acid-albumin-dextrose-catalase medium was added in this experiment. After incubated at 37° C. for 4 weeks and centrifuged, the pellet was washed with PBS containing 0.05% Tween-80 and then filtered through an 8-μm filter membrane to reduce aggregation. The mixture was aliquoted into 0.5 ml tubes, stored at −80° C. refrigerator, or for infecting mice.

Animals reception and grouping: The mice used in this experiment were female Balb/c mice weighing 19-20 grams, purchased from the Charls Rever Laboratories or Harlan of the United States. Animals arrived at the facility three days before infection and were randomly assigned to different cage boxes, 4-5 mice per cage, after a general health check. Then, the animals were kept in the standard experimental conditions, and were given enough food and water.

Infection of mice and drug treatment: Bacteria suspension was diluted to the designated OD with Middlebrook 7H9 medium so that the final concentration of bacteria was estimated to be around 2*106 CFU/mL The actual bacterial amount of the bacterial solution used for the infection would be measured as follows: the bacterial solution used for the infection was serially diluted by 10-fold, 50 μl of bacterial solution in each dilution was coated on a 6-well plate; the medium was 7H11 agar plate, and the plate was cultured at 37° C. for 14-18 days before counting. All mice were infected by inhalation.

After infected for three days, 5 mice were euthanized and the lung tissue was taken out and ground. The bacteria load of the lung was measured. Specifically, the lung of mouse was removed, added to 3 ml of HBSS, and homogenized. 100 μl of this stock solution was added into 900 μl of HBSS to make a 10-fold dilution. Then the 1:10 sample was diluted using the same method. The same operation was conducted until 1:10000. Each dilution well was mixed thoroughly. 50 μl of bacterial solution in each dilution was coated on a 6-well plate. The medium was 7H11 agar plate. The plate was cultured at 37° C. for 14-18 days before counting. Each dilution was done in duplicate to obtain the average.

10 days after infection, another eight mice were euthanized, and the amount of the bacteria in the lungs was measured after the lung tissue was removed and ground. All remaining mice were weighed and the weighing results were recorded. The positive drug rifampicin was formulated with 20% hydroxypropyl beta-cyclodextrin at a final concentration of 1.5 mg per milliliter. The concentration of other synthetic drugs was 2.5 milligrams per milliliter. Mice of different groups were treated with different drugs according to the description in the following table and administered by gavage in a volume of 10 ml per kilogram body weight according to body weight. The entire dosing cycle lasted for four weeks and the mice were administered once on on each working day.

Experimental designs of the treatment groups were shown in Table 3.

TABLE 3

Experimental designs of the treatment groups

| Treatment group | Compound | Dose (mg/kg) | number of mice in each group |
|---|---|---|---|
| T3 | — | — | 5 |
| T10 | — | — | 8 |
| T35 CMC | 0.5% CMC | — | 8 |
| Positive control RMP | rifampin | 15 | 8 |
| T35 Vehicle | 20% CD (pH-3) | — | 8 |
| Positive control group | Bedaquiline | 25 | 8 |
| Test group 1 | Compound 115 (Example 22) | 25 | 8 |

TABLE 3-continued

Experimental designs of the treatment groups

| Treatment group | Compound | Dose (mg/kg) | number of mice in each group |
|---|---|---|---|
| Test group 2 | Compound 133 (Example 25) | 25 | 8 |

Note:
T3—the third day;
T10—the tenth day;
T35—the 35$^{th}$ days;
CMC—carboxymethylcellulose;
RMP—rifampicin; 20% CD (pH-3) - 20%β-cyclodextrin (pH ~3).

After infected for 35 days, all mice were euthanized, and the lung tissues were taken out and ground. The bacteria load of the lungs was calculated and the experimental results were shown in FIG. 1.

Results analysis: By comparing the amount of the bacteria in the lungs of the uninfected group on day 3, day 10 and day 35, it can be seen that the amount of the bacteria in the lungs showed a continuous increase without any treatment. The positive control, rifampicin, significantly reduced the amount of the bacteria in the lungs of the mice compared with the solvent treated group, with a reduction of 1.8 log, whereas the synthetic positive control, Bedaquiline, significantly reduced to 5.2 log. Two tested compounds, 115 and 133, also showed significant bactericidal or bacteriostatic effect on tubercle bacillus which was basically similar to the synthetic positive control and significantly reduced 5.2-5.4 log. These results indicate that the two novel compounds found in the present invention have a great potential to be a potent antibiotic having remarkable efficacy against tubercle bacillus.

The invention claimed is:

1. A compound of formula (I), or a pharmaceutically acceptable salt, hydrate, stereoisomer or tautomer thereof,

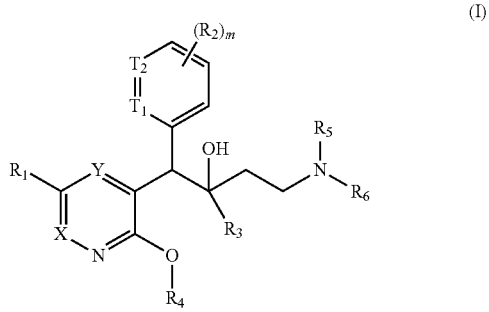

(I)

wherein,
$R^1$ is selected from H, F, Cl, Br, I, CN, OH, SH, $NH_2$, CHO, COOH, $C(=O)NH_2$, $S(=O)NH_2$, $S(=O)_2NH_2$, or the following group optionally substituted with 0, 1, 2 or 3 $R^{01}$: $C_{1-10}$ hydrocarbyl, $C_{1-10}$ heterohydrocarbyl, $C_{3-10}$ cyclohydrocarbyl, $C_{3-10}$ heterocyclohydrocarbyl, $C_{1-10}$ hydrocarbyl substituted with $C_{3-10}$ cyclohydrocarbyl or $C_{3-10}$ heterocyclohydrocarbyl, $C_{1-10}$ heterohydrocarbyl substituted with $C_{3-10}$ cyclohydrocarbyl or $C_{3-10}$ heterocyclohydrocarbyl;
m is 0, 1, 2 or 3;
$R^2$ is selected from H, halogen, haloalkyl, OH, CN, $NH_2$, or the following group optionally substituted with 0, 1, 2 or 3 $R^{01}$: $C_{1-10}$ alkyl, $C_{1-10}$ alkoxy or $C_{1-10}$ alkylthiol;
$R^3$ is selected from the following group optionally substituted with 0, 1, 2 or 3 $R^{01}$: 6-12 membered aryl, 6-12 membered heteroaryl, 6-12 membered aryl-alkylene, 6-12 membered heteroaryl-alkylene, 3-6 membered cycloalkyl, 3-6 membered heterocycloalkyl, 3-6 membered cycloalkyl-alkylene or 3-6 membered heterocycloalkyl-alkylene;
$R^4$ represents $C_{1-8}$-alkyl optionally substituted with 0, 1, 2 or 3 $R^{01}$;
$R^5$ and $R^6$ are each independently selected from H, $C_{1-8}$-alkyl or benzyl, wherein the $C_{1-8}$ alkyl is optionally substituted with 0, 1, 2 or 3 F, Cl, Br, I, CN, OH, $NH_2$ or $CF_3$;
$T_1$ and $T_2$ are each independently selected from CH and N;
X is selected from CH, $-C(C_{6-12}$ aryl)-, $-C$(halogen)-, $-C(C_{1-10}$ alkyl)-, $-C(C_{1-10}$ alkoxy)-, $-C[N(di-C_{1-10}$ alkyl)]- and N;
Y is selected from CH and N;
$R^{01}$ is selected from F, Cl, Br, I, CN, OH, $N(CH_3)_2$, $NH(CH_3)$, $NH_2$, CHO, COOH, $C(=O)NH_2$, $S(=O)NH_2$, $S(=O)_2NH_2$, $CF_3$, $CF_3O$, $(NH_2)CH_2$, $(HO)CH_2$, $CH_3C(=O)$, $CH_3OC(=O)$, $CH_3S(=O)_2$, $CH_3S(=O)$ $C_{1-8}$-alkoxy and $C_{1-8}$-alkyl;
"hetero" represents a heteroatom or a heteroatom group selected from $-C(=O)NH-$, $-NH-$, $-C(=NH)-$, $-S(=O)_2NH-$, $-S(=O)NH-$, $-O-$, $-S-$, N, =O, =S, $-C(=O)O-$, $-C(=O)-$, $-C(=S)-$, $-S(=O)-$, $-S(=O)_2-$ or $-NHC(=O)NH-$;
the number of the hetero atoms or hetero atom groups is each independently selected from 0, 1, 2 or 3;
optionally, $R^5$ and $R^6$ are together attached to the same atom to form a 3-6 membered ring.

2. The compound, or pharmaceutically acceptable salt, hydrate, stereoisomer or tautomer thereof according to claim 1, wherein $R^1$ is selected from H, F, Cl, Br, I, CN, OH, SH, $NH_2$, CHO, COOH, $C(=O)NH_2$, $S(=O)NH_2$, $S(=O)_2NH_2$, $R^{11}$ or

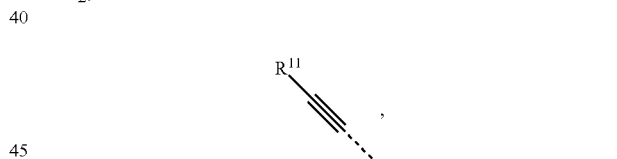

wherein, $R^{11}$ is selected from the following group optionally substituted with 0, 1, 2 or 3 $R^{01}$: $C_{1-6}$ alkyl, $C_{1-6}$ heteroalkyl, N,N-di($C_{1-6}$ alkyl)amino-$(CH_2)_{0-3}$, $C_{3-6}$ cycloalkyl, 3-6 membered heterocycloalkyl, 5-6 membered cyclohydrocarbyl and 5-6 heterocyclohydrocarbyl.

3. The compound, or pharmaceutically acceptable salt, hydrate, stereoisomer or tautomer thereof according to claim 2, wherein $R^1$ is selected from H, F, Cl, Br, I, $R^{101}$ and

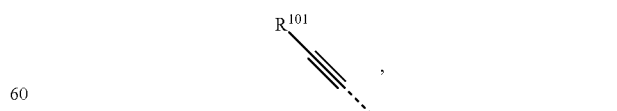

wherein, $R^{101}$ is selected from the following group optionally substituted with 1, 2 or 3 F, Cl, Br, I, $CH_3$, $CF_3$, $CH_3O$ or $CF_3O$: phenyl, pyridyl, thienyl, furyl, thiazolyl, isothiazolyl, $C_{1-6}$ alkyl, N,N-di($C_{1-6}$ alkyl)amino-$(CH_2)_{0-3}$, $C_{3-4}$ cycloalkyl,

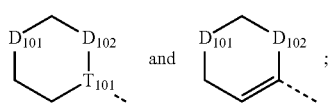

$D_{101}$ is selected from $CH_2$, O, S, NH and $N(CH_3)$;
$D_{102}$ is $CH_2$ or a single bond; and
$T_{101}$ is CH or N.

4. The compound, or pharmaceutically acceptable salt, hydrate, stereoisomer or tautomer thereof according to claim 3, wherein $R^1$ is selected from:

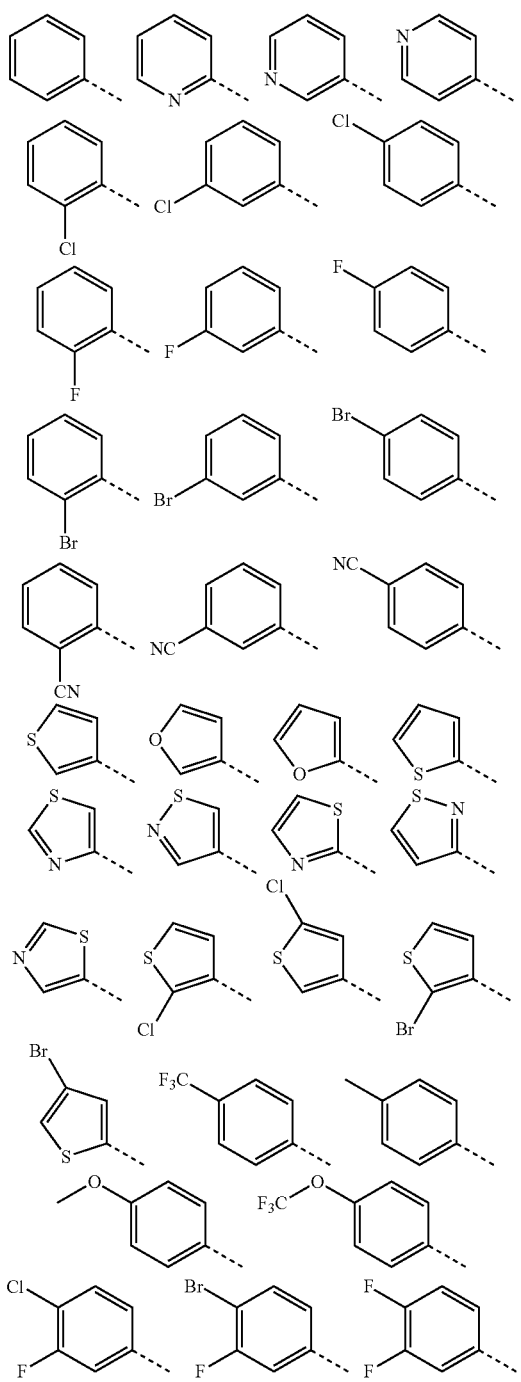

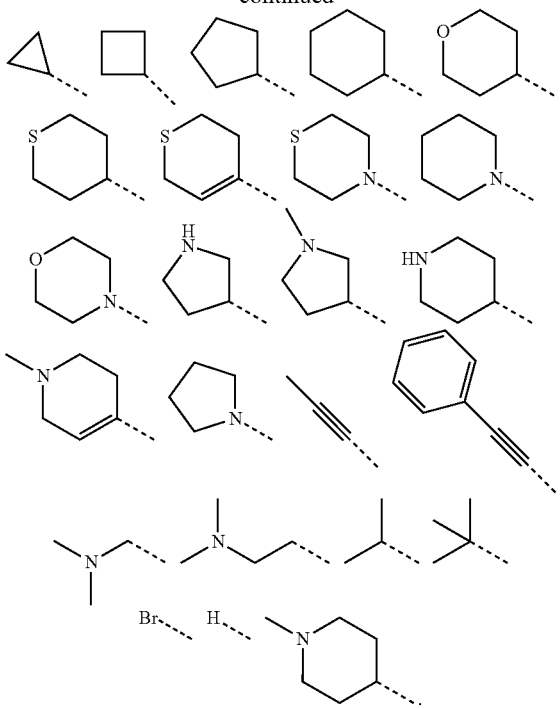

5. The compound, or pharmaceutically acceptable salt, hydrate, stereoisomer or tautomer thereof according to claim 1, wherein $R^2$ is selected from H, halogen, hydroxyl, or the following group optionally substituted with 0, 1, 2 or 3 $R^{01}$: $C_{1-6}$ alkyl or $C_{1-6}$ alkoxy.

6. The compound, or pharmaceutically acceptable salt, hydrate, stereoisomer or tautomer thereof according to claim 5, wherein $R^2$ is selected from H, halogen, hydroxyl, $CH_3O$ and $CF_3$.

7. The compound, or pharmaceutically acceptable salt, hydrate, stereoisomer or tautomer thereof according to claim 1, wherein $R^3$ is selected from the following group optionally substituted with 0, 1, 2 or 3 $R^{01}$: phenyl-$(CH_2)_{0-3}$, naphthyl-$(CH_2)_{0-3}$ and $C_{3-6}$ cycloalkyl-$(CH_2)_{0-3}$.

8. The compound, or pharmaceutically acceptable salt, hydrate, stereoisomer or tautomer thereof according to claim 7, wherein $R^3$ is selected from:

-continued

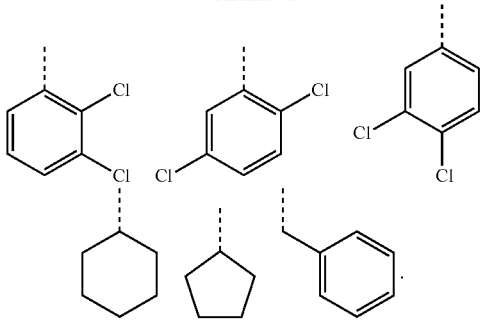

9. The compound, or pharmaceutically acceptable salt, hydrate, stereoisomer or tautomer thereof according to claim 1, wherein $R^4$, $R^5$ and $R^6$ are each independently selected from $C_{1-6}$ alkyl optionally substituted with 0, 1, 2 or 3 F, Cl, Br, I, CN, OH, SH, $NH_2$, CHO, COOH, $C(=O)NH_2$, $S(=O)NH_2$ or $S(=O)_2NH_2$.

10. The compound, or pharmaceutically acceptable salt, hydrate, stereoisomer or tautomer thereof according to claim 9, wherein $R^4$, $R^5$ and $R^6$ are independently selected from $CH_3$ and

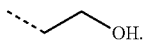

11. The compound, or pharmaceutically acceptable salt, hydrate, stereoisomer or tautomer thereof according to claim 1, wherein the structure unit

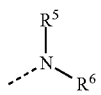

is selected from

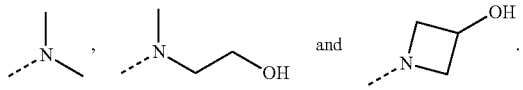

12. The compound, or pharmaceutically acceptable salt, hydrate, stereoisomer or tautomer thereof according to claim 1, wherein the compound is selected from:
1) 2-(5-(4-(dimethylamino)-2-hydroxyl-2-(naphthalen-1-yl)-1-phenylbutyl)-3-(6-methoxypyridin-3-yl))benzonitrile;
2) 1-(5-(2-bromophenyl)-2-methoxypyridin-3-yl)-4-(dimethylamino)-2-(naphthalen-1-yl)-1-phenylbutan-2-ol;
3) 1-(5-cyclopropyl-2-methoxypyridin-3-yl)-4-(dimethylamino)-2-(naphthalen-1-yl)-1-phenylbutan-2-ol;
4) 4-(dimethylamino)-1-(6-methoxy-[3,4'-bipyridin]-5-yl)-2-(naphthalen-1-yl)-1-phenylbutan-2-ol;
5) 4-(dimethylamino)-1-(6-methoxy-[3,3'-bipyridin]-5-yl)-2-(naphthalen-1-yl)-1-phenylbutan-2-ol;
6) 4-(dimethylamino)-1-(2-methoxy-5-(pyrrolidin-3-yl)pyridin-3-yl)-2-(naphthalen-1-yl)-1-phenylbutan-2-ol;
7) 4-(dimethylamino)-1-(2-methoxy-5-(1-methylpyrrol-3-yl)pyridin-3-yl)-2-(naphthalen-1-yl)-1-phenylbutan-2-ol;
8) 1-(5-cyclopentyl-2-methoxypyridin-3-yl)-4-(dimethylamino-2-(naphthalen-1-yl)-1-phenylbutan-2-ol;
9) 4-(dimethylamino)-1-(2-methoxy-5-(tetrahydro-2H-pyran-4-yl)pyridin-3-yl)-2-(naphthalen-1-yl)-1-phenylbutan-2-ol;
10) 4-(dimethylamino)-1-(2-methoxy-5-(piperidin-4-yl)pyridin-3-yl)-2-(naphthalen-1-yl)-1-phenylbutan-2-ol;
11) 4-(dimethylamino)-1-(2-methoxy-5-(1-methylpiperidin-4-yl)pyridin-3-yl)-2-(naphthalen-1-yl)-1-phenylbutan-2-ol;
12) 4-(dimethylamino)-1-(6-methoxy-1'-methyl-1',2',3',6'-tetrahydro-[3,4'-bipyridin]-5-yl)-2-(naphthalen-1-yl)-1-phenylbutan-2-ol;
13) 4-(dimethylamino)-1-(5-(2-fluorophenyl)-2-methoxypyridin-3-yl)-2-(naphthalen-1-yl)-1-phenylbutan-2-ol;
14) 4-(dimethylamino)-1-(5-(3-fluorophenyl)-2-methoxypyridin-3-yl)-2-(naphthalen-1-yl)-1-phenylbutan-2-ol;
15) 4-(dimethylamino)-1-(5-(4-fluorophenyl)-2-methoxypyridin-3-yl)-2-(naphthalen-1-yl)-1-phenylbutan-2-ol;
16) 4-(dimethylamino)-1-(6'-methoxy-[2,3'-bipyridin]-5'-yl)-2-(naphthalen-1-yl)-1-phenylbutan-2-ol;
17) 4-(dimethylamino)-1-(5-((dimethylamino)methyl)-2-methoxypyridin-3-yl)-2-(naphthalen-1-yl-1-phenylbutan-2-ol;
18) 4-(dimethylamino)-1-(5-(2-(dimethylamino)ethyl)-2-methoxypyridin-3-yl)-2-(naphthalen-1-yl)-1-phenylbutan-2-ol;
19) 1-(5-cyclohexyl-2-methoxypyridin-3-yl)-4-(dimethylamino)-2-(naphthalen-1-yl)-1-phenylbutan-2-ol;
20) 1-5-(2-chlorophenyl)-2-methoxypyridin-3-yl)-4-(dimethylamino)-2-(naphthalen-1-yl)-1-phenylbutan-2-ol;
21) 1-5-(3-chlorophenyl)-2-methoxypyridin-3-yl)-4-(dimethylamino)-2-(naphthalen-1-yl)-1-phenylbutan-2-ol;
22) 1-(5-(4-chlorophenyl)-2-methoxypyridin-3-yl)-4-(dimethylamino)-2-(naphthalen-1-yl)-1-phenylbutan-2-ol;
23) 4-(dimethylamino)-1-(2-methoxypyridin-3-yl)-2-(naphthalen-1-yl)-1-phenylbutan-2-ol;
24) 1-(5-(3-bromophenyl)-2-methoxypyridin-3-yl)-4-(dimethylamino)-2-(naphthalen-1-yl)-1-phenylbutan-2-ol;
25) 1-(5-(4-bromophenyl)-2-methoxypyridin-3-yl)-4-(dimethylamino)-2-(naphthalen-1-yl)-1-phenylbutan-2-ol;
26) 4-(dimethylamino)-1-(2-methoxy-5-(thiophen-3-yl)pyridin-3-yl)-2-(naphthalen-1-yl)-1-phenylbutan-2-ol;
27) 4-(dimethylamino)-1-(2-methoxy-5-(thiophen-2-yl)pyridin-3-yl)-2-(naphthalen-1-yl)-1-phenylbutan-2-ol;
28) 4-(dimethylamino)-1-(5-(isothiazol-3-yl)-2-methoxypyridin-3-yl)-2-(naphthalen-1-yl)-1-phenylbutan-2-ol;
29) 3-(5-(4-(dimethylamino)-2-hydroxyl-2-(naphthalen-1-yl)-1-phenylbutyl)-6-methoxypyridin-3-yl)-benzonitrile;
30) 4-(5-(4-(dimethylamino)-2-hydroxyl-2-(naphthalen-1-yl)-1-phenylbutyl)-6-methoxypyridin-3-yl)-benzonitrile;
31) 4-(dimethylamino)-1-(2-methoxy-5-(thiazol-4-yl)pyridin-3-yl)-2-(naphthalen-1-yl)-1-phenylbutan-2-ol;
32) 4-(dimethylamino)-1-(5-(isothiazol-4-yl)-2-methoxypyridin-3-yl)-2-(naphthalen-1-yl)-1-phenylbutan-2-ol;
33) 4-(dimethylamino)-1-(2-methoxy-5-(thiazol-2-yl)pyridin-3-yl)-2-(naphthalen-1-yl)-1-phenylbutan-2-ol, 34) 4-(dimethylamino)-1-(2-methoxy-5-(thiazol-5-yl)pyridin-3-yl)-2-(naphthalen-1-yl)-1-phenylbutan-2-ol;
35) 4-(dimethylamino)-1-(5-isopropyl-2-methoxypyridin-3-yl)-2-(naphthalen-1-yl)-1-phenylbutan-2-ol;
36) 4-(dimethylamino)-1-(5-(furan-3-yl)-2-methoxypyridin-3-yl)-2-(naphthalen-1-yl)-1-phenylbutan-2-ol;
37) 4-(dimethylamino)-1-(5-(furan-2-yl)-2-methoxypyridin-3-yl)-2-(naphthalen-1-yl)-1-phenylbutan-2-ol;
38) 1-(5-bromo-2-methoxypyridin-3-yl)-4-(dimethylamino)-2-(naphthalen-1-yl)-1-phenylbutan-2-ol;
39) 1-(5-(5-chlorothiophen-3-yl)-2-methoxypyridin-3-yl)-4-(dimethylamino)-2-(naphthalen-1-yl)-1-phenylbutan-2-ol;
40) 1-(5-(2-chlorothiophen-3-yl)-2-methoxypyridin-3-yl)-4-(dimethylamino)-2-(naphthalen-1-yl)-1-phenylbutan-2-ol;
41) 1-(5-(3,6-dihydro-2H-thiopyran-4-yl)-2-methoxypyridin-3-yl)-4-(dimethylamino)-2-(naphthalen-1-yl)-1-phenylbutan-2-ol;
42) 4-(dimethylamino)-1-(2-methoxy-5-(tetrahydro-2H-thiopyran-4-yl)pyridin-3-yl)-2-(naphthalen-1-yl)-1-phenylbutan-2-ol;
43) 4-(dimethylamino)-1-(2-methoxy-5-(pyrrolidin-1-yl)pyridin-3-yl)-2-(naphthalen-1-yl)-1-phenylbutan-2-ol;
44) 4-(dimethylamino)-1-(2-methoxy-5-prop-1-ynyl-3-pyridyl)-2-(1-naphthyl)-1-phenylbutan-2-ol;
45) 1-(5-(5-bromothiophen-3-yl)-2-methoxypyridin-3-yl)-4-(dimethylamino)-2-(naphthalen-1-yl)-1-phenylbutan-2-ol;
46) 4-(dimethylamino)-1-(2-methoxy-5-(4-(trifluoromethyl)phenyl)pyridin-3-yl)-2-(naphthalen-1-yl)-1-phenylbutan-2-ol;
47) 4-(dimethylamino)-1-(2-methoxy-5-(4-methoxyphenyl)pyridin-3-yl)-2-(naphthalen-1-yl)-1-phenylbutan-2-ol;
48) 1-(5-(4-bromo-3-fluorophenyl)-2-methoxypyridin-3-yl)-4-(dimethylamino)-2-(naphthalen-1-yl)-1-phenylbutan-2-ol;
49) 1-(5-(4-chloro-3-fluorophenyl)-2-methoxypyridin-3-yl)-4-(dimethylamino)-2-(naphthalen-1-yl)-1-phenylbutan-2-ol;
50) 4-(dimethylamino)-1-[2-methoxy-5-(2-phenylethynyl)-3-pyridyl]-2-(1-naphthyl)-1-phenyl-butan-2-ol;
51) 1-(5-(3,4-difluorophenyl)-2-methoxypyridin-3-yl)-4-(dimethoxyamino)-2-(naphthalen-1-yl)-1-phenylbutan-2-ol);
52) 4-(dimethylamino)-1-(2-methoxy-6-phenylpyridin-3-yl)-2-(naphthalen-1-yl)-1-phenylbutan-2-ol;
53) 4-(dimethylamino)-1-(2-methoxy-6-phenylpyridin-3-yl)-1,2-di phenyl butan-2-ol,
54) 4-(dimethylamino)-2-(2-fluorophenyl)-1-(2-methoxy-5-phenylpyridin-3-yl)-1-phenylbutan-2-ol;
55) 2-(2,3-difluorophenyl)-4-(dimethylamino)-1-(2-methoxy-5-phenylpyridin-3-yl)-1-phenylbutan-2-ol;
56) 2-(3,5-difluorophenyl)-4-(dimethylamino)-1-(2-methoxy-5-phenylpyridin-3-yl)-1-phenylbutan-2-ol;
57) 2-(2, 5-difluorophenyl)-4-(dimethylamino)-1-(2-methoxy-5-phenylpyridin-3-yl)-1-phenylbutan-2-ol;
58) 4-dimethylamino-1-(2-methoxy-5-phenylpyridin-3-yl)-2-(naphthalen-1-yl)-1-phenylbutan-2-ol;
59) 4-dimethylamino-1-(2-ethoxy-5-phenylpyridin-3-yl)-2-(naphthalen-1-yl)-1-phenylbutan-2-ol;
60) 1-(4-chlorophenyl)-4-(dimethylamino)-1-(2-methoxy-5-phenylpyridin-3-yl)-2-phenylbutan-2-ol;
61) 1-(3-chlorophenyl)-4-(dimethylamino)-1-(2-methoxy-5-phenyl pyridin-3-yl)-2-phenylbutan-2-ol;
62) 4-(dimethylamino)-1-(2-fluorophenyl)-1-(2-methoxy-5-phenylpyridin-3-yl)-2-phenylbutan-2-ol;
63) 4-(dimethylamino)-1-(3-fluorophenyl)-1-(2-methoxy-5-phenylpyridin-3-yl)-2-phenylbutan-2-ol;
64) 4-(dimethylamino)-1-(4-fluorophenyl)-1-(2-methoxy-5-phenylpyridin-3-yl)-2-phenylbutan-2-ol;
65) 1-(2,3-dimethoxyphenyl)-4-(dimethylamino)-1-(2-methoxy-5-phenylpyridin-3-yl)-2-phenylbutan-2-ol;
66) 2-(3, 5-difluorophenyl)-1-(2,3-dimethoxyphenyl)-4-(dimethylamino)-1-(2-methoxy-5-phenylpyridin-3-yl)butan-2-ol;
67) 2-(3-chlorophenyl)-1-(2,3-dimethoxyphenyl)-4-(dimethylamino)-1-(2-methoxy-5-phenylpyridin-3-yl)butan-2-ol;
68) 2-(3,5-dichlorophenyl)-1-(2,3-dimethoxyphenyl)-4-(dimethylamino)-1-(2-methoxy-5-phenylpyridin-3-yl)butan-2-ol,
69) 4-(dimethylamino)-1-(2-fluoro-3-methoxyphenyl)-1-(2-methoxy-5-phenylpyridin-3-yl)-2-phenylbutan-2-ol;
70) 4-(dimethylamino)-1-(2-methoxy-5-phenylpyridin-3-yl)-2-phenyl-1-(pyridin-2-yl)butan-2-ol;
71) 4-(dimethylamino)-1-(2-methoxy-5-phenylpyridin-3-yl)-2-phenyl-1-(pyridin-3-yl)butan-2-ol;
72) 4-(dimethylamino)-1-(2-methoxy-5-phenylpyridin-3-yl)-1-(3-methoxyphenyl)-2-phenylbutan-2-ol;
73) 4-(dimethylamino)-1-(2-methoxy-5-phenylpyridin-3-yl)-1-(4-methoxyphenyl)-2-phenylbutan-2-ol;
74) 4-(dimethylamino)-1-(2-methoxy-5-phenylpyridin-3-yl)-2-phenyl-1-(2-(trifluoromethyl)phenyl)butan-2-ol;
75) 4-(dimethylamino)-1-(2-methoxy-5-phenylpyridin-3-yl)-2-(naphthalen-1-yl)-1-(3-trifluoromethyl)phenyl)butan-2-ol;
76) 1-(5-(4-chlorophenyl)-2-methoxypyridin-3-yl)-2-(3,5-dichlorophenyl)-4-(dimethylamino)-1-phenylbutan-2-ol;
77) 1-(5-(4-chlorophenyl)-2-methoxypyridin-3-yl)-2-(2,5-difluorophenyl)-4-(dimethylamino)-1-phenylbutan-2-ol;
78) 1-(5-(4-chlorophenyl)-2-methoxypyridin-3-yl)-4-(dimethylamino)-2-(3-fluorophenyl)-1-phenylbutan-2-ol;
79) 2-(3-chlorophenyl)-1-(5-(4-chlorophenyl)-2-methoxypyridin-3-yl)-4-(dimethylamino)-1-phenylbutan-2-ol;
80) 1-(5-(4-chlorophenyl)-2-methoxypyridin-3-yl)-2-(2,3-dichlorophenyl)-4-(dimethylamino)-1-phenylbutan-2-ol;
81) 1-(5-(4-chlorophenyl)-2-methoxypyridin-3-yl)-2-(2,5-dichlorophenyl)-4-(dimethylamino)-1-phenylbutan-2-ol;
82) 1-(5-(4-chlorophenyl)-2-methoxypyridin-3-yl)-2-(3,4-dichlorophenyl)-4-(dimethylamino)-1-phenylbutan-2-ol;
83) 1-(5-(4-bromophenyl)-2-methoxypyridin-3-yl)-2-(2,5-difluorophenyl)-4-(dimethylamino)-1-phenylbutan-2-ol;
84) 1-(5-(4-bromophenyl)-2-methoxypyridin-3-yl)-4-(dimethylamino)-2-(3-fluorophenyl)-1-phenylbutan-2-ol;
85) 1-(5-(4-bromophenyl)-2-methoxypyridin-3-yl)-2-(3,5-dichlorophenyl)-4-(dimethylamino)-1-phenylbutan-2-ol;
86) 1-(5-(4-bromophenyl)-2-methoxypyridin-3-yl)-2-(3-chlorophenyl)-4-(dimethylamino)-1-phenylbutan-2-ol;
87) 4-(dimethylamino)-1-(2-methoxy-5-thiomorpholinpyridin-3-yl)-2-(naphthalen-1-yl)-1-phenylbutan-2-ol;
88) 4-(dimethylamino)-1-(2-methoxy-5-morpholinopyridin-3-yl)-2-(naphthalen-1-yl)-1-phenylbutan-2-ol, 89) 1-(5-tert-butyl-2-methoxypyridin-3-yl)-4-dimethylamino-2-(naphthalen-1-yl)-1-phenylbutan-2-ol;
90) 1-(6-chloro-5-(4-chlorophenyl)-2-methoxypyridin-3-yl)-4-dimethylamino-2-(naphthalen-1-yl)-1-phenylbutan-2-ol;
91) 2-cyclohexyl-4-dimethylamino-1-(2-methoxy-5-phenylpyridin-3-yl)-1-phenyl butan-2-ol,
92) 2-cyclopentyl-4-(dimethylamino)-1-(2-methoxy-5-phenylpyridin-3-yl)-1-phenylbutan-2-ol;
93) 2-benzyl-4-dimethylamino-1-2-methoxy-5-phenylpyridin-3-yl)-1-phenylbutan-2-ol;
94) 4-((2-hydroxylethyl)(methyl)amino)-1-(2-methoxy-5-phenylpyridin-3-yl)-2-(naphthalen-1-yl)-1-phenylbutan-2-ol;
95) 1-(3-hydroxyl-4-(2-methoxy-5-phenylpyridin-3-yl)-3-(naphthalen-1-yl)-4-phenylbutyl)azetidin-3-ol;
96) 1-(5-(4-bromophenyl)-2-methoxypyridin-3-yl)-2-(2,3-difluorophenyl)-4-(dimethylamino)-1-phenylbutan-2-ol,
97) 1-(5-(4-chlorophenyl)-2-methoxy-3-pyridyl)-2-(2,3-difluorophenyl)-4-dimethylamino-1-phenylbutan-2-ol;
98) 1-(5-(4-bromophenyl)-2-methoxypyridin-3-yl)-2-(3,5-difluorophenyl)-4-dimethylamino-1-phenylbutan-2-ol;
99) 1-(5-(4-chlorophenyl)-2-methoxypyridin-3-yl)-2-(3,5-difluorophenyl)-4-dimethylamino-1-phenylbutan-2-ol;
100) 1-(4-chlorophenyl)-1-(5-(4-chlorophenyl)-2-methoxypyridin-3-yl)-4-dimethylamino-2-naphthalen-1-yl)butan-2-ol;
101) 1-(5-(4-bromophenyl)-2-methoxypyridin-3-yl)-1-(4-chlorophenyl)-4-dimethylamino-2-(naphthalen-1-yl)butan-2-ol;
102) 4-(dimethylamino)-1-(2-methoxy-5-(p-tolyl)pyridin-3-yl)-2-(naphthalen-1-yl)-1-phenylbutan-2-ol;
103) 4-(dimethylamino)-1-(2-methoxy-5-(4-(trifluoromethoxy)phenyl)pyridin-3-yl)-2-(naphthalen-1-yl)-1-phenylbutan-2-ol;
104) 1-(5-(4-chloro-3-methoxyphenyl)-2-methoxypyridin-3-yl)-4-(dimethylamino)-2-(naphthalen-1-yl)-1-phenylbutan-2-ol;
105) 2-(2-bromophenyl)-1-(5-(4-chlorophenyl)-2-methoxypyridin-3-yl)-4-(dimethylamino)-1-phenylbutan-2-ol,
106) 2-(3-bromophenyl)-1-(5-(4-chlorophenyl)-2-methoxypyridin-3-yl)-4-(dimethylamino)-1-phenylbutan-2-ol;
107) 2-(4-bromophenyl)-1-(5-(4-chlorophenyl)-2-methoxypyridin-3-yl)-4-(dimethylamino)-1-phenylbutan-2-ol;
108) 1-(5-(4-chlorophenyl)-2-methoxypyridin-3-yl)-2-(3,5-dichlorophenyl)-1-(2,3-dimethoxyphenyl)-4-(dimethylamino)butan-2-ol;
109) 2-(3-chlorophenyl)-1-(5-(4-chlorophenyl)-2-methoxypyridin-3-yl)-1-(2,3-dimethoxyphenyl)-4-(dimethylamino)butan-2-ol;
110) 1-(5-(4-chlorophenyl)-2,6-dimethoxypyridin-3-yl)-4-(dimethylamino)-2-(naphthalen-1-yl)-1-phenylbutan-2-ol.

13. A method for treating a *Mycobacterium tuberculosis* disease comprising the step of administering the compound of claim 1 to a subject in need thereof.

* * * * *